US012544382B2

(12) United States Patent
Zhao et al.

(10) Patent No.: US 12,544,382 B2
(45) Date of Patent: Feb. 10, 2026

(54) 2, 4, 6-TRI-SUBSTITUTED PYRIMIDINE COMPOUND AS ATR KINASE INHIBITOR

(71) Applicant: BEIJING TIDE PHARMACEUTICAL CO., LTD., Beijing (CN)

(72) Inventors: Yanping Zhao, Beijing (CN); Hongjun Wang, Beijing (CN); Bin Liu, Beijing (CN); Yuanyuan Jiang, Beijing (CN); Weiting Zhong, Beijing (CN); Huifen Xu, Beijing (CN); Honglei Zhang, Beijing (CN); Chuangchuang Huang, Beijing (CN); Nana Tian, Beijing (CN); Jing Zhao, Beijing (CN); Jing Li, Beijing (CN); Weina Liu, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 1021 days.

(21) Appl. No.: 17/616,571

(22) PCT Filed: Jun. 5, 2020

(86) PCT No.: PCT/CN2020/094532
§ 371 (c)(1),
(2) Date: Dec. 3, 2021

(87) PCT Pub. No.: WO2020/244613
PCT Pub. Date: Dec. 10, 2020

(65) Prior Publication Data

US 2022/0378799 A1 Dec. 1, 2022

(30) Foreign Application Priority Data

Jun. 6, 2019 (CN) ........................ 201910490080.6
Sep. 17, 2019 (CN) ........................ 201910876919.X
May 22, 2020 (CN) ........................ 202010441539.6

(51) Int. Cl.
*A61K 31/5377* (2006.01)
*A61P 35/00* (2006.01)
*C07D 413/14* (2006.01)
*C07D 471/04* (2006.01)

(52) U.S. Cl.
CPC .......... *A61K 31/5377* (2013.01); *A61P 35/00* (2018.01); *C07D 413/14* (2013.01); *C07D 471/04* (2013.01)

(58) Field of Classification Search
CPC ... A61K 31/5377; A61K 31/506; A61P 35/00; C07D 413/14; C07D 471/04; C07D 405/14
See application file for complete search history.

(56) References Cited

U.S. PATENT DOCUMENTS 5,376,645 A 12/1994 Stella et al.
2007/0135466 A1 6/2007 Ledeboer et al.
2008/0171743 A1 7/2008 Finlay et al.
2008/0262021 A1 10/2008 Capraro et al.
2009/0018134 A1 1/2009 Pike et al.
2015/0087673 A1 3/2015 Hitoshi et al.
2019/0055240 A1 2/2019 Di Francesco et al.
2020/0399260 A1* 12/2020 Qian ........................ A61P 35/00

FOREIGN PATENT DOCUMENTS

CN 101010318 A 8/2007
CN 101535296 A 9/2009
CN 101765597 A 6/2010
CN 101790525 A 7/2010
CN 102372711 A 3/2012
CN 102448958 A 5/2012
CN 103613591 A 3/2014
(Continued)

OTHER PUBLICATIONS

Brown; Bioisosteres in Medicinal Chemistry, Wiley-VCH, 2012 (Year: 2012).*
(Continued)

*Primary Examiner* — Jeffrey S Lundgren
*Assistant Examiner* — W. Justin Youngblood
(74) *Attorney, Agent, or Firm* — Lando & Anastasi, LLP

(57) ABSTRACT

Compounds of general formula (A) can be used for treating ATR kinase-mediated diseases, for example, hyperplastic diseases such as cancers. Also provided are a pharmaceutical composition of the compounds of general formula (A), a use of the pharmaceutical composition for treating the ATR kinase-mediated diseases and a preparation method for the pharmaceutical composition (A)

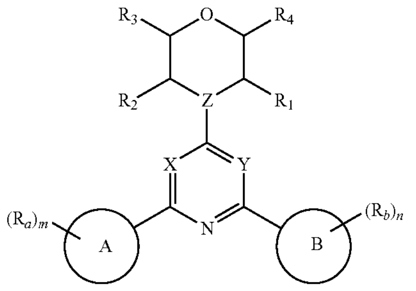

17 Claims, No Drawings

(56) References Cited

FOREIGN PATENT DOCUMENTS

| | | | |
|---|---|---|---|
| CN | 110343095 | A | 10/2019 |
| CN | 110467610 | A | 11/2019 |
| IN | 2281MUM2012 | | 6/2014 |
| WO | 03097641 | A2 | 11/2003 |
| WO | 2005028444 | A1 | 3/2005 |
| WO | 2005030130 | A2 | 4/2005 |
| WO | 2008023180 | A1 | 2/2008 |
| WO | 2008032077 | A1 | 3/2008 |
| WO | 2008048981 | A2 | 4/2008 |
| WO | 2008089307 | A2 | 7/2008 |
| WO | 2008089310 | A2 | 7/2008 |
| WO | 2009007749 | A2 | 1/2009 |
| WO | 2009007751 | A2 | 1/2009 |
| WO | 2009093981 | A1 | 7/2009 |
| WO | 2011005119 | A1 | 1/2011 |
| WO | 2011154737 | A1 | 12/2011 |
| WO | 2012044641 | A1 | 4/2012 |
| WO | 2012151562 | A1 | 11/2012 |
| WO | 2013010136 | A2 | 1/2013 |
| WO | 2013028263 | A1 | 2/2013 |
| WO | 2013192367 | A1 | 12/2013 |
| WO | 2015055071 | A1 | 4/2015 |
| WO | 2015073804 | A2 | 5/2015 |
| WO | 2019014618 | A1 | 1/2019 |
| WO | 2019036641 | A1 | 2/2019 |
| WO | 2019050889 | A1 | 3/2019 |
| WO | 2019154365 | A1 | 8/2019 |
| WO | 2020259601 | A1 | 12/2020 |
| WO | 2021023272 | A1 | 2/2021 |
| WO | 2021233376 | A1 | 11/2021 |
| WO | 2021238999 | A1 | 12/2021 |

OTHER PUBLICATIONS

Jorda, et al.; Journal of Medicinal Chemistry; v54, pp. 2980-2993; 2011 (Year: 2011).*

Foote, Kevin M. et al., "Discovery and Characterization of AZD6738, a Potent Inhibitor of Ataxia Telangiectasia Mutated and Rad3 Related (ART) Kinase with Application as an Anticancer Agent", Journal of Medical Chemistry, pp. 9889-9907 (2018).

Degorce et al., "Discovery of Novel 3-Quinoline Carboxamides as Potent, Selective and Orally Bioavailable Inhibitors of Ataxia Telangiectasia Mutated (ATM) Kinase", Journal of Medicinal Chemistry, 2016, 56, pp. 6281-6292.

Goldberg et al., "The Discovery of 7-Methyl-2-[(7-methyl[1,2,4]triazolo[1,5-a]pyridin-6-yl)amino]-9-(tetrahydro-2H-pyran-4-yl)-7,9-dihydro-8H-purin-8-one (AZD7648), a Potent and Selective DNA-Dependent Protein Kinase (DNA-PK) Inhibitor", Journal of Medicinal Chemistry, 2020, 63, pp. 3461-3471.

Mortensen et al., Discovery and SAR exploration of a novel series of imidazo[4,5-b]pyrazin-2-ones as potent and selective mTOR kinase inhibitors. Bioorganic & Medicinal Chemistry Letters, 21 (2011) pp. 6793-6799.

* cited by examiner

2, 4, 6-TRI-SUBSTITUTED PYRIMIDINE COMPOUND AS ATR KINASE INHIBITOR

CROSS-REFERENCE TO RELATED APPLICATIONS

This application is a U.S. national phase application under 35 U.S.C. § 371 of International Application No. PCT/CN2020/094532, filed Jun. 5, 2020, which claims the benefit of Chinese Application Nos. 201910490080.6, filed Jun. 6, 2019, 201910876919.X, filed Sep. 17, 2019, and 202010441539.6, filed May 22, 2020.

TECHNICAL FIELD

The present disclosure relates to 2,4,6-tri-substituted pyrimidine compounds as ATR kinase inhibitor. More specifically, the compound of the present disclosure is effective in the treatment of diseases mediated by ATR kinase, for example, proliferative diseases such as cancers. The present disclosure also provides a pharmaceutical composition of the compound, use of the compound for treating diseases mediated by ATR kinase and its preparation.

BACKGROUND

ATR (Ataxia telangiectasia and Rad3-related protein) is a class of protein kinase involved in genome stability and DNA damage repair. It belongs to PIKK family. The activation of ATR can be activated by stagnant replication forks or DNA single strand breakage (SSB). The activated ATR will recruit repair proteins or repair factors to repair the damaged parts and delay the mitotic process (especially in the G2/M phase of mitosis), which not only stabilizes the replication fork, but also ensures the stability of the gnome.

In addition, the DNA damage repair system in most tumor cells is abnormal, which usually lacks a certain repair pathway (such as p53 or ATM mutation), making them more dependent on ATR for survival. In normal cells, due to its robust and complete repair pathway, inhibition of ATR kinase alone will not produce a great impact. Therefore, inhibition of ATR may have a more significant effect on the treatment of cancer without great toxic side effects on normal cells.

Moreover, the inhibition of ATR can be combined with radiotherapy or chemotherapy drugs to synergistically enhance the effect. Widely used chemotherapeutic drugs include antimetabolites (such as gemcitabine), DNA cross-linking agents (such as cisplatin, carboplatin), and alkylating agents (such as temozolomide), topoisomerase inhibitors (such as topotecan, irinotecan), etc. When tumor cells are affected by chemotherapy or radiotherapy, the ATR signaling pathway was activated to a greater extent to repair damaged DNA. Therefore, when using radiotherapy or chemotherapy to treat cancer, at the same time inhibiting ATR, the therapeutic effect on cancer can be greatly enhanced.

So far, there is still no ATR inhibitor on the market, so it is still necessary to discover more effective and safer ATR inhibitors.

SUMMARY OF THE INVENTION

The present disclosure provides a compound of formula (I), which can be used for treating diseases mediated by ATR kinase, for example, proliferative diseases such as cancers.

In one aspect, the present disclosure provides a compound of formula (A), or a pharmaceutically acceptable salt, enantiomer, diastereomer, racemate, solvate, hydrate, polymorph prodrug, or isotopic variant thereof, or mixture thereof:

(A)

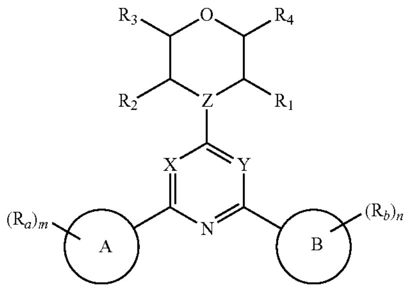

wherein,

X is $CR_5$ or N; Y is $CR_6$ or N; and wherein at least one of X and Y is N;

Z is $CR_\#$ or N;

$R_1$, $R_2$, $R_3$, $R_4$ and $R_\#$ are independently selected from H, $C_{1-6}$ alkyl and $C_{1-6}$ haloalkyl; or $R_1$ and $R_2$, $R_3$ and $R_4$ are connected to form bond, $C_{1-6}$ alkylene, $C_{2-6}$ alkenylene or $C_{2-6}$ alkynylene;

$R_5$ and $R_6$ are independently selected from H, halogen, $C_{1-6}$ alkyl or $C_{1-6}$ haloalkyl;

when Z is $CR_\#$, wherein $R_\#$ and $R_1$ can be connected to form $C_{3-5}$ cycloalkyl or 3- to 5-membered heterocyclyl;

ring A is selected from $C_{6-10}$ aryl and 5- to 10-membered heteroaryl;

ring B is 5- to 10-membered heteroaryl;

$R_a$ is independently selected from H, halogen, —CN, -L-NRR', -L-OR, —C(O)R, —C(O)OR, —C(O)NRR', —NRC(O)R', —OC(O)NRR', —NRC(O)NRR', alkyl, haloalkyl, alkoxy, $C_{1-6}$ haloalkoxy, -L-$S(O)_p$R*, -L-S(═O)(═NR)R*, cycloalkyl and -L-4- to 8-membered heterocyclyl, each of which is optionally substituted with R** group;

wherein L is independently selected from bond, —O—, —S—, —NR—, —C(O)—, $C_{1-6}$ alkylene, $C_{2-6}$ alkenylene and $C_{2-6}$ alkynylene; p=1 or 2;

R* is selected from $C_{1-6}$ haloalkyl, -L'-OR, -L'-$C_{3-7}$cycloalkyl and -L'-4- to 8-membered heterocyclyl; wherein L' is independently selected from bond, $C_{1-6}$ alkylene, $C_{2-6}$ alkenylene, $C_{2-6}$ alkynylene, alkylene and —NH—$C_{1-6}$ alkylene;

$R_b$ is independently selected from H, halogen, —CN, -L-OR, -L-$C_{1-6}$ alkyl, -L-$C_{1-6}$ alkoxy, -L-$C_{3-7}$ cycloalkyl, -L-3- to 8-membered heterocyclyl. —NRR', —C(O)R, —C(O)OR, —C(O)NRR', —OC(O)R'. —NRC(O)R', —OC(O)NRR' and —NRC(O)NRR', each of which is optionally substituted with R** group;

R** is independently selected from H, halogen, —CN, —C(═O)R, $C_{1-6}$ alkyl, $C_{1-6}$ haloalkyl, $C_{1-6}$ alkoxy, $C_{1-6}$ haloalkoxy, 4- to 8-membered heterocyclyl, —$S(O)_p$—$C_{1-6}$ alkyl, —$S(O)_6$—$C_{1-6}$ haloalkyl and —NRR';

R and R' are independently selected from H, $C_{1-6}$ alkyl and $C_{1-6}$ haloalkyl, or R, R' are taken together with the nitrogen atoms to which they are attached to form 4- to 8-membered heterocyclyl;

m=0, it, 2, 3, 4 or 5;

n=0, 1, 2, 3, 4 or 5.

In another aspect, the present disclosure provides a compound of formula (I), or a pharmaceutically acceptable salt, enantiomer, diastereomer, racemate, solvate, hydrate, polymorph, prodrug, or isotopic variant thereof, or mixture thereof:

(I)

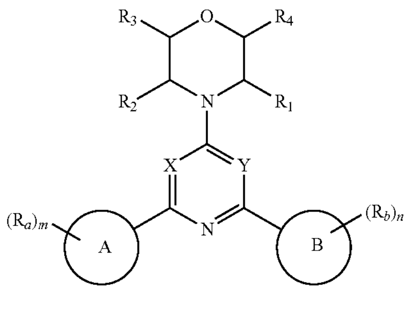

wherein,

X is CH or N; Y is CH or N; and wherein at least one of X and Y is N;

$R_1$, $R_2$, $R_3$ and $R_4$ are independently selected from H, $C_{1-6}$ alkyl and $C_{1-6}$ haloalkyl; or $R_1$ and $R_2$, $R_3$ and $R_4$ are connected to form bond. $C_{1-6}$ alkylene, $C_{2-6}$ alkenylene or $C_{2-6}$ alkynylene;

ring A is selected from $C_{6-10}$ aryl and 5- to 10-membered heteroaryl;

ring B is 5- to 10-membered heteroaryl;

$R_a$ is independently selected from H, halogen, —CN, -L-NRR', -L-OR, —C(O)R, —C(O)OR, —C(O)NRR', —OC(O)R', —NRC(O)R', —OC(O)NRR', —NRC(O)NRR', $C_{1-6}$ alkyl, $C_{1-6}$ haloalkyl, alkoxy, $C_{1-6}$ haloalkoxy, -L-S(O)$_p$R*, -L-S(═O)(═NR)R*, -L-$C_{3-7}$ cycloalkyl and -L-4- to 8-membered heterocyclyl, each of which is optionally substituted with R** group;

$R_b$ is independently selected from H, halogen, —CN, —OH, $C_{1-6}$ alkyl, $C_{1-6}$ alkoxy, -L-$C_{3-7}$ cycloalkyl, -L-3- to 8-membered heterocyclyl, —NRR', —C(O)R, —C(O)OR, —C(O)NRR', —OC(O)R', —NRC(O)R', —OC(O)NRR' and —NRC(O)NRR';

m=0, 1, 2, 3, 4 or 5;

n=0, 1, 2, 3, 4 or 5;

wherein L is independently selected from bond, —O—, —S—, —NR—, —C(O)—, $C_{1-6}$ alkylene, $C_{2-6}$ alkenylene and $C_{2-6}$ alkynylene;

R* is selected from $C_{1-6}$ alkyl, $C_{1-6}$ haloalkyl, -L'-NRR', -L'-OR, -L'-$C_{3-7}$ cycloalkyl and -L'-4- to 8-membered heterocyclyl;

L' is independently selected from bond, $C_{1-6}$ alkylene, $C_{2-6}$ alkenylene, $C_{2-6}$ alkynylene, —O—$C_{1-6}$ alkylene and —NH—$C_{1-6}$ alkylene;

R** is independently selected from H, halogen, —CN, —C(═O)R, $C_{1-6}$ alkyl, $C_{1-6}$ haloalkyl, $C_{1-6}$ alkoxy, $C_{1-6}$ haloalkoxy, 4- to 8-membered heterocyclyl, —S(O)$_p$—$C_{1-6}$ alkyl, —S(O)$_p$—$C_{1-6}$ haloalkyl and —NRR';

R and R' are independently selected from H, $C_{1-6}$ alkyl and $C_{1-6}$ haloalkyl, or R, R' are taken together with the nitrogen atoms to which they are attached to form 4- to 8-membered heterocyclyl;

p=1 or 2.

In another aspect, the present disclosure provides a pharmaceutical composition comprising a compound disclosed herein, and optionally pharmaceutically acceptable excipients.

In another aspect, the present disclosure provides a pharmaceutical composition comprising a compound disclosed herein and pharmaceutically acceptable excipients, which further comprises other therapeutic agent(s).

In another aspect, the present disclosure provides a kit comprising a compound disclosed herein, other therapeutic agent(s), and pharmaceutically acceptable carriers, adjuvants or vehicles.

In another aspect, the present disclosure provides a use of a compound disclosed herein in the manufacture of a medicament for treating and/or preventing a disease mediated by ATR kinase.

In another aspect, the present disclosure provides a method of treating and/or preventing a disease mediated by ATR kinase in a subject, comprising administering to the subject a compound disclosed herein or a composition disclosed herein.

In another aspect, the present disclosure provides a compound disclosed herein or a composition disclosed herein, for use in treating and/or preventing a disease mediated by ATR kinase.

In a specific embodiment, the disease includes: proliferative diseases (such as cancer), especially, solid tumors (such as carcinoma and sarcoma), leukemia and lymphoma, especially breast cancer, colorectal cancer, lung cancer (including small cell lung cancer, non-small cell lung cancer and bronchoalveolar cancer), prostate cancer and bile duct cancer, bone cancer, bladder cancer, head and neck cancer, kidney cancer, liver cancer, gastrointestinal cancer, esophageal cancer, ovarian cancer, pancreatic cancer, skin cancer, testicular cancer, thyroid cancer, uterine cancer, cervical cancer and vulvar cancer, and leukemia [including acute lymphoblastic leukemia (ALL) and chronic myeloid leukemia (CML)], multiple myeloma and lymphoma.

Other objects and advantages of the present disclosure will be apparent to those skilled in the art from the specific embodiments, examples and claims disclosed herein.

Definition

Chemical Definitions

Definitions of specific functional groups and chemical terms are described in more detail below.

When a range of values is listed, it is intended to encompass each value and sub-range within the range. For example "$C_{1-6}$ alkyl" is intended to include $C_1$, $C_2$, $C_3$, $C_4$, $C_5$, $C_6$, $C_{1-6}$, $C_{1-5}$, $C_{3-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

"$C_{1-6}$ alkyl" refers to a radical of a straight or branched, saturated hydrocarbon group having 1 to 6 carbon atoms. In some embodiments, $C_{1-4}$ alkyl is preferred. Examples of $C_{1-6}$ alkyl include methyl ($C_3$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), pentyl ($C_5$), neopentyl ($C_5$), 3-methyl-2-butyl ($C_5$), tert-pentyl ($C_5$) and n-hexyl ($C_6$). The term "$C_{1-6}$ alkyl" also includes heteroalkyl, wherein one or more (e.g., 1, 2, 3 or 4) carbon atoms are substituted with heteroatoms (e.g., oxygen, sulfur, nitrogen, boron, silicon, phosphorus). Alkyl groups can be optionally substituted with one or more substituents, for example, with 1 to 5 substituents, 1 to 3 substituents or 1 substituent. Conventional abbreviations of alkyl include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$) or i-Bu (—$CH_2CH(CH_3)_2$).

"$C_{2-6}$ alkenyl" refers to a radical of a straight or branched hydrocarbon group having 2 to 6 carbon atoms and at least one carbon-carbon double bond. In some embodiments, $C_{2-4}$ alkenyl is preferred. Examples of $C_{2-6}$ alkenyl include vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. The term "$C_{2-6}$ alkenyl" also includes heteroalkenyl, wherein one or more (e.g., 1, 2, 3 or 4) carbon atoms are replaced by heteroatoms (e.g., oxygen, sulfur, nitrogen, boron, silicon, phosphorus). The alkenyl groups can be optionally substituted with one or more substituents, for example, with 1 to 5 substituents, 1 to 3 substituents or 1 substituent.

"$C_{2-6}$ alkynyl" refers to a radical of a straight or branched hydrocarbon group having 2 to 6 carbon atoms, at least one carbon-carbon triple bond and optionally one or more carbon-carbon double bonds. In some embodiments, $C_{2-4}$ alkynyl is preferred. Examples of $C_{2-6}$ alkynyl include, but are not limited to, ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), etc. The term "$C_{2-6}$ alkynyl" also includes heteroalkynyl, wherein one or more (e.g., 1, 2, 3 or 4) carbon atoms are replaced by heteroatoms (e.g., oxygen, sulfur, nitrogen, boron, silicon, phosphorus). The alkynyl groups can be substituted with one or more substituents, for example, with 1 to 5 substituents, 1 to 3 substituents or 1 substituent.

"$C_{1-6}$ alkylene, $C_{2-6}$ alkenylene or $C_{2-6}$ alkynylene" refers to a divalent group of the "$C_{1-6}$ alkyl, $C_{2-6}$ alkenyl or $C_{2-6}$ alkynyl" as defined above.

"$C_{1-6}$ alkylene" refers to a divalent group formed by removing another hydrogen of the $C_{1-6}$ alkyl, and can be a substituted or unsubstituted alkylene. In some embodiments, $C_{1-4}$ alkylene is particularly preferred. The unsubstituted alkylene groups include, but are not limited to, methylene ($-CH_2-$), ethylene ($-CH_2CH_2-$), propylene ($-CH_2CH_2CH_2-$), butylene ($-CH_2CH_2CH_2CH_2-$), pentylene ($-CH_2CH_2CH_2CH_2CH_2-$), hexylene ($-CH_2CH_2CH_2CH_2CH_2CH_2-$), etc. Examples of substituted alkylene groups, such as those substituted with one or more alkyl (methyl) groups, include, but are not limited to, substituted methylene ($-CH(CH_3)-$, $-C(CH_3)_2-$), substituted ethylene ($-CH(CH_3)CH_2-$, $-CH_2CH(CH_3)-$, $-C(CH_3)_2CH_2-$, $-CH_2C(CH_3)_2-$), substituted propylene ($-CH(CH_3)CH_2CH_2-$, $-CH_2CH(CH_3)CH_2-$, $-CH_2CH_2CH(CH_3)-$, $-C(CH_3)_2CH_2CH_2-$, $-CH_2C(CH_3)_2CH_2-$, $-CH_2CH_2C(CH_3)_2-$), etc.

"$C_{2-6}$ alkenylene" refers to a $C_{2-6}$ alkenyl group wherein another hydrogen is removed to provide a divalent radical of alkenylene, and which may be substituted or unsubstituted alkenylene. In some embodiments, $C_{2-4}$ alkenylene is particularly preferred. Exemplary unsubstituted alkenylene groups include, but are not limited to, ethenylene ($-CH{=}CH-$) and propenylene (e.g., $-CH{=}CHCH_2-$, $-CH_2-CH{=}CH-$). Exemplary substituted alkenylene groups, e.g., substituted with one or more alkyl (methyl) groups, include but are not limited to, substituted ethylene ($-C(CH_3){=}CH-$, $-CH{=}C(CH_3)-$), substituted propylene (e.g., $-C(CH_3){=}CHCH_2-$, $-CH-C(CH_3)CH_2-$, $-CH{=}CHCH(CH_3)-$, $-CH{=}CHC(CH_3)_2-$, $-CH(CH_3)_2CH-$). $-C(CH_3)_2-CH{=}CH-$, $-CH_2-C(CH_3){=}CH-$, $-CH_2-CH{=}C(CH_3)-$), and the like.

"$C_{2-6}$ alkynylene" refers to a $C_{2-6}$ alkynyl group wherein another hydrogen is removed to provide a divalent radical of alkynylene, and which may be substituted or unsubstituted alkynylene. In some embodiments, $C_{2-4}$ alkynylene is particularly preferred. Exemplary alkynylene groups include, but are not limited to, ethenylene ($-(C{\equiv}C)$, substituted or unsubstituted propynylene ($-C{\equiv}CCH_2-$), and the like.

"$C_{1-6}$ alkoxy" refers to the group $-OR$ wherein R is a substituted or unsubstituted $C_{1-6}$ alkyl. In some embodiments, $C_{1-4}$ alkoxy group is particularly preferred. Specific alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy. The alkoxy can be optionally substituted with one or more substituents, for example, with 1 to 5 substituents, 1 to 3 substituents or 1 substituent.

"Halo" or "halogen" refers to fluorine (F), chlorine (Cl), bromine (Br) and iodine (I).

Thus, "$C_{1-6}$ haloalkyl" and "$C_{1-6}$ haloalkoxy" refer to the above "$C_{1-6}$ alkyl" and "$C_{1-6}$ alkoxy", which are substituted by one or more halogen. In some embodiments, $C_{1-4}$ haloalkyl is particularly preferred, and more preferably $C_{1-2}$ haloalkyl. In some embodiments, $C_{1-4}$ haloalkoxy group is particularly preferred, and more preferably $C_{1-2}$ haloalkoxy group. Exemplary haloalkyl groups include, but are not limited to, $-CF_3$, $-CH_2F$, $-CHF_2$, $-CHFCH_2F$, $-CH_2CHF_2$, $-CF_2CF_3$, $-CCl_3$, $-CH_2Cl$, $-CHCl_2$, 2,2,2-trifluoro-1,1-dimethyl-ethyl, and the like. Exemplary haloalkoxy groups include, but are not limited to: $-OCH_2F$, $-OCHF_2$, $-OCF_3$, and the like. The haloalkyl and haloalkoxy can be substituted at any available point of attachment, for example, with 1 to 5 substituents, 1 to 3 substituents or 1 substituent.

"$C_{3-7}$ cycloalkyl" refers to a radical of a non-aromatic cyclic hydrocarbon group having from 3 to 7 ring carbon atoms and zero heteroatoms. In some embodiments, $C_{3-5}$ cycloalkyl is preferred. In other embodiments, $C_{3-6}$ cycloalkyl is preferred. In other embodiments, $C_{5-6}$ cycloalkyl is preferred. The cycloalkyl also includes a ring system in which the cycloalkyl described herein is fused with one or more aryl or heteroaryl groups, wherein the point of attachment is on the cycloalkyl ring, and in such case, the number of carbon atoms continues to represent the number of carbon atoms in the cycloalkyl system. Exemplary cycloalkyl groups include, but are not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_5$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), etc. The cycloalkyl can be substituted with one or more substituents, for example, with 1 to 5 substituents, 1 to 3 substituents or 1 substituent.

"3- to 11-membered heterocyclyl" refers to a radical of 3- to 11-membered non-aromatic ring system having ring carbon atoms and 1 to 5 ring heteroatoms, wherein each of the heteroatoms is independently selected from nitrogen, oxygen, sulfur, boron, phosphorus and silicon. In the heterocyclyl containing one or more nitrogen atoms, the point of attachment can be a carbon or nitrogen atom as long as the valence permits. In some embodiments, 3- to 9-membered heterocyclyl is preferred, which is a radical of 3- to 9-membered non-aromatic ring system having ring carbon atoms and 1 to 5 ring heteroatoms. In some embodiments, 3- to 8-membered heterocyclyl is preferred, which is a radical of 3- to 8-membered non-aromatic ring system having ring carbon atoms and 1 to 4 ring heteroatoms, 3- to 6-membered heterocyclyl is preferred, which is a radical of 3- to 6-membered non-aromatic ring system having ring carbon atoms and 1 to 3 ring heteroatoms, 3- to 5-membered heterocyclyl is preferred, which is a radical of 3- to 5-membered non-aromatic ring system having ring carbon atoms and 1 to 2 ring heteroatoms. 4- to 8-membered heterocyclyl is preferred, which is a radical of 4- to 8-membered non-aromatic ring system having ring carbon atoms and 1 to 3 ring heteroatoms. 5- to 6-membered heterocyclyl is more preferred, which is a radical of 5- to 6-membered non-aromatic ring system having ring carbon atoms and 1 to 3 ring heteroatoms. The heterocyclyl also includes a ring system wherein the heterocyclyl described above is fused with one or more cycloalkyl groups, wherein the point of attachment is on the cycloalkyl ring, or the heterocyclyl described above is fused with one or inure amyl or heteroaryl groups, wherein the point of attachment is on the heterocyclyl ring and in such cases, the number of ring members continues to represent the number of ring members in the heterocyclyl ring system. Exemplary 3-membered heterocyclyl groups containing one heteroatom include, but are not limited to, aziridinyl, oxiranyl and thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothienyl, pyrrolidinyl, dihydropyrrolyl and pyrrolyl-2,5-dione. Exemplary 5-membered heterocyclyl groups containing two heteroatoms include, but are not limited to, dioxolanyl, oxasulfuranyl, disulfuranyl, and oxazolidin-2-one. Exemplary 5-membered, heterocyclyl groups containing three heteroatoms include, but are not limited to, oxadiazolinyl, and thiadiazolinyl. Exemplary 6-membered heterocyclyl groups containing one heteroatom include, but are not limited to, piperidyl, tetrahydropyranyl, dihydropyridyl and thianyl. Exemplary 6-membered heterocyclyl groups containing two heteroatoms include, but are not limited to, piperazinyl, morpholinyl, dithianyl and dioxanyl. Exemplary 6-membered heterocyclyl groups containing three heteroatoms include, but are not limited to, triazinanyl. Exemplary 7-membered heterocycyl groups containing one heteroatom include, but are not limited to, azepanyl, oxepanyl and thiepanyl. Exemplary 5-membered heterocyclyl groups fused with a $C_6$ aryl (also referred as 5,6-bicyclic heterocyclyl herein) include, but are not limited to, indolinyl, isoindolinyl, dihydrobenzofuranyl, dihydrobenzothiophenyl, benzoxazolinonyl, etc. Exemplary 6-membered heterocyclyl groups fused with a $C_6$ aryl (also referred as 6,6-bicyclic heterocyclyl herein) include, but are not limited to, tetrahydroquinolinyl, tetrahydroisoquinolinyl, etc. The heterocyclyl can be substituted with one or more substituents, for example, with 1 to 5 substituents, 1 to 3 substituents or 1 substituent.

"$C_{6-10}$ aryl" refers to a radical of monocyclic or polycyclic (e.g., bicyclic) 4n+2 aromatic ring system having 6-10 ring carbon atoms and zero heteroatoms (e.g., having 6 or 10 shared π electrons in a cyclic array). In some embodiments, the aryl group has six ring carbon atoms ("$C_6$ aryl"; for example, phenyl). In some embodiments, the aryl group has ten ring carbon atoms ("$C_{10}$ aryl"; for example, naphthyl. e.g., 1-naphthyl and 2-naphthyl). The aryl group also includes a ring system in which the aryl ring described above is fused with one or more cycloalkyl or heterocyclyl groups, and the point of attachment is on the aryl ring, in which case the number of carbon atoms continues to represent the number of carbon atoms in the aryl ring system. The aryl can be substituted with one or more substituents, for example, with 1 to 5 substituents, 1 to 3 substituents or 1 substituent.

"5- to 10-membered heteroaryl" refers to a radical of 5- to 10-membered monocyclic or bicyclic 4n+2 aromatic ring system (e.g., having 6 or 10 shared a electrons in a cyclic array) having ring carbon atoms and 1-4 ring heteroatoms, wherein each heteroatom is independently selected from nitrogen, oxygen and sulfur. In the heteroaryl group containing one or more nitrogen atoms, the point of attachment can be a carbon or nitrogen atom as long as the valence permits. Heteroaryl bicyclic systems may include one or more heteroatoms in one or two rings. Heteroaryl also includes ring systems wherein the heteroaryl ring described above is fused with one or inure cycloalkyl or heterocyclyl groups, and the point of attachment is on the heteroaryl ring. In such case, the number the carbon atoms continues to represent the number of carbon atoms in the heteroaryl ring system. In some embodiments, 5- to 6-membered heteroaryl groups are particularly preferred, which are radicals of 5- to 6-membered monocyclic or bicyclic 4n+2 aromatic ring systems having ring carbon atoms and 1-4 ring heteroatoms. Exemplary 5-membered heteroaryl groups containing one heteroatom include, but are not limited to, pyrrolyl, furyl and thienyl. Exemplary 5-membered heteroaryl groups containing two heteroatoms include, but are not limited to, imidazolyl, pyrazolyl, oxazolyl, isoxazolyl, thiazolyl and isothiazolyl. Exemplary 5-membered heteroaryl groups containing three heteroatoms include, but are not limited to, triazolyl, oxadiazolyl. (such as, 1,2,4-oxadiazoyl), and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzoisoxazolyl, benzoxadiazolyl, benzothiazolyl, benzoisothiazolyl, benzothiadiazolyl, indolizinyl and purinyl. Exemplary 6,6-bicyclic heteroaryl groups include, but are not limited to, naphthyridinyl, pteridinyl, quinoxalinyl, phthalazinyl and quinazolinyl. The heteroaryl can be substituted with one or more substituents, for example, with 1 to 5 substituents, 1 to 3 substituents or 1 substituent.

Specific examples of preferred heteroaryl groups include: pyrrolyl, imidazolyl, pyrazolyl, 2-pyridyl, 3-pyridyl, 4-pyridyl, pyrimidinyl, pyrazinyl, pyridazinyl, triazolyl (4H-1,2,4-triazolyl, 1H-1,2,3-triazolyl, 2H-1,2,3-triazolyl, pyranyl, 2-furanyl, 2-furyl, 3-furyl, 2-thienyl, 3-thienyl, oxazolyl, isoxazolyl, oxazolyl (1,2,4-oxazolyl, 1,3,4-oxazolyl, 1,2,5-oxazolyl, thiazolyl, thiadiazolyl (1,2,4-thiadiazolyl, 1,3,4-thiadiazolyl, 1,2,5-thiadiazolyl).

"carbonyl", whether used alone or in conjunction with other terms (e.g., aminocarbonyl), is represented by —C(O)—.

"Oxo" represents =O.

"Thioxo" represents =S.

Alkyl, alkenyl, alkynyl, carbocyclyl, heterocyclyl, aryl and heteroaryl as defined herein are optionally substituted groups.

Exemplary substituents on carbon atoms include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})$ OR$^{aa}$, —OC(—NR$^{bb}$)R$^{aa}$, —OC(═NR$^{bb}$)OR$^{aa}$, —C(═NR$^{bb}$)N(R$^{bb}$)$_2$, —OC(═NR$^{bb}$)N(R$^{bb}$)$_2$, —NR$^{bb}$C(═NR$^{bb}$)N(R$^{bb}$)$^2$, —C(═O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(═O)R$^{aa}$, —OS(═O)R$^{aa}$, —Si(R$^{aa}$)$_3$, —OSi(R$^{aa}$)$_3$, —C(═S)N(R$^{bb}$)$_2$, —C(═O)SR$^{aa}$, —C(═S)SR$^{aa}$, —SC(═S)SR$^{aa}$, —SC(═O)SR$^{aa}$, —OC(═O)SR$^{aa}$, —SC(═O)OR$^{aa}$, —SC(═O)R$^{aa}$, —P(═O)$_2$R$^{aa}$, —OP(═O)$_2$R$^{aa}$, —P(═O)(R$^{aa}$)$_2$, —OP(═O)(R$^{aa}$)$_2$, —OP(═O)(OR$^{aa}$)$_2$, —P(O)$_2$N(R$^{bb}$)$_2$, —OP(═O)$_2$N(R$^{bb}$)$_2$, —P(═O)(NR$^{bb}$)$_2$, —OP(═O)(NR$^{bb}$)$_2$, —NR$^{bb}$P(═O)(OR$^{cc}$)$_2$, —NR$^{bb}$P(═O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, haloalkyl, alkenyl, alkynyl, carbocyclyl, heterocyclyl, aryl and heteroaryl, wherein each of the alkyl, alkenyl, alkenyl, carbocyclyl, heterocyclyl, aryl and heteroaryl is independently substituted with 0, 1, 2, 3, 4 or 5 R$^{dd}$ groups;

or two geminal hydrogen on a carbon atom are replaced with ═O, ═S, ═NN(R$^{bb}$)$_2$, ═NNR$^{bb}$C(═O)R$^{aa}$, ═NNR$^{bb}$C(═O)OR$^{aa}$, ═NNR$^{bb}$S(═O)$_2$R$^{aa}$, ═NR$^{bb}$ or ═NOR$^{cc}$ groups;

each of the R$^{aa}$ is independently selected from alkyl, haloalkyl, alkenyl, alkynyl, carbocyclyl, heterocyclyl, aryl and heteroaryl, or two of the R$^{aa}$ groups are combined to form a heterocyclyl or heteroaryl ring, wherein each of the alkyl, alkenyl, alkynyl, carbocyclyl, heterocyclyl, aryl and heteroaryl is independently substituted with 0, 1, 2, 3, 4 or 5 R$^{dd}$ groups;

each of the R$^{bb}$ is independently selected from hydrogen, —OH, —OR$^{aa}$, —N(R$^{cc}$)$_2$, —CN, —C(═O)R$^{aa}$, —C(═O)N(R$^{cc}$)$_2$, —CO$_2$R$^{aa}$, —SO$_2$R$^{aa}$, —C(═NR$^{cc}$)OR$^{aa}$, —C(═NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(═S)N(R$^{cc}$)$_2$, —C(═O)SR$^{cc}$, —C(═S)SR$^{cc}$, —P(═O)$_2$R$^{aa}$, —P(═O)(R$^{aa}$)$_2$, —P(═O)$_2$N(R$^{cc}$)$_2$, —P(═O)(NR$^{cc}$)$_2$, alkyl, haloalkyl, alkenyl, alkynyl, carbocyclyl, heterocyclyl, aryl and heteroaryl, or two R$^{bb}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 R$^{dd}$ groups;

each of the R$^{cc}$ is independently selected from hydrogen, alkyl, haloalkyl, alkenyl, alkynyl, carbocyclyl, heterocyclyl, aryl and heteroaryl, or two R$^{cc}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 R$^{dd}$ groups;

each of the R$^{dd}$ is independently selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, SSR$^{ee}$, —C(═O)R$^{ee}$, —CO$_2$H, —CO$_2$R$^{ee}$, —OC(═O)R$^{ee}$, —OCO$_2$R$^{ee}$, —C(═O)N(R$^{ff}$)$_2$, —OC(═O)N(R$^{ff}$)$_2$, —NR$^{ff}$C(═O)R$^{ee}$, —NR$^{ff}$CO$_2$R$^{ee}$, —NR$^{ff}$C(═O)N(R$^{ff}$)$_2$, —C(═NR$^{ff}$)OR$^{ee}$, —OC(═NR$^{ff}$)R$^{ee}$, —OC(═NR$^{ff}$)OR$^{ee}$, —C(═NR$^{ff}$)N(R$^{ff}$)$_2$, —OC(═NR$^{ff}$)N(R$^{ff}$)$_2$, —NR$^{ff}$C(═NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(═O)R$^{ee}$, —Si(R$^{ee}$)$_3$, —OSi(R$^{ee}$)$_3$, —C(═S)N(R$^{ff}$)$_2$, —C(═O)SR$^{ee}$, —C(═S)SR$^{ee}$, —SC(═S)SR$^{ee}$, —P(═O)$_2$R$^{ee}$, —P(═O)(R$^{ee}$)$_2$, —OP(═O)(R$^{ee}$)$_2$, —OP(═O)(OR$^{ee}$)$_2$, alkyl, haloalkyl, alkenyl, alkynyl, carbocyclyl, heterocyclyl, aryl, heteroaryl wherein each of the alkyl, alkenyl, alkynyl, carbocyclyl, heterocyclyl, aryl and heteroaryl is independently substituted with 0, 1, 2, 3, 4 or 5 R$^{66}$ groups, or two geminal R$^{dd}$ substituents can be combined to form ═O or ═S;

each of the R$^{ee}$ is independently selected from alkyl, haloalkyl, alkenyl, alkynyl, carbocyclyl, aryl, heterocyclyl, and heteroaryl, wherein each of the alkyl, alkenyl, alkynyl, carbocyclyl, heterocyclyl, aryl and heteroaryl is independently substituted with 0, 1, 2, 3, 4 or 5 R$^{gg}$ groups;

each of the R$^{ff}$ is independently selected from hydrogen, alkyl, haloalkyl, alkenyl, alkynyl, carbocyclyl, heterocyclyl, aryl and heteroaryl, or two R$^{ff}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 R$^{gg}$ groups;

each of the R$^{gg}$ is independently selected from halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, 13 NH$_3$$^+$X$^-$, —N(OC$_{2-6}$ alkyl)(C$_{1-6}$ alkyl), —N(OH)(C$_{1-6}$ alkyl), —NH(OH), —SH, —SC$_{1-6}$ alkyl, —SS(C$_{2-6}$ alkyl), —C(═O)(C$_{1-6}$ alkyl), —CO$_2$H, —CO$_2$(C$_{2-6}$ alkyl), —OC(═O)(C$_{1-6}$ alkyl), —OCO$_2$(C$_{1-6}$ alkyl), —C(═O)NH$_2$, —C(═O)N(C$_{1-6}$ alkyl)$_2$, —OC(═O)NH(C$_{1-6}$ alkyl), —NHC(═O)(C$_{1-6}$ alkyl), —N(C$_{1-6}$ alkyl)C(═O)(C$_{1-6}$ alkyl), —NHCO$_2$(C$_{1-6}$ alkyl), —NHC(═O)N(C$_{1-6}$ alkyl)$_2$, —NHC(═O)NH(C$_{1-6}$ alkyl), —NHC(═O)NH$_2$, —C(═NH)O(C$_{1-6}$ alkyl), —OC(═NH)(C$_{1-6}$ alkyl), —OC(═NH)(C$_{1-6}$ alkyl, —C(═NH)N(C$_{1-6}$ alkyl)$_2$, —C(═NH)NH(C$_{1-6}$ alkyl), —C(═NH)NH$_2$, —OC(═NH)N(C$_{1-6}$ alkyl)$_2$, —OC(NH)NR(C$_{1-6}$ alkyl), —OC(NH)NH$_2$, —NHC(NH)N(C$_{1-6}$ alkyl)$_2$, —NHC(═NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(═S)N(C$_{1-6}$ alkyl)$_2$, C(═S)NH(C$_{1-6}$ alkyl), C(═S)NH$_2$, —C(═O)S(C$_{1-6}$ alkyl), —C(═S)SC$_{1-6}$ alkyl, —SC(═S)SC$_{1-6}$ alkyl, —P(═O)$_2$(C$_{1-6}$ alkyl), —P(═O)(C$_{1-6}$ alkyl), —OP(═O)(C$_{1-6}$ alkyl)$_2$, —OP(═O)(OC$_{1-6}$ alkyl)$_2$, C$_{1-6}$ alkyl, C$_{1-6}$ haloalkyl, C$_2$-C$_6$ alkenyl, C$_2$-C$_6$ alkynyl, C$_3$-C$_7$ carbocyclyl, C$_6$-C$_{10}$ aryl, C$_3$-C$_7$ heterocyclyl, C$_5$-C$_{10}$ heteroaryl; or two geminal R$^{gg}$ substituents may combine to form ═O or ═S; wherein X$^-$ is a counterion.

Exemplary substituents on nitrogen atoms include, but are not limited, to, hydrogen, —OH, —OR$^{aa}$, —N(R$^{cc}$)$_2$, —CN, —C(═O)R$^{aa}$, —C(═O)N(R$^{cc}$)$_2$, —CO$_2$R$^{aa}$, —SO$_2$R$^{aa}$, —C(═NR$^{bb}$)R$^{aa}$, —C(═NR$^{aa}$)OR$^{aa}$, —C(═NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(═S)N(R$^{cc}$)$_2$, —C(═O)SR$^{cc}$, —C(═S)SR$^{cc}$, —P(═O)$_2$R$^{aa}$, —P(═O)(R$^{aa}$)$_2$, —P(═O)$_2$N(R$^{cc}$)$_2$, —P(═O)(NR$^{cc}$)$_2$, haloalkyl, alkenyl, alkynyl, carbocyclyl, heterocyclyl, aryl and heteroaryl, or two R$^{cc}$ groups attached to a nitrogen atom combine to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 R$^{dd}$ groups, and wherein R$^{aa}$, R$^{bb}$, R$^{cc}$ and R$^{dd}$ are as described herein.

Other Definitions

The term "cancer" includes, but is not limited to, the following cancers: breast, ovary, cervix, prostate, testis, esophagus, stomach, skin, lung, bone, colon, pancreas, thyroid, biliary tract, buccal cavity and pharynx (mouth), lips, tongue, oral cavity, pharynx, small intestine, colorectal, large intestine, rectum, cancer of brain and central nervous system, glioblastoma, neuroblastoma, keratoacanthoma, epidermoid carcinoma, large cell carcinoma, adenocarcinoma, adenoma, follicular carcinoma, undifferentiated carcinoma, papillary carcinoma, seminoma, melanoma, sarcoma, bladder cancer, liver cancer, kidney cancer, bone marrow disorder, lymphatic disorder, Hodgkin's disease, hairy cell carcinoma and leukemia.

The term "treating" as used herein relates to reversing, alleviating or inhibiting the progression or prevention of the disorders or conditions to which the term applies, or of one or more symptoms of such disorders or conditions. The noun "treatment" as used herein relates to the action of treating, which is a verb, and the latter is as just defined.

The term "pharmaceutically acceptable salt" as used herein refers to those carboxy late and amino acid addition salts of the compounds of the present disclosure, which are suitable for the contact with patients' tissues within a reliable medical judgment, and do not produce inappropriate toxicity, irritation, allergy, etc. They are commensurate with a reasonable benefit/risk ratio, and are effective for their intended use. The term includes, if possible, the zwitterionic form of the compounds of the disclosure.

The pharmaceutically acceptable base addition salts are formed with metals or amines, such as alkali metal and alkaline earth metal hydroxides or organic amines. Examples of the metals used as cations include sodium, potassium, magnesium, calcium, etc. Examples of suitable amines are air N,N-dibenzylethylenediamine chloroprocaine, choline, diethanolamine, ethylenediamine, N-methylglucamine and procaine.

The base addition salt of the acidic compound can be prepared by contacting the free acid form with a sufficient amount of the required base to form a salt in a conventional manner. The free acid can be regenerated by contacting the salt form with an acid in a conventional manner and then isolating the free acid. The free acid forms are somewhat different from their respective salt forms in their physical properties, such tis solubility in polar solvents. But for the purposes of the present disclosure, the salts are still equivalent to their respective free acids.

The salts can be prepared from the inorganic acids, which include sulfates, pyrosulfates, bisulfates, sulfites, bisulfites, nitrates, phosphates, monohydrogen phosphates, dihydrogen phosphates, metaphosphates, pyrophosphates, chlorides, bromides and iodides. Examples of the acids include hydrochloric acid, nitric acid, sulfuric acid, hydrobromic acid, hydroiodic acid, phosphoric acid, etc. The representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, methanesulfonate, glucoheptanate, lactobionate, lauryl sulfonate, isethionate, etc. The salts can also be prepared from the organic acids, which include aliphatic monocarboxylic and dicarboxylic acids, phenyl-substituted alkanoic acids, hydroxyalkanoic acids, alkanedioic acid, aromatic acids, aliphatic and aromatic sulfonic acids, etc. The representative salts include acetate, propionate, octanoate, isobutyrate, oxalate, malonate, succinate, suberate, sebacate, fumarate, maleate, mandelate, benzoate, chlorobenzoate, methyl benzoate, dinitrobenzoate, naphthoate, besylate, tosylate, phenylacetate, citrate, lactate, maleate, tartrate, methanesulfonate, etc. The pharmaceutically acceptable salts can include cations based on alkali metals and alkaline earth metals, such as sodium, lithium, potassium, calcium, magnesium, etc., as well as non-toxic ammonium, quaternary ammonium, and amine cations including, but not limited to, ammonium, tetramethylammonium, tetraethylammonium, methylamine, dimethylamine, trimethylamine, trietylamine, ethylamine, etc. Salts of amino acids are also included, such as arginine salts, gluconates, galacturonates, etc. (for example, see Berge S. M. et al., "Pharmaceutical Salts," J. Pharm Sci., 1977; 66: 1-19 for reference).

Examples of pharmaceutically acceptable non-toxic amides of the compounds of the disclosure include $C_1$-$C_6$ alkyl esters, wherein the alkyl group is straight or branched. Acceptable esters also include $C_5$-$C_7$ cycloalkyl esters as well as arylalkyl esters, such as, but not limited to, benzyl esters. $C_1$-$C_4$ alkyl esters are preferred. Esters of the compounds of the disclosure can be prepared according to the conventional methods, for example, March's Advanced Organic Chemistry, 5 Edition, M, B. Smith & J. March, John Wiley & Sons, 2001.

Examples of pharmaceutically acceptable non-toxic amides of the compounds of the disclosure include amides derived from ammonia, primary $C_1$-$C_6$ alkylamines and secondary $C_1$-$C_6$ dialkylamines, wherein the alkyl group is straight or branched. In the case of the secondary amine, the amine may also be in the form of a 5- or 6-membered heterocycle containing one nitrogen atom. Amides derived from ammonia, $C_1$-$C_3$ alkyl primary amine and $C_1$-$C_2$ dialkyl secondary amine are preferred. Amides of the compounds of the present disclosure can be prepared according to the conventional methods, for example, March's Advanced Organic Chemistry, 5 Edition, M, B. Smith & J. March, John Wiley & Sons, 2001.

"Subjects" to which administration is contemplated include, but are not limited to, humans (e.g., males or females of any age group, e.g., paediatric subjects (e.g., infants, children, adolescents) or adult subjects (e.g., young adults, middle-aged adults or older adults) and/or non-human animals, such as mammals, e.g., primates (e.g., cynomolgus monkeys, rhesus monkeys), cattle, pigs, horses, sheep, goats, rodents, cats and/or dogs. In some embodiments, the subject is a human. In some embodiments, the subject is a non-human animal. The terms "human", "patient" and "subject" can be used interchangeably herein.

"Disease," "disorder," and "condition" can be used interchangeably herein.

Unless indicated, otherwise the term "treatment" as used herein includes the effect on a subject who is suffering from a particular disease, disorder, or condition, which reduces the severity of the disease, disorder, or condition, or delays or slows the progression of the disease, disorder or condition ("therapeutic treatment"). The term also includes the effect that occurs before the subject begins to suffer from a specific disease, disorder or condition ("prophylactic treatment").

Generally, the "effective amount" of a compound refers to an amount sufficient to elicit a target biological response. As understood by those skilled in the art, the effective amount of the compound of the disclosure can vary depending on the following factors, such as the desired biological endpoint, the pharmacokinetics of the compound, the diseases being treated, the mode of administration, and the age, health status and symptoms of the subjects. The effective amount includes therapeutically effective amount and prophylactically effective amount.

Unless indicated, otherwise the "therapeutically effective amount" of the compound as used herein is an amount sufficient to provide therapeutic benefits in the course of treating a disease, disorder or condition, or to delay or minimize one or more symptoms associated with the disease, disorder or condition. The therapeutically effective amount of a compound refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

Unless indicated, otherwise the "prophylactically effective amount" of the compound as used herein is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a compound refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the compounds of the present disclosure and other therapeutic agents. For example, the compounds of the present disclosure can be administered simultaneously or sequentially in separate unit dosage with other therapeutic agents, or simultaneously in a single unit dosage with other therapeutic agents.

DETAILED DESCRIPTION OF THE EMBODIMENTS

As used herein, the term "compound disclosed herein" refers to the following compounds of formulae (I) to (VI), or a pharmaceutically acceptable salt, enantiomer, diastereomer, racemate, solvate, hydrate, polymorph, prodrug, or isotopic variant thereof, or mixture thereof.

In the present disclosure, compounds are named using standard nomenclature. For compounds having an asymmetric center, it should be understood, unless otherwise stated, that all optical isomers and mixtures thereof are included. Furthermore, unless otherwise specified, all isomer compounds and carbon-carbon double bonds included in the present disclosure may occur in the form of Z and E. Compounds which exist in different tautomeric forms, one of which is not limited to any particular tautomer, but is intended to cover all tautomeric forms. General formula is used for certain compounds, including descriptions and variables. Unless otherwise specified, each variable in such a formula is defined independently of any other variable and multiple variables that independently define any one of the variables in each occurrence.

In one embodiment, the present disclosure refers to a compound of formula (A), or a pharmaceutically acceptable salt, enantiomer, diastereomer, racemate, solvate, hydrate, polymorph, prodrug, or isotopic variant thereof, or mixture thereof:

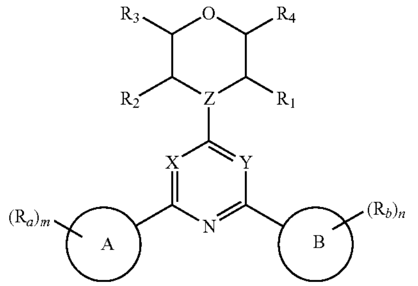

(A)

wherein,

X is $CR_5$ or N; Y is $CR_6$ or N; and wherein at least one of X and Y is N;

Z is $CR_4$ or N;

$R_1$, $R_2$, $R_3$, $R_4$ and $R_\#$ are independently selected from H, $C_{1-6}$ alkyl and $C_{1-6}$ haloalkyl; or $R_1$ and $R_2$, $R_3$ and $R_4$ are connected to form bond, $C_{1-6}$ alkylene, $C_{2-6}$ alkenylene or $C_{2-6}$ alkynylene;

$R_5$ and $R_6$ are independently selected from H, halogen, $C_{1-6}$ alkyl or $C_{1-6}$ haloalkyl;

when Z is $CR_\#$, wherein $R_\#$ and $R_1$ can be connected to form $C_{3-5}$ cycloalkyl or 3- to 5-membered heterocyclyl;

ring A is selected from $C_{6-10}$ aryl and 5- to 10-membered heteroaryl;

ring B is 5- to 10-membered heteroaryl;

$R_a$ is independently selected from H, halogen, —CN, -L-NRR', -L-OR, —C(O)R, —C(O)OR, —C(O)NRR', —OC(O)R', —NRC(O)R', —OC(O)NRR', —NRC(O)NRR', $C_{1-6}$ alkyl, $C_{1-6}$ haloalkyl, $C_{1-6}$ alkoxy, $C_{1-6}$ haloalkoxy, -L-S(=O)$_p$R*, -L-S(=O)(=NR)R*, -L-$C_{3-7}$ cycloalkyl and -L-4- to 8-membered heterocyclyl, each of which is optionally substituted with R** group;

wherein L is independently selected from bond, —O—, —S—, —NR—, —C(O)—, $C_{1-6}$ alkylene, $C_{2-6}$ alkenylene and $C_{2-6}$ alkynylene; p=1 or 2;

R* is selected from $C_{1-6}$ alkyl, $C_{1-6}$ haloalkyl, -L'-NRR', -L'-OR, -L-$C_{3-4}$ cycloalkyl and -L'-4- to 8-membered heterocyclyl; wherein L' is independently selected from bond, $C_{1-6}$ alkylene, $C_{2-6}$ alkenylene, $C_{2-6}$ alkynylene, —O—$C_{1-6}$ alkylene and —NH—$C_{1-6}$ alkylene;

$R_b$ is independently selected from H, halogen, —CN, -L-OR, -L-$C_{1-6}$ alkyl, -L-$C_{1-6}$ alkoxy, -L-$C_{3-7}$ cycloalkyl, -L-3- to 8-membered heterocyclyl, —NRR', —C(O)R, —C(O)OR, —C(O)NRR', —OC(O)R', —NRC(O)R', —OC(O)NRR' and —NRC(O)NRR', each of which is optionally substituted with R** group;

R** is independently selected from H, halogen, —CN, —C(=O)R, $C_{1-6}$ alkyl, $C_{1-6}$ haloalkyl, $C_{1-6}$ alkoxy, $C_{1-6}$ haloalkoxy, 4- to 8-membered heterocyclyl, —S(O)$_p$—$C_{1-6}$ alkyl, —S(O)$_p$—$C_{1-6}$ haloalkyl and —NRR';

R and R' are independently selected from H, $C_{1-6}$ alkyl and $C_{1-6}$ haloalkyl, or R, R' are taken together with the nitrogen atoms to which they are attached to form 4- to 8-membered heterocyclyl;

m=0, 1, 2, 3, 4 or 5;

n=0, 1, 2, 3, 4 or 5.

In another aspect, the present disclosure refers to a compound of formula (I), or a pharmaceutically acceptable salt, enantiomer, diastereomer, racemate, solvate, hydrate, polymorph, prodrug, or isotopic variant thereof, or mixture thereof:

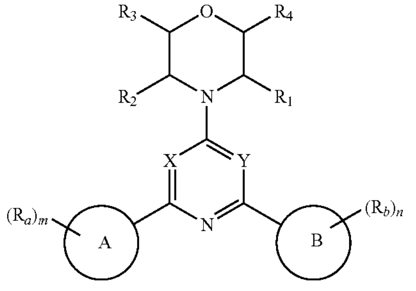

(I)

wherein,

X is CH or N; Y is CH or N; and wherein at least one of X and Y is N;

$R_1$, $R_2$, $R_3$, and $R_4$ are independently selected from H, $C_{1-6}$ alkyl and $C_{1-6}$ haloalkyl; or $R_1$ and $R_2$, $R_3$ and $R_4$ are connected to form bond. $C_{1-6}$ alkylene, $C_{2-6}$ alkenylene or $C_{2-6}$ alkynylene;

ring A is selected from $C_{6-10}$ aryl and 5- to 10-membered heteroaryl;

ring B is 5- to 10-membered heteroaryl;

$R_a$ is independently selected from H, halogen, —CN, -L-NRR', -L-OR, —C(O)R, —C(O)OR, —C(O)NRR', —OC(O)R', —NRC(O)R', —OC(O)NRR', —NRC(O)NRR', $C_{1-6}$ alkyl, $C_{1-6}$ haloalkyl, alkoxy, $C_{1-6}$ haloalkoxy, -L-S(O)$_p$R*, -L-S(=O)(=NR)R*, -L-$C_{3-7}$ cycloalkyl and -L-4- to 8-membered heterocyclyl, each of which is optionally substituted with R** group;

$R_b$ is independently selected from H, halogen, —CN, —OH, $C_{1-6}$ alkyl, $C_{1-6}$ alkoxy, -L-$C_{3-7}$ cycloalkyl, -L-3- to 8-membered heterocyclyl, —NRR', —C(O)R, —C(O)OR, —C(O)NRR', —OC(O)R', —NRC(O)R', —OC(O)NRR' and —NRC(O)NRR';

m=0, 1, 2, 3, 4 or 5;

n=0, 1, 2, 3, 4 or 5;

wherein L is independently selected from bond, —O—, —S—, —NR—, —C(O)—, $C_{1-6}$ alkylene, $C_{2-6}$ alkenylene and $C_{2-6}$ alkynylene;

R* is selected from $C_{1-6}$ alkyl, $C_{1-6}$ haloalkyl, -L'-NRR', -L'-OR, -L-$C_{3-7}$ cycloalkyl and -L'-4- to 8-membered heterocyclyl;

L' is independently selected from bond, $C_{1-6}$ alkylene, $C_{2-6}$ alkenylene, $C_{2-6}$ alkynylene, alkylene and —NH—$C_{1-6}$ alkylene;

R** is independently selected from H, halogen. —CN, —C(=O)R, $C_{1-6}$ alkyl, $C_{1-6}$ haloalkyl, $C_{1-6}$ alkoxy, haloalkoxy, 4- to 8-membered heterocyclyl, —S(O)$_p$—$C_{1-6}$ alkyl, —S(O)$_p$—$C_{1-6}$ haloalkyl and —NRR;

R and R' are independently selected from H, $C_{1-6}$ alkyl and $C_{1-6}$ haloalkyl, or R, R' are taken together with the nitrogen atoms to which they are attached to form 4- to 8-membered heterocyclyl;

p=1 or 2.

X, Y and Z in a specific embodiment, X is $CR_5$, and Y is N; in another specific embodiment, X is CH, and Y is N; in another specific embodiment, X is N, and Y is $CR_6$; in another specific embodiment, X is N, and Y is CH; in another specific embodiment, X is N, and Y is N.

In a specific embodiment, Z is $CR_{\#}$; in another specific embodiment, Z is N.

$R_1$, $R_2$, $R_3$, $R_4$ and $R_{\#}$

In a specific embodiment, $R_1$ is H; in another specific embodiment, $R_1$ is $C_{1-6}$ alkyl, for example, (R)—$C_{1-6}$ alkyl, for example, (R)-methyl; in another specific embodiment, $R_1$ is $C_{1-6}$ haloalkyl, for example, (R)—$C_{1-6}$ haloalkyl. In a specific embodiment, $R_2$ is H, in another specific embodiment, $R_2$ is $C_{1-6}$ alkyl, for example, (R)—$C_{1-6}$ alkyl, for example, (R)-methyl; in another specific embodiment, $R_2$ is $C_{1-6}$ haloalkyl, for example, (R)—$C_{1-6}$; haloalkyl. In a specific embodiment, $R_3$ is H; in another specific embodiment, $R_3$ is $C_{1-6}$ alkyl, for example, (R)—$C_{1-6}$ alkyl, for example, (R)-methyl; in another specific embodiment, $R_3$ is $C_{1-6}$ haloalkyl, for example, (R)—$C_{1-6}$ haloalkyl. In a specific embodiment, $R_4$ is H; in another specific embodiment, $R_4$ is $C_{1-6}$ alkyl, for example, (R)—$C_{1-6}$ alkyl, for example, (R)-methyl; in another specific embodiment, $R_4$ is $C_{1-6}$ haloalkyl, for example, (R)—$C_{1-6}$ haloalkyl in a specific embodiment, $R_{\#}$ is H; in another specific embodiment, $R_{\#}$ is $C_{1-6}$ alkyl, for example, (R)—$C_{1-6}$ alkyl, for example, (R)-methyl; in another specific embodiment. $R_{\#}$ is $C_{1-6}$ haloalkyl, for example, (R)—$C_{1-6}$ haloalkyl.

In another specific embodiment, at least one of $R_1$ and $R_2$ is $C_{1-6}$ alkyl, for example, (R)—$C_{1-6}$ alkyl, for example, (R)-methyl.

In another specific embodiment, $R_1$ and $R_2$, $R_3$ and $R_4$ are connected to form bond; in another specific embodiment, $R_1$ and $R_2$, $R_3$ and $R_4$ are connected to form $C_{1-6}$ alkylene, for example, methylene, ethylene or propylene; in another specific embodiment, $R_1$ and $R_2$, $R_3$ and $R_4$ are connected to form $C_{2-6}$ alkenylene; in another specific embodiment, $R_1$ and $R_2$, $R_3$ and $R_4$ are connected to form $C_{2-6}$ alkynylene.

In another specific embodiment, when Z is $CR_{\#}$, wherein $R_{\#}$, $R_1$ are taken together with the atoms to which they are attached to form $C_{3-5}$ cycloalkyl; in another specific embodiment, the said $C_{3-5}$ cycloalkyl is cyclopropyl; in another specific embodiment, the said $C_{3-5}$ cycloalkyl is cyclobutyl; in another specific embodiment, the said $C_{3-5}$ cycloalkyl is cyclopentyl; in another specific embodiment, when Z is $CR_{\#}$, wherein $R_{\#}$, $R_1$ are taken together with the atoms to which they are attached to form 3-5 heterocyclyl; in another specific embodiment, the said 3- to 5-membered heterocyclyl is oxiranyl, aziridinyl or thiorenyl, an another specific embodiment, the said 3- to 5-membered heterocyclyl is oxetanyl, azetidinyl or thietanyl; in another specific embodiment, the said 3- to 5-membered heterocyclyl is tetrahydrofuranyl, pyrrolidinyl or thiolanyl.

Ring A

In a specific embodiment, ring A is $C_{6-10}$ aryl, for example, phenyl; in another specific embodiment, ring A is 5- to 10-membered heteroaryl, for example, 5- to 6-membered heteroaryl.

In another specific embodiment, ring A is selected from

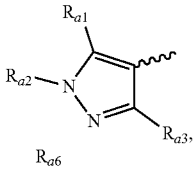

,

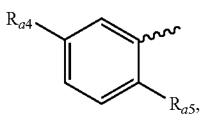

,

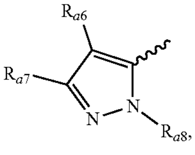

,

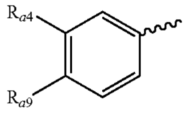

and

-continued

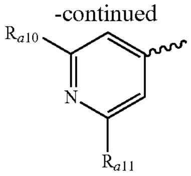

;

in another specific embodiment, ring A is selected from

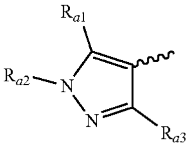

and

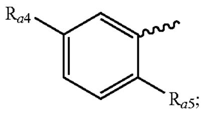

in another specific embodiment, ring A is

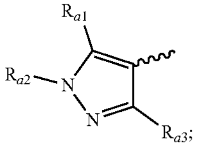

wherein $R_{a1}$-$R_{a11}$ are as defined in the context.

Ring B

In a specific embodiment, ring B is 5- to 10-membered heteroaryl, such as bicyclic 9- to 10-membered heteroaryl; in another specific embodiment, ring B is

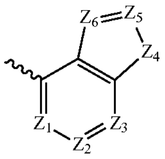

or

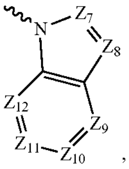

, represents the point of attachment to the rest of the molecule, 0, 1, 2, or 3 of $Z_1$-$Z_{12}$ are heteroatoms selected from O, S and N, as long as the chemistry permits; and each of $Z_1$-$Z_{12}$ is optionally oxidized to early =O group; alternatively, wherein at least one of $Z_1$-$Z_{12}$ is a heteroatom selected from O, S and N, as long as the chemistry permits; and $Z_1$-$Z_{12}$ are optionally oxidized to carry =O group; in another specific embodiment, ring B is selected from

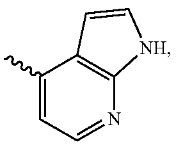

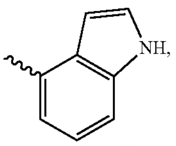

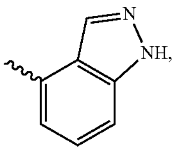

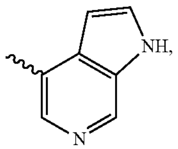

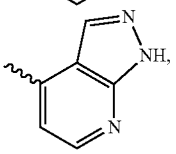

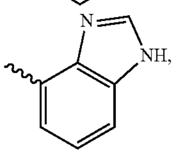

-continued

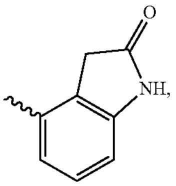

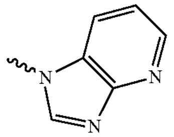

and

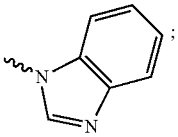

;

in another specific embodiment, ring B is selected from

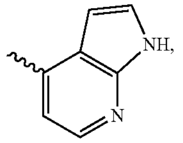

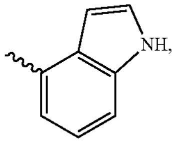

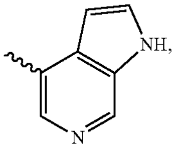

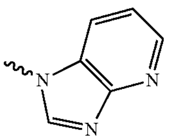

and

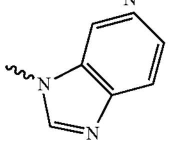

;

in another specific embodiment, ring B is

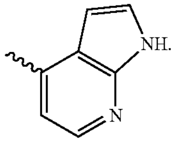

In the specific embodiment as mentioned above, 0, 1, 2, or 3 of $Z_1$-$Z_{12}$ are N atoms; alternatively, at least one of $Z_1$-$Z_{12}$ is a N atom; in another specific embodiment, $Z_1$-$Z_3$ contains at most one N atom; in another specific embodiment, $Z_4$-$Z_6$ contains at most two N atoms; in another specific embodiment, $Z_4$ is N atom.

$R_a$

In a specific embodiment, $R_a$ is independently selected from H, -L-NRR', -L-OR, —NRC(O)NRR', $C_{1-6}$ alkyl, $C_{1-6}$ haloalkyl, $C_{1-6}$ alkoxy, haloalkoxy. -L-S(=O)(=NR)R*, -L-S(O)$_p$R*, -L-$C_{3-7}$ cycloalkyl and -L-4- to 8-membered heterocyclyl, each of which is optionally substituted with R** group; in another specific embodiment, one of $R_a$ is H; in another specific embodiment, one of $R_a$ is halogen; in another specific embodiment, one of $R_a$ is —CN, in another specific embodiment, one of $R_a$ is -L-NRR'; in another specific embodiment, one of $R_a$ is -L-OR; in another specific embodiment, one of $R_a$ is —C(O)R; in another specific embodiment, one of $R_a$ is —C(O)OR; in another specific embodiment, one of $R_a$ is —C(O)NRR'; in another specific embodiment, one of $R_a$ is —OC(O)R'; in another specific embodiment, one of $R_a$ is —NRC(O)R'; in another specific embodiment, one of $R_a$ is —OC(O)NRR'; in another specific embodiment, one of $R_a$ is —NRC(O)NRR'; in another specific embodiment, one of $R_a$ is $C_{1-6}$ alkyl; in another specific embodiment, one of $R_a$ is $C_{1-6}$ haloalkyl; in another specific embodiment, one of $R_a$ is $C_{1-6}$ alkoxy; in another specific embodiment, one of $R_a$ is $C_{1-6}$ haloalkoxy; in another specific embodiment, one of $R_a$ is -L-S(O)$_p$R*; in another specific embodiment, one of $R_a$ is -L-S(=O)(=NR)R*; in another specific embodiment, one of $R_a$ is -L-$C_{3-7}$ cycloalkyl, in another specific embodiment, one of $R_a$ is -L-4- to 8-membered heterocyclyl, in the specific embodiment as mentioned above, wherein the said $R_a$ is substituted with 1, 2 or 3 R** groups.

$R_b$

In a specific embodiment, $R_b$ is independently selected from H, halogen, —CN, —OH, $C_{1-6}$ alkyl, $C_{1-6}$ alkoxy, —NRR' and —NRC(O)R'; in another specific embodiment, one of $R_b$ is H; in another specific embodiment, one of $R_b$ is halogen; in another specific embodiment, one of $R_b$ is —CN; in another specific embodiment, one of $R_b$ is -L-OR; in another specific embodiment, one of $R_b$ is —OH; in another specific embodiment, one of $R_b$ is -L-$C_{1-6}$ alkyl; in another specific embodiment, one of $R_b$ is $C_{1-6}$ alkyl; in another specific embodiment, one of $R_b$ is -L-$C_{1-6}$ alkoxy; in another specific embodiment, one of $R_b$ is $C_{1-6}$ alkoxy; in another specific embodiment, one of $R_b$ is -L-$C_{3-7}$ cycloalkyl; in another specific embodiment, one of $R_b$ is -L-3- to 8-membered heterocyclyl; in another specific embodiment; one of $R_6$ is —NRR'; in another specific embodiment, one of $R_6$ is C(O)R; in another specific embodiment, one of $R_6$ is —C(O)OR; in another specific embodiment, one of $R_b$ is —C(O)NRR'; in another specific embodiment, one of $R_b$ is —OC(O)R'; in another specific embodiment, one of $R_b$ is —NRC(O)R'; in another specific embodiment, one of $R_b$ is —OC(O)NRR', in another specific embodiment, one of $R_b$ is —NRC(O)NRR'.

m in a specific embodiment, m=0; in another specific embodiment, m=1; M another specific embodiment, m=2; in another specific embodiment, m=3; in another specific embodiment, m=4, in another specific embodiment, m=5.

n

In a specific embodiment, n=0; in another specific embodiment, n=1; in another specific embodiment, n=2; in another specific embodiment, n=3; in another specific embodiment, n=4; in another specific embodiment, n=5.

L

In a specific embodiment, L is independently selected from bond, —C(O)— and $C_{1-6}$ alkylene; in another specific embodiment, L is bond; in another specific embodiment, L is —O—; in another specific embodiment, L is —S—; in another specific embodiment, L is —NR—; in another specific embodiment, L is —C(O)—, in another specific embodiment, L is —$C_{1-6}$ alkylene, in another specific embodiment, L is —$C_{2-6}$ alkenylene; in another specific embodiment, L is —$C_{2-6}$ alkynylene.

R*

In a specific embodiment, R' is $C_{1-6}$ alkyl; in another specific embodiment, R* is $C_{1-6}$ haloalkyl; in another specific embodiment, R* is -L'-NRR'; in another specific embodiment, R* is -L'-OR; in another specific embodiment, R* is -L'-$C_{3-7}$ cycloalkyl; in another specific embodiment, R* is to -L'-4- to 8-membered heterocyclyl.

L'

In a specific embodiment, L' is bond; in another specific embodiment, L' is $C_{1-6}$ alkylene, in, another specific embodiment, L' is $C_{2-6}$ alkenylene; in another specific embodiment, L' is $C_2$ alkynylene; in another specific embodiment, L' is —O—$C_{1-6}$ alkylene; in another specific embodiment, U is —NH—$C_{1-6}$ alkylene.

R**

In a specific embodiment, R is H; in another specific embodiment, R is halogen; in another specific embodiment, R is —CN, in another specific embodiment, R is —C(=O)R; in another specific embodiment, R is $C_{1-6}$ alkyl; in another specific embodiment, R is $C_{1-6}$ haloalkyl; in another specific embodiment, R is $C_{1-6}$ alkoxy; in another specific embodiment, R is $C_{1-6}$ haloalkoxy; in another specific embodiment, R is 4- to 8-membered heterocyclyl; in another specific embodiment, R is —S(O)$_p$—$C_{1-6}$ alkyl; in another specific embodiment, R is —S(O)$_p$—$C_{1-6}$ haloalkyl; in another specific embodiment. R is —NRR'.

R and R'

In a specific embodiment, R and R' are independently H; in another specific embodiment, R and R' are independently $C_{1-6}$ alkyl; in another specific embodiment, R and R' are independently $C_{1-6}$ haloalkyl; in another specific embodiment, R, R' are taken together with the nitrogen atoms to which they are attached to form 4- to 8-membered heterocyclyl.

p

In a specific embodiment, p=1; in another specific embodiment, p=2.

Any technical solution in any one of the above specific embodiments, or any combination thereof, may be combined with any technical solution in other specific embodiments or any combination thereof. For example, any technical solution of X or any combination thereof may be combined with any technical solution of Y, $R_1$-$R_4$, ring A, ring B, $R_a$, $R_b$, R*, R**, L, L', p, R, R' or any combination thereof. The present disclosure is intended to include all combination of such technical solutions, which are not exhaustively listed here to save space.

In a more specific embodiment, the present disclosure provides a compound of formula (II), or a pharmaceutically acceptable salt, enantiomer, diastereomer, racemate, solvate, hydrate, polymorph, prodrug, or isotopic variant thereof, or mixture thereof:

(II)

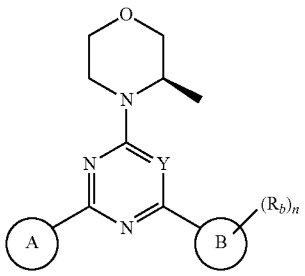

wherein, Y, ring A, ring B, $R_b$ and n are as defined above.

In another specific embodiment, the present disclosure provides a compound of formula (II), or a pharmaceutically acceptable salt, enantiomer, diastereomer, racemate, solvate, hydrate, polymorph, prodrug, or isotopic variant thereof, or mixture thereof:

wherein,

Y is CH or N;

ring A is selected from:

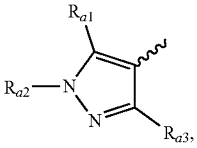

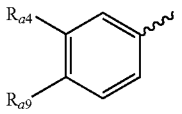

and

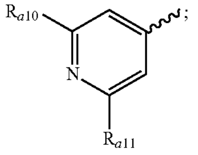

$R_{a1}$ is selected from H, $C_{1-6}$ alkyl and $C_{1-6}$; haloalkyl;

$R_{a2}$ is selected from $C_{1-6}$ alkyl and $C_{1-6}$ haloalkyl;

$R_{a3}$ is selected from H, $C_{1-6}$ alkyl and $C_{1-6}$ haloalkyl;

$R_{a4}$ is selected from H and $S(O)_pR^*$, wherein p=1 or 2, R* is selected from $C_{1-6}$ alkyl and $C_{1-6}$ haloalkyl;

$R_{a9}$ is selected from H and —NRC(O)NRR', wherein R and R' are independently selected from H, $C_{1-6}$ alkyl and $C_{1-6}$ haloalkyl;

$R_{a10}$ is selected from $C_{1-6}$ alkyl, $C_{1-6}$ haloalkyl, $C_{1-6}$ alkoxy and $C_{1-6}$ haloalkoxy;

$R_{a11}$ is selected from H and —NRR', wherein R and R' are independently selected from H, $C_{1-6}$ alkyl, $C_{1-6}$ haloalkyl;

ring 13 is selected from:

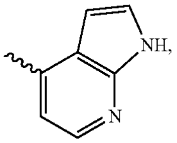

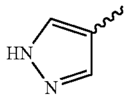

and

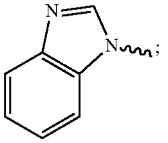

$R_b$ is selected from H, halogen, $C_{1-6}$ alkyl and $C_{1-6}$ haloalkyl;

n=0, 1, 2, 3 or 4.

In another specific embodiment, the present disclosure provides a compound of formula (II), or a pharmaceutically acceptable salt, enantiomer, diastereomer, racemate, solvate, hydrate, polymorph, prodrug, or isotopic variant thereof, or mixture thereof:

wherein, ring A is selected from:

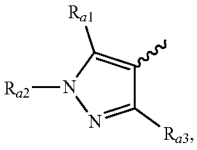

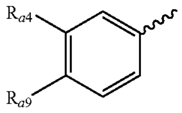

and

-continued

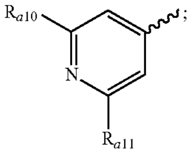

$R_{a1}$ is H or methyl;

$R_{a2}$ is methyl or isopropyl;

$R_{a3}$ is H or methyl;

$R_{a4}$ is H or —$SO_2Me$;

$R_{a9}$ is H or —$NH_2C(O)NH_2Et$;

$R_{a10}$ is $CF_2H$ or $C_{1-6}$ alkoxy;

$R_{a11}$ is H;

B is selected from

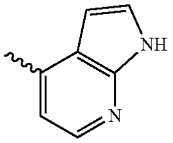

and

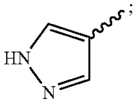

$R_b$ is H or methyl;

n=0, 1 or 2.

In another specific embodiment, the present disclosure provides a compound of formula (III), or a pharmaceutically acceptable salt, enantiomer, diastereomer, racemate, solvate, hydrate, polymorph, prodrug, or isotopic variant thereof, or mixture thereof:

(III)

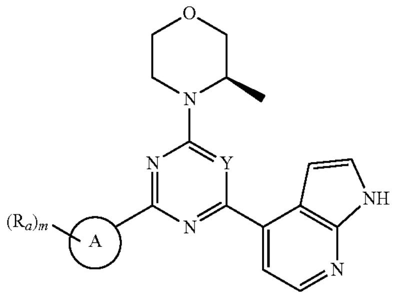

wherein, Y, ring A, $R_a$ and mare as defined above.

In another specific embodiment, the present disclosure provides a compound of formula (III), or a pharmaceutically acceptable salt, enantiomer, diastereomer, racemate, solvate, hydrate, polymorph, prodrug, or isotopic variant thereof, or mixture thereof:

wherein, ring A is:

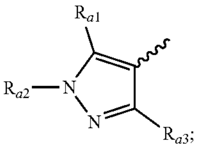

$R_{a1}$ is selected from $C_{1-6}$ alkyl and $C_{1-6}$ haloalkyl;

$R_{a2}$ is selected from $C_{1-6}$ alkyl and $C_{1-6}$ haloalkyl;

$R_{a3}$ is selected from $C_{1-6}$ alkyl and $C_{1-6}$ haloalkyl.

In another specific embodiment, the present disclosure provides a compound of formula (III), or a pharmaceutically acceptable salt, enantiomer, diastereomer, racemate, solvate, hydrate, polymorph, prodrug, or isotopic variant thereof, or mixture thereof:

wherein, ring A is:

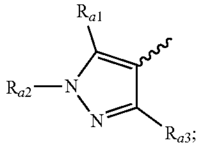

$R_{a1}$ is methyl;

$R_{a2}$ is methyl or isopropyl;

$R_{a3}$ is methyl.

In another specific embodiment, the present disclosure provides a compound of formula (IV), or a pharmaceutically acceptable salt, enantiomer, diastereomer, racemate, solvate, hydrate, polymorph, prodrug, or isotopic variant thereof, or mixture thereof:

(IV)

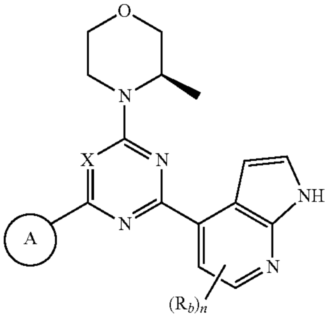

wherein,

X is CH or N;

ring A is selected from:

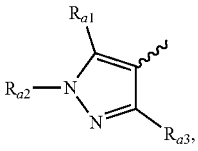

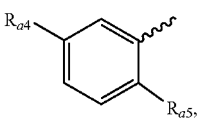

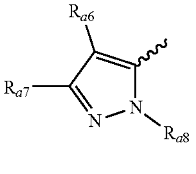

and

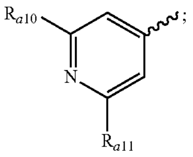

$R_{a1}$ is selected from H, $C_{1-6}$ alkyl and $C_{1-6}$ haloalkyl;

$R_{a2}$ is selected from $C_{1-6}$ alkyl, $C_{1-6}$ haloalkyl, -L-NRR', -L-OR, -L-4- to 8-membered heterocyclyl and -L-S(O)$_p$R*, each of which is optionally substituted with R** group; wherein L is selected from bond, $C_{1-6}$ alkylene, $C_{2-6}$ alkenylene and $C_{2-6}$ alkynylene, p=1 or 2, R* is selected from $C_{1-6}$ alkyl, $C_{3-7}$ cycloalkyl, 4- to 8-membered heterocyclyl, $C_{1-6}$ haloalkyl and —NRR'; R** is selected from H, halogen, —OR, —C(O)R, $C_{1-6}$ alkyl, $C_{1-6}$ haloalkyl, 4- to 8-membered heterocyclyl, —S(O)$_p$—$C_{1-6}$ alkyl, —S(O)$_p$—$C_{1-6}$ haloalkyl and —NRR', wherein R and R' are independently selected from H, $C_{1-6}$ alkyl and $C_{1-6}$ haloalkyl;

$R_{a3}$ is selected from H, $C_{1-6}$ alkyl and $C_{1-6}$ haloalkyl;

$R_4$ is selected from $C_{1-6}$ alkyl, -L-S(=O)(=NR)R*, -L-S(O)$_p$R* and -L-4- to 8-membered heterocyclyl, each of which is optionally substituted with R** group; wherein, p=1 or 2, L is selected from bond, —NR—, —C(O)— and $C_{1-6}$ alkylene, R* is selected from $C_{1-6}$ alkyl, $C_{1-6}$ haloalkyl, -L'-NRR', -L'-OR and -L'-4- to 8-membered heterocyclyl; and wherein L' is selected from bond, $C_{1-6}$ alkylene, $C_{2-6}$ alkenylene, $C_{2-6}$ alkynylene and —NH—$C_{1-6}$ alkylene, R and R' are independently selected from H, $C_{1-6}$ alkyl and $C_{1-6}$ haloalkyl, or R, R' are taken together with the nitrogen atoms to which they are attached to form 4- to 8-membered heterocyclyl, R** is selected from H, —CN, —NRR', alkyl, $C_{1-6}$haloalkyl, —S(O)$_p$—$C_{1-6}$ alkyl and —S(O)$_p$—$C_{1-6}$ haloalkyl, wherein p=1 or 2;

$R_{a5}$ is selected from $C_{1-6}$ alkyl, $C_{1-6}$ haloalkyl, $C_{3-7}$ cycloalkyl, $C_{1-6}$ alkoxy and $C_{1-6}$ haloalkoxy;

$R_{a6}$ is H;

$R_{a7}$ is H;

$R_{a8}$ is selected from $C_{1-6}$ alkyl, $C_{1-6}$ haloalkyl and $C_{3-7}$ cycloalkyl;

$R_{a10}$ is selected from $C_{1-6}$ alkyl and $C_{1-6}$ haloalkyl, each of which is optionally substituted with —CN;

$R_{a11}$ is H;

$R_b$ is selected from H, halogen, —CN, —OH, $C_{1-6}$ alkyl, $C_{1-6}$ alkoxy, cycloalkyl, -L-3- to 8-membered heterocyclyl, —NRR', —C(O)R;

n=0, 1, 2 or 3.

In another specific embodiment, the present disclosure provides a compound of formula (IV), or a pharmaceutically acceptable salt, enantiomer, diastereomer, racemate, solvate, hydrate, polymorph, prodrug, or isotopic variant thereof, or mixture thereof:

wherein,

X is CH or N;

ring A is selected from:

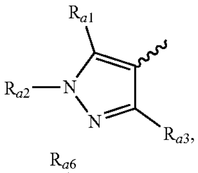

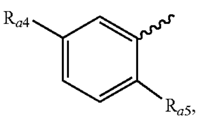

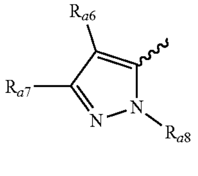

and

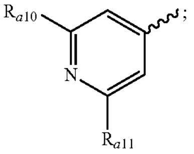

$R_{a1}$ is selected front H, $C_{1-6}$ alkyl and $C_{1-6}$ haloalkyl;

$R_{a2}$ is selected from $C_{1-6}$ alkyl, $C_{1-6}$ haloalkyl, -L-NRR', -L-OR and -L-4- to 8-membered heterocyclyl, wherein L is bond or $C_{1-6}$ alkylene, R and R' are independently selected from H, $C_{1-6}$ alkyl or $C_{1-6}$ haloalkyl;

$R_{a3}$ is selected from H, $C_{1-6}$ alkyl and $C_{1-6}$ haloalkyl;

$R_{a4}$ is selected from —S(O)$_p$R*, wherein p=1 or 2, R* is selected from $C_{1-6}$ alkyl, 4- to 8-membered heterocyclyl, $C_{1-6}$ haloalkyl and -L'-NRR', and wherein U is selected from bond, $C_{1-6}$ alkylene, $C_{2-6}$ alkenylene, $C_{2-6}$ alkynylene and —NH—$C_{1-6}$ alkylene, R and R' are independently selected from H, $C_{1-6}$ alkyl and $C_{1-6}$ haloalkyl, or R, R' are taken together with the nitrogen atoms to which they are attached to form 4- to 8-membered heterocyclyl;

$R_{a5}$ is selected from $C_{1-6}$ alkyl, $C_{1-6}$ haloalkyl, cycloalkyl, $C_{1-6}$ alkoxy and $C_{1-6}$ haloalkoxy;

$R_{a6}$ is H;

$R_7$ is H;

$R_{a8}$ is selected from $C_{1-6}$ alkyl, $C_{1-6}$ haloalkyl and $C_{3-7}$ cycloalkyl;

$R_{a10}$ is selected from $C_{1-6}$ alkyl and $C_{1-6}$ haloalkyl, each of which is optionally substituted with —CN;

$R_{a11}$ is H;

$R_b$ is selected from H, halogen, —CN, —OH, $C_{1-6}$ alkyl, $C_{1-6}$ alkoxy, cycloalkyl, -L-3- to 8-membered heterocyclyl, —NRR', —C(O)R;

n=0, 1, 2 or 3.

In another specific embodiment, the present disclosure provides a compound of formula (IV), or a pharmaceutically acceptable salt, enantiomer, diastereomer, racemate, solvate, hydrate, polymorph, prodrug, or isotopic variant thereof, or mixture thereof:

wherein,

X is CH or N;

ring A is selected from:

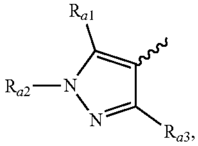

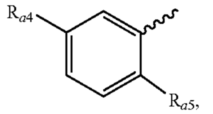

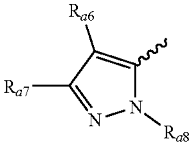

and

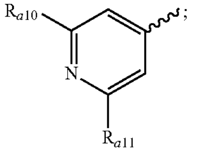

$R_{a1}$ is H or methyl;

$R_{a2}$ is methyl, isopropyl, —$CH_2CH_2CH_2OH$, —$CH_2CH_2OMe$, —$CH_2CH_2NMe_2$, —$CH_2CH_2CH_2NMe_2$, azetidin-3-ylmethyl, oxetan-3-ylmethyl, pyran-4-yl, tetrahydropyrrolyl or piperidinyl;

$R_{a3}$ is H, methyl or $CF_3$;

$R_{a4}$ is —$SO_2N(Me)_2$, —$SO_2Me$, —$SO_2iPr$ or —$SO_2$-piperidin-4-yl;

$R_{a5}$ is methyl, methoxy, isopropyl or trifluoromethyl;

$R_{a6}$ is H;

$R_{a7}$ is H;

$R_{a8}$ is Me;

$R_{a10}$ is isopropyl optionally substituted with —CN;

$R_{a11}$ is H;

$R_b$ is H, halogen, methoxy or —$CH_2$-azetidin-3-yl;

n=0, 1, 2 or 3.

In another specific embodiment, the present disclosure provides a compound of formula (IV), or a pharmaceutically acceptable salt, enantiomer, diastereomer, racemate, solvate, hydrate, polymorph, prodrug, or isotopic variant thereof, or mixture thereof:

(IV)

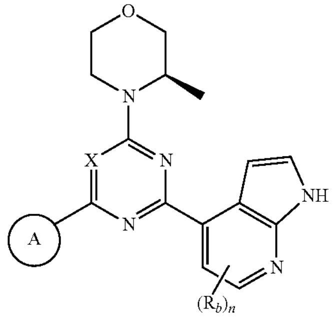

wherein,

X is CH or N;

ring A is selected from:

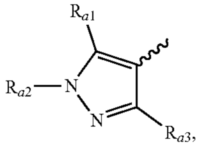

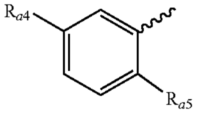

and

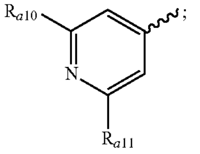

$R_{a1}$ is selected from $C_{1-6}$ alkyl and $C_{1-6}$ haloalkyl;

$R_{a2}$ is selected from $C_{1-6}$ alkyl, $C_{1-6}$ haloalkyl, -L-NRR', -L-4- to 8-membered heterocyclyl, -L-S(O)$_p$R*, each of which is optionally substituted with R** group, wherein L is selected from bond, $C_{1-6}$ alkylene, $C_{2-6}$ alkenylene and $C_{2-6}$ alkynylene, p=1 or 2, R* is selected from $C_{2-6}$ alkyl, $C_{1-6}$ haloalkyl and —NRR', and wherein R and R' are independently selected from H, $C_{1-6}$ alkyl and $C_{1-6}$ haloalkyl, or R, R' are taken together with the nitrogen atoms to which they are attached to form 4- to 8-membered heterocyclyl; R** is selected from halogen, $C_{2-6}$ alkyl, $C_{1-6}$ haloalkyl, —S(O)$_p$—$C_{1-6}$ alkyl and —S(O)$_p$—$C_{1-6}$ haloalkyl, wherein p=1 or 2;

$R_{a3}$ is selected from H, $C_{1-6}$ alkyl and $C_{1-6}$ haloalkyl;

$R_{a4}$ is selected from $C_{1-6}$ alkyl, -L-S(=O)(=NR)R*, -L-S(O)$_p$R* and -L-4- to 8-membered heterocyclyl, each of which is optionally substituted with R** group; wherein, p=1 or 2, L is selected from bond, —NR—, —C(O)— and $C_{1-6}$ alkylene, R* is selected from $C_{1-6}$ alkyl, $C_{1-6}$ haloalkyl, -L'-NRR', -L'-OR and -L'-4- to 8-membered heterocyclyl; and wherein L' is selected from bond. $C_{1-6}$ alkylene. $C_{2-6}$ alkenylene, $C_{2-6}$ alkynylene and —NH—$C_{1-6}$ alkylene, R and are independently selected from H, $C_{1-6}$ alkyl and $C_{1-6}$ haloalkyl, or R, R' are taken together with the nitrogen atoms to which they are attached to form 4- to 8-membered heterocyclyl; R** is selected from —CN, $C_{1-6}$ alkyl, $C_{1-6}$ haloalkyl, —$S(O)_p$—$C_{1-6}$ alkyl and —$S(O)_p$—$C_{1-6}$ haloalkyl, wherein p=1 or 2;

$R_{a5}$ is selected from $C_{1-6}$ alkyl, $C_{1-6}$ haloalkyl, $C_{3-7}$ cycloalkyl, $C_{1-6}$ alkoxy and $C_{1-6}$ haloalkoxy;

$R_{a10}$ is selected from $C_{1-6}$ alkyl and $C_{1-6}$ haloalkyl, each of which is optionally substituted with —CN;

$R_{a11}$ is H;

$R_b$ is selected from H, halogen, —CN, —OH, alkyl, $C_{1-6}$ alkoxy, cycloalkyl, -L-3- to 8-membered heterocyclyl, —NRR', —C(O)R;

n=0, 1, 2 or 3.

In another specific embodiment, the present disclosure provides a compound of formula (IV), or a pharmaceutically acceptable salt, enantiomer, diastereomer, racemate, solvate, hydrate, polymorph, prodrug, or isotopic variant thereof, or mixture thereof:

wherein,

X is CH or N;

ring A is

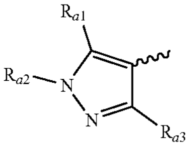
or
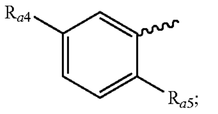

$R_{a1}$ is selected from $C_{1-6}$ alkyl and $C_{1-6}$ haloalkyl;

$R_{a2}$ is selected from $C_{1-6}$ alkyl, $C_{1-6}$ haloalkyl and -L-4- to 8-membered heterocyclyl;

$R_{a3}$ is selected from H, $C_{1-6}$ alkyl and $C_{1-6}$ haloalkyl;

$R_{a4}$ is selected from —$S(O)_pR^*$, wherein p=1 or 2, R* is selected from $C_{1-6}$ alkyl, $C_{1-6}$ haloalkyl, -4- to 8-membered heterocyclyl and -L'-NRR', and wherein L' is selected from bond, $C_{1-6}$ alkylene, $C_{2-6}$ alkenylene, $C_{2-6}$ alkynylene, and —NH—$C_{1-6}$ alkylene, R and R' are independently selected from H, $C_{1-6}$ alkyl and $C_{1-6}$ haloalkyl, or R, R' are taken together with the nitrogen atoms to which they are attached to form 4- to 8-membered heterocyclyl;

$R_{a5}$ is selected from $C_{1-6}$ alkyl, $C_{1-6}$ haloalkyl, cycloalkyl, $C_{1-6}$ alkoxy and $C_{1-6}$ haloalkoxy;

$R_{a10}$ is selected from $C_{1-6}$ alkyl and $C_{1-6}$ haloalkyl, each of which is optionally substituted with —CN;

$R_{a11}$ is H;

$R_b$ is selected from H, halogen, —CN, —OH, $C_{1-6}$ alkyl, $C_{1-6}$ alkoxy, cycloalkyl, -L-3- to 8-membered heterocyclyl, —NRR', —C(O)R;

L is selected from bond and $C_{1-6}$alkylene;

n=0, 1, 2 or 3.

In another specific embodiment, the present disclosure provides a compound of formula (IV), or a pharmaceutically acceptable salt, enantiomer, diastereomer, racemate, solvate, hydrate, polymorph, prodrug, or isotopic variant thereof, or mixture thereof:

wherein,

X is CH or N;

ring A is

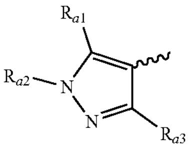
or
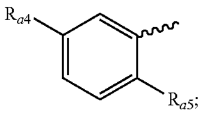

$R_{a1}$ is methyl;

$R_{a2}$ is —$CH_2CH_2CH_2OH$, —$CH_2CH_2NMe_2$, —$CH_2CH_2CH_2NMe_2$, —$CH_2CH_2OMe$, azetidin-3-ylmethyl, oxetan-3-ylmethyl, pyran-4-yl, tetrahydropyrrolyl or piperidinyl;

$R_{a3}$ is H, methyl, $CF_3$;

$R_{a4}$ is —$SO_2N(Me)_2$, —$SO_2Me$, —$SO_2iPr$ or —$SO_2$-piperidin-4-yl;

$R_{a5}$ is methyl, isopropyl, methoxy or trifluoromethyl;

$R_b$ is H, halogen, methoxy or —$CH_2$-azetidin-3-yl;

n=0, 1, 2 or 3.

In another specific embodiment, the present disclosure provides a compound of formula (V), or a pharmaceutically acceptable salt, enantiomer, diastereomer, racemate, solvate, hydrate, polymorph, prodrug, or isotopic variant thereof, or mixture thereof:

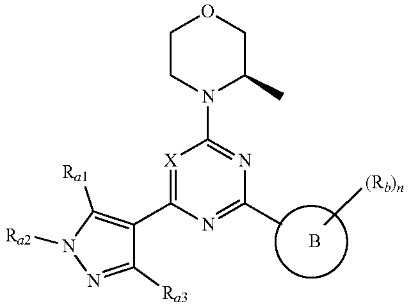
(V)

wherein,

X is CH or N;

$R_{a1}$ is selected from $C_{1-6}$ alkyl and $C_{1-6}$ haloalkyl;

$R_{a2}$ is selected from -L-$S(O)_pR^*$, -L-S(=O)(=NR)R*, $C_{1-6}$ alkyl and -L-4- to 8-membered heterocyclyl, each of which is optionally substituted with R** group;

$R_{a3}$ is selected from $C_{1-6}$ alkyl and $C_{1-6}$ haloalkyl;

ring B is

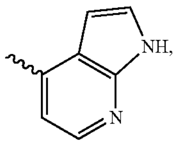
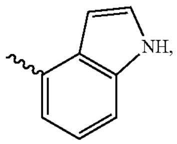
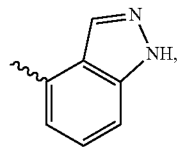
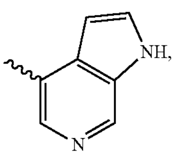
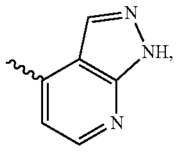
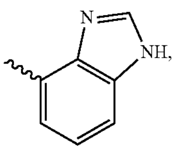
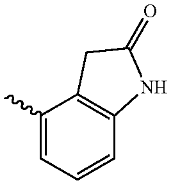
and
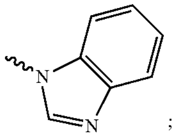
;

$R_b$ is selected from H, halogen, —CN, —OH, $C_{1-6}$ alkyl, $C_{1-6}$ alkoxy, cycloalkyl, -L-3- to 8-membered heterocyclyl, —NRR' and —NRC(O)R';

n=0, 1, 2, 3, 4 or 5;

p=1 or 2;

R* is selected from $C_{1-6}$ alkyl or $C_{1-6}$ haloalkyl;

L is selected from bond, —O—, —S—, —NR—, —C(O)— or $C_{1-6}$ alkylene;

R** is independently selected from H, halogen, —CN, —C(═O)R, $C_{1-6}$ alkyl, $C_{1-6}$ haloalkyl, $C_{1-6}$ alkoxy, $C_{1-6}$ haloalkoxy, 4- to 8-membered heterocyclyl, —$S(O)_p$—$C_{1-6}$ alkyl, —$S(O)_p$—$C_{1-6}$ haloalkyl and —NRR;

R and R' are independently selected from H, $C_{1-6}$ alkyl and $C_{1-6}$ haloalkyl.

In another specific embodiment, the present disclosure provides a compound of formula (V), or a pharmaceutically acceptable salt, enantiomer, diastereomer, racemate, solvate, hydrate, polymorph, prodrug, or isotopic variant thereof, or mixture thereof:

wherein,

X is CH or N;

$R_{a1}$ is selected from $C_{1-6}$ alkyl and $C_{1-6}$ haloalkyl;

$R_{a2}$ is selected from $C_{1-6}$ alkyl, $C_{1-6}$ haloalkyl and -L-4- to 8-membered heterocyclyl;

$R_{a3}$ is selected from $C_{1-6}$ alkyl and $C_{1-6}$ haloalkyl;

ring B is selected from:

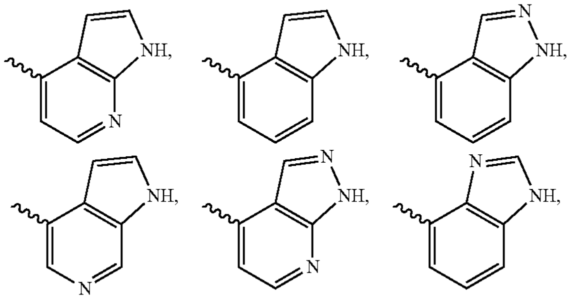

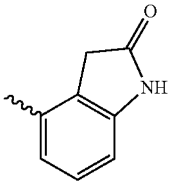

and

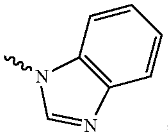

;

$R_b$ is selected from H, halogen, —CN, —OH, $C_{1-6}$ alkyl, $C_{1-6}$ alkoxy, cycloalkyl, -L-3- to 8-membered heterocyclyl, —NRR' and —NRC(O)R', wherein R and R' are independently selected from H, $C_{1-6}$ alkyl and $C_{1-6}$ haloalkyl;

L is selected from bond and $C_{1-6}$ alkylene;

n=0, 1, 2, 3, 4 or 5.

In another specific embodiment, the present disclosure provides a compound of formula (V), or a pharmaceutically acceptable salt, enantiomer, diastereomer, racemate, solvate, hydrate, polymorph, prodrug, or isotopic variant thereof, or mixture thereof:

wherein,

X is CH or N;

$R_{a1}$ is methyl;

$R_{a2}$ is methyl, isopropyl or piperidinyl;

$R_{a3}$ is methyl or trifluoromethyl;

ring B is selected from:

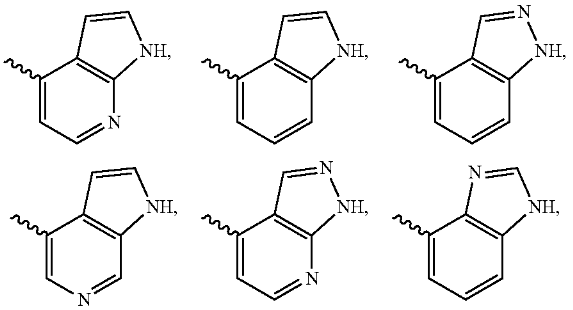

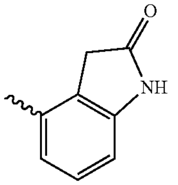

and

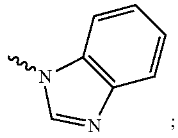

;

$R_b$ is selected from H, halogen, methyl, methoxy, —$CH_2$-azetidin-3-yl, —NHMe and —NHC(O)Me;

n=0, 1 or 2.

In another specific embodiment, the present disclosure provides a compound of formula (VI), or a pharmaceutically acceptable salt, enantiomer, diastereomer, racemate, solvate, hydrate, polymorph, prodrug, or isotopic variant thereof, or mixture thereof:

(VI)

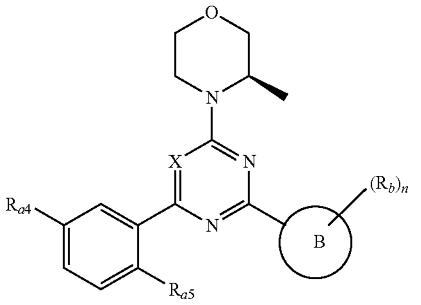

wherein,

X is CH or N;

$R_{a4}$ is -L-$S(O)_2$R*, which is optionally substituted with R** group wherein. L is selected from bond and alkylene, R* is selected from $C_{1-6}$ alkyl, $C_{1-6}$ haloalkyl. -L'-NRR' and -L'-4- to 8-membered heterocyclyl; and wherein L' is selected from bond and $C_{1-6}$ alkylene, R and R' are independently selected from H, $C_{1-6}$ alkyl, or R, are taken together with the nitrogen atoms to which they are attached to form 4- to 8-membered heterocyclyl; R** is selected from H, —CN, C(═O)R, $C_{1-6}$ alkyl, $C_{1-6}$ haloalkyl, —$S(O)_p$—$C_{1-6}$ alkyl, —$S(O)_p$—$C_{1-6}$ haloalkyl and —NRR', wherein p=1 or 2;

$R_{a5}$ is selected from methyl, methoxy, isopropyl or trifluoromethyl;

ring B is selected from:

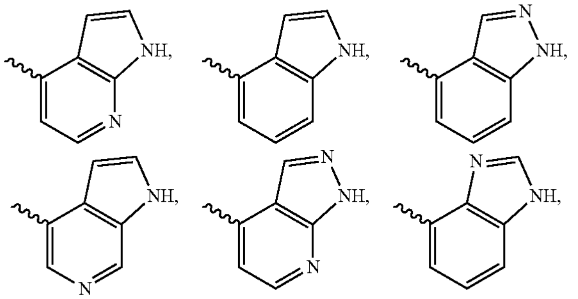

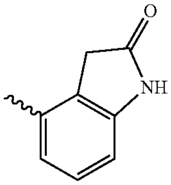

and

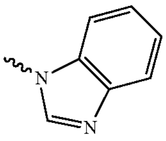

;

$R_b$ is selected from H, halogen, —CN, —OH, $C_{1-6}$ alkyl, $C_{1-6}$ alkoxy, cycloalkyl, -L-3- to 8-membered heterocyclyl, —NRR' and —NRC(O)R', wherein R and R' are independently selected from H, $C_{1-6}$ alkyl and $C_{1-6}$ haloalkyl;

n=0, 1, 2, 3, 4 or 5.

In another specific embodiment, the present disclosure provides a compound of formula (VI), or a pharmaceutically acceptable salt, enantiomer, diastereomer, racemate, solvate, hydrate, polymorph, prodrug, or isotopic variant thereof, or mixture thereof:

wherein,

X is CH or N;

$R_{a4}$ is selected from —$S(O)_2R^*$, wherein, R* is selected from $C_{1-6}$ alkyl, -L'-NRR' and 4- to 8-membered heterocycyl, and wherein R and R' are independently selected from H, $C_{1-6}$ alkyl and $C_{1-6}$ haloalkyl, or R, R' are taken together with the nitrogen atoms to which they are attached to form 4- to 8-membered heterocyclyl, L' is selected from bond and $C_{1-6}$ alkylene;

$R_{a5}$ is selected from methyl, methoxy, isopropyl or trifluoromethyl;

ring B is selected from:

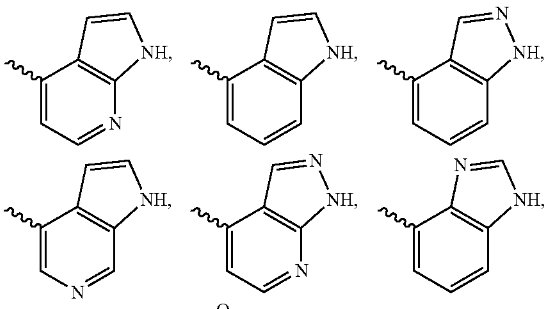

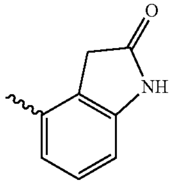

and

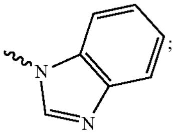

;

$R_b$ is selected from H, halogen —CN, —OH, $C_{1-6}$ alkyl, $C_{1-6}$ alkoxy, cycloalkyl, -L-3- to 8-membered heterocyclyl, —NRR' and —NRC(O)R', wherein R and R' are independently selected from H, alkyl and $C_{1-6}$ haloalkyl;

L is selected from bond and $C_{1-6}$ alkylene;

alternatively, n=0, 1 or 2.

In another specific embodiment, the present disclosure provides a compound of formula (VI), or a pharmaceutically acceptable salt, enantiomer, diastereomer, racemate, solvate, hydrate, polymorph, prodrug, or isotopic variant thereof, or mixture thereof:

wherein,

X is CH or N;

$R_{a4}$ is —$SO_2N(Me)_2$, —$SO_2Me$, —$SO_2iPr$ or —$SO_2$-piperidin-4-yl;

$R_{a5}$ is selected from methyl, methoxy, isopropyl or trifluoromethyl;

ring B is selected from:

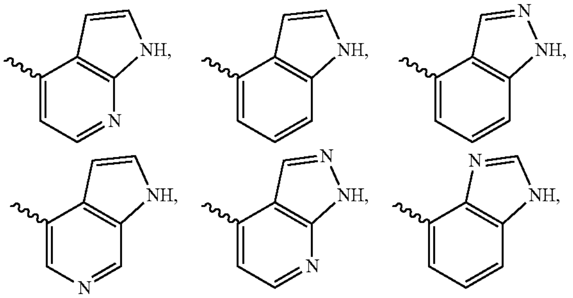

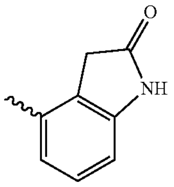

and

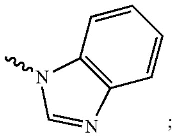

;

$R_b$ is selected from H, halogen, methyl, methoxy, —$CH_2$-azetidin-3-yl, —NHMe and —NHC(O)Me;

n=0, 1 or 2.

In another specific embodiment, the present disclosure provides a compound of formula (VII), or a pharmaceutically acceptable salt, enantiomer, diastereomer, racemate, solvate, hydrate, polymorph, prodrug, or isotopic variant thereof, or mixture thereof;

(VII)

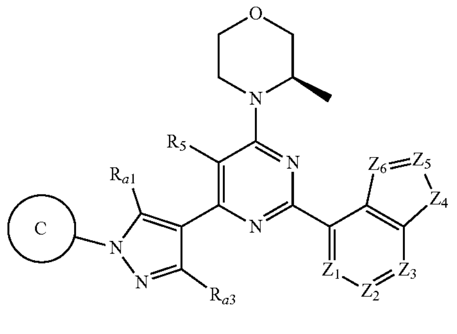

wherein, ring C is $C_{3-7}$ cycloalkyl or 4- to 8-membered heterocyclyl, each of which is substituted with $R_{a12}$ (alternatively 5- to 6-membered heterocyclyl substituted with $R_{a12}$ alternatively 5- to 6-membered heterocyclyl containing N atom(s) substituted with $R_{a12}$);

$R_{a1}$ is $C_{1-6}$ alkyl, $C_{1-6}$ haloalkyl, alkoxy or $C_{1-6}$ haloalkoxy (alternatively methyl, trifluoromethyl or methoxy);

$R_{a3}$ is $C_{1-6}$ alkyl or $C_{1-6}$ haloalkyl (alternatively methyl or trifluoromethyl);

$R_{a12}$ is H, $C_{1-6}$ alkyl or $C_{1-6}$ haloalkyl;

$R_5$ is H, halogen, $C_{1-6}$ alkyl or $C_{1-6}$ haloalkyl;

$Z_1$ is N or $CR_{b1}$;

$Z_2$ is N or $CR_{b2}$;

$Z_3$ is N or $CR_{b3}$;

$Z_4$ is $NR_{b4}$ or $C(R_{b4})_2$;

$Z_5$ is N or $CR_{b5}$;

$Z_6$ is N or $CR_{b6}$;

$R_{b1}$, $R_{b2}$, $R_{b3}$, $R_{b4}$, $R_{b5}$ and $R_{b6}$ are independently selected from H, halogen, $C_{1-6}$ alkyl, $C_{1-6}$ haloalkyl, $C_{1-6}$ alkoxy and $C_{1-6}$ haloalkoxy (alternatively selected from H, halogen and methoxy);

alternatively, at least one of $R_{a1}$ and $R_{a3}$ is $C_{1-6}$ haloalkyl.

In another specific embodiment, the present disclosure provides a compound of formula (VII), or a pharmaceutically acceptable salt, enantiomer, diastereomer, racemate, solvate, hydrate, polymorph, prodrug, or isotopic variant thereof, or mixture thereof:

ring C is $C_{3-7}$ cycloalkyl or 4- to 8-membered heterocyclyl, each of which is substituted with $R_{a12}$ (alternatively 5- to 6-membered heterocyclyl substituted with $R_{a12}$, alternatively 5- to 6-membered heterocyclyl containing N atom(s) substituted with $R_{a12}$);

$R_{a1}$ is $C_{4-6}$ alkyl or $C_{1-6}$ haloalkyl (alternatively methyl or trifluoromethyl);

$R_{a3}$ is $C_{1-6}$ alkyl or $C_{1-6}$ haloalkyl (alternatively methyl or trifluoromethyl);

$R_{a12}$ is H, $C_{1-6}$ alkyl or $C_{1-6}$ haloalkyl;

$R_5$ is H, halogen, $C_{1-6}$ alkyl or $C_{1-6}$ haloalkyl;

$Z_1$ is N or $CR_{b1}$;

$Z_2$ is N or $CR_{b2}$;

$Z_1$ is N or $CR_{b3}$;

$Z_4$ is $NR_{b4}$ or $C(R_{b4})_2$;

$Z_5$ is N or $CR_{b5}$;

$Z_6$ is N or $CR_{b6}$;

$R_{b2}$ is H or halogen (alternatively H or F);

$R_{b3}$ is H;

$R_{b1}$, $R_{b4}$, $R_{b5}$, and $R_{b6}$ are independently selected from H, halogen, $C_{1-6}$ alkyl, $C_{1-6}$ haloalkyl, $C_{1-6}$ alkoxy and $C_{1-6}$ haloalkoxy (alternatively selected from H, halogen and methoxy);

alternatively, at least one of $R_{a1}$ and $R_{a3}$ is $C_{1-6}$ haloalkyl.

In another specific embodiment, the present disclosure provides a compound of formula (VIII), or a pharmaceutically acceptable salt, enantiomer, diastereomer, racemate, solvate, hydrate, polymorph, prodrug, or isotopic variant thereof, or mixture thereof:

(VIII)

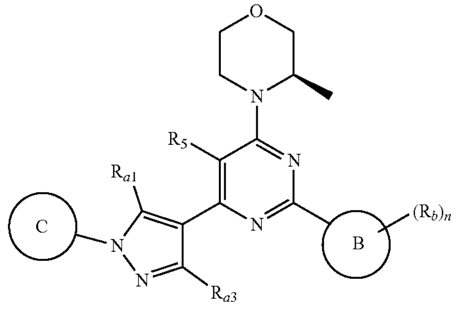

wherein, ring C is

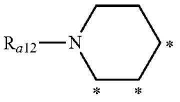
, wherein the point of attachment with the rest of the molecule is at one of the positions shown by *;

$R_{a1}$ is $C_{1-6}$ alkyl or $C_{1-6}$ haloalkyl (alternatively is methyl or trifluoromethyl);

$R_{a3}$ is $C_{1-6}$ alkyl or $C_{1-6}$ haloalkyl (alternatively is methyl or trifluoromethyl);

$R_{a12}$ is H or $C_{1-6}$ alkyl (alternatively is H or methyl);

$R_5$ is H or halogen (alternatively is H or F);

ring B is selected from

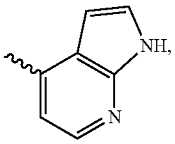
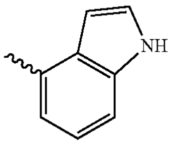
and
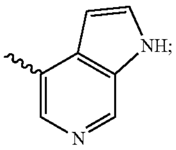

$R_b$ is H, methoxy or halogen (alternatively is H or halogen);

n is 0, 1, 2 or 3;

alternatively, at least one of $R_{a1}$ and $R_{a3}$ is $C_{1-6}$ haloalkyl.

In another specific embodiment, the present disclosure provides a compound of formula (VIII), or a pharmaceutically acceptable salt, enantiomer, diastereomer, racemate, solvate, hydrate, polymorph, prodrug, or isotopic variant thereof, or mixture thereof:

ring C is

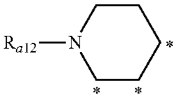
, wherein the point of attachment with the rest of the molecule is at one of the positions shown by *;

$R_{a1}$ is methyl or trifluoromethyl;

$R_{a3}$ is methyl or trifluoromethyl;

$R_{a12}$ is H or methyl;

$R_5$ is H or F;

ring B is selected from.

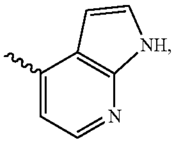

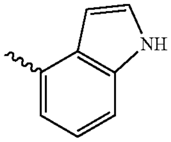

and

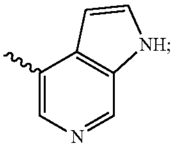

$R_b$ is H;

n is 0, 1, 2 or 3;

alternatively, at least one of $R_{a1}$ and $R_{a3}$ is $C_{1-6}$ haloalkyl.

In another specific embodiment, the present disclosure provides a compound of formula (IX), or a pharmaceutically acceptable salt, enantiomer, diastereomer, racemate, solvate, hydrate, polymorph, prodrug, or isotopic variant thereof, or mixture thereof:

(IX)

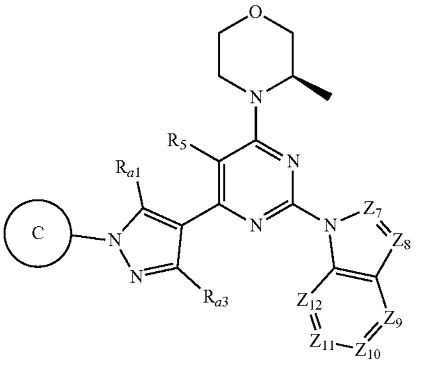

wherein, ring C is $C_{3-7}$ cycloalkyl or 4- to 8-membered heterocyclyl, each of which is substituted with $R_{a12}$ (alternatively 5- to 6-membered heterocyclyl substituted with $R_{a12}$, alternatively 5- to 6-membered heterocyclyl containing N atom(s) substituted with $R_{a12}$;

$R_{a1}$ is $C_{1-6}$ alkyl or $C_{1-6}$ haloalkyl;

$R_{a3}$ is $C_{1-6}$ alkyl or $C_{1-6}$ haloalkyl;

$R_{a12}$ is H, alkyl or $C_{1-6}$ haloalkyl;

$R_5$ is H, halogen, $C_{1-6}$ alkyl or haloalkyl;

$Z_7$ is N or $CR_{b7}$;

$Z_8$ is N or $CR_{b8}$;

$Z_9$ is N or $CR_{b9}$;

$Z_{10}$ is N or $CR_{b10}$;

$Z_{11}$ is N or $CR_{b11}$;

$Z_{12}$ is N or $CR_{b12}$;

wherein, $R_{b7}$ is H, -L-OR, -L-$C_{1-6}$ alkyl, -L-$C_{3-7}$ cycloalkyl, —NRR', —NRC(O)R' or —NRC(O)NRR';

$R_{b8}$; $R_{b9}$, $R_{b10}$, $R_{b11}$ and $R_{b12}$ are independently selected from H, halogen, —CN, $C_{1-6}$ alkyl, $C_{1-6}$ haloalkyl, $C_{1-6}$ alkoxy and $C_{1-6}$ haloalkoxy (alternatively selected front H, halogen, —CN and methoxy);

L is independently selected from bond; —O—, —S—, —NR—, —C(O)—, $C_{1-6}$ alkylene, $C_{2-6}$ alkenylene and $C_{2-6}$ alkynylene;

R and R' are independently selected from H, $C_{1-6}$ alkyl and $C_{1-6}$ haloalkyl.

In another specific embodiment, the present disclosure provides a compound of formula (IX), or a pharmaceutically acceptable salt, enantiomer, diastereomer, racemate, solvate, hydrate, polymorph, prodrug, or isotopic variant thereof, or mixture thereof:

wherein, ring C is $C_{3-7}$ cycloalkyl or 4- to 8-membered heterocyclyl, each of which is substituted with $R_{a12}$ (alternatively 5- to 6-membered heterocyclyl substituted with $R_{a12}$, alternatively 5- to 6-membered heterocyclyl containing N atoms) substituted with $R_{a12}$);

$R_{a1}$ is $C_{1-6}$ alkyl or $C_{1-6}$ haloalkyl;

$R_{a3}$ is $C_{1-6}$ alkyl or $C_{1-6}$ haloalkyl;

$R_{a12}$ is H, $C_{1-6}$ alkyl or $C_{1-6}$ haloalkyl;

$R_5$ is H, halogen, $C_{1-6}$ alkyl or $C_{1-6}$ haloalkyl;

$Z_7$ is N or $CR_{b7}$;

$Z_8$ is N or $CR_{b8}$;

$Z_9$ is N or $CR_{b9}$;

$Z_{10}$ is N or $CR_{b10}$;

$Z_{11}$ is N or $CR_{b11}$;

$Z_{12}$ is N or $CR_{b12}$;

wherein, $R_{b7}$ is selected from —NRR', —NRC(O)R' or —NRC(O) NRR';

$R_{b8}$, $R_{b9}$, $R_{b10}$, $R_{b11}$ and $R_{b12}$ are independently selected from H, halogen. —CN, $C_{1-6}$ alkyl, $C_{1-6}$ haloalkyl, $C_{1-6}$ alkoxy and $C_{1-6}$ haloalkoxy (alternatively selected from H, halogen, —CN and methoxy);

L is independently selected from bond, —O—, —S—, —NR—, —C(O)—, $C_{1-6}$ alkylene, $C_{2-6}$ alkenylene and $C_{2-6}$ alkynylene;

R and R' are independently selected from H, $C_{1-6}$ alkyl and $C_{1-6}$ haloalkyl.

In another specific embodiment, the present disclosure provides a compound of formula (X), or a pharmaceutically acceptable salt, enantiomer, diastereomer, racemate, solvate, hydrate, polymorph, prodrug, or isotopic variant thereof, or mixture thereof;

(X)

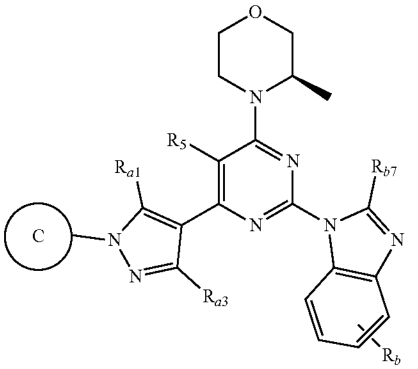

wherein, ring C is

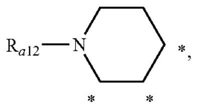

wherein the point of attachment with the rest of the molecule is at one of the positions shown by *;

$R_{a1}$ is $C_{1-6}$ alkyl or $C_{1-6}$ haloalkyl (alternatively is methyl or trifluoromethyl);

$R_{a3}$ is $C_{1-6}$ alkyl or $C_{1-6}$ haloalkyl (alternatively is methyl or trifluoromethyl);

$R_{a12}$ is H or $C_{1-6}$ alkyl (alternatively is H or methyl);

$R_5$ is H;

$R_{b7}$ is selected from —NRR', —NRC(O)R' or —NRC(O)NRR'; wherein, R and R' are independently selected from H, $C_{1-6}$ alkyl and $C_{1-6}$ haloalkyl (alternatively, $R_{b7}$ selected from $NH_2$, NHMe, NHEt, NHC(O)Me or NHC(O)Et);

$R_b$ is H or halogen (alternatively is H or F).

In another specific embodiment, the present disclosure provides a compound of formula (X), or a pharmaceutically acceptable salt, enantiomer, diastereomer, racemate, solvate, hydrate, polymorph, prodrug, or isotopic variant thereof, or mixture thereof:

wherein, ring C is

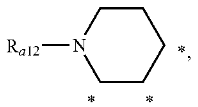

wherein the point of attachment with the rest of the molecule is at one of the positions shown by *;

$R_{a1}$ is methyl or trifluoromethyl;

$R_{a3}$ is methyl or trifluoromethyl;

$R_{a12}$ is H or methyl;

$R_5$ is H;

$R_{b7}$ is selected from $NH_2$, NHMe or NHC(O)Me;

$R_b$ is H or F.

In another specific embodiment, the present disclosure provides a compound of formula (XI), or a pharmaceutically acceptable salt, enantiomer, diastereomer, racemate, solvate, hydrate, polymorph; prodrug, or isotopic variant thereof, or mixture thereof:

(XI)

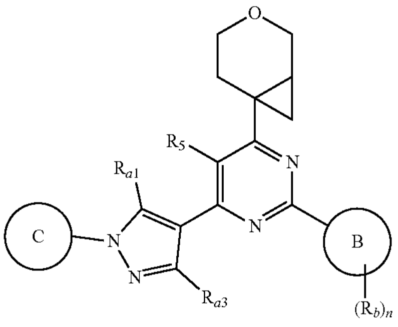

wherein, ring C is $C_{3-7}$ cycloalkyl or 4- to 8-membered heterocyclyl, each of which is substituted with $R_{a12}$ (alternatively 5- to 6-membered heterocyclyl substituted with $R_{a12}$, alternatively 5- to 6-membered heterocyclyl containing N atom(s) substituted with $R_{a12}$;

$R_{a1}$ is $C_{1-6}$ alkyl or $C_{1-6}$ haloalkyl (alternatively is methyl or trifluoromethyl);

$R_{a3}$ is $C_{1-6}$ allyl or $C_{1-6}$ haloalkyl (alternatively is methyl or trifluoromethyl);

$R_{a12}$ is H, $C_{1-6}$ alkyl or $C_{1-6}$ haloalkyl (alternatively is H or methyl);

$R_5$ is H, halogen, $C_{1-6}$ alkyl or $C_{1-6}$ haloalkyl (alternatively is H or F);

ring B is selected from:

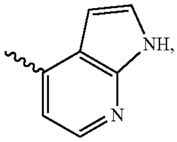,
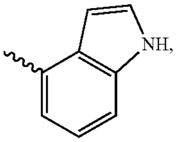,
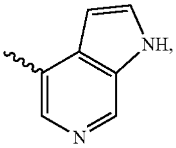,

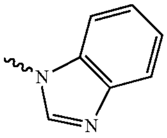 or 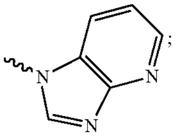;

$R_b$ is selected from H, halogen, —CN, -L-$C_{1-6}$ alkyl, $C_{1-6}$ alkoxy, -L-$C_{3-7}$ cycloalkyl, -L-3- to 8-membered heterocyclyl, —NRR', —NRC(O)R' and —NRC(O)NRR', wherein R and R' are independently selected from H, $C_{1-6}$ alkyl and $C_{1-6}$ haloalkyl.

The preferred compound disclosed herein includes but is not limited to the following compound, or the pharmaceutically acceptable salt, enantiomer, diastereomer, racemate, solvate, hydrate, polymorph, prodrug, or isotopic variant thereof, or mixture thereof:

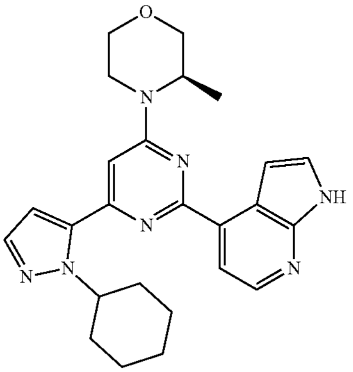

-continued
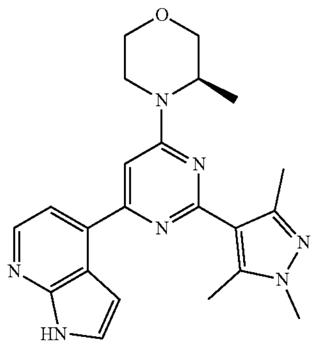
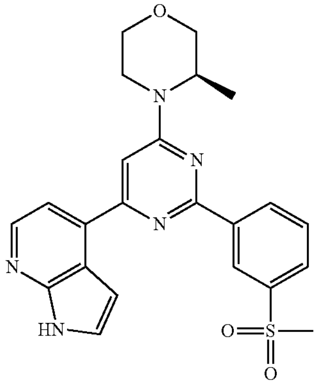
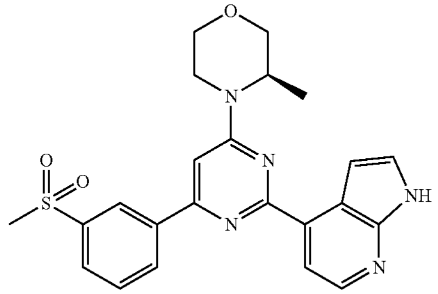
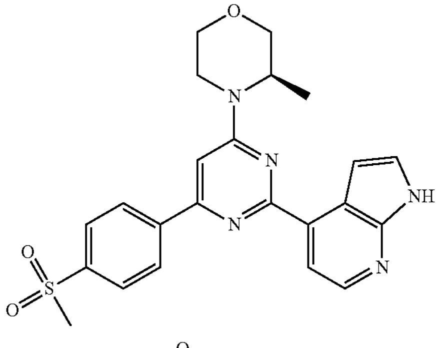
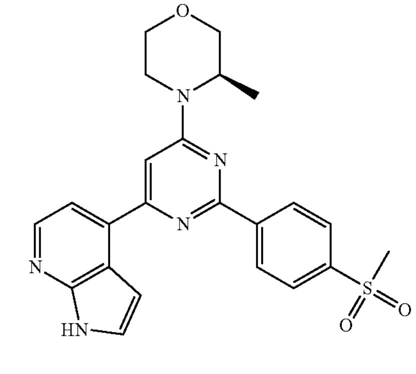
-continued
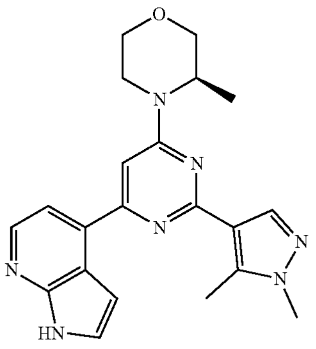
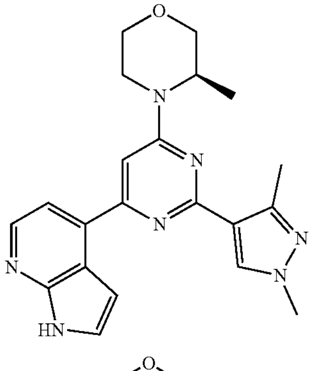
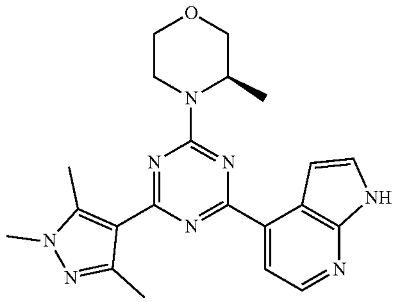
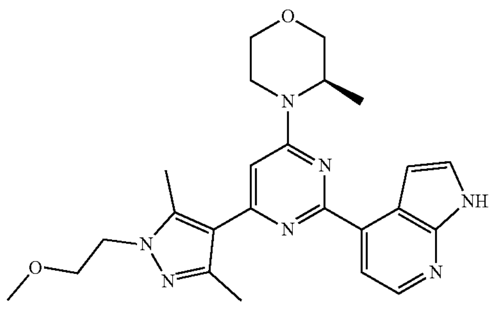
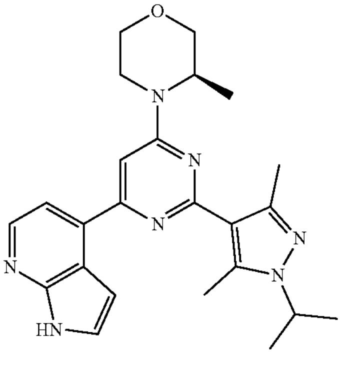

-continued
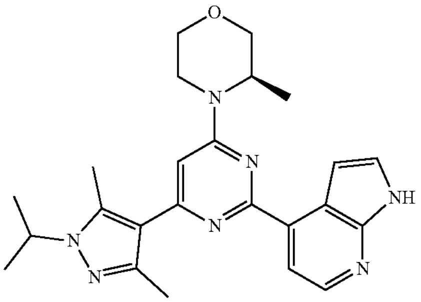
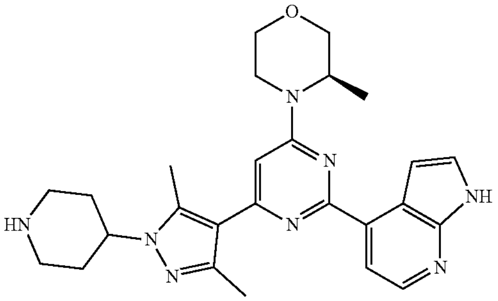
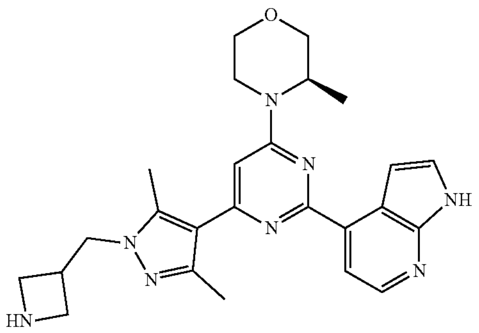
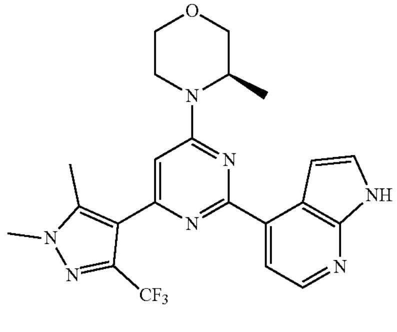
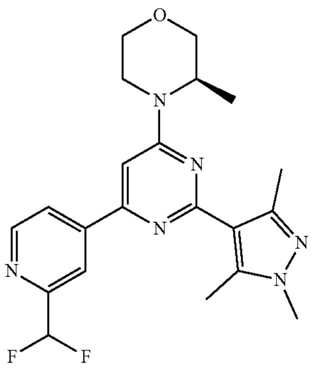
-continued
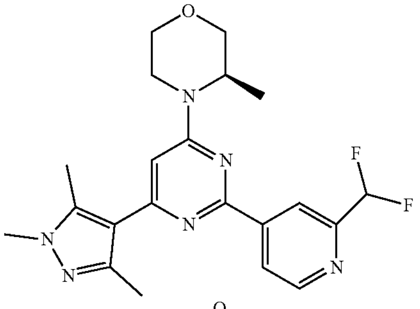
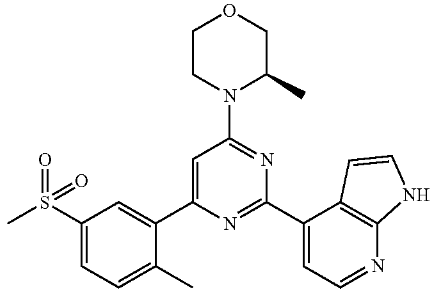
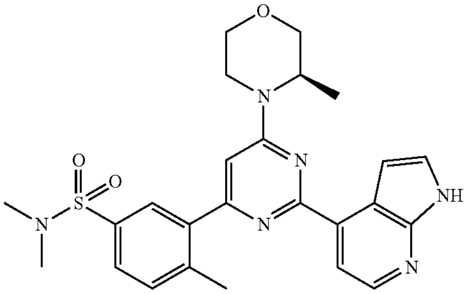
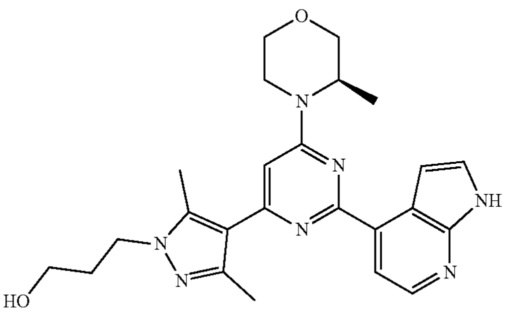
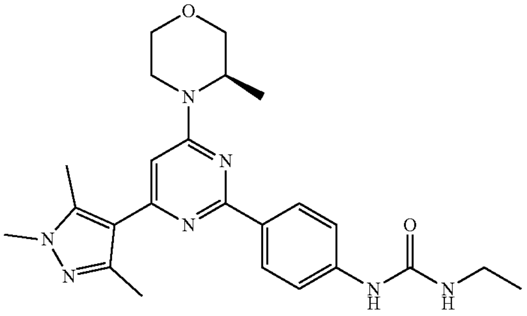

-continued
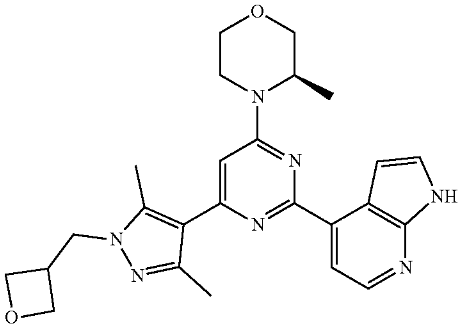
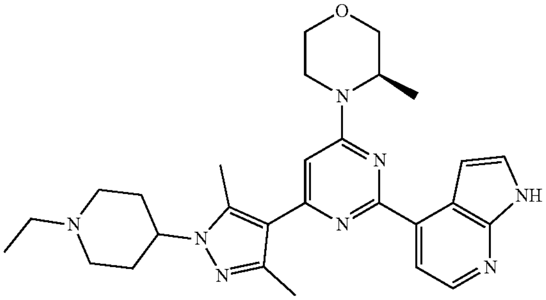
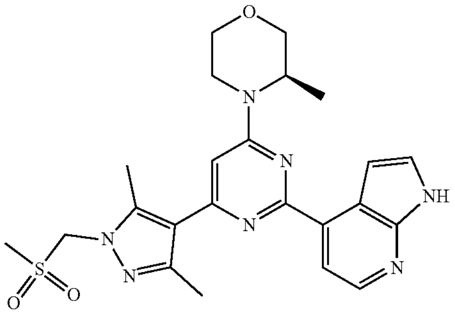
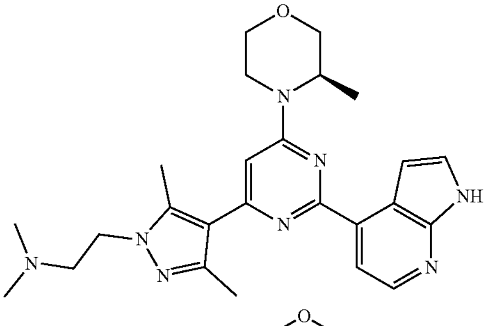
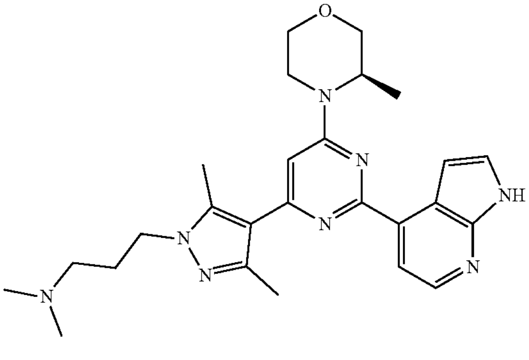
-continued
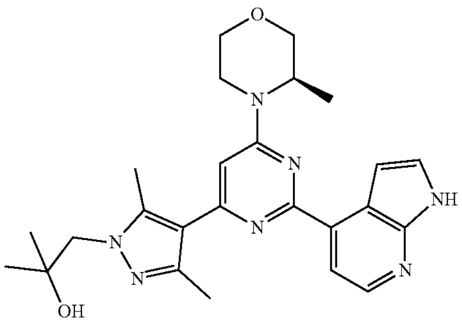
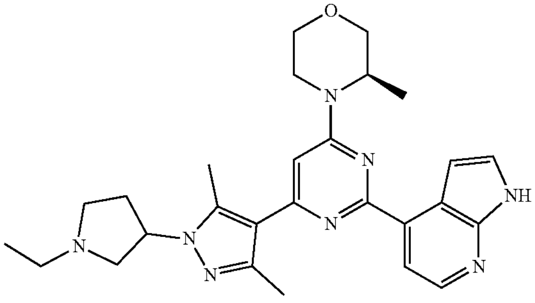
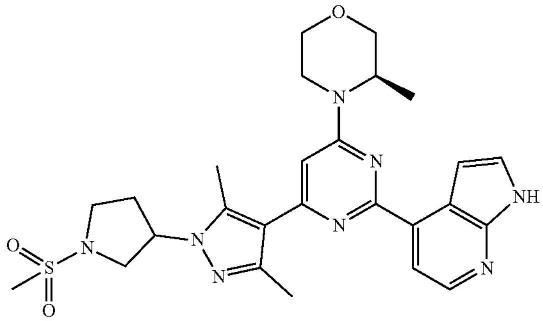
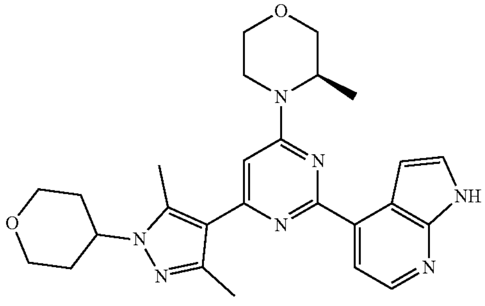
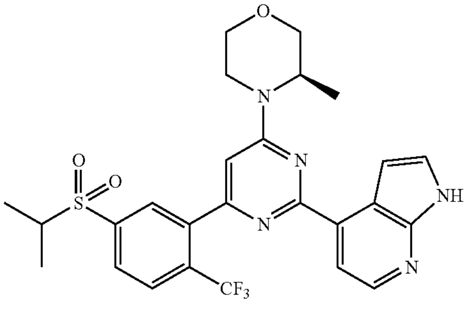

-continued
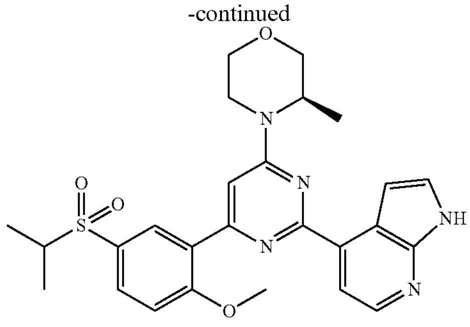
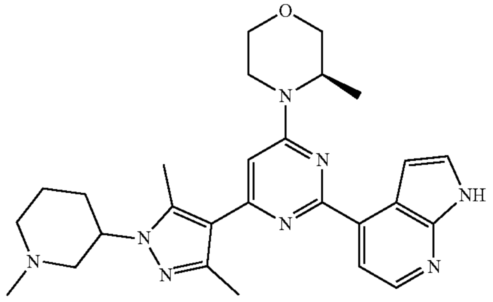
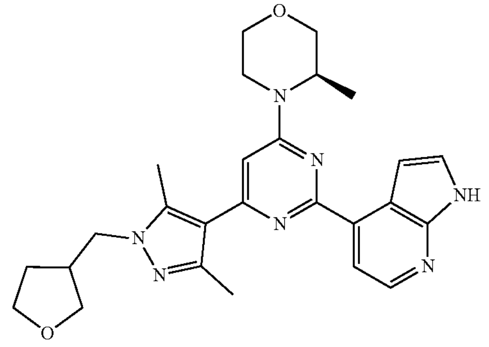
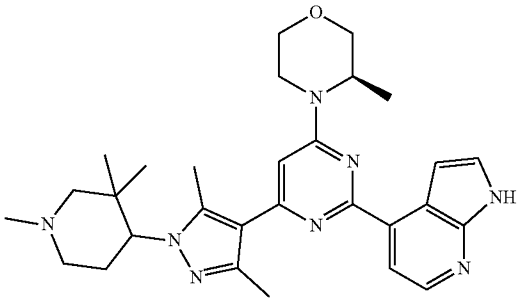
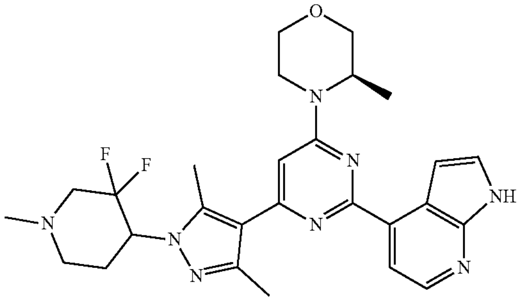
-continued
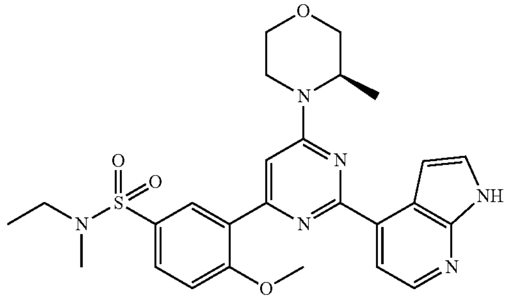
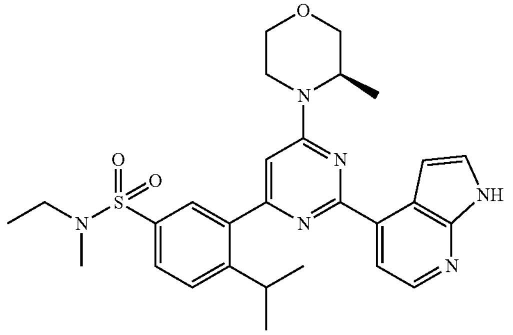
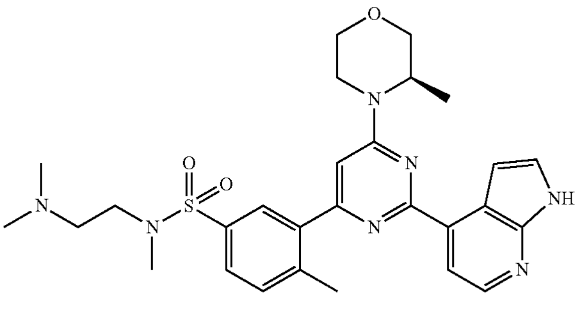
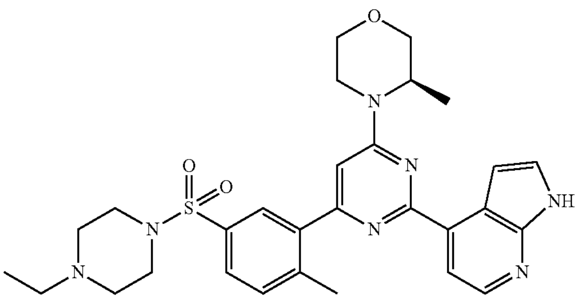
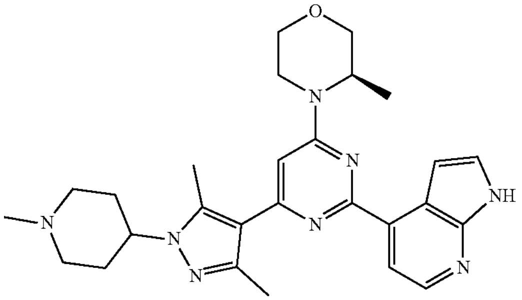

-continued
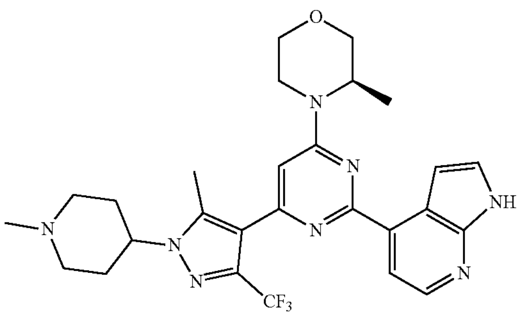
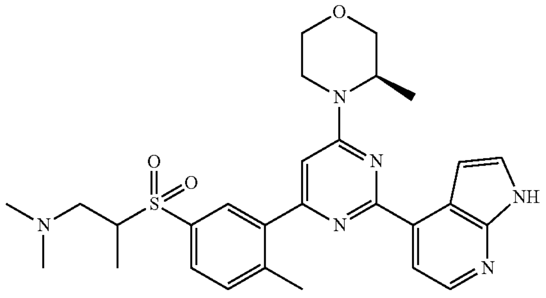
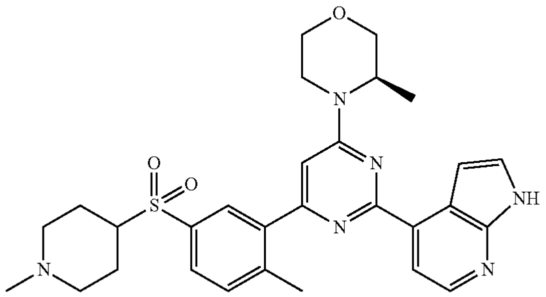
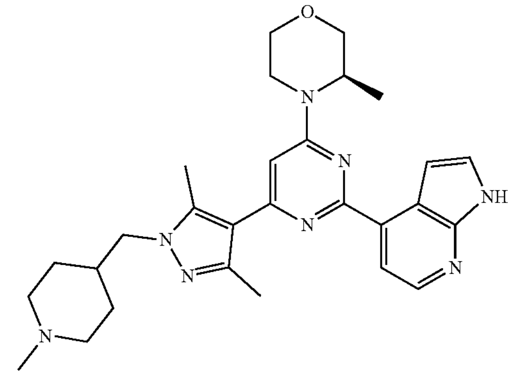
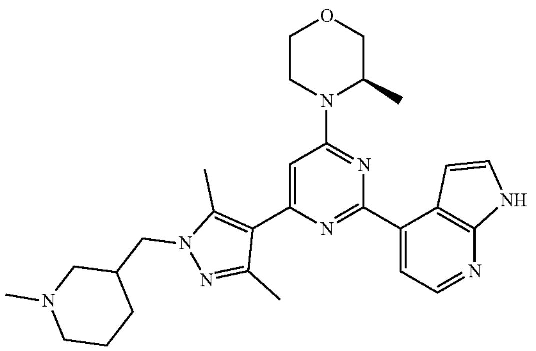
-continued
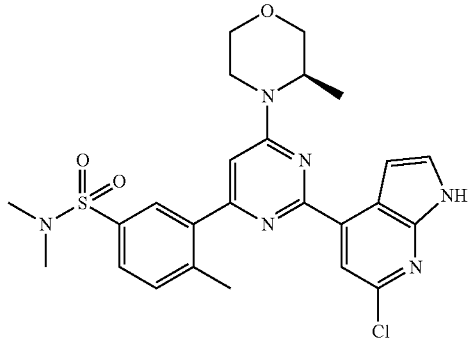
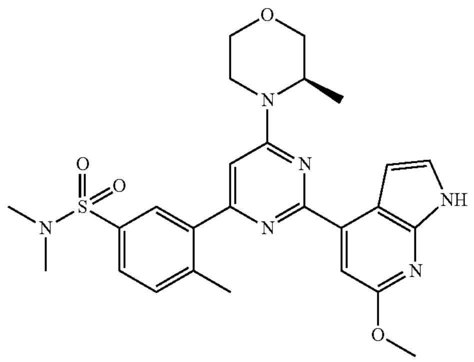
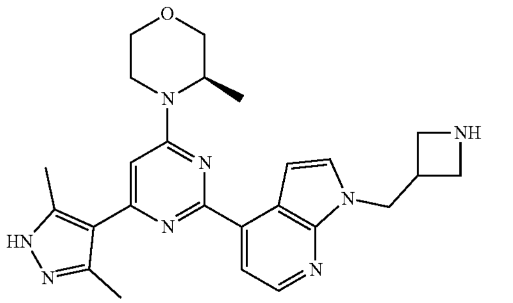
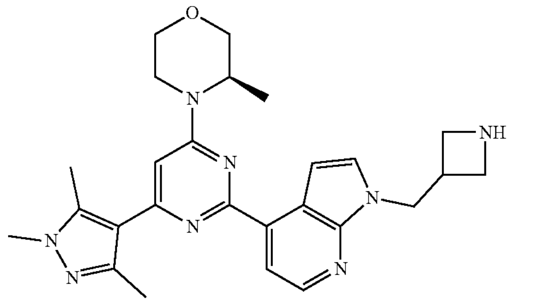
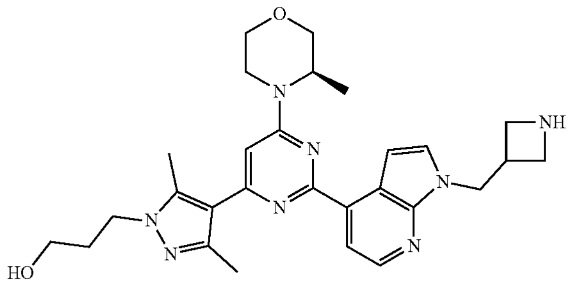

-continued
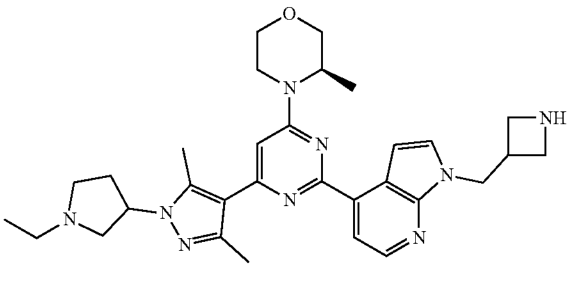
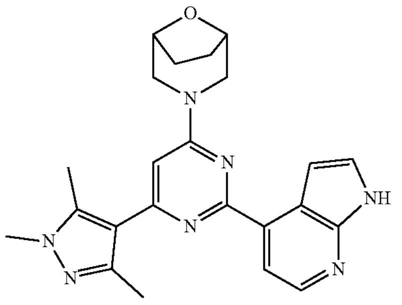
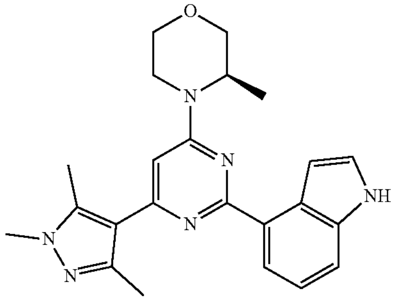
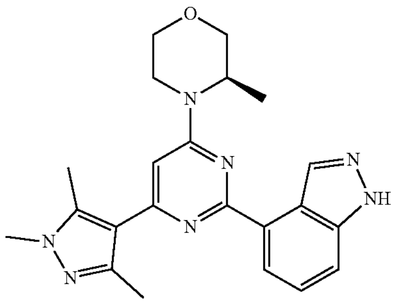
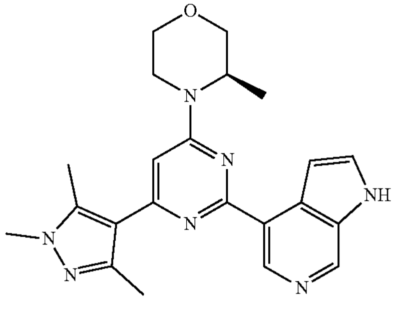
-continued
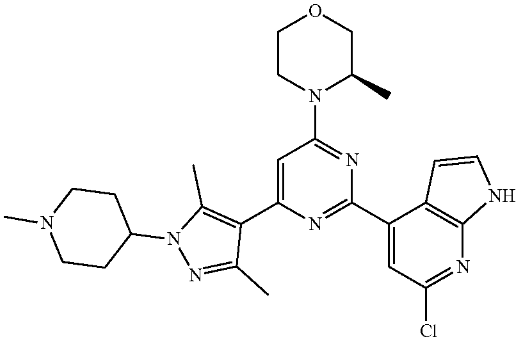
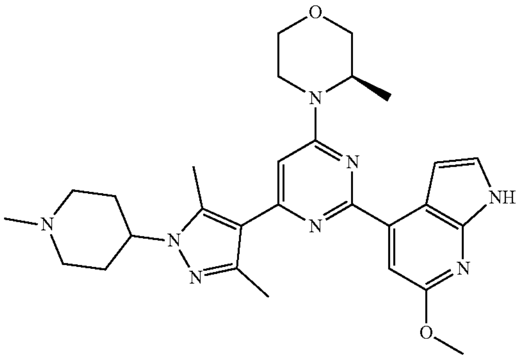
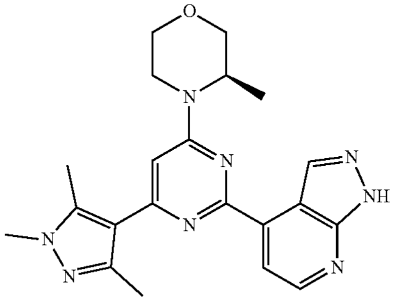
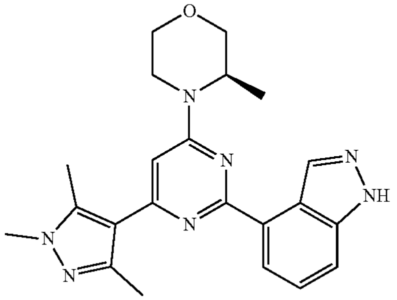
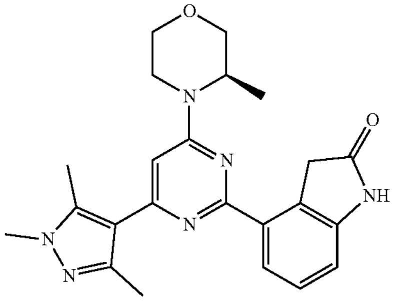

-continued
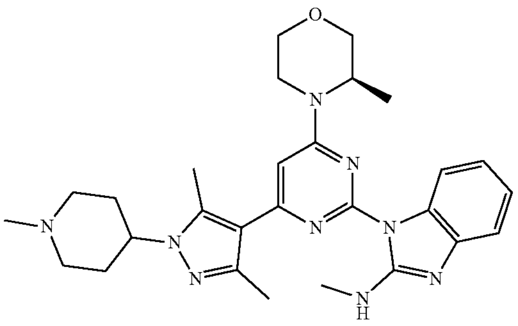
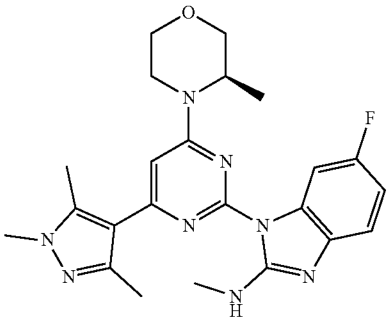
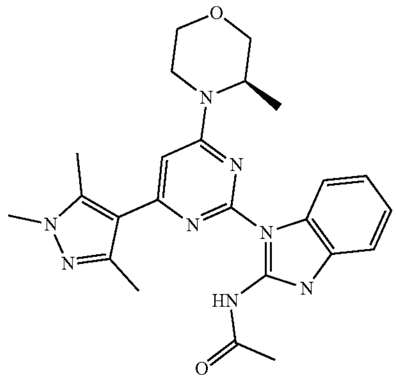
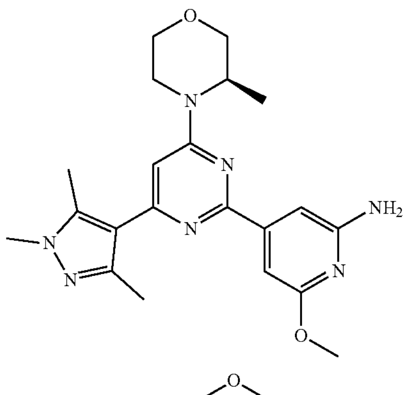
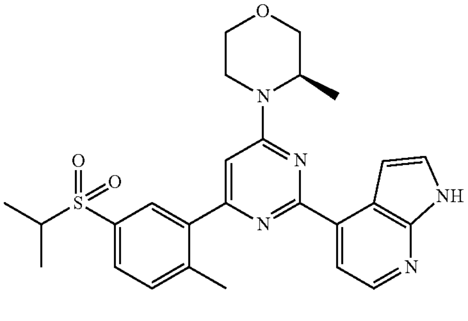
-continued
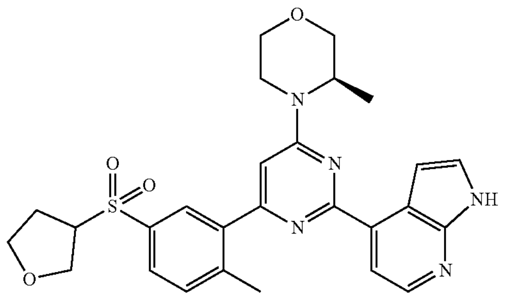
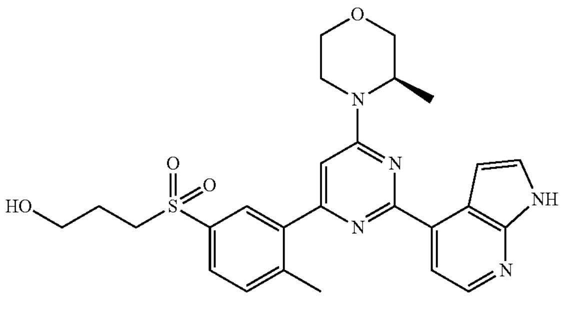
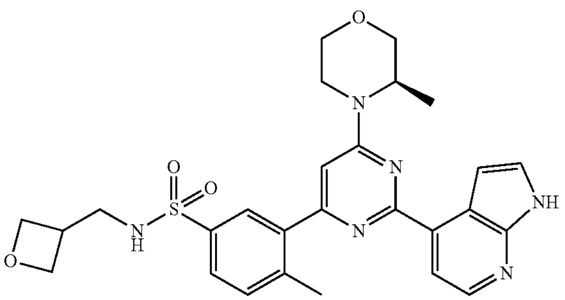
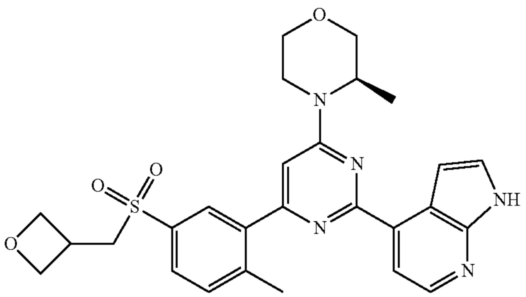
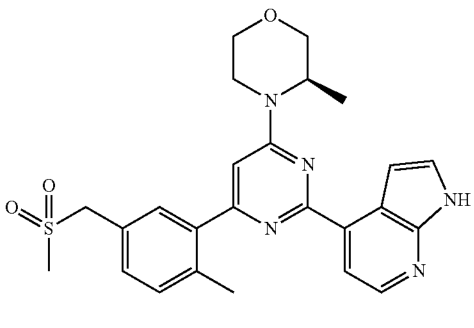

-continued
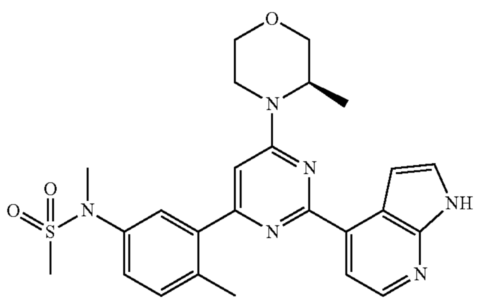
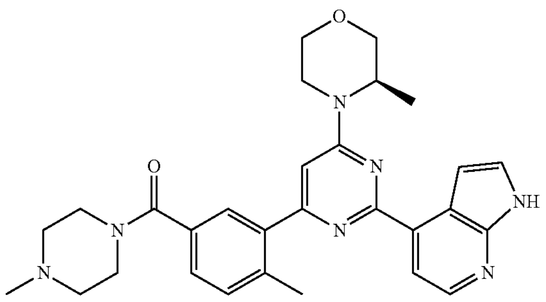
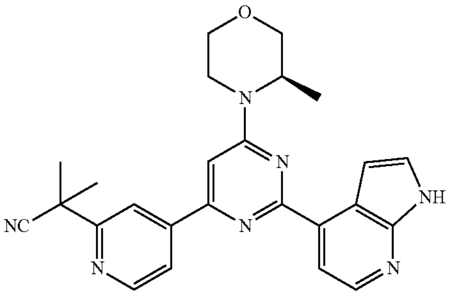
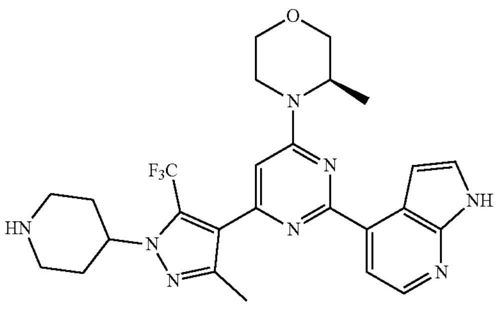
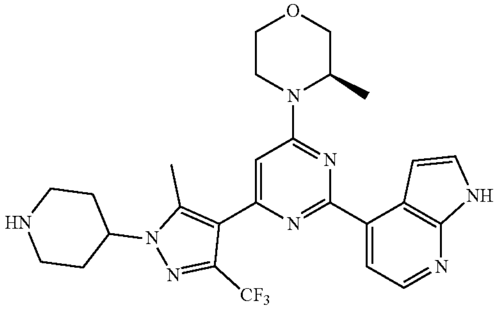
-continued
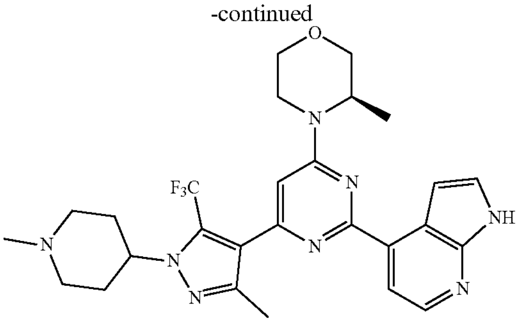
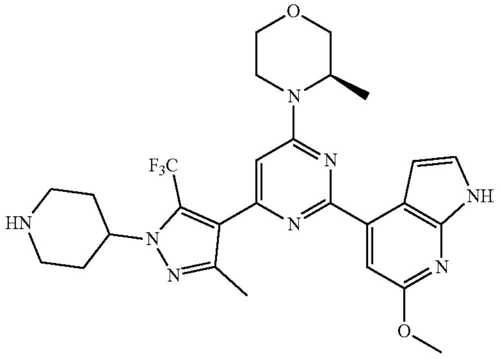
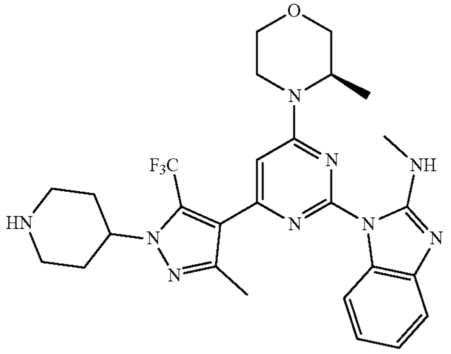
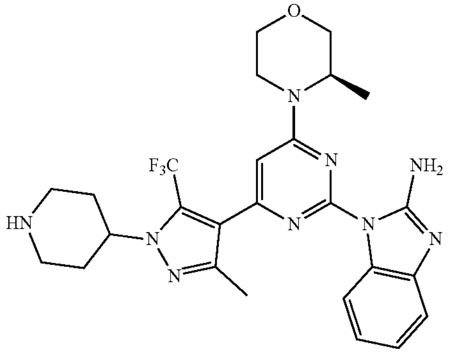
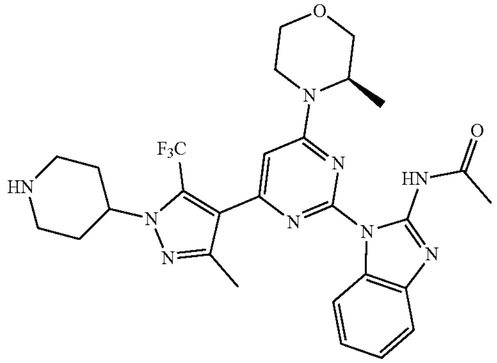

-continued
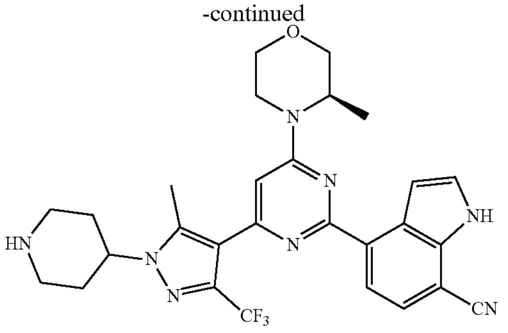
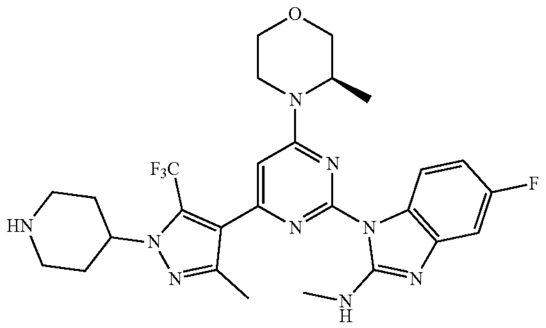
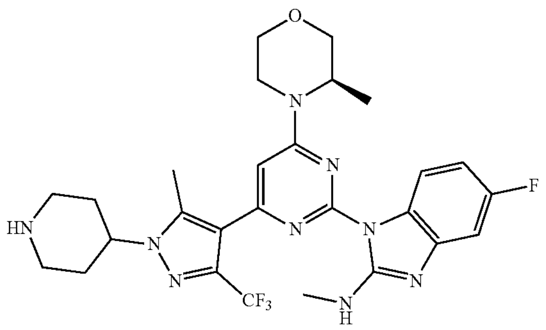
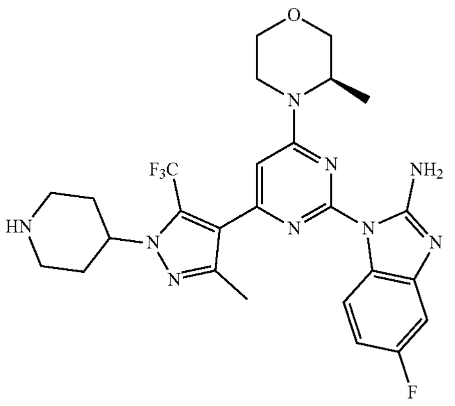
-continued
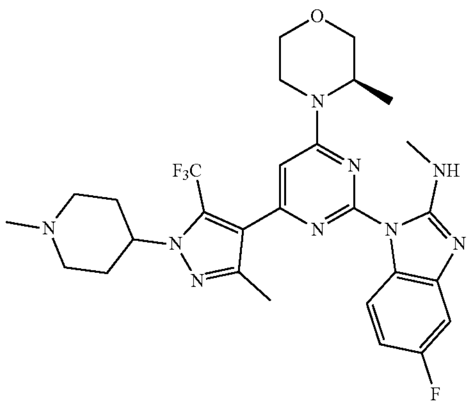
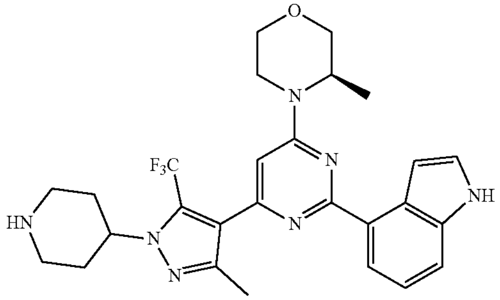
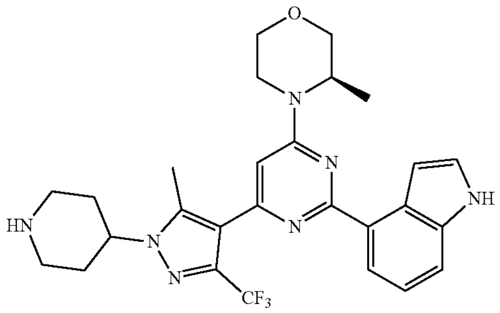
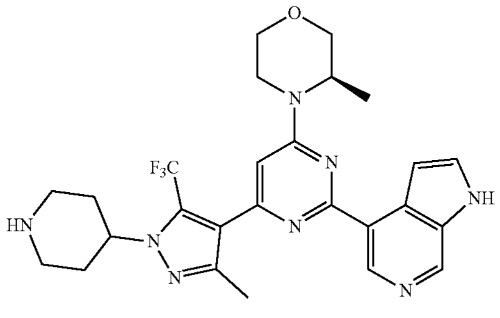
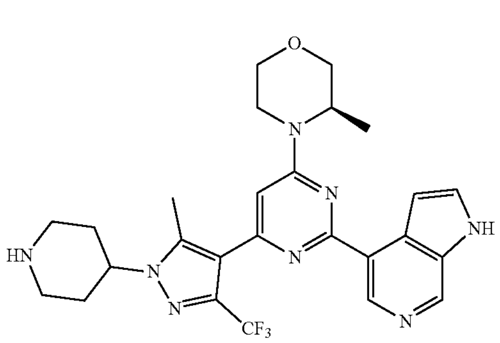

-continued
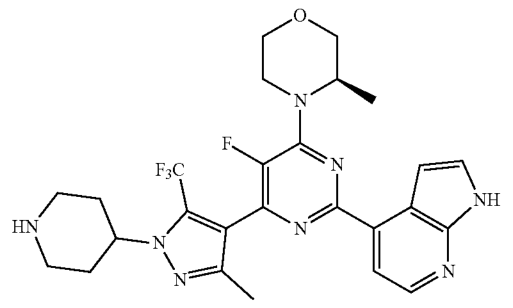
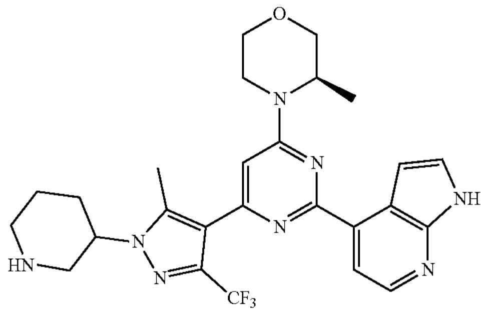
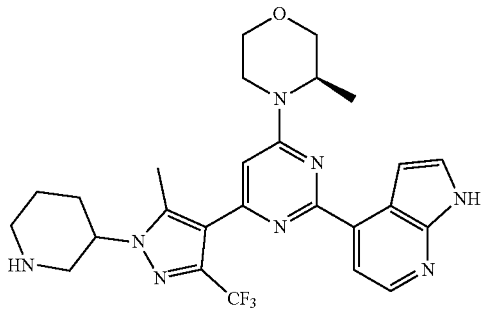
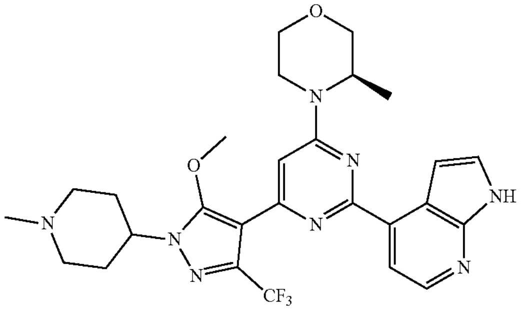
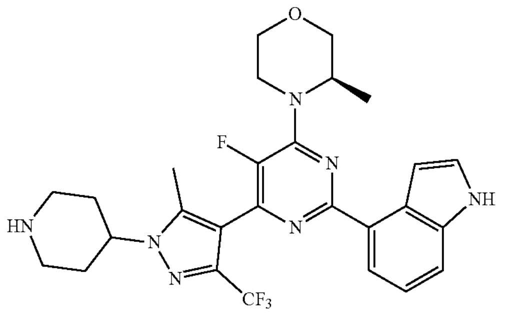
-continued
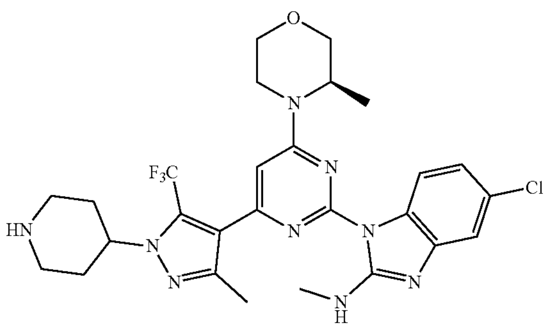
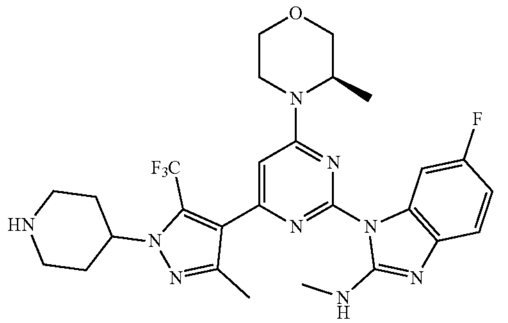
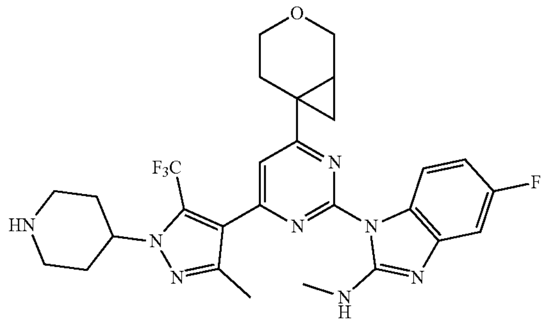
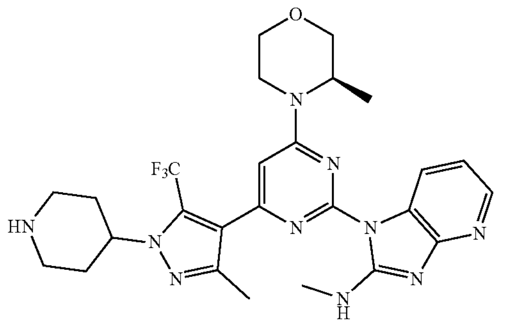
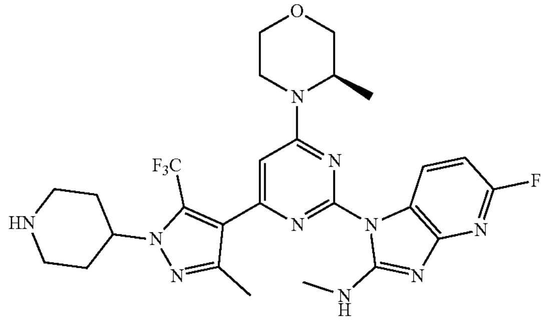

-continued
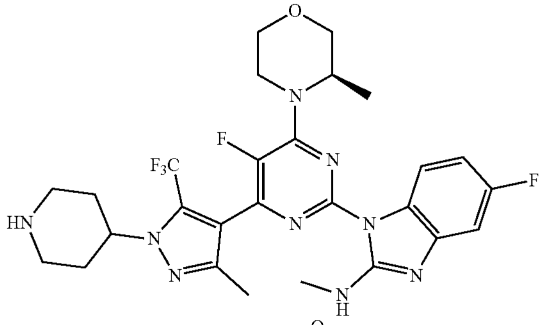
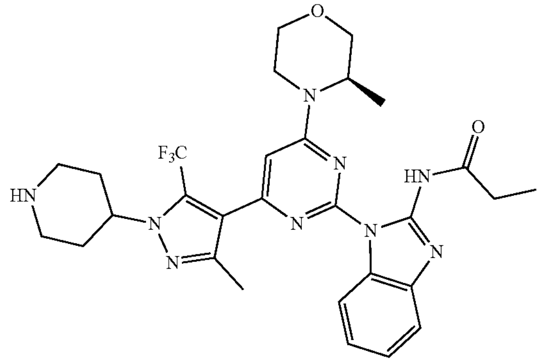
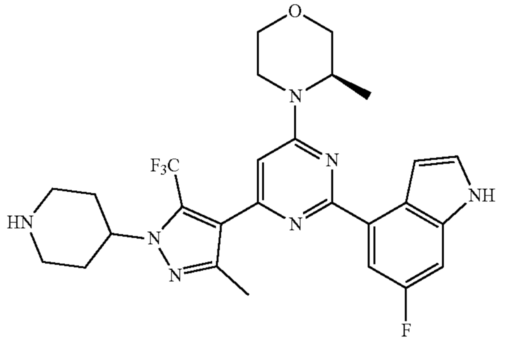
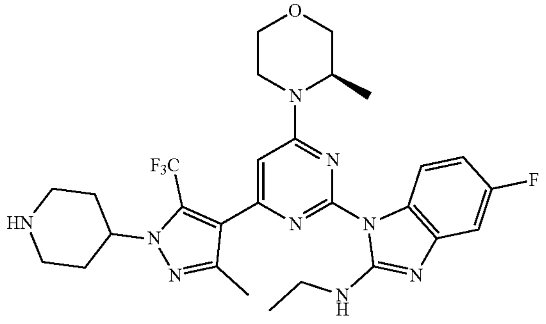
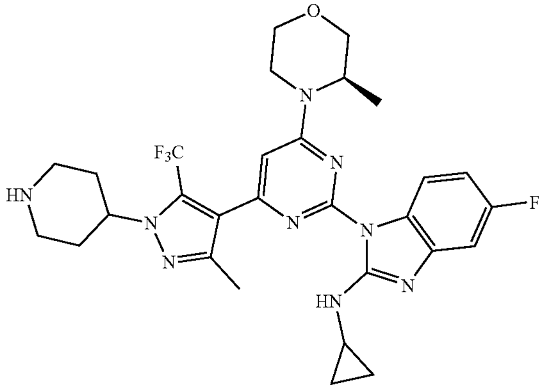
-continued
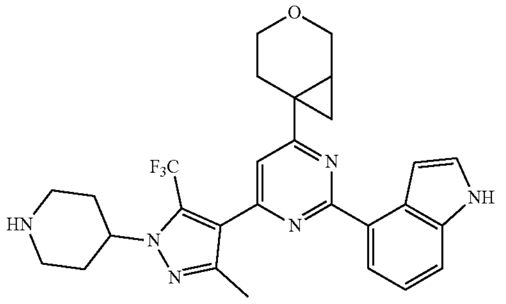
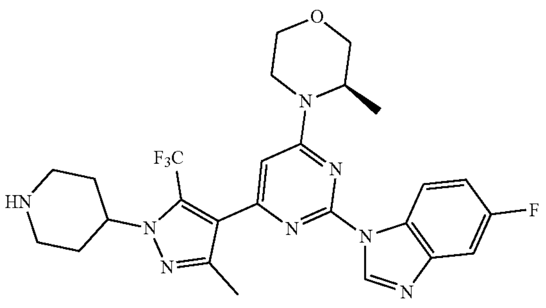
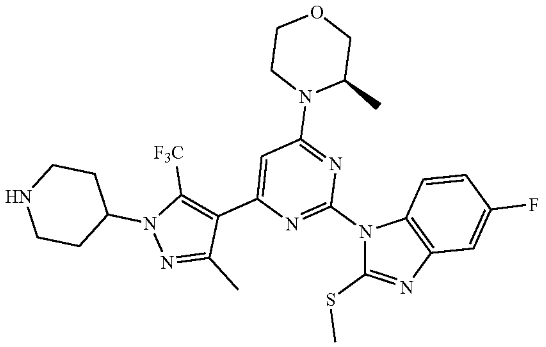
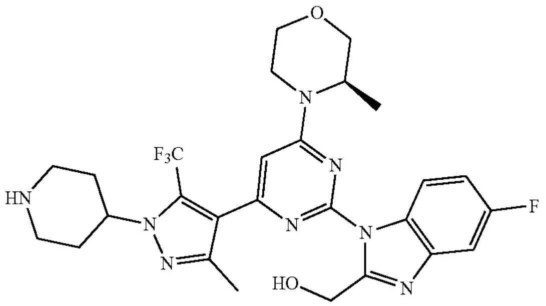
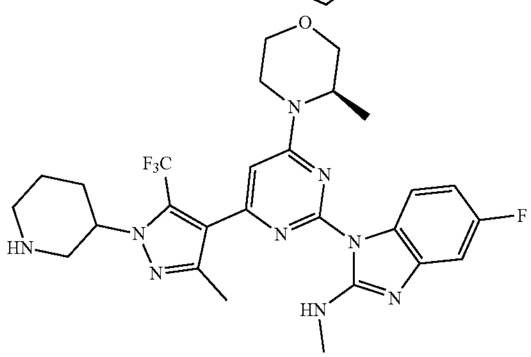

-continued
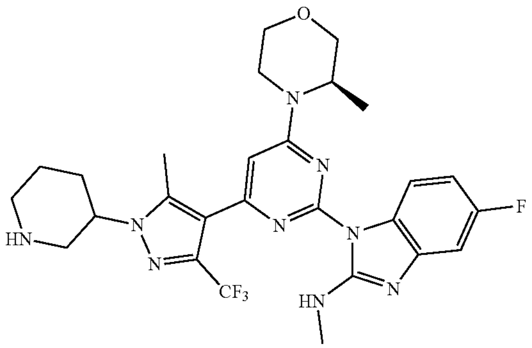
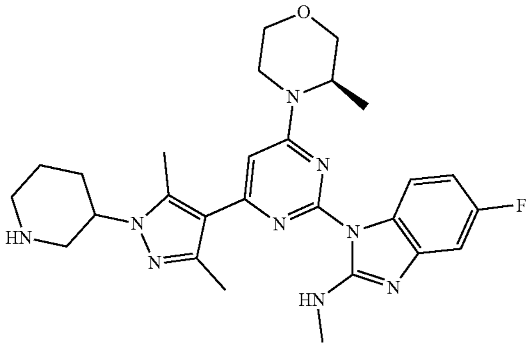
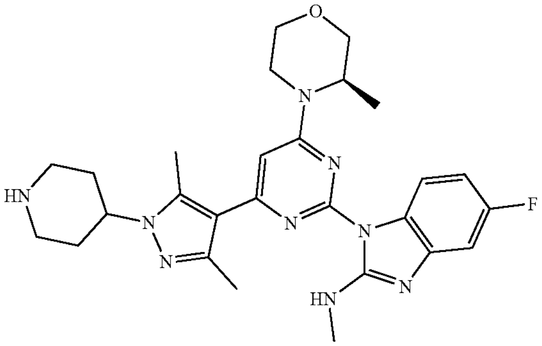
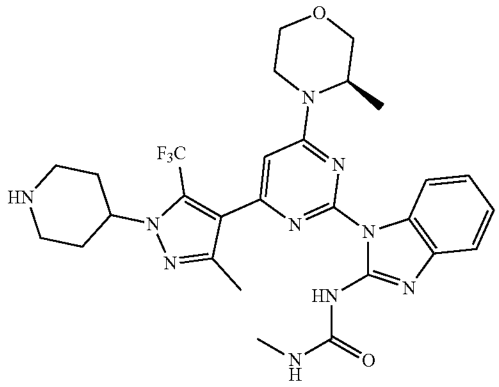
-continued
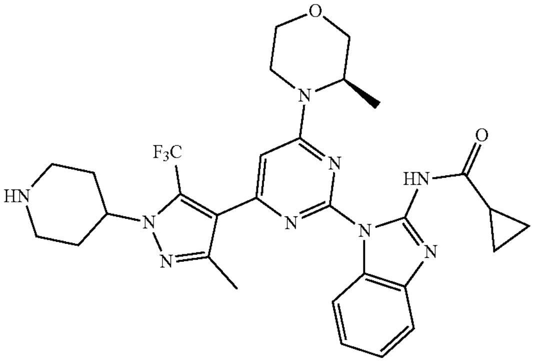
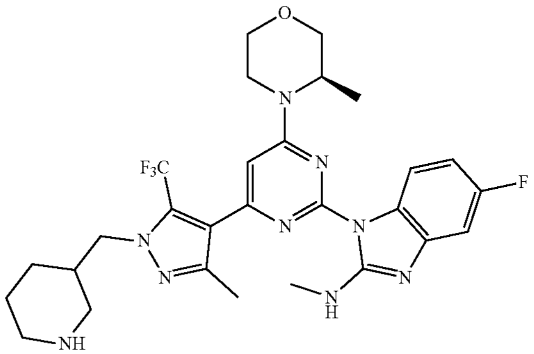
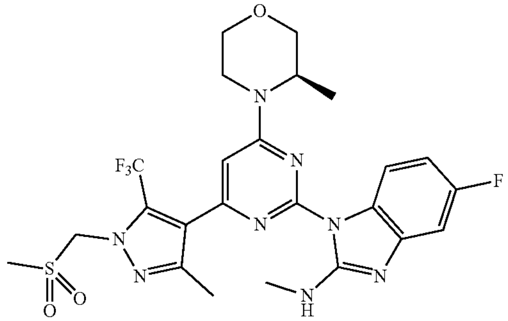
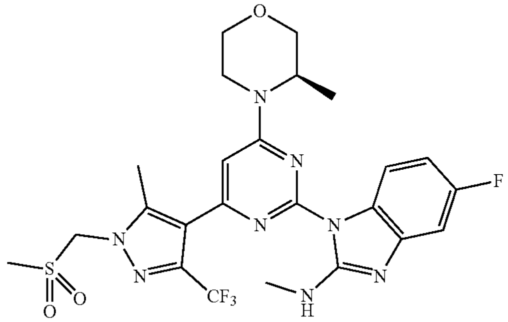
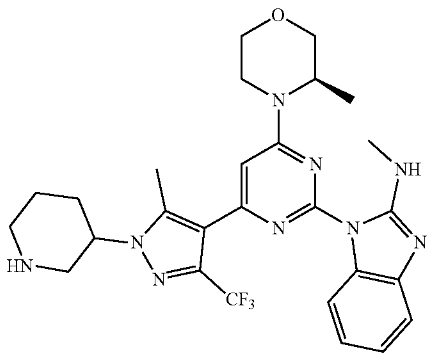

-continued
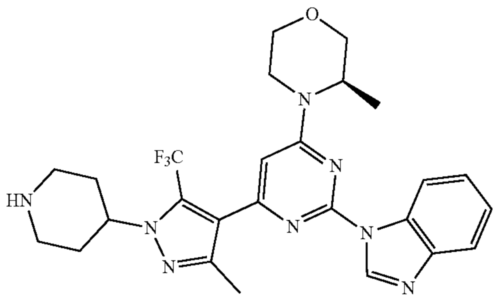
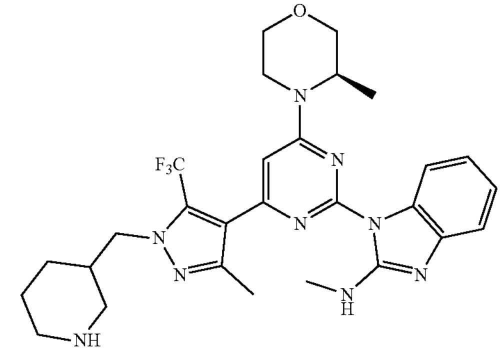
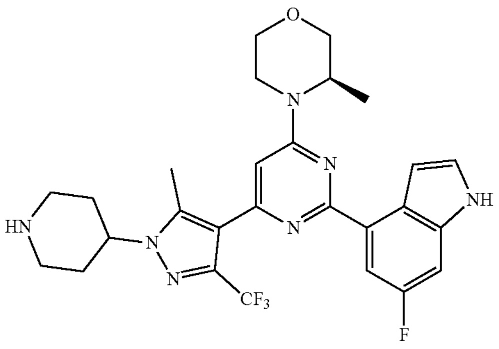
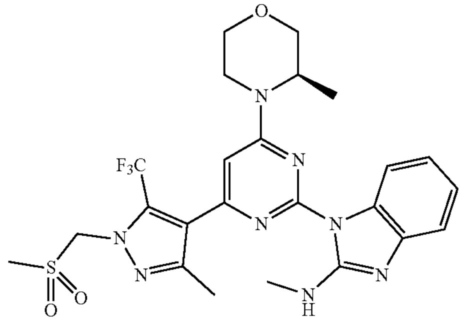
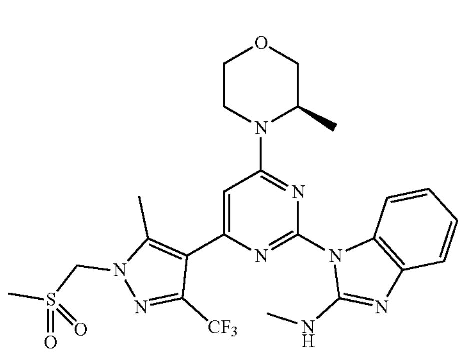
-continued
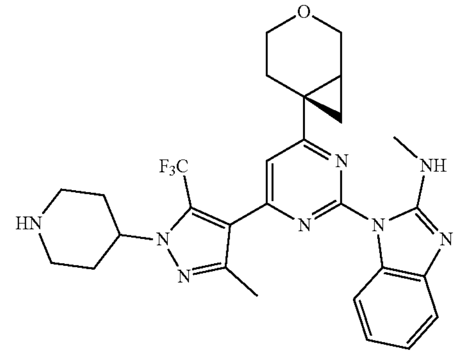
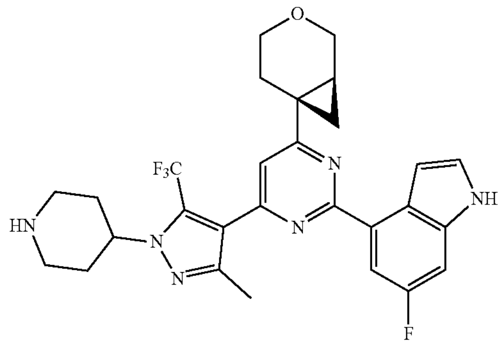
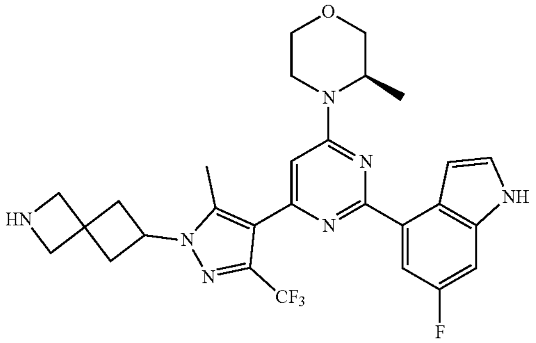
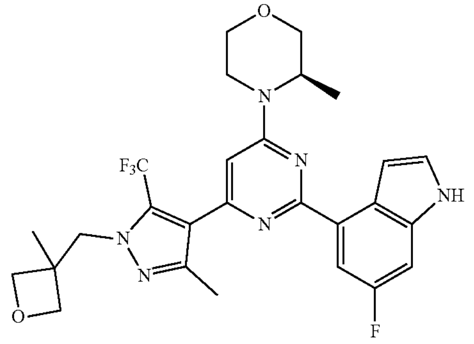
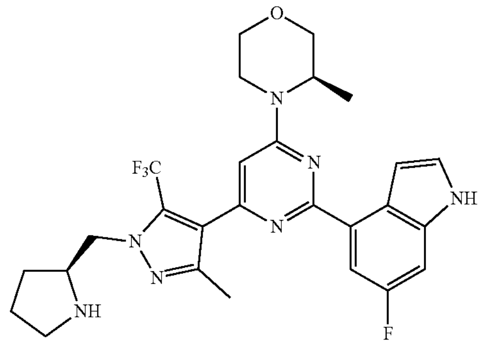

-continued

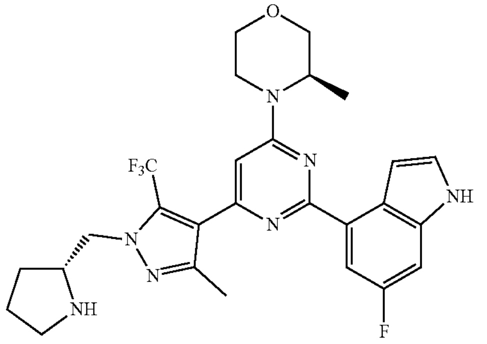

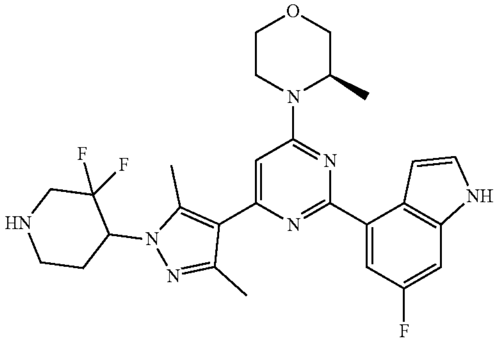

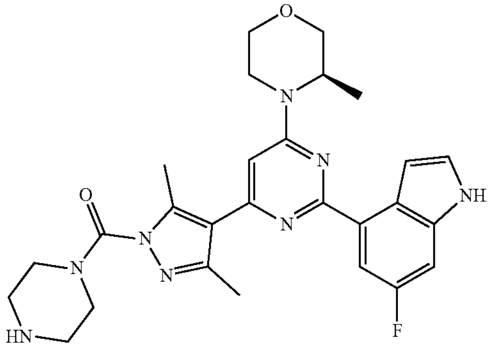

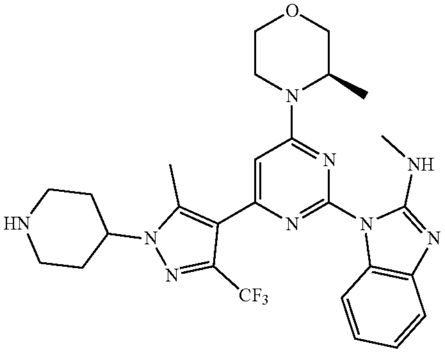

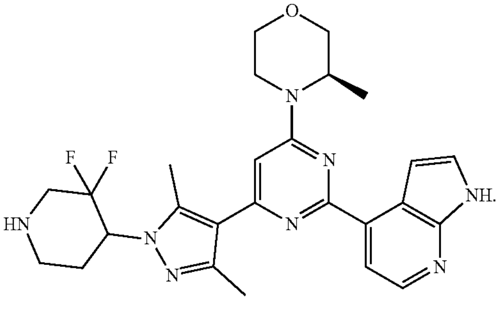

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including, racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or preferred isomers can be prepared by asymmetric synthesis.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds of the present disclosure.

The term "solvate" refers to forms of a compound or a salt thereof, which are associated with a solvent, usually by a solvolysis reaction. This physical association may include hydrogen bonding. Conventional solvents include water, methanol, ethanol, acetic acid. DMSO. THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a (definite ratio to the number of the compound molecules in the hydrate. Therefore, hydrates of a compound can be represented, for example, by a general formula R·x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R·0.5 $H_2O$)) and polyhydrates (x is a number greater than 1, for example, dihydrates (R·2 $H_2O$) and hexahydrates (R·6 $H_2O$)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes, which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present disclosure that comprise be above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^{3}H$ and $^{14}C$), can be used for the measurement of the distribution of drug and/or substrate in tissue. Tritium, which is $^{3}H$ and carbon-14, which is $^{14}C$ isotope, are particularly preferred, because they are easy to prepare and detect. Furthermore, replaced by heavier isotopes, such as deuterium, which is $^{2}H$, may provide therapeutic benefits due to the higher metabolic stability, such as prolonging the half-life in vivo or decreasing the dosage requirements, and thus may be preferred in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is convened into an active form that has medical effects in vivo by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward 13. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 1.15-130, each of which are incorporated herein by reference.

The prodrugs are any covalently bonded compounds of the present disclosure, which release the parent compound in vivo when the prodrug is administered to a patient. Prodrugs are typically prepared by modifying functional groups in such a way that the modifications can be cleaved either by routine manipulation or decompose in vivo to yield the parent compound. Prodrugs include, for example, compounds of the present disclosure wherein the hydroxyl, amino or sulfhydryl groups are bonded to any group that, when administered to a patient, cleaves to form the hydroxyl, amino or sulfhydryl groups. Thus, representative examples of prodrugs include (hut are not limited to) the acetate/acetamide, formate/formamide and benzoate/benzamide derivatives of the hydroxyl, amino or sulfhydryl functional groups of the compounds of formula (I). Furthermore, in the case of carboxylic acid (—COOH), esters such as methyl esters and ethyl esters, etc. can be employed. The ester itself may be active in their own and/or hydrolyzable under in vivo conditions in the human body. Suitable pharmaceutically acceptable in vivo hydrolysable ester groups include those groups that can readily break down in the human body to release the parent acids or salts thereof.

The present disclosure also provides a pharmaceutical formulation comprising a therapeutically effective amount of a compound of formula (I), or therapeutically acceptable salts thereof, and pharmaceutically acceptable carriers, diluents or excipients thereof. All of these forms belong to the present disclosure.

Pharmaceutical Compositions, Formulations and Kits

In another aspect, the present disclosure provides a pharmaceutical composition comprising a compound of the present disclosure (also referred to as the "active ingredient") and a pharmaceutically acceptable excipient. In certain embodiments, the pharmaceutical composition comprises an effective amount of the compound of the present disclosure. In certain embodiments, the pharmaceutical composition comprises a therapeutically effective amount of the compound of the present disclosure. In certain embodiments, the pharmaceutical composition comprises a prophylactically effective amount of the compound of the present disclosure.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacetylene, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (e.g., vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present disclosure may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired closing form.

With oral dosing, one to five and especially two to four and typically three oral closes per clay are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of the present disclosure can also be administered in sustained release forms or from sustained release ding delivery systems. A description of representative sustained release materials can be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Treatment

As stated herein, it is known that ATR kinase have roles in tumourigenesis as well as numerous other diseases. We have found that the compounds of formula (I) possess potent anti-tumour activity which it is believed is obtained by way of inhibition of ATR kinase.

The compounds of the present disclosure are of value as anti-tumour agents. Particularly, the compounds of the present disclosure are of value as anti-proliferative, apoptotic and/or anti-invasive agents in the containment and/or treatment of solid and/or liquid tumour disease. Particularly, the compounds of the present disclosure are expected to be useful in the prevention or treatment of those tumours which are sensitive to inhibition of ATR. Further, the compounds of the present disclosure are expected to be useful in the prevention or treatment of those tumours which are mediated alone or in part by ATR. The compounds may thus be used to produce an ATR enzyme inhibitory effect in a warm-blooded animal in need of such treatment.

As stated herein, inhibitors of ATR kinase should be of therapeutic value for the treatment of proliferative disease such as cancer and in particular solid tumours such as carcinoma and sarcomas and the leukaemias and lymphoid malignancies and in particular for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including acute lymphoctic leukaemia (ALL) and chronic myelogenous leukaemia (CML)], multiple myeloma and lymphomas.

Anti-cancer effects which are accordingly useful in the treatment of cancer in a patient include, but are not limited to, anti-tumour effects, the response rate, the time to disease progression and the survival rate. Anti-tumour effects of a method of treatment of the present disclosure include but are not limited to, inhibition of tumour growth tumour growth delay, regression of tumour, shrinkage of tumour, increased time to regrowth of tumour on cessation of treatment; slowing of disease progression. Anti-cancer effects include prophylactic treatment as well as treatment of existing disease.

A ATR kinase inhibitor, or a pharmaceutically acceptable salt thereof, may also be useful for the treatment patients with cancers, including, but not limited to, haematologic malignancies such as leukaemia, multiple myeloma, lymphomas such as Hodgkins disease, non-Hodgkin's lymphomas (including mantle cell lymphoma), and myelodysplastic syndromes, and also solid tumours and their metastases such as breast cancer, lung cancer (non-small cell lung cancer (NSCL), small cell lung cancer (SCLC), squamous cell carcinoma), endometrial cancer, tumours of the central nervous system such as gliomas, dysembryoplastic neuroepithelial tumour, glioblastoma multiforme, mixed gliomas, medulloblastoma, retinoblastoma, neuroblastoma, germinoma and teratoma, cancers of the gastrointestinal tract such as gastric cancer, oesophagal cancer, hepatocellular (liver) carcinoma, cholangiocarcinoma, colon and rectal carcinomas, cancers of the small intestine, pancreatic cancers, cancers of the skin such as melanomas (in particular metastatic melanoma), thyroid cancers, cancers of the head and neck and cancers of the salivary glands, prostate, testis, ovary, cervix, uterus, vulva, bladder, kidney eluding renal cell carcinoma, clear cell and renal oncocytoma), squamous cell carcinomas, sarcomas such as osteosarcoma, chondrosarcoma, leiomyosarcoma, soft tissue sarcoma, Ewing's sarcoma, gastrointestinal stromal tumour (GIST), Kaposi's sarcoma, and paediatric cancers such as rhabdomyosarcomas and neuroblastomas.

The compounds of the present disclosure and the methods of treatment comprising the administering or use of a ATR kinase inhibitor, or a pharmaceutically acceptable salt thereof, are expected to be particularly useful for the treatment of patients with lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment of patients with acute myeloid leukaemia.

The effective dose of the compound of the present disclosure is usually at an average daily dose of 0.01 mg to 50 mg compound/kg of patient weight, alternatively 0.1 mg to 25 mg compound/kg of patient weight, in single or multiple administrations. Generally, the compound of the present disclosure can be administered to the patient who needs this treatment in the daily dose range of about 1 mg to about 3500 mg per patient, alternatively 10 mg to 1000 mg. For example, the daily dose per patient can be 10, 20, 30, 40, 50, 60, 70, 80, 90, 100, 150, 200, 250, 300, 350, 400, 500, 600, 700, 800, 900 or 1000 mg. It can be administered once or several times a day, weekly (or several days apart) or on an intermittent schedule. For example, on a weekly basis (e.g. every Monday), the compound can be administered one or more times a day, variably for several weeks, for example, 4-10 weeks. Or, the compound may be administered daily for several days (e.g. 2-10 days), and then a few days (e.g. 1-30 days) without administering the compound, repeating the cycle arbitrarily or repeating a given number of times, e.g. 4-10 cycles. For example, the compound of the present disclosure can be administered daily for 5 days, and then interrupted for 9 days, and then administered daily for 5 days, then interrupted for 9 days, and so on, repeating the cycle arbitrarily or repeating 4-10 times in total.

Combination Therapy

The treatment defined herein may be applied as a sole therapy or may involve, in addition to the compounds of the present disclosure, conventional surgery or radiotherapy or chemotherapy. Accordingly, the compounds of the present disclosure can also be used in combination with existing therapeutic agents for the treatment of cancer.

Suitable agents to be used in combination include:

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate; cytosine arabinoside, hydroxyurea and gemcitabine); antitumour antibiotics (far example anthracyclines like adriamycin, bleomycin, doxorubicin, daunomycin epirubicin, idarubicin, mitomycin-C, dactinomycin and mithramycin); antimitotic, agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide; flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like AZD0530 and dasatinib); and metalloproteinase inhibitors like marimastat and inhibitors of urokinase plasminogen activator receptor function;

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as gefitinib, erlotinib and CI 1033; and erbB2 tyrosine kinase inhibitors such as lapatinib), inhibitors of the hepatocyte growth factor family; inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, for example the anti-vascular endothelial cell growth factor antibody bevacizumab (Avastin™) and VEGF receptor tyrosine kinase inhibitors such as ZD6474, AZD2171 vatalanib and sunitinib, and compounds that work by other mechanisms (for example linomide, inhibitors of integral αvβ3 function and angio statin);

(vi) vascular damaging agents such as combretastatin;

(vii) antisense therapies, for example those which are directed to the targets listed above, such as ISIS 2503;

(viii) gene therapy approaches, including approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell allergy, approaches using transfected immune cells such as cytokine-transfected dendritic cells, approaches using cytokine-transfected tumour cell lines and approaches using anti-idiotypic antibodies.

EXAMPLES

The materials or reagents used herein are commercially available or are prepared by synthetic methods generally known in the art. The following reaction routes exemplify the specific synthetic methods of the compounds of the present disclosure.

Preparation of Key Intermediates a1-a13:

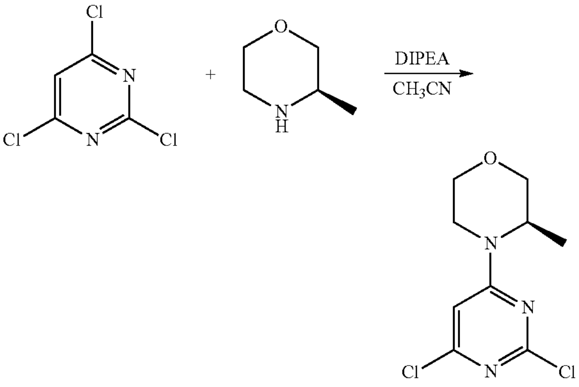

a1

2,4,6-trichloropyrimidine (13.74 mmol, 2.5 g). (R)-2-methylmorpholine (13.8 mmol, 1.4 g) and DIPEA (30 mmol, 3.87 g) were added to a reaction flask, after dissolving in 50 mL of acetonitrile, the mixture was reacted at 90° C. for 2 hours. The reaction was stopped, the solvent was dried by rotary evaporation, 50 mL of water was added, extracted with ethyl acetate, dried over anhydrous $Na_2SO_4$, and separated by column chromatography to afford intermediate a1 (2.3 g. yield: 68%), LC-MS: [M+H]+: 248.

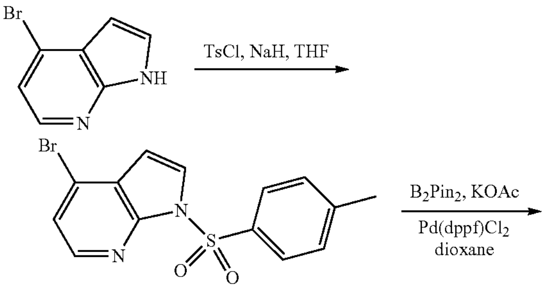

a2

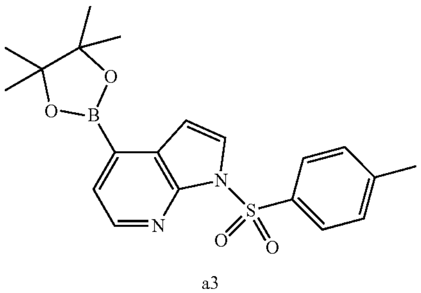

a3

In an ice bath, 4-bromo-7-azaindole (25.5 mmol, 5 g) and p-toluenesulfonyl chloride (38.25 mmol, 7.27 g) were added to a reaction flask, dissolved in 7.00 mL of anhydrous tetrahydrofuran, 60% NaH (30 mmol, 1.2 g) was slowly added, and the mixture was reacted at room temperature for 6 hours. The reaction was stopped, 50 mL of water was slowly added, the organic solvent was dried by rotary evaporation, extracted with dichloromethane, dried over anhydrous $Na_2SO_4$, and separated by column chromatography to afford intermediate a2 (9.0 g, quantitative yield), LC-MS: [M+H]+: 350.

Under nitrogen protection, intermediate a2 (25.5 mmol, 9.0 g) and bis(pinacolato)diboron (30.6 mmol, 7.77 g) were dissolved in 1,4-dioxane, potassium acetate (51 mmol, 5 g) and Pd(dppf)$Cl_2$ (2.5 mmol, 0.83 g) were added, and the mixture was reacted at 90° C. for 12 hours. The reaction was stopped, filtered, the organic solvent was dried by rotary evaporation, and separated by column chromatography to afford intermediate a3 (10.0 g, yield: 98%), LC-MS: [M+H]+: 399.

The following intermediate was synthesized with reference to intermediate a3:

-continued

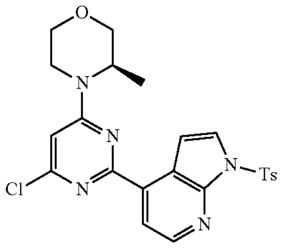

a4

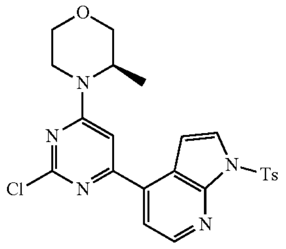

a5

Under nitrogen protection, intermediate a1 (4 mmol, 1.0 g) and intermediate a3 (6 mmol, 2.4 g) were dissolved in 10 mL mixture of 1,4-dioxane and water (v/v: 9/1), sodium carbonate (8 mmol, 848 mg) and Pd(dppf)$Cl_2$ (0.4 mmol, 293 mg) were added, and the mixture was heated to reflux and reacted for 12 hours. The reaction was stopped, filtered, the organic solvent was dried by rotary evaporation, water was added, extracted with ethyl acetate, and separated by column chromatography to afford intermediate a4 (700 mg) and intermediate a5 (400 mg), total yield: 57%, LC-MS: $[M+H]^+$: 484.

| The Intermediate's structure | Altered material's structure | LC-MS/$[M + H]^+$ |
| --- | --- | --- |
| 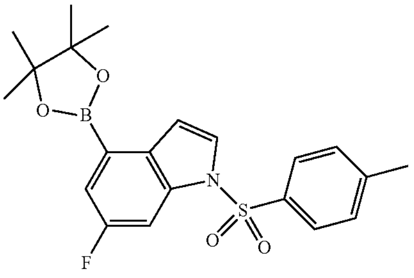 a13 | 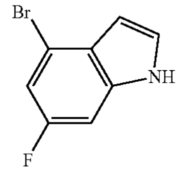 | 416 |

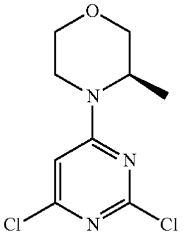

a1

+

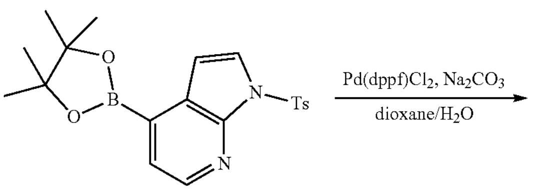

a3

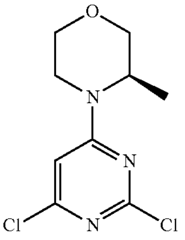

a1

+

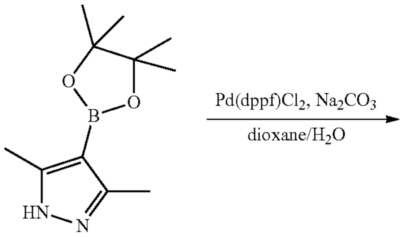

a6

-continued

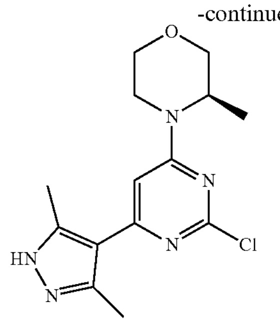

a7

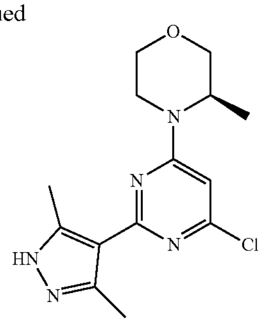

a8

Under nitrogen protection, intermediate a1 (2.0 mmol, 500 mg) and (3,5-dimethyl-1H-pyrazol-4-yl)boronic acid, pinacol cyclic ester a6 (2.0 mmol, 440 mg) were dissolved in 15 mL mixture of 1,4-dioxane and water (v/v: 9/1), potassium carbonate (6.1 mmol, 830 mg) and Pd(dppf)$Cl_2$ (0.4 mmol, 293 mg) were added, and the mixture was heated to reflux and reacted for 12 hours. The reaction was stopped, filtered, the organic solvent was dried by rotary evaporation, water was added, extracted with ethyl acetate, and separated by column chromatography to afford intermediate a7 (200 mg, yield: 33%) and intermediate a8 (60 mg, yield: 10%), LC-MS: $[M+H]^+$: 308.

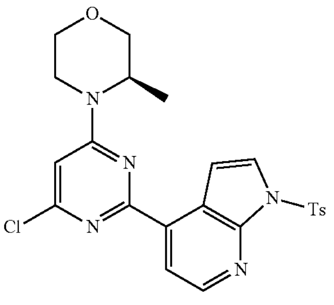

a4

+

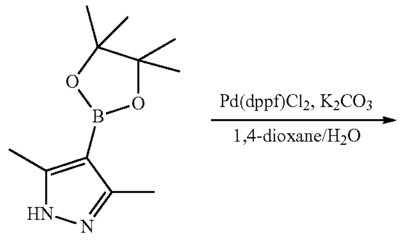

a6

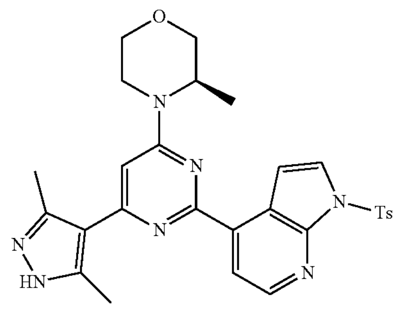

a9

Under nitrogen protection, intermediate a4 (1.04 mmol, 500 trig) and intermediate a6 (1.1 mmol, 253 mg) were dissolved in 10 mL mixture of 1,4-dioxane and water (v/v: 9/1), potassium carbonate (3.2 mmol, 430 mg) and Pd(dppf)$Cl_2$ (0.2 mmol, 151 mg) were added, and the mixture was heated to reflux and reacted for 12 hours. The reaction was stopped, filtered, the organic solvent was dried by rotary evaporation, water was added, extracted with ethyl acetate, and separated by column chromatography to afford intermediate a9 (320 mg, yield: 57%), LC-MS: $[M+H]^+$: 544.

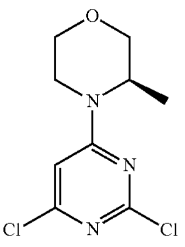

a1

+

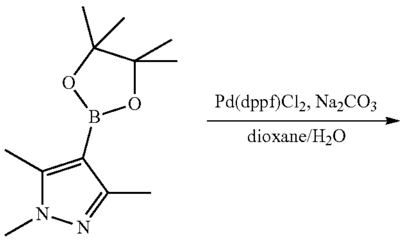

a10

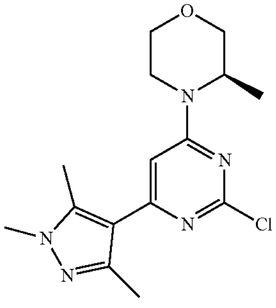

a11

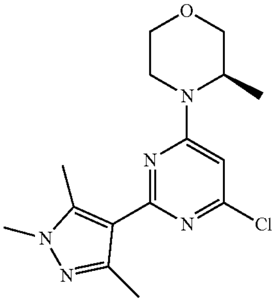

a12

Under nitrogen protection, intermediate a1 (2.0 mmol, 500 mg) and (1,3,5-trimethyl-1H-pyrazol-4-yl) boronic acid, pinacol cyclic ester a10 (2.0 mmol, 472 mg) were dissolved in 10 mL mixture of 1,4-dioxane and water (v/v: 9/1), sodium carbonate (6.0 mmol, 636 mg) and Pd(dppf)$Cl_2$ (0.2 mmol, 151 mg) were added, then the mixture was heated to reflux and reacted for 16 hours. The reaction was stopped, filtered, the organic solvent was dried by rotary evaporation, water was added, extracted with ethyl acetate, and separated by column chromatography to afford intermediate a11 (280 mg, yield: 43%) and intermediate a12 (110 mg, yield: 17%), LC-MS: $[M+H]^+$: 322.

Preparation of Key Intermediates b1-b18:

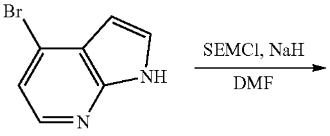

-continued

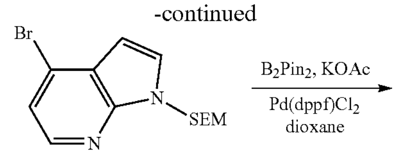

b1

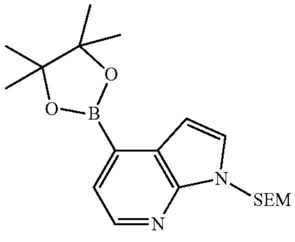

b2

In an ice bath 4-bromo-7-azaindole (10.2 mmol, 2 g) was added to a reaction flask, dissolved in 50 mL of DMF, and 60% NaH (15.2 mmol, 610 mg) was slowly added. Half an hour later, SEMCl (15.2 mmol, 2.5 g) was added, and the reaction was continued at room temperature for 1 hour. The reaction was stopped, 100 mL of water was slowly added, extracted with ethyl acetate, and dried over anhydrous $Na_2SG$; to afford intermediate b1 (quantitative yield), LC-MS: $[M+H]^+$: 327.

Under nitrogen protection, intermediate b1 (10.2 mmol, 3.3 g) and bis(pinacolato)diboron (20.3 mmol, 5.2 g) were dissolved in 1,4-dioxane, potassium acetate (20.3 mmol, 2.0 g) and $Pd(dppf)Cl_2$ (1.1 mmol, 742 mg) were added, and the mixture was reacted at 90° C. for 3 hours. The reaction was stopped, filtered, the organic solvent was dried by rotary evaporation, and separated by column chromatography to afford intermediate b2 (5.8 g. yield: 70%), LC-MS: $[M+H]^+$: 375.

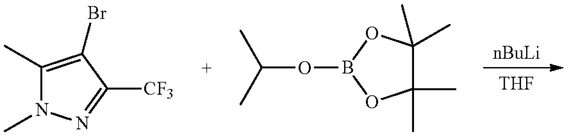

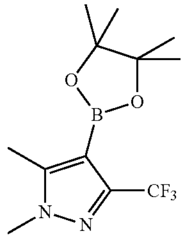

b3

At −78° C., 1,5-dimethyl-4-bromo-3-trifluoromethyl-114-pyrazole (0.41 mmol, 100 mg) was dissolved in 10 mL of anhydrous THF, butyl lithium (0.18 mL, 2.5M) was added dropwise, 30 minutes later, isopropoxyboronic acid, pinacol cyclic ester (0.49 mmol, 91 mg) was added, and the reaction was continued at −78° C. for 3 hours. 20 mL of saturated aqueous ammonium chloride was added to quench the reaction, which was extracted with dichloromethane, the organic phase was dried over anhydrous sodium sulfate, and directly used in the next step. LC-MS: $[M+H]^+$: 291.

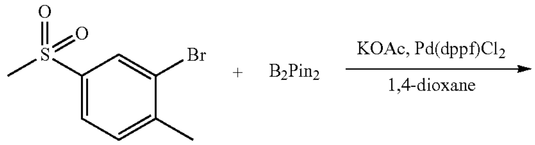

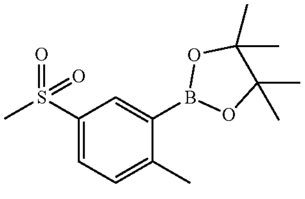

b4

Under nitrogen protection, compound 3-bromo-4-methylphenyl methyl sulfone (2.0 mmol, 500 mg) and bis(pinacolato)diboron (4.0 mmol, 1.0 g) were dissolved in 10 mL of 1,4-dioxane, potassium acetate (6.0 mmol, 590 mg) and $Pd(dppf)Cl_2$ (0.2 mmol, 150 mg) were added, and the mixture was reacted at 90° C. for 2 hours. The reaction was stopped, filtered, the organic solvent was removed under reduced pressure to afford intermediate b4 (quantitative yield), LC-MS: $[M+H]^+$: 297.

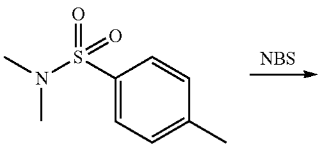

b5-2

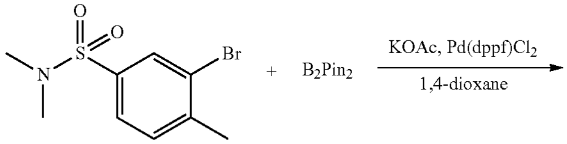

b5-1

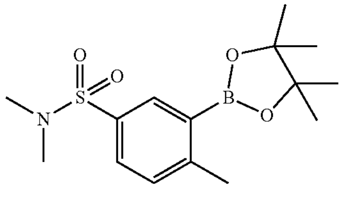

b5

In an ice bath, compound N,N-dimethyl p-toluenesulfonamide b5-2 (5 mmol, 1 g) was dissolved in 12 mL of concentrated sulfuric acid, NBS (5.5 mmol, 983 mg) was added, the temperature was slowly raised to room temperature, and stirred for 3 hours. The mixture was slowly poured into ice water to quench the reaction, suction filtered, and dried to afford the compound b5-1 (1.3 g, yield: 93%). LC-MS: $[M+H]^+$: 278.

Under nitrogen protection, compound b5-1 (2.2 mmol, 600 mg) and bis(pinacolato)diboron (4.3 mmol, 1.1 g) were dissolved in 15 mL of 1,4-dioxane, potassium acetate (6.5 mmol, 635 mg) and $Pd(dppf)Cl_2$ (0.22 mmol, 158 mg) were added, and the mixture was reacted at 100° C. for 2 hours. The reaction was stopped, filtered, the organic solvent was removed under reduced pressure, and separated by column chromatography to afford intermediate b5 (quantitative yield), LC-MS: $[M+H]^+$: 326,

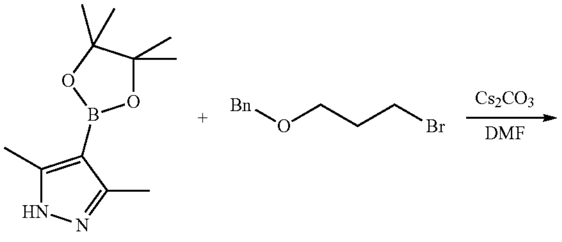

a6

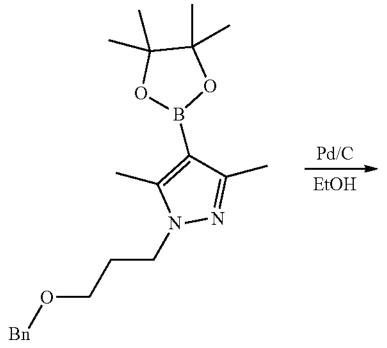

b6-1

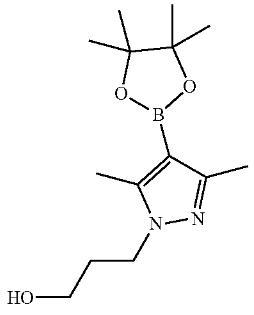

b6

Intermediate a6 (1.0 mmol, 222 tug) was dissolved in 10 mL of DMF, cesium carbonate (1.0 mmol, 326 mg) and 3-bromopropyl benzyl ether (1.2 mmol, 275 mg) were added, and the mixture was reacted at 70° C. for 12 hours. The reaction was stopped, water was added, extracted with ethyl acetate, washed with brine, dried over anhydrous sodium sulfate, filtered, and separated by column chromatography to afford oily intermediate b6-1 (260 rug, yield: 70%), LC-MS: $[M+H]^+$: 371.

20 mg Palladium on Carbon was added to a solution of Intermediate b6-1 (0.27 mmol, 100 mg) in 5 mL of ethanol and reacted overnight under catalytic hydrogenation (4 atm). After suction filtering, white solid b6 (88 mg, quantitative yield) was afforded, LC-MS: $[M+H]^+$: 281.

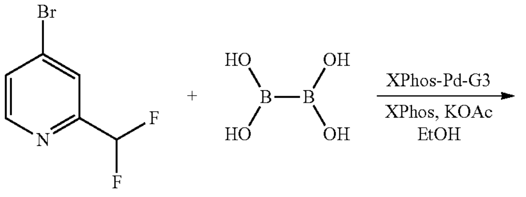

-continued

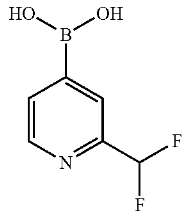

b7

Under nitrogen protection, compound 4-bromo-2-difluoromethylpyridine (1.7 mmol, 350 mg) and tetrahydroxydiboron (3.2 mmol, 288 mg) were dissolved in 10 mL of ethanol, potassium acetate (6.4 mmol, 630 mg), X-Phos (0.21 mmol, 102 mg) and X-Phos-Pd-G3 (0.11 mmol, 90 mg) were added, and the mixture was reacted at 80° C. for 3 hours. The reaction was stopped, filtered, the organic solvent was removed under reduced pressure to afford intermediate b7, LC-MS: $[M+H]^+$: 174.

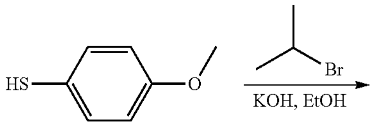

1

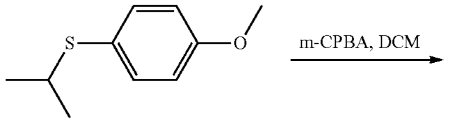

b8-2

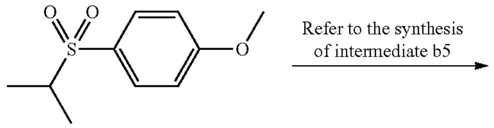

b8-1

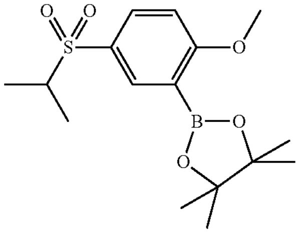

b8

P-methoxybenzenethiol (7.2 mmol, 1.0 g), potassium hydroxide (10.8 mmol, 604 mg) were added to a reaction flask, dissolved in 20 mL of ethanol, bromoisopropane (7.2 mmol, 878 mg) was added dropwise, and the mixture was reacted at 50° C. After TLC monitored that the reaction was complete, the mixture was filtered, the solvent was removed under reduced pressure, and separated by column chromatography to afford intermediate b8-2, quantitative yield.

In an ice bath, intermediate b8-2 (8.24 mmol 1.5 g) was dissolved in 30 mL of dichloromethane, m-CPBA (20 mmol, 3.4 g) was slowly added, and the mixture was reacted at room temperature overnight. 50 mL of water was added, and extracted with dichloromethane to afford intermediate b8-1, quantitative yield.

Intermediate b8 was afforded by using intermediate b8-1 as raw material and referring to the synthesis of intermediate b5, yield: 42%.

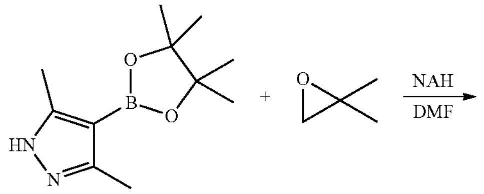

a6

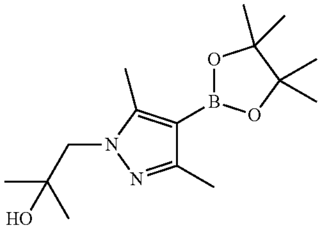

b9

Intermediate a6 (0.23 mmol, 50 mg), NaH (0.25 mmol, 9 ng) were added to a reaction flask, dissolved in 8 mL of DMF, 1,2-epoxy-2-methylpropane (0.25 mmol, 18 mg) was added dropwise, and the mixture was reacted at 80° C. overnight. 15 mL of water was added, extracted with 10 mL of ethyl acetate, the solvent was removed under reduced pressure, and separated by column chromatography to afford intermediate b9, yield: 44%, LC-MS: $[M+H]^+$: 295.

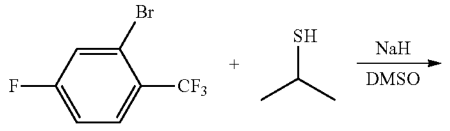

b10-1

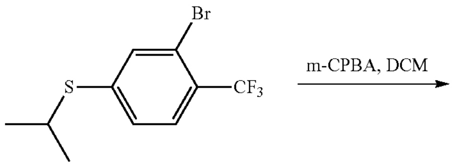

b10-2

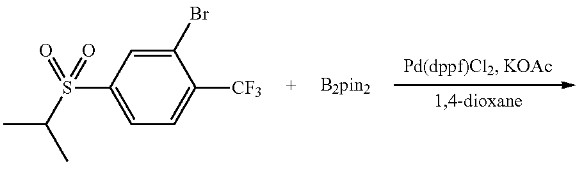

b10-3

-continued

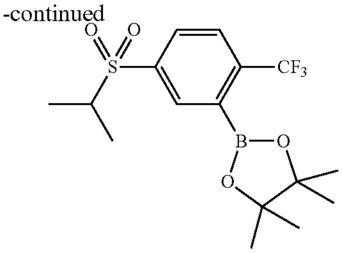

b10

In an ice bath, intermediate b10-1 (2.06 mmol, 500 mg) was dissolved in 10 mL of DMSO, isopropyl mercaptan (2.47 mmol, 188 mg) was slowly added, and the mixture was reacted at room temperature for 2 hours. 50 mL of water was added, extracted with ethyl acetate to afford crude intermediate b10-2, which was directly proceeded in the next step.

In an ice hath, the crude b10-2 from the previous step was dissolved in 30 mL of dichloromethane, m-CPBA (12.5 mmol, 2.1 g) was slowly added, and the mixture was reacted at room temperature for 10 hours. The reaction was stopped, 50 mL of water was added, extracted with dichloromethane, and separated by flash column chromatography to afford 690 mg intermediate b10-3, two-step total yield: 99%.

Under nitrogen protection, intermediate b10-3 (0.91 mmol, 300 mg) and bis(pinacolato)diboron (1.09 mmol, 276 mg) were dissolved in 12 mL of 1,4-dioxane, potassium acetate (2.7 mmol, 266 mg) and $Pd(dppf)Cl_2$ (0.18 mmol, 132 mg) were added, and the mixture was reacted at 100° C. for 2 hours. The reaction was stopped, filtered, the organic solvent was removed under reduced pressure, and separated by column chromatography to afford intermediate b10 (240 mg, yield: 70%).

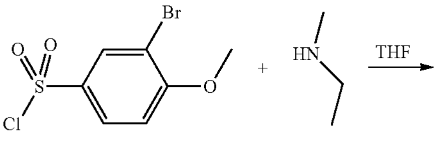

b11-1

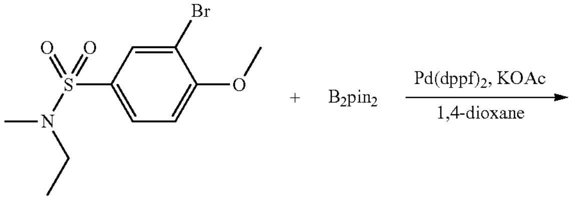

b11-2

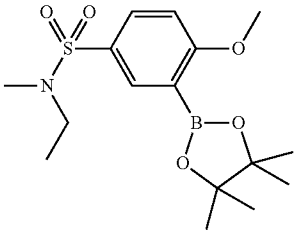

b11

In an ice bath, the raw material methyl ethyl amine (3.57 mmol, 211 mg) was dissolved in 8 mL of b11-1 (2.38 mmol, 680 mg) was slowly added dropwise, and after the mixture was reacted at room temperature for 2 hours, the reaction was stopped. 30 mL of water was added, extracted with ethyl acetate, and separated by flash column chromatography to afford intermediate b11-2 (450 mg, yield: 62%). LC-MS: $[M+H]^+$: 309.

Under nitrogen protection, intermediate b11-2 (1.46 mmol, 450 mg) and his(pinacolato)diboron (1.75 mmol, 445 mg) were dissolved in 12 mL of 1,4-dioxane, potassium acetate (2.92 mmol, 291 mg) and $Pd(dppf)Cl_2$ (0.10 mmol, 107 mg) were added; and the mixture was reacted at 100° C. for 2 hours. The reaction was stopped, filtered, the solvent was removed under reduced pressure, and separated by flash column chromatography to afford intermediate b11 (480 mg, yield: 93%). LC-MS: $[M+H]^+$: 356.

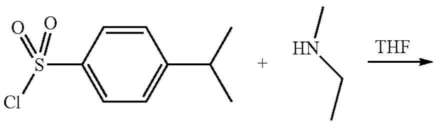

b12-1

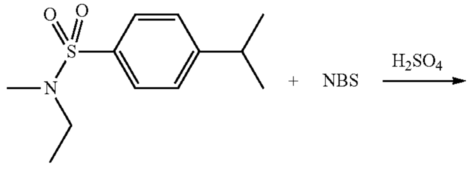

b12-2

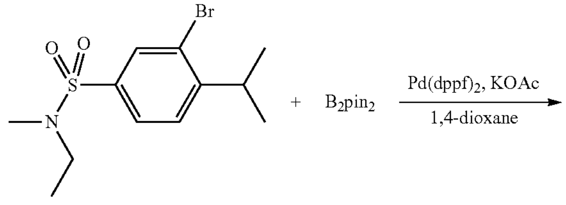

b12-3

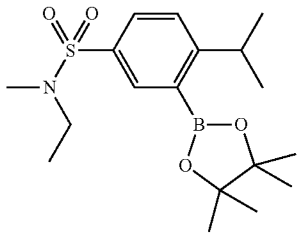

b12

In an ice bath, the raw material methyl ethyl aide (20.3 mmol, 1.2 g) was dissolved in 15 mL of THF, b12-1 (6.8 mmol, 1.5 g) was slowly added dropwise, and after the mixture was reacted at room temperature for 2 hours, the reaction was stopped. 40 mL of water was added, extracted with ethyl acetate, and separated by flash column chromatography to afford intermediate b12-2 (1.6 g, yield: 97%).

In an ice bath, intermediate b12-2 (2.07 mmol, 500 mg) was slowly dissolved in 3 mL of concentrated sulfuric acid, N-bromosuccinimide (2.18 mmol, 388 mg) was added in batches, and after the mixture was reacted at room temperature for 2 hours, the reaction was stopped. The mixture was slowly poured into 30 mL of ice-water mixture, saturated sodium bicarbonate aqueous solution was added to adjust the pH to about 10, and extracted with ethyl acetate to afford crude intermediate b12-3.

Under nitrogen protection crude b12-3 (550 mg) and bis(pinacolato)diboron (2.6 mmol, 65:5 mg) were dissolved in 10 mL of 1,4-dioxane, potassium acetate (5.1 mmol, 505 mg) and $Pd(dppf)Cl_2$ (0.17 mmol, 126 mg) were added, and the mixture was reacted at 100° C. for 2 hours. The reaction was stopped, filtered, the solvent was removed under reduced pressure to afford intermediate b12, which was directly used in the next step. LC-MS: $[M+H]^+$: 368.

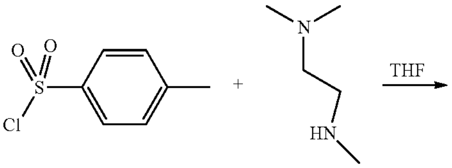

b13-1

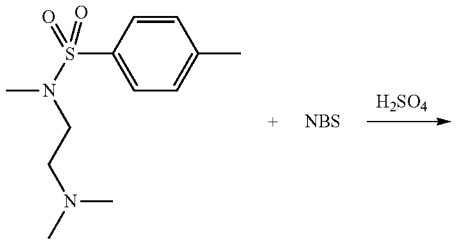

b13-2

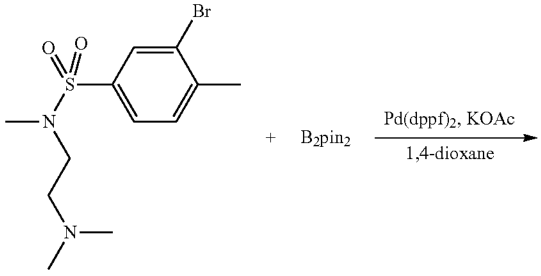

b13-3

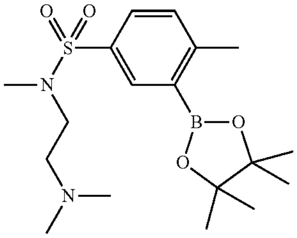

b13

In an ice bath, the raw material b13-1 (23.5 mmol, 2.4 g) was dissolved in 15 mL of THF, p-toluenesulfonyl chloride (7.85 mmol, 1.5 g) was slowly added dropwise, and after the mixture was reacted at room temperature for 2 hours, the reaction was stopped. 40 mL of water was added, extracted with ethyl acetate, and separated by flash column chromatography to afford intermediate b13-2 (2.0 g, yield: 99%).

In an ice bath, intermediate b13-2 (1.95 mmol, 500 mg) was slowly dissolved in 3 mL of concentrated sulfuric acid, after N-bromosuccinimide (2.05 mmol, 365 mg) was added in batches, flee mixture was reacted at room temperature for 2 hours. The mixture was slowly poured into 30 mL of ice-water mixture, saturated sodium bicarbonate aqueous solution was added to adjust the pH to about 10, and extracted with ethyl acetate to afford 900 mg oily crude intermediate b13-3.

Under nitrogen protection, intermediate b13-3 (550 mg, crude) and bis(pinacolato)diboron (2.5 mmol, 626 mg) were dissolved in 10 mL of 1,4-dioxane, potassium acetate (4.9 mmol, 483 mg) and Pd(dppf)$Cl_2$ (0.16 mmol, 120 mg) were added, and the mixture was reacted at 10011 for 2 hours. The reaction was stopped, filtered, the solvent was removed under reduced pressure to afford intermediate b13, which was directly used in the next step. LC-MS: $[M+H]^+$: 383.

The following intermediates were synthesized with reference to compound b13:

| Structure | The structure of raw material replacing b13-1 | LC-MS/ $[M + H]^+$ |
|---|---|---|
| 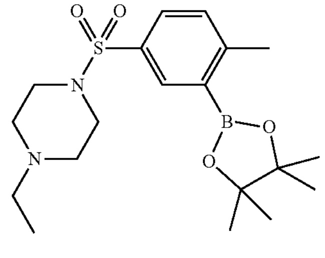 b14 | 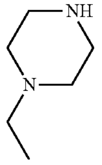 b14-1 | 395 |

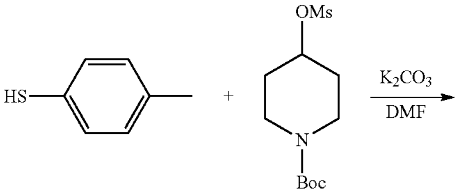

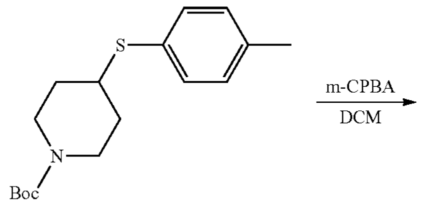

b15-1

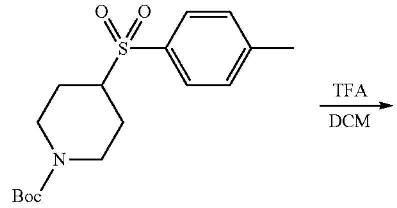

b15-2

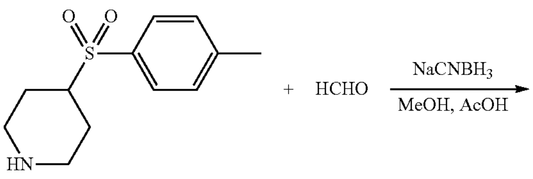

b15-3

-continued

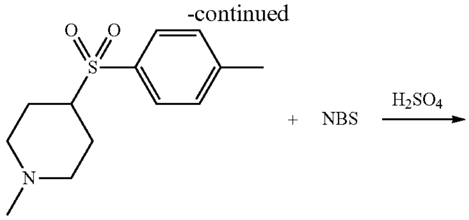

b15-4

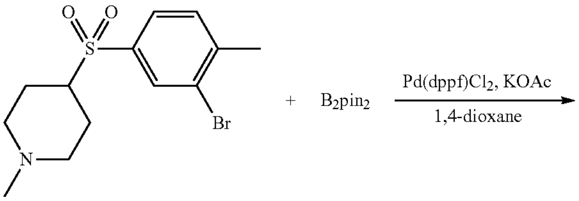

b15-5

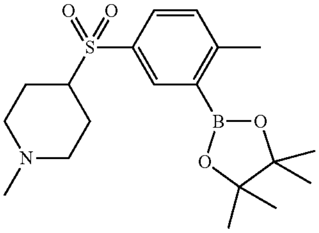

b15

P-toluenethiol (0.81 mmol, 100 mg), potassium carbonate (2.41 mmol, 333 mg) and tert-butyl 4-((methylsulfonyl)oxy) piperidine-1-carboxylate (0.97 mmol, 270 mg) were dissolved in 8 mL of DMF, and the reaction was heated to 70° C. and reacted for 2 hours. The reaction was stopped, 30 mL of water was added, extracted with ethyl acetate, and concentrated to afford 230 mg crude intermediate b15-1.

In an ice bath, intermediate b15-1 (3.09 mmol, 1.0 g) was dissolved in 50 mL of dichloromethane, m-chloroperoxybenzoic acid (15.4 mmol, 2.66 g) was slowly added, and the mixture was reacted at room temperature for 4 hours. 50 mL of ice water was added to the mixture, extracted with ethyl acetate, and separated by flash column chromatography to afford intermediate b15-2 (600 mg, yield: 58%). LC-MS: $[M+H]^+$: 340.

Intermediate b15-2 (1.77 mmol, 600 mg) was dissolved in 6 mL of dichloromethane, 2 mL of trifluoroacetic acid was slowly added, and the mixture was reacted at room temperature for 1 hour. The reaction was stopped, the solvent was removed under reduced pressure. 20 mL of saturated sodium bicarbonate aqueous solution was added to the mixture, and extracted with dichloromethane to afford intermediate b15-3. LC-MS: $[M+H]^+$: 240.

Intermediate b15-3 (1.77 mmol, 423 mg) was dissolved in 5 mL of methanol, 2 mL of 40% formaldehyde aqueous solution and 4 drops of acetic acid were added. After stirring for 10 minutes, $NaCNBH_3$ (8.8 mmol, 555 mg) was added, and the mixture was reacted at room temperature for 3 hours. The reaction was stopped, and the solvent was removed under reduced pressure. 30 mL of saturated sodium bicarbonate aqueous solution was added to the mixture, extracted with dichloromethane, and separated by Clash column chromatography to afford intermediate b15-4 (yield: 89%), LC-MS: $[M+H]^+$: 254.

In an ice bath, intermediate b15-4 (1.58 mmol, 400 mg) was slowly dissolved in 3 mL of concentrated sulfuric acid, N-bromosuccinimide (1.74 mmol, 307 mg) was added in batches, and the reaction was continued at room temperature for 3 hours. The mixture was slowly poured into 30 mL of ice-water mixture, and the pH of the system was adjusted to about 8 with 1N NaOH solution, extracted with dichloromethane, dried over anhydrous sodium sulfate, and separated by flash column chromatography to afford intermediate b15-5 (300 mg, yield: 58%). LC-MS: $[M+H]^+$: 333.

Under nitrogen protection, intermediate b15-5 (0.57 mmol, 190 mg) and bis(pinacolato)diboron (0.68 mmol, 174 mg) were dissolved in 5 mL of 1,4-dioxane, potassium acetate (1.72 mmol, 168 mg) and $Pd(dppf)Cl_2$ (0.11 mmol, 84 mg) were added, and the mixture was reacted at 100° C. for 2 hours. The reaction was stopped, filtered, the solvent was removed under reduced pressure to afford intermediate b15, which was directly used in the next step. LC-MS: $[M+H]^+$: 380.

In an ice bath, intermediate b16-2 (1.76 mmol, 350 mg) was slowly dissolved in 3 mL of concentrated sulfuric acid, N-bromosuccinimide, (1.33 mmol, 235 mg) was added in batches, and reacted at room temperature for 3 hours. The mixture was slowly poured into 30 mL of ice-water mixture, and the pH of the system was adjusted to about 8 with 1N NaOH solution, extracted with dichloromethane, dried over anhydrous sodium sulfate, and separated by flash column chromatography to afford intermediate b16-3 (350 mg, yield: 95%).

Under nitrogen protection, intermediate b16-3 (0.9 mmol, 250 mg) and bis(pinacolato)diboron (1.08 mmol, 276 mg) were dissolved in 8 mL of 1,4-dioxane, potassium acetate (1.8 mmol, 176 mg) and $Pd(dppf)Cl_2$ (0.09 mmol, 66 mg) were added, and the mixture was reacted at 100° C. for 2 hours. The reaction was stopped, filtered, the solvent was removed under reduced pressure to afford intermediate b16, which was directly used in the next step.

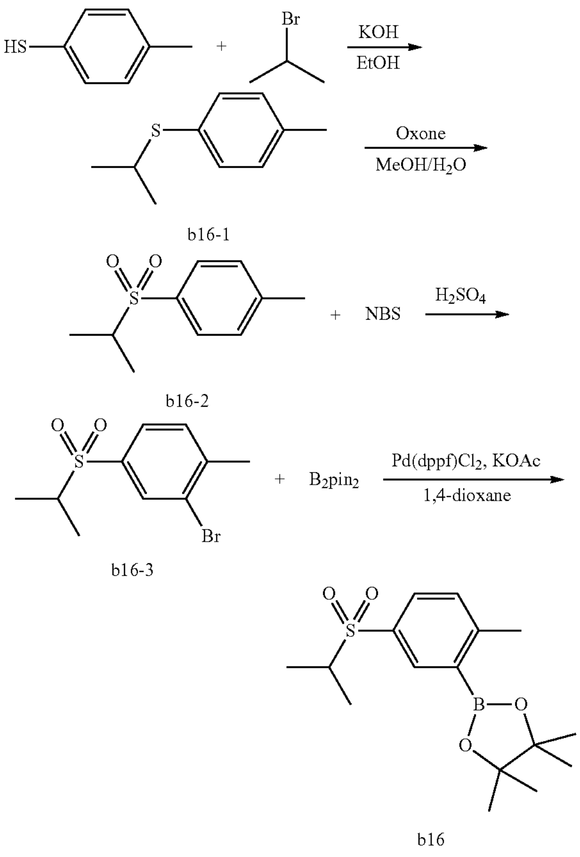

b16-1 b16-2 b16-3 b16

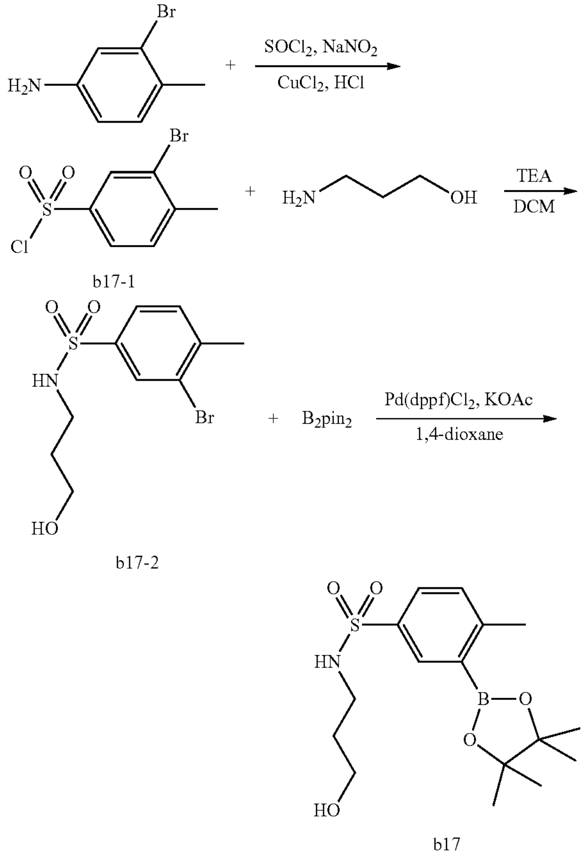

b17-1 b17-2 b17

P-toluenethiol (4.01 mmol, 500 mg), potassium hydroxide (10.05 mmol, 553 mg) and 2-bromopropane (6.04 mmol, 737 mg) were dissolved in 12 mL of ethanol, the reaction was heated to 50° C. and reacted for 8 hours. The reaction was stopped, 30 mL of water was added, and extracted with dichloromethane to afford crude intermediate b16-1.

In an ice bath, intermediate b16-1 (1.81 mmol, 300 no was dissolved in mixture of 10 mL methanol and 2 mL water, potassium monopersulfate (Oxone, 4.5 mmol, 278 mg) was slowly added, and the mixture was reacted at room temperature for 4 hours. 30 mL of water was added to the mixture, extracted with ethyl acetate, and separated by flash column chromatography to afford intermediate b16-2 (350 mg, yield: 99%).

At −10° C., 3-bromo-4-methyl-aniline (5.37 mmol, 1.0 g) and $CuCl_2$ (0.54 mmol, 60 mg) were dissolved in 20 mL of concentrated hydrochloric acid, 2 mL aqueous solution of sodium nitrite (5.9 mmol, 410 mg) was slowly added and stirred for 30 minutes. Thionyl chloride (24 mmol, 189 g) was slowly dissolved in 10 mL of water and the solution was slowly added dropwise to the reaction, and continued to stir at −10° C. for 1 hour. The temperature of the reaction was warmed to room temperature, after reacting for 2 hours, the reaction was stopped. 40 mL of ice water was added to the mixture, extracted with dichloromethane, and dried over anhydrous sodium sulfate to afford intermediate b17-1 (250 mg, yield: 17%).

In an ice bath, 4-hydroxybutylamine (11.13 mmol, 84 mg) and triethylamine (1.85 mmol, 188 mg) were dissolved in 10 mL of dichloromethane, intermediate b17-1 (0.93 mmol, 250 mg) was slowly added, and after the mixture was reacted at room temperature for 6 hours, the reaction was stopped. 30 mL of water was added, extracted with dichloromethane, dried over anhydrous sodium sulfate, and separated by flash column chromatography to afford intermediate b17-2 (150 mg, yield: 53%). LC-MS: 309.

Under nitrogen protection, intermediate b17-2 (0.49 mmol, 150 mg) and bis(pinacolato)diboron (0.58 mmol, 150 mg) were dissolved in 8 mL of 1,4-dioxane, potassium acetate (1.46 mmol, 160 mg) and Pd(dppf)$Cl_2$ (0.097 mmol, 70 mg) were added, and the mixture was reacted at 100° C. for 2 hours. The reaction was stopped, filtered, the solvent was removed under reduced pressure to afford intermediate b17, which was directly used in the next step. LC-MS: $[M+H]^+$: 356.

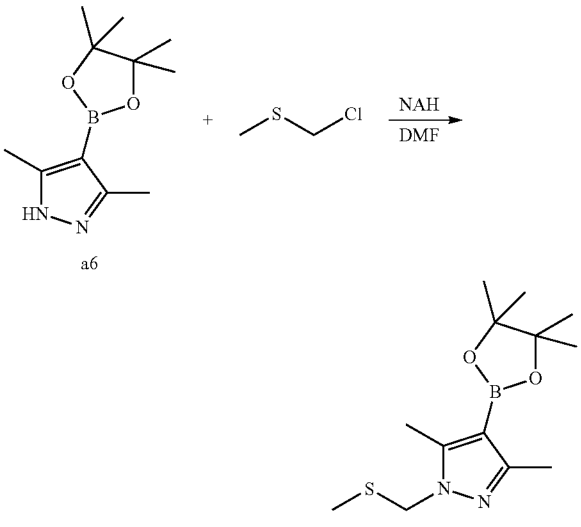

a6 b18

In an ice bath, the raw material a6 (0.45 mmol, 100 mg) was dissolved in 8 mL of DMF, NaH (0.54 mmol, 22 mg) was slowly added. After stirring for 30 minutes, (chloromethyl)(methyl)sulfane (0.54 mmol, 52 mg) was added dropwise, the reaction was heated to 60° C. and reacted for 10 hours, and the reaction was stopped. 30 mL of water was slowly added to the reaction, extracted with ethyl acetate, dried over anhydrous sodium sulfate, and separated by flash column chromatography to afford intermediate b18 (60 mg, yield: 47%). LC-MS: $[M+H]^+$: 283.

Preparation of Key Intermediates c1-c15:

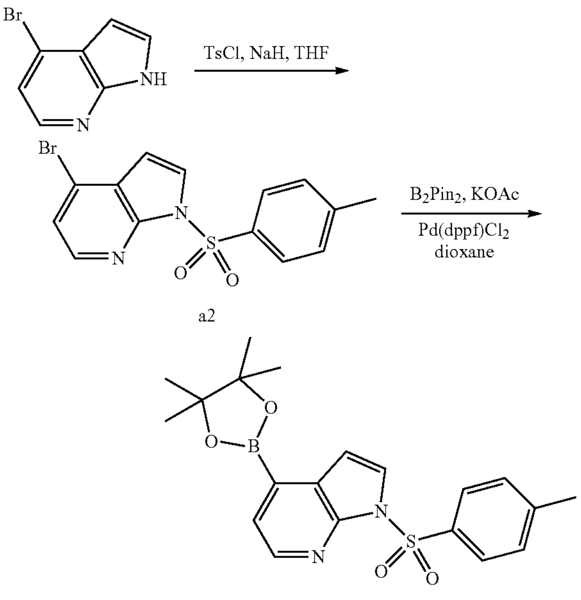

a2 a3

The operation steps were the same as above.

The following compounds were synthesized with reference to intermediate a3:

| Structure | Altered material's structure | LC-MS/$[M + H]^+$ |
|---|---|---|
| 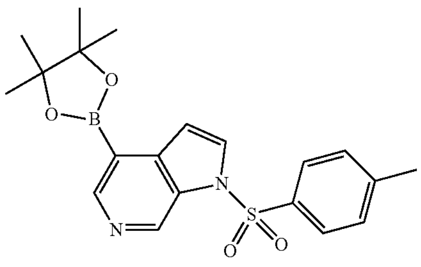 c-1 | 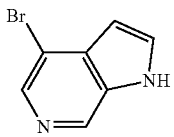 c1-1 | 399 |

-continued

| Structure | Altered material's structure | LC-MS/[M + H]+ |
|---|---|---|
| 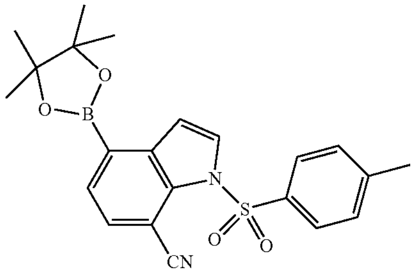 c2 | 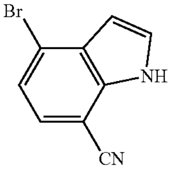 c2-1 | 423 |

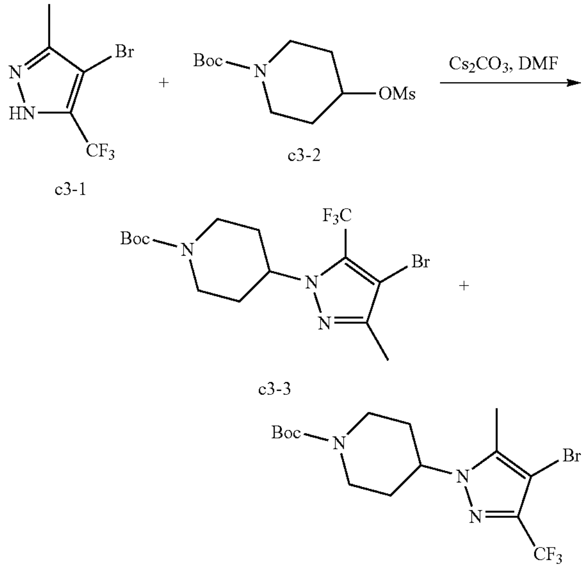

c3-1 c3-2 c3-3 c4-1

The raw material c3-1 (36.7 mmol, 7 g) and cesium carbonate (92.1 mmol, 30.03 g) was added to a reaction flask, dissolved in 100 mL of DMF, and the raw material c3-2 (36.8 mmol, 8.43 g) was slowly added. After the reaction was heated to 80° C. and reacted for 4 hours, the reaction was stopped, 300 mL of water was slowly added, extracted with ethyl acetate, dried over anhydrous $Na_2SO_4$, and separated by flash column chromatography to afford intermediate c3-3 (3.4 g, yield: 23%) and intermediate c4-1 (7.0 g, yield: 47%), LC-MS: $[M+H]^+$: 412.

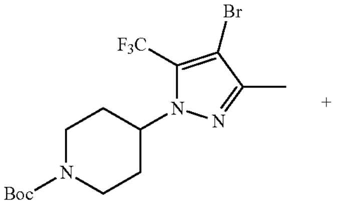

c3-3

-continued

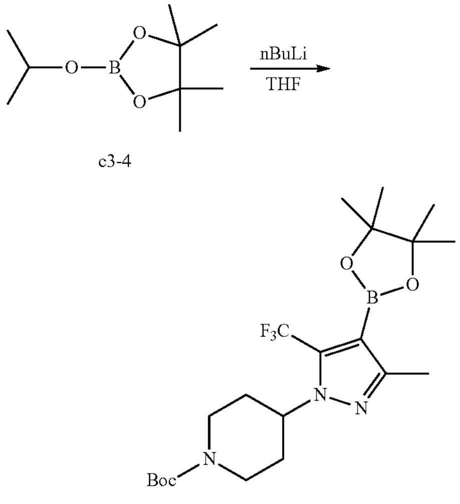

c3-4 c3

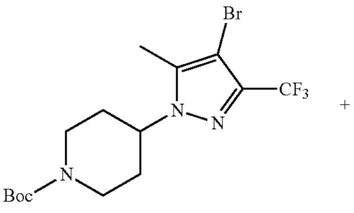

c4-1

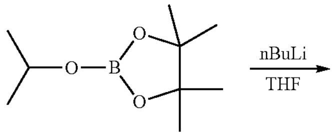

c3-4

-continued

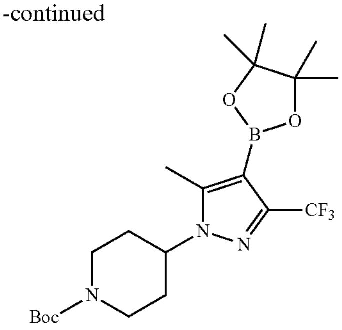

c4

At −78° C., intermediate c3-3 (6.3 mmol, 2.6 g) was dissolved in 60 mL of anhydrous THF, butyl lithium (3.0 mL, 2.5M) was added dropwise, 30 minutes later, isopropoxyboronic acid, pinacol cyclic ester c3-4 (9.5 mmol, 1.88 mL) was added, after the reaction was continued at −78° C. for 3 hours, 150 mL of saturated ammonium chloride aqueous solution was added to quench the reaction, and extracted with dichloromethane. The organic phase was dried over anhydrous sodium sulfate to afford crude intermediate c3. LC-MS: $[M+H]^+$: 460.

Crude intermediate c4 was afforded by using intermediate c4-1 as raw material and referring to the synthesis of intermediate c3. LC-MS: $[M+H]^+$: 460.

The following compounds were synthesized with reference to intermediate c3:

| Structure | The structure of raw material replacing c3-2 | LC-MS/$[M + H]^+$ |
|---|---|---|
| 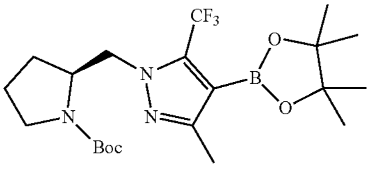 c12 | 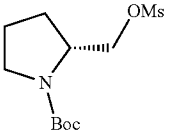 c12-1 | 460 |
| 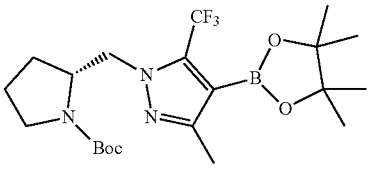 c13 | 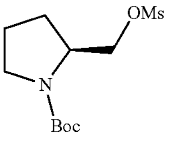 c13-1 | 460 |

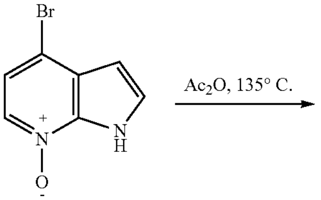

c5-1

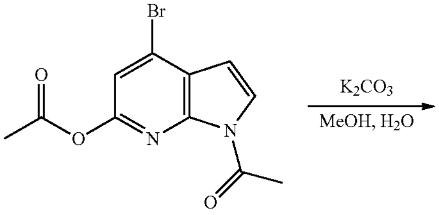

c5-2

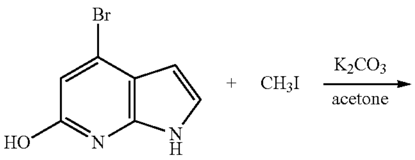

c5-3

-continued

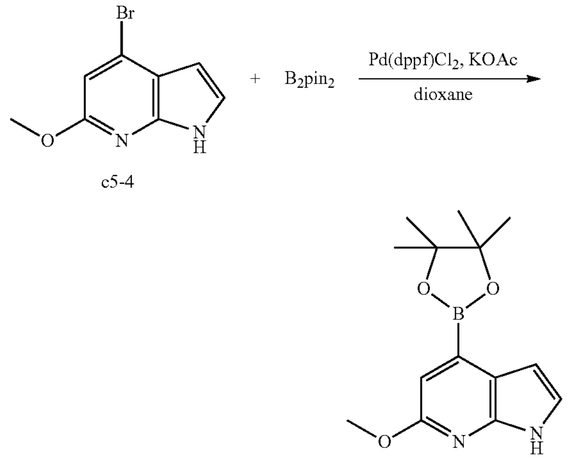

c5-4 c5

4-Bromo-7-azaindole 7-oxide c5-1 (4.7 mmol, 1 g) was dissolved in 15 mL of acetic anhydride in a reaction flask, the solution was reacted at 135° C. for 8 hours. After the reaction was cooled to room temperature, 50 mL of water was added, extracted with dichloromethane, dried over anhydrous sodium sulfate, and separated by column chromatography to afford intermediate c5-2 (13 g. yield: 93%). LC-MMS: $[M+H]^+$: 297.

Intermediate c5-2 (4.36 mmol, 1.3 g), potassium carbonate (17.5 mmol, 2.4 g) were dissolved in 20 mL of methanol, 5 mL of water was added, after the mixture was reacted at mom temperature for 12 hours, filtered, the solvent was removed under reduced pressure, and separated by column chromatography to afford intermediate c5-3 (235 mg, yield: 25%). LC-MS: $[M+H]^+$: 213.

Intermediate c5-3 (0.236 mmol, 50 mg), potassium carbonate (1.118 mmol, 162 mg) were added to a reaction flask, and dissolved in 5 mL of acetone. Methyl iodide (0.236 mmol, 14 µL) was slowly added dropwise, and the mixture was reacted at 50° C. overnight. The reaction was stopped, filtered, the solvent was removed under reduced pressure, and separated by column chromatography to afford intermediate c5-4 (16 mg, yield: 30%), LC-MS: $[M+H]^+$: 227.

Under nitrogen protection, intermediate c5-4 (0.11 mmol, 25 mg) and bis(pinacolato)diboron (0.13 mmol, 33 mg) were dissolved in 4 mL of 1,4-dioxane, potassium acetate (0.33 mmol, 32 mg) and $Pd(dppf)Cl_2$ (0.011 mmol, 9 mg) were added, then the mixture was heated to reflux and reacted for 3 hours. The reaction was stopped, filtered, the solvent was removed under reduced pressure to afford intermediate crude c5. LC-MS: $[M+H]^+$: 276.

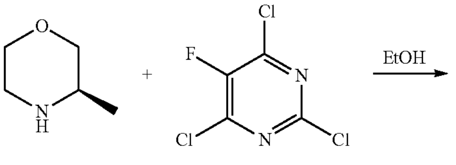

c6-1

-continued

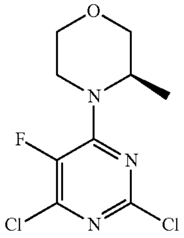

c6

At −20° C., the raw material c6-1 (1.0 mmol, 200 mg) was added to a reaction flask, dissolved in 12 mL of ethanol. A solution of (R)-2-methylmorpholine (1.1 mmol, 111 mg) in 2 mL ethanol was added dropwise, and the mixture was reacted at room temperature for 12 hours. The reaction was stopped, the solvent was evaporated under reduced pressure, and separated by column chromatography to afford intermediate c6 (127 mg, yield: 48%), LC-MS: $[M+H]^+$: 266.

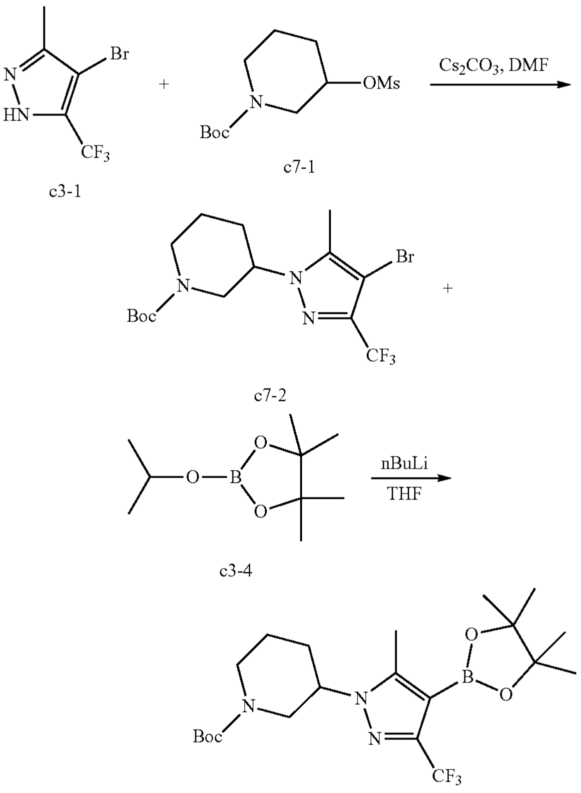

c3-1 c7-1 c7-2 c3-4 c7

The raw material c3-1 (2.19 mmol, 500 mg) and the raw material c7-1 (2.63 mmol, 731 mg) were added to a reaction flask, and dissolved in 10 mL of DMF. After cesium carbonate (6.57 mmol, 2.14 g) was added, the mixture was reacted at 80° C. for 5 hours. The reaction was stopped, filtered, the solvent was evaporated under reduced pressure, and separated by flash column chromatography to afford intermediate c7-2 (240 mg, yield: 27%), LC-MS: $[M+H-tBu]^+$: 356.

At −78° C., intermediate c7-2 (0.6 mmol, 247 mg) was dissolved in 6 ml of anhydrous THF, butyl lithium (0.29 mL, 2.5M) was added dropwise, and 30 minutes later, isopropoxyboronic acid, pinacol cyclic ester c3-4 (0.78 mmol, 155 μL) was added. After the reaction was continued at −78° C. for 3 hours, 100 mL of saturated ammonium chloride aqueous solution was added to quench the reaction, and extracted with dichloromethane. The organic phase was dried over anhydrous sodium sulfate to afford elude intermediate c7 (240 mg, yield: 88%) LC-MS: $[M+H]^+$: 460.

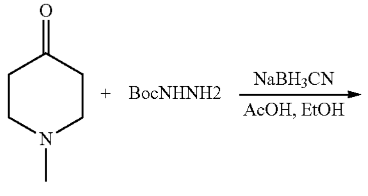

c8-1

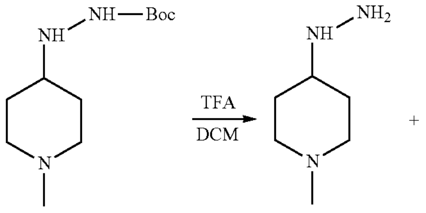

c8-2 c8-3

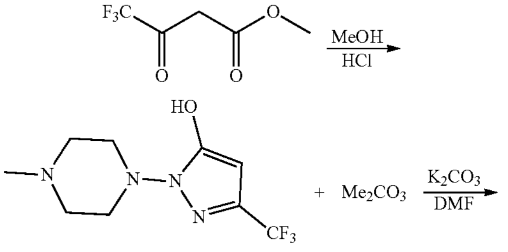

c8-4

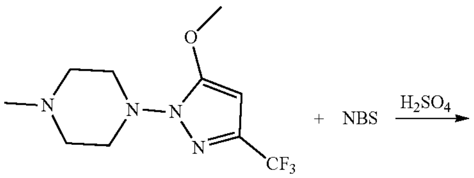

c8-5

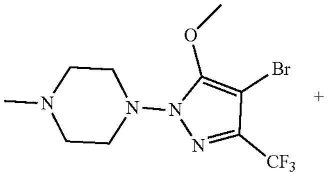

c8-6

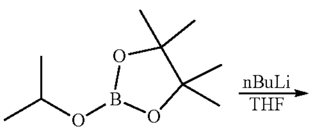

-continued

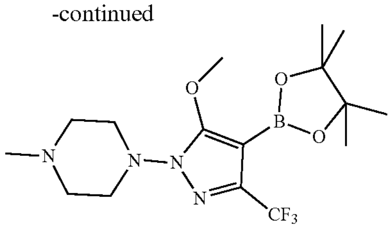

c8

N-methyl-4-piperidone c8-11 (17.6 mmol, 2 g) and Boc-hydrazine (17.6 mmol, 2.3 g) were dissolved in 60 mL of ethanol, and the mixture was reacted at room temperature for 2 days. After the solvent was removed under reduced pressure, the mixture was placed in an ice bath and dissolved in 20 mL acetic acid and 5 mL water, $NaBH_3CN$ (26.5 mmol, 1.67 g) was slowly added, and the reaction was continued for 3 hours. The reaction was stopped, the solvent was removed under reduced pressure, and the pH of the mixture was adjusted to about 9 with saturated $NaHCO_3$ aqueous solution, extracted with dichloromethane. The organic phase was dried over anhydrous sodium sulfate to afford intermediate c8-2 (3.1 g, yield: 77%). LC-MS: $[M+H]^+$: 230.

Intermediate c8-2 (13.5 mmol, 3.1 g) was dissolved in 30 mL of dichloromethane, 6 mL of trifluoroacetic acid was added dropwise, and after the mixture was reacted at room temperature for 2 hours, the solvent was removed under reduced pressure to afford intermediate c8-3 (quantitative yield).

Intermediate c8-3 (6.76 mmol, 878 mg) and methyl trifluoroacetoacetate (7.44 mmol, 1.26 g) were added to a reaction flask, after the mixture was dissolved in 12 mL of methanol, it was heated to reflux and reacted for 1.5 hours. After 1 mL of concentrated hydrochloric acid was added to the mixture, the reaction was continued for 12 hours. The reaction was stopped, the solvent was removed under reduced pressure, and separated by flash column chromatography to afford intermediate c8-4 (1.68 g, quantitative yield). LC-MS: $[M+H]^+$: 250.

In an ice bath, intermediate c8-4 (6.7 mmol, 1.68 g) and potassium carbonate (20.2 mmol, 4.82 g) were dissolved in 20 mL of DMF, dimethyl carbonate (13.4 mmol, 1.2 g) was slowly added, and after the mixture was reacted at room temperature for 12 hours, the reaction was stopped, 50 mL of water was added, extracted with ethyl acetate, the solvent was removed under reduced pressure, and separated by flash column chromatography to afford intermediate c8-5 (400 mg, yield: 23%). LC-MS: $[M+H]^+$: 264.

In an ice bath, intermediate c8-5 (1.14 mmol, 300 mg) was dissolved in 6 mL of concentrated sulfuric acid, NBS (1.14 mmol, 200 mg) was slowly added in batches, and the mixture was reacted at room temperature for 8 hours, the mixture was poured into 50 nil of ice water and adjusted the pH to about 9 with saturated $NaHCO_3$ aqueous solution, extracted with dichloromethane, the solvent was removed under reduced pressure, and dried over anhydrous sodium sulfate to afford intermediate c8-6 (400 mg, quantitative yield). LC-MS: $[M+H]^+$: 342.

At −78° C., intermediate c8-6 (1.46 mmol, 500 mg) was dissolved in 15 mL of anhydrous THF, butyl lithium (0.7 mL, 2.5M) was added dropwise, 30 minutes later, isopropoxyboronic acid, pinacol cyclic ester c3-4 (1.75 mmol, 326 mg) was added, after the reaction was continued at −78° C. for 3 hours, 50 mL of saturated ammonium chloride aqueous solution was added to quench the reaction, and extracted with dichloromethane. The organic phase was dried over anhydrous sodium sulfate to afford crude intermediate c8 (500 mg, yield: 87%). LC-MS: $[M+H]^+$: 390.

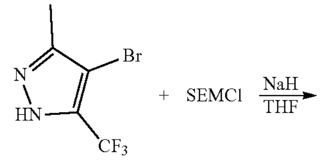

c3-1

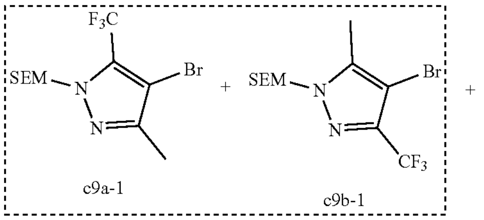

c9a-1 c9b-1

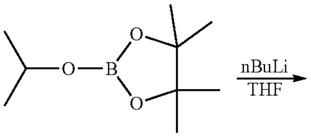

c3-4

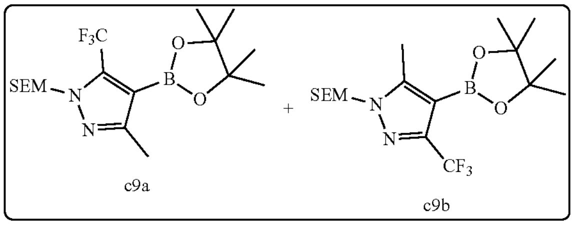

c9a c9b

In an ice bath, under nitrogen protection, the raw material c3-1 (5 mmol, 1.15 g) and 2-(trimethylsilyl) ethoxymethyl chloride SEMCl (5 mmol, 0.9 mL) were added to a reaction flask, and dissolved in 25 mL of THE NaH (5 mmol, 200 mg) was added in batches, after the mixture was stirred for 1 hour, the reaction was stopped. 50 mL of ice water was slowly added to the mixture to quench the reaction, extracted with ethyl acetate, dried over anhydrous sodium sulfate, and separated by flash column chromatography to afford mixture of intermediate c9a-1 and c9b-1 (1.3 g, yield: 73%), LC-MS: $[M+H]^+$: 359.

At −78° C., the mixture of intermediate c9a-1 and c9b-1 (3.63 mmol, 1.3 g) was dissolved in 35 ml of anhydrous THF, butyl lithium (1.74 mL, 2.5M) was added dropwise, 30 minutes later, isopropoxyboronic acid, pinacol cyclic ester c3-4 (5.45 mmol, 1.1 mL) was added. The reaction was continued at −78° C. for 3 hours, 100 ml of saturated ammonium chloride aqueous solution was added to quench the reaction, and extracted with dichloromethane. The organic phase was dried over anhydrous sodium sulfate to afford crude intermediate c9a and c9b (1.8 g), which was directly used in the next step. LC-MS: $[M+H]^+$: 407.

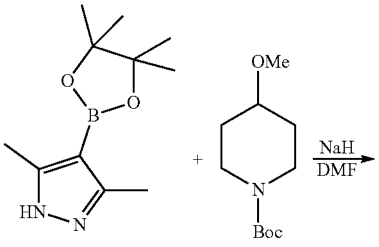

a6

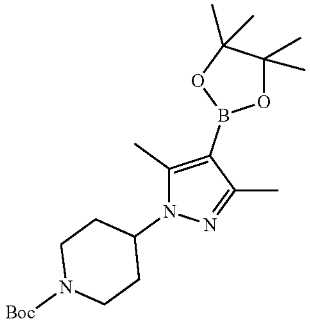

c10

In an ice bath, under nitrogen protection, the raw material a6 (2.25 mmol, 500 mg) was dissolved in 15 mL of DMF, NaH (4.5 mmol, 180 mg) was added in batches, stirred for 30 minutes later, tert-butyl 4-((methylsulfonyl)oxy)piperidine-1-carboxylate, (3.37 mmol, 943 mg) was slowly added, the reaction was heated to 90° C. and continued to react for 2 hours. The reaction was stopped, 50 mL of ice water was slowly added to the mixture to quench the reaction, extracted with ethyl acetate, dried over anhydrous sodium sulfate to afford crude intermediate c10 (2.0 g), which was directly used in the next step. LC-MS: $[M+H]^+$: 406,

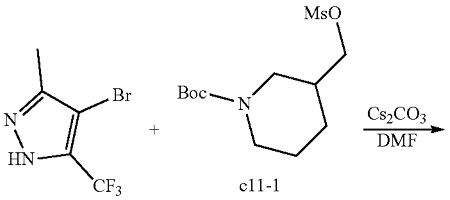

c3-1 c11-1

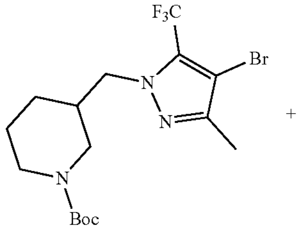

c11-2

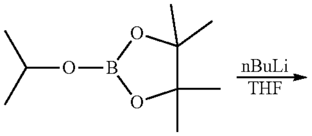

c3-4

-continued

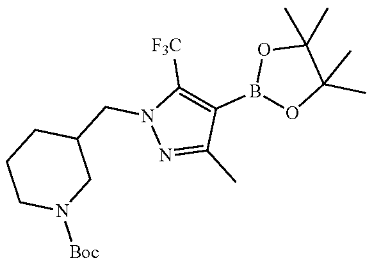

c11

The raw material c3-1 (2.19 mmol, 500 mg) and the raw material c11-1 (2.63 mmol, 769 mg) were added to a reaction flask, dissolved in 10 mL of DMF. After cesium carbonate (6.57 mmol, 2.14 g) was added, the mixture was reacted at 80° C. for 10 hours. The reaction was stopped, filtered, the solvent was removed under reduced pressure, and separated by flash column chromatography to afford intermediate c11-2 (170 mg, yield: 19%), LC-MS: $[M+H]^+$: 331.

At −78° C., intermediate c11-2 (0.4 mmol, 170 mg) was dissolved in 10 mL of anhydrous THY', butyl lithium (0.8 mL, 2.5M) was added dropwise, and 30 minutes later, isopropoxyboronic acid, pinacol cyclic ester c3-4 (1 mmol, 200 μL) was added. After the reaction was continued at −78° C. for 3 hours, 50 mL of saturated ammonium chloride aqueous solution was added to quench the reaction, and extracted with dichloromethane. The organic phase was dried over anhydrous sodium sulfate to afford crude intermediate c11 (100 mg, yield: 53%), which was directly used in the next step. LC-MS: $[M+H]^+$: 474.

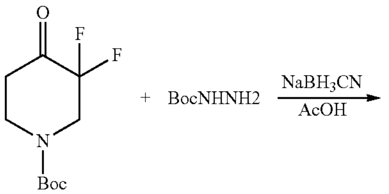

c14-1

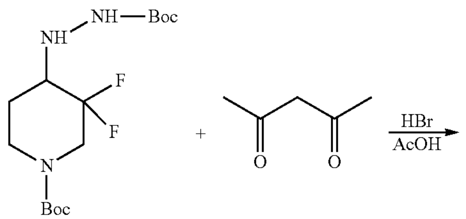

c14-2

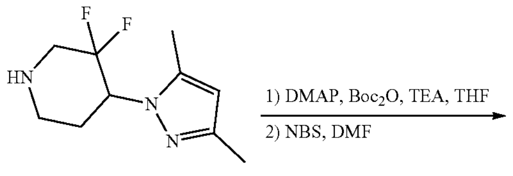

c14-3

-continued

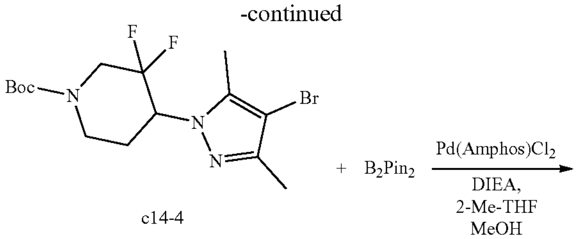

c14-4

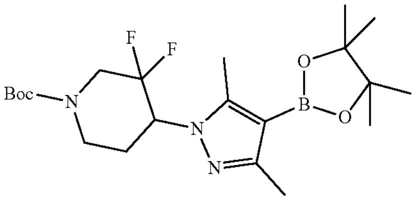

c14

The raw material c14-1 (14.3 mmol, 3.3 g) and N-Boc-hydrazine (15.7 mmol, 2.11 g) were dissolved in 30 mL of acetic acid. After the mixture was stirred for 5 minutes, $NaBH_3CN$ (43 mmol, 2.7 g) was slowly added, the mixture was reacted at room temperature for 10 hours. The reaction was stopped, 100 mL of ice water was added to the mixture to quench the reaction, and the solvent was removed under reduced pressure. The pH of the mixture was adjusted to about 9 with saturated $NaHCO_3$ aqueous solution, and extracted with dichloromethane. The organic phase was dried over anhydrous sodium sulfate, and separated by flash column chromatography to afford intermediate c14-2 (3.2 g, yield: 65%).

Intermediate c14-2 (8.83 mmol, 3.1 g) and acetylacetone (10.6 mmol, 1.1 mL) were added to a reaction flask, and dissolved in 30 mL of acetic acid. 3 mL of hydrobromic acid (45%) was slowly added to the mixture, and the mixture was reacted at room temperature for 2 hours. The reaction was stopped, and the solvent was removed under reduced pressure to afford crude intermediate c14-3 (3 g, crude). LC-MS: $[M+H]^+$: 216.

Crude intermediate c14-3 (7.8 mmol, 1.68 g), Boc anhydride (11.7 mmol, 2.5 g), triethylamine (23.4 mmol, 3.4 mL) and DMAP (0.78 mmol, 95 mg) were dissolved in 20 mL of tetrahydrofuran, and the mixture was reacted at room temperature for 12 hours. The reaction was stopped, 100 mL of water was added, extracted with ethyl acetate, washed with saturated sodium chloride aqueous solution, and dried over anhydrous sodium sulfate to afford yellow oily product (1.37 g). The yellow oily product was dissolved in 10 mL of DMF and placed in an ice bath, NBS (5 mmol, 882 mg) was added slowly in batches, the mixture was reacted at room temperature for 8 hours, 50 mL of ice water was added, extracted with ethyl acetate, dried over anhydrous sodium sulfate, and separated by flash column chromatography to afford intermediate c14-4 (1.1 g, three-step total yield: 32%). LC-MS: $[M+H]^+$: 395.

Under nitrogen protection, intermediate c14-4 (1.3 mmol, 500 mg), his(pinacolato)diboron (1.52 mmol, 300 mg), DIEA (3.8 mmol, 0.66 mL) and $Pd(Amphos)Cl_2$ (0.13 mmol, 90 mg) were added to a microwave reaction flask, and dissolved in 20 mL mixture of 2-Me-THE and MeOH (v/v, 1/1). After the mixture was heated to 100° C. in microwave and reacted for 1 hour, the reaction was stopped. The mixture was filtered, 30 mL of water was added, and extracted with ethyl acetate to afford crude intermediate c14, which was directly used in the next step. LC-MS: [M+H]+: 442.

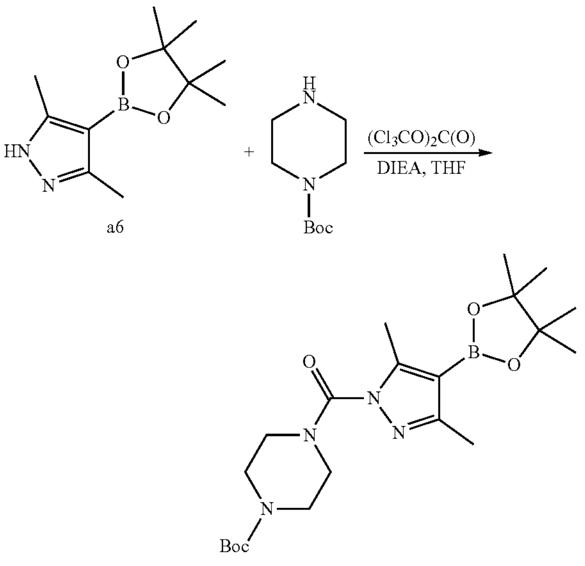

a6 c15

In an ice bath, the raw material a6 (2.0 mmol, 444 mg), N-Roc-piperazine (3.0 mmol, 559 mg), DIEA (5.0 mmol, 645 mg) were dissolved in 15 mL of tetrahydrofuran. After the mixture was stirred for 5 minutes, triphosgene (4.0 mmol, 1.08 g) was slowly added to the system, and the reaction was stopped after stirring for 2 hours in an ice bath. 40 mL of water was added to the mixture, extracted with dichloromethane, and separated by flash column chromatography to afford intermediate c15 (180 mg, yield: 21%). LC-MS: [M+H]+: 435.

Preparation of Key Intermediates d1-d9:

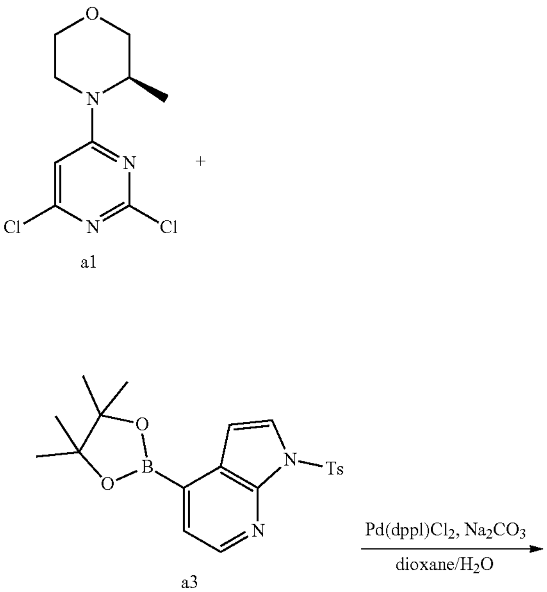

al a3

-continued

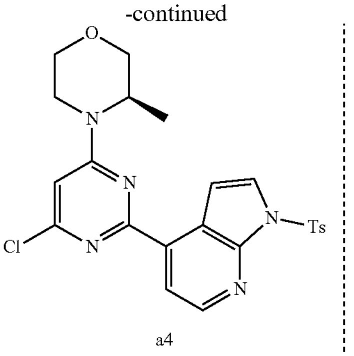

a4

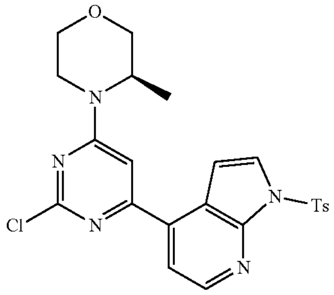

a5

The operation steps were the same as above.

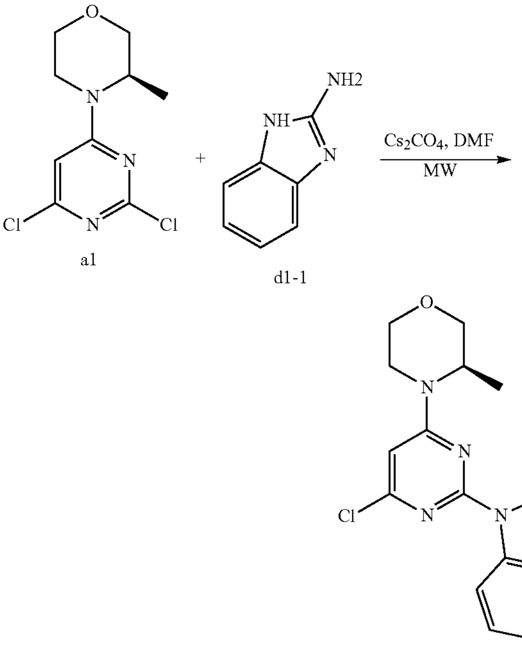

al dl-1 dl

Intermediate a1 (2.02 mmol, 500 mg) and 2-aminobenzimidazole d1-1 (2.11 mmol, 282 mg) were added to a microwave reaction flask, dissolved in 10 mL of DMF. After cesium carbonate (4.03 mmol, 1.3 g) was added, the mixture was reacted at 100° C. in microwave for 1.5 hours. The reaction was stopped, 40 mL of water was added, extracted with ethyl acetate, dried over anhydrous sodium sulfate, and separated by flash column chromatography to afford intermediate d1 (600 mg, yield: 86%), LC-MS: [M+H]+: 345,

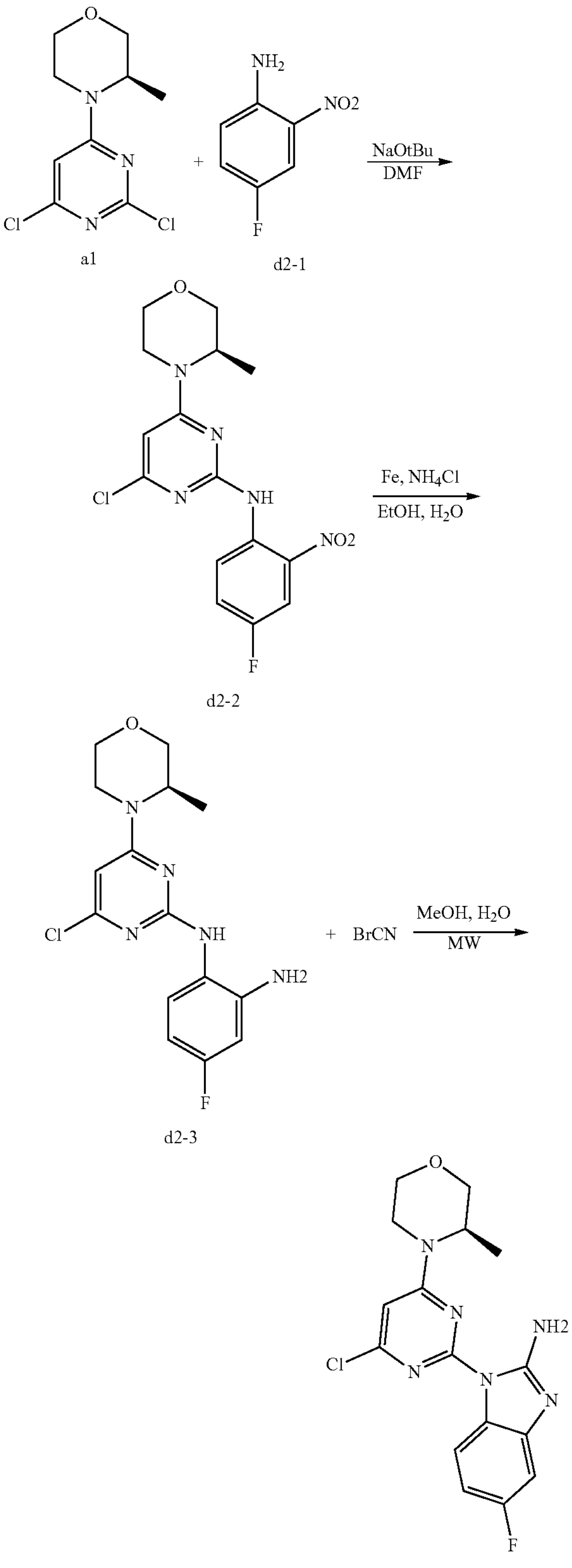

a1, d2-1, d2-2, d2-3, d2

Intermediate a1 (2.02 mmol, 500 mg) and 2-nitro-4-fluoro-aniline d2-1 (2.4 mmol, 375 mg) were added to a microwave reaction flask, and dissolved in 8 mL of DMF. After sodium tert-butoxide (4 mmol, 384 mg) was added, the mixture was reacted at 100° C. in microwave for 1 hour. The reaction was stopped. 30 mL of water was added, extracted with ethyl acetate, dried over anhydrous sodium sulfate, and separated by flash column chromatography to afford intermediate d2-2 (700 mg, yield: 95%), LC-MS: $[M+H]^+$: 368.

Intermediate d2-2 (2.72 mmol, 1 g), reduced iron powder (9.5 mmol, 532 mg) and ammonium chloride (9.5 mmol, 508 mg) were added to a reaction flask, and the mixture was dissolved in 20 mL ethanol and 4 mL of water. The mixture was reacted at 100° C. for 1.5 hours. The reaction was stopped, suction filtered, 60 of water was added, extracted with ethyl acetate, and dried over anhydrous sodium sulfate to afford intermediate d2-3 (900 mg, yield: 98%), LC-MS: [M+H]+: 338.

Intermediate d2-3 (1.78 mmol, 600 mg), bromonitrile (5.3 mmol, 565 mg) were added to a reaction flask, dissolved in 10 mL methanol and 4 mL water. The mixture was reacted at 60° C. in microwave for 1.5 hours. The reaction was stopped. 40 mL of water was added, extracted with ethyl acetate, dried over anhydrous sodium sulfate, and separated by flash column chromatography to afford intermediate d2 (400 mg, yield: 62%), LC-MS: $[M+H]^+$: 363.

The following compounds were synthesized with reference to intermediate d2:

| Structure | The structure replacing d2-1 | LC-MS/ $[M + H]^+$ |
|---|---|---|
| 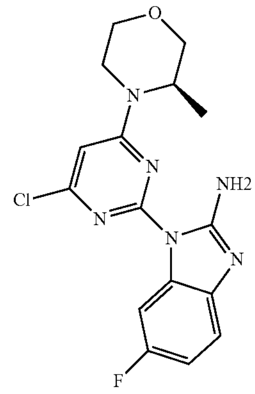 d6 | 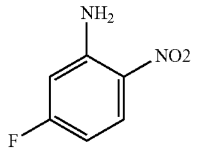 d6-1 | 363 |
| 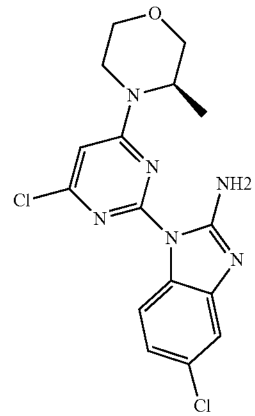 d8 | 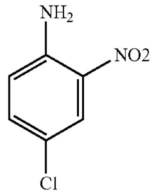 d8-1 | 380 |

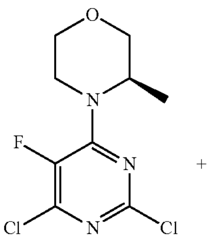

c6

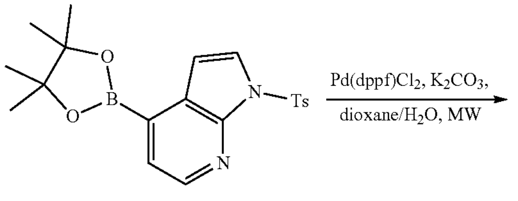

a3

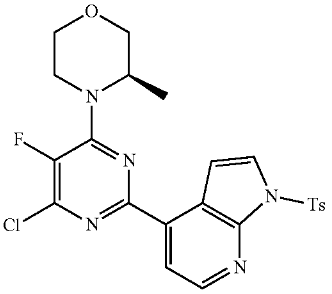

d3

Under nitrogen protection, intermediate c6 (1 mmol, 265 mg) and intermediate a3 (1 mmol, 398 mg) were dissolved in 10 mL mixture of 1,4-dioxane and water (v/v: 9/1), potassium carbonate (3 mmol, 414 mg) and $Pd(dppf)Cl_2$ (0.1 mmol, 73 mg) were added, and the mixture was heated at 110° C. in microwave for 30 minutes. The reaction was stopped, filtered, 10 mL of water was added, extracted with ethyl acetate, and separated by column chromatography to afford intermediate d3 (100 mg) yield: 20%, LC-MS: $[M+H]^+$: 502.

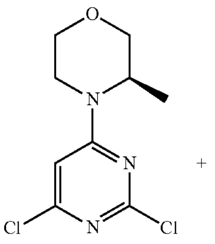

a1

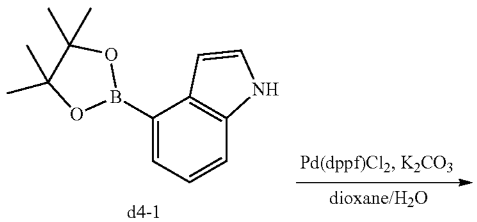

d4-1

-continued

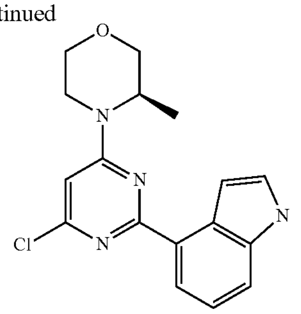

d4

Under nitrogen protection, intermediate a1 (0.8 mmol, 200 mg) and 4-indolylboronic acid, pinacol cyclic ester d4-1 (0.88 mmol, 214 mL were dissolved in 10 mL mixture of 1,4-dioxane and water (v/v: 9/1), potassium carbonate (1.6 mmol, 221 mg) and $Pd(dppf)Cl_2$ (0.08 mmol, 59 mg) were added, and the mixture was heated to 110° C. and reacted for 2 hours. The reaction was stopped, filtered, 30 mL of water was added, extracted with ethyl acetate, and separated by column chromatography to afford intermediate d4 (50 rag) yield: 19%, LC-MS: $[M+H]^+$: 329.

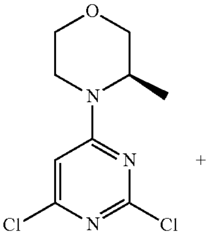

a1

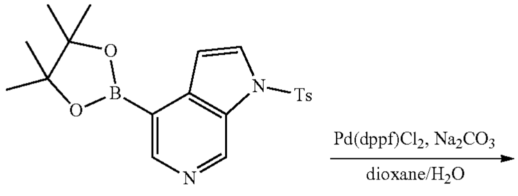

c1

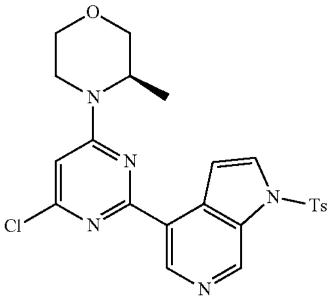

d5

Under nitrogen protection, intermediate a1 (1.28 mmol, 317 and intermediate c1 (2.57 mmol, 1.02 g) were dissolved in 15 mL mixture of 1,4-dioxane and water (v/v: 9/1), sodium carbonate (5.12 mmol, 543 mg) and $Pd(dppf)Cl_2$ (0.13 mmol, 95 mg) were added, then the mixture was heated to reflux and reacted for 12 hours. The reaction was stopped, filtered, the organic solvent was dried by rotary evaporation, 30 mL of water was added, extracted with ethyl acetate, and separated by column chromatography to afford intermediate d5 (300 mg), yield: 49%, LC-MS: $[M+H]^+$: 484.

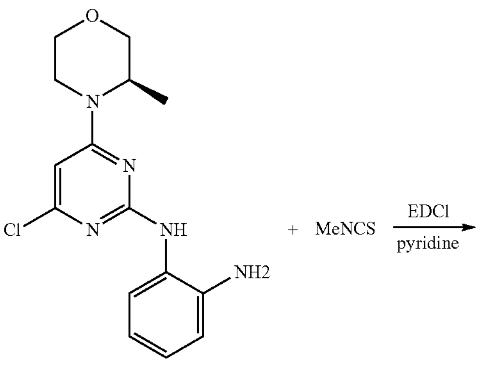

d2-3

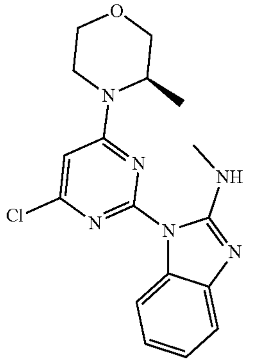

d7

Intermediate d2-3 (6.25 mmol, 2.0 g) was added to a reaction flask and dissolved in 20 mL of pyridine. Methyl isothiocyanate (7.5 mmol, 548 mg) was slowly added, and the mixture was reacted at 90° C. for 0.5 hours. The reaction was cooled to room temperature. EDCI (9.38 mmol, 1.8 g) was added, the mixture was continued to heat up to 90° C. and reacted for 10 hours, and the reaction was stopped. 100 mL of water was added to the mixture, extracted with ethyl acetate, dried over anhydrous sodium sulfate, and separated by flash column chromatography to afford intermediate d7 (1.2 g, yield: 54%), LC-MS: $[M+H]^+$: 359.

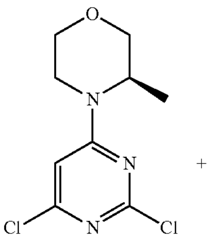

a1

-continued

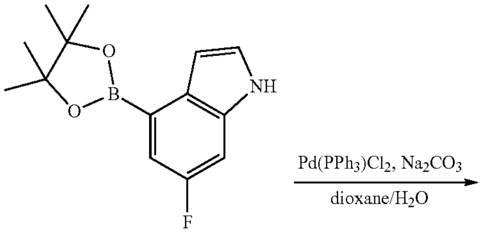

d9-1

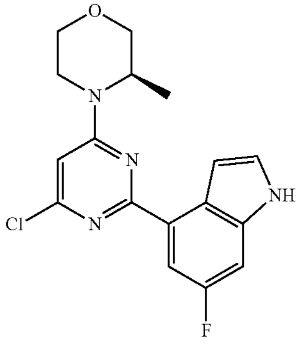

d9

Under nitrogen protection, intermediate a1 (14.0 mmol, 3.47 g) and 6-fluoro-4-(4,4,5,5-tetramethyl-1,3,2-dioxaborolan-2-yl)-1H-indole d9-1 (21.0 mmol, 5.48 g) were dissolved in 80 mL mixture of 1,4-dioxane and water (v/v: 9/1), sodium carbonate (42 mmol, 4.4 g) and $Pd(PPh_3)Cl_2$ (1.4 mmol, 984 mg) were added, and the mixture was heated to 90° C. and stirred 6 hours continuously. The reaction was stopped, filtered, 200 mL of water was added, extracted with ethyl acetate, and separated by column chromatography to afford intermediate d9 (1.75 g, yield: 37%), LC-MS: $[M+H]^+$: 347.

Preparation of Key Intermediate e1:

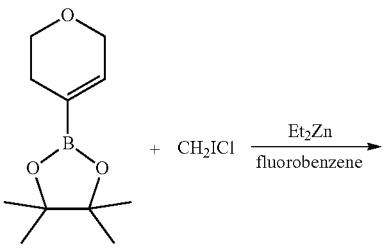

e1-1

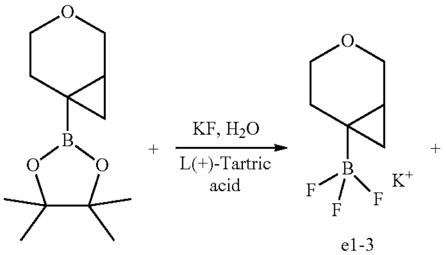

e1-2 e1-3

-continued

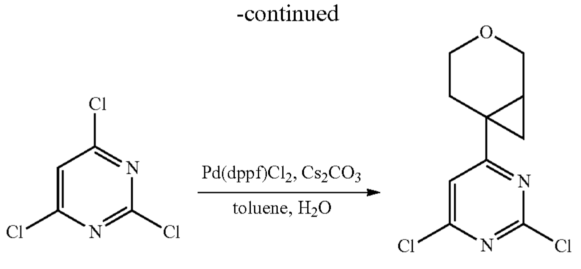

el

Under nitrogen protection, at −5° C., the raw material e1-1 (5 mmol, 1.05 g) was dissolved in 15 mL of fluorobenzene, diethyl zinc (12.5 ml 25 mmol, 2N in toluene) and chloroiodomethane in fluorobenzene (4.4 g/1.8 mL, 25 mmol, added in three portions) were slowly added, and the mixture was reacted at room temperature for 12 hours. The reaction was placed in an ice bath, 40 mL of saturated ammonium chloride aqueous solution was added to quench the reaction, extracted with ethyl acetate, dried over anhydrous sodium sulfate, and separated by column chromatography to afford intermediate e1-2 (730 mg, yield: 65%).

Under nitrogen protection, intermediate e1-2 (3.23 mmol, 730 mg) was dissolved in 16 mL mixture of methanol/acetonitrile (1/1, v/v), KF aqueous solution (749 mg/3 mL) was slowly added. After the mixture was stirred for 10 minutes, L-tartaric acid (6.46 mmol, 968 mg) and tetrahydrofuran (350 μL) were added, and the reaction was continued at room temperature for 1.5 h. The reaction was stopped, filtered, the filtrate was concentrated to afford intermediate e1-3 (600 mg, crude).

Under nitrogen protection, intermediate e1-3 (7.4 mmol, 1.5 g), cesium carbonate (22.2 mmol, 7.2 g) and 2,4,6-trichloropyrimidine (7.4 mmol, 1.35 g) were dissolved in 36 mL mixture of toluene/water (5/1, v/v), and $Pd(dppf)Cl_2$ (0.74 mmol, 540 mg) was added. The mixture was heated to 110° C. and reacted overnight. The reaction was stopped, filtered, concentrated, and separated by flash column chromatography to afford yellow oily intermediate el (500 mg, yield: 27%), LC-MS: $[M+H]^+$: 246.

Example 1

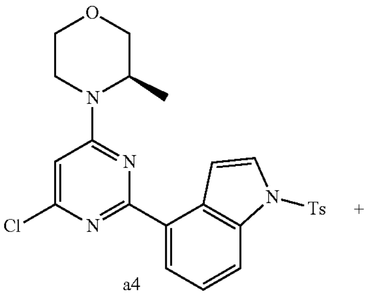

a4

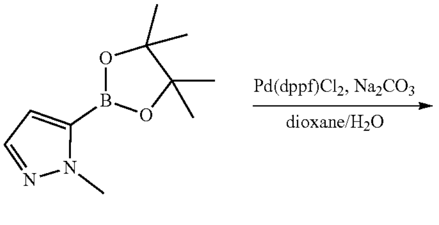

-continued

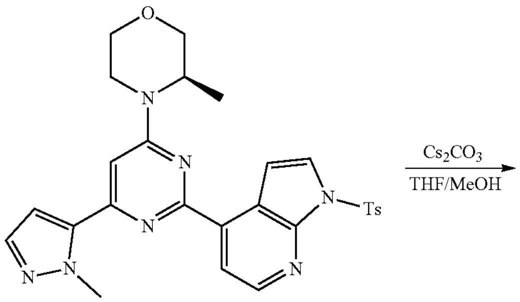

A1-1

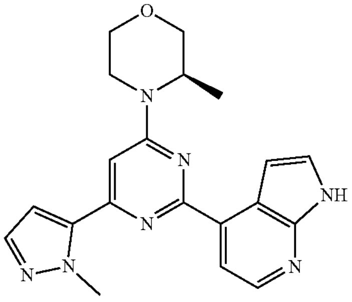

A1

Under nitrogen protection, intermediate a4 (0.21 mmol, 100 mg) and (1-methyl-1H-pyrazol-5-yl)boronic acid, pinacol cyclic ester (0.4 mmol, 84 mg) were dissolved in 5 mL mixture of 1,4-dioxane and water (v/v: 9/1), potassium carbonate (0.5 mmol, 848 mg) and $Pd(dppf)Cl_2$ (0.02 mmol, 15 mg) were added, and the reaction was heated at 100° C. in microwave for 1 hour. The reaction was stopped, filtered, the organic solvent was dried by rotary evaporation, water was added, extracted with ethyl acetate, and separated by column chromatography to afford compound A1-1. Compound A1-1 was dissolved in mixture of tetrahydrofuran and methanol, cesium carbonate (0.4 mmol, 131 mg) was added, the mixture was refluxed overnight until the reaction was complete. The mixture was filtered, the solvent was dried by rotary evaporation, and separated by preparative chromatography to afford the title compound A1 (yield: 41%), LC-MS: $[M+H]^+$: 376.

The compounds synthesized by the route of example 1 are as follows:

| Structure | The structure of boronic ester | LC-MS/ [M + H]$^+$ | $^1$H NMR yield |
|---|---|---|---|
| 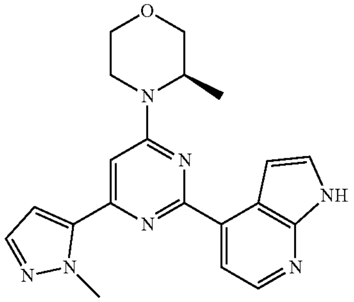 A1 | 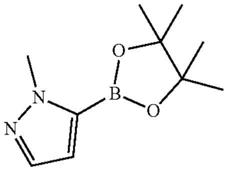 | 376 | $^1$H NMR (400 MHz, DMSO-$d_6$) δ 11.91 (s, 1H), 8.38 (s, 1H), 8.04 (s, 1H), 7.63 (s, 1H), 7.55 (s, 1H), 7.22 (s, 1H), 7.13 (s, 1H), 7.04 (s, 1H), 4.69 (s, 1H), 4.29 (s, 4H), 4.03 (d, J = 10.7 Hz, 1H), 3.82 (d, J = 11.3 Hz, 1H), 3.70 (d = J = 10.9 Hz, 1H), 3.55 (t, J = 11.5 Hz, 1H), 3.34 (d, J = 12.0 Hz, 1H), 1.31 (d, J = 6.0 Hz, 3H), 41% |
| 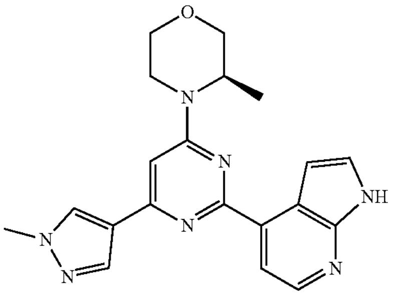 A2 | 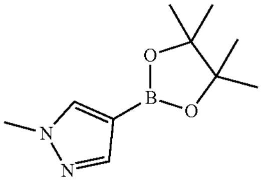 | 376 | $^1$H NMR (300 MHz, DMSO-$d_6$) δ 11.75 (s, 1H), 8.48 (s, 1H), 8.33 (d, J = 5.0 Hz, 1H), 8.21 (d, J = 0.7 Hz, 1H), 8.07 (d, J = 5.0 Hz, 1H), 7.58 (dd, J = 3.4, 2.5 Hz, 1H), 7.32 (dd, J = 3.4, 1.9 Hz, 1H), 7.04 (s, 1H), 4.65 (d, J = 7.6 Hz, 1H), 4.25 (d, J = 13.2 Hz, 1H), 4.02 (dd, J = 11.2, 3.6 Hz, 1H), 3.94 (s, 3H), 3.82 (d, J = 11.4 Hz, 1H), 3.69 (dd, J = 11.4, 3.1 Hz, 1H), 3.54 (td, J = 11.8, 2.9 Hz, 1H), 3.26 (dd, J = 12.5, 3.8 Hz, 1H), 1.28 (d, J = 6.7 Hz, 3H). 30% |
| 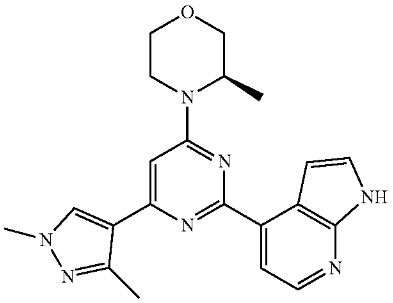 A3 | 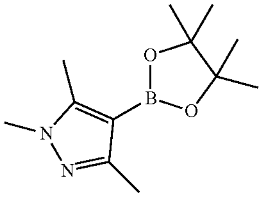 | 404 | $^1$H NMR (400 MHz, DMSO-$d_6$) δ 11.76 (s, 1H), 8.33 (d, J = 5.0 Hz, 1H), 8.01 (d, J = 5.0 Hz, 1H), 7.57 (t, J = 2.9 Hz, 1H), 7.24 (dd, J = 3.4, 1.9 Hz, 1H), 6.64 (s, 1H), 4.57 (s, 1H), 4.21 (d, J = 13.2 Hz, 1H), 4.06-3.96 (m, 1H), 3.81 (d, J = 11.4 Hz, 1H), 3.74 (s, 3H), 3.69 (dd, J = 11.3, 3.0 Hz, 1H), 3.61-3.49 (m, 1H), 3.27 (td, J = 12.9, 12.5, 4.2 Hz, 1H), 2.52 (s, 3H), 2.38 (s, 3H), 1.29 (d, J = 6.7 Hz, 3H). 55% |
| 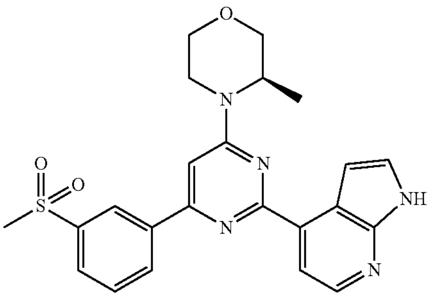 A4 | 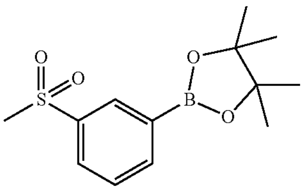 | 450 | $^1$H NMR (400 MHz, DMSO-$d_6$) δ 11.81 (s, 1H), 8.81 (t, J = 1.9 Hz, 1H), 8.69-8.64 (m, 1H), 8.38 (d, J = 5.0 Hz, 1H), 8.10 (dd, J = 7.7, 5.6 Hz, 2H), 7.87 (t, J = 7.8 Hz, 1H), 7.62 (d, J = 3.5 Hz, 1H), 7.45 (s, 1H), 7.31 (d, J = 3.4 Hz, 1H), 4.79 (s, 1H), 4.39 (d, J = 13.3 Hz, 1H), 4.05 (d, J = 11.6 Hz, 1H), 3.84 (d, J = 11.5 Hz, 1H), 3.72 (d, J = 10.8 Hz, 1H), 3.57 (t, J = 11.6 Hz, 1H), 3.37 (d, J = 13.6 Hz, 1H), 3.33 (s, 3H), 1.33 (d, J = 6.7 Hz, 3H). 72% |

-continued

| Structure | The structure of boronic ester | LC-MS/ [M + H]+ | 1H NMR yield |
|---|---|---|---|
| 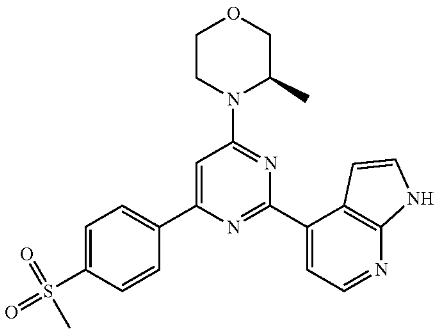 A5 | 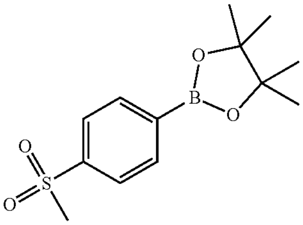 [SMILES: CC1(C)OB(c2ccc(S(C)(=O)=O)cc2)OC1(C)C] | 450 | 1H NMR (400 MHz, DMSO-$d_6$) (δ 11.82 (s, 1H), 8.59-8.52 (m, 2H), 8.37 (d, J = 5.0 Hz, 1H), 8.11 (dd, J = 6.7, 1.8 Hz, 3H), 7.62 (t, J = 3.0 Hz, 1H), 7.45 (s, 1H), 7.31 (dd, J = 3.3, 1.9 Hz, 1H), 4.77 (s, 1H), 4.39 (d, J = 13.4 Hz, 1H), 4.08-4.01 (m, 1H), 3.84 (d, J = 11.5 Hz, 1H), 3.77-3.68 (m, 1H), 3.57 (t, J = 11.3 Hz, 1H), 3.36 (dd, J = 13.2, 3.7 Hz, 1H), 3.30 (s, 3H), 1.32 (d, J = 6.7 Hz, 3H). 25% |
| 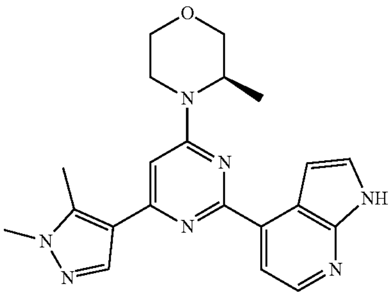 A6 | 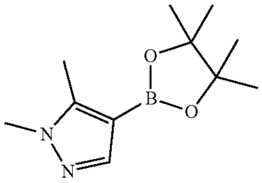 | 390 | 1H NMR (400 MHz, DMSO-$d_6$) δ 11.75 (s, 1H), 8.34 (d, J = 5.1 Hz, 1H), 8.12 (s, 1H), 8.00 (d, J = 5.0 Hz, 1H), 7.58 (t, J = 3.0 Hz, 1H), 7.22 (d, J = 2.5 Hz, 1H), 6.93 (s, 1H), 4.66 (d, J = 7.7 Hz, 1H), 4.23 (d, J = 13.3 Hz, 1H), 4.05-3.98 (m, 1H), 3.81 (d, J = 6.3 Hz, 4H), 3.69 (d, J = 12.1 Hz, 1H), 3.54 (t, J = 11.8 Hz, 1H), 3.29-3.23 (m, 1H), 2.76 (s, 3H), 1.28 (d, J = 6.7 Hz, 3H). 26% |
| 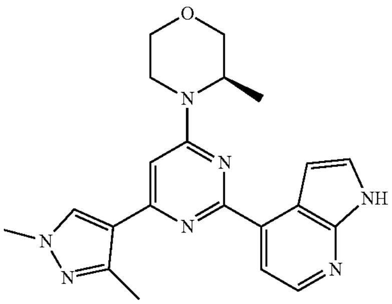 A7 | 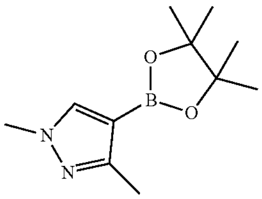 | 390 | 1H NMR (400 MHz, DMSO-$d_6$) δ 11.76 (s, 1H), 8.41 (s, 1H), 8.34 (d, J = 5.1 Hz, 1H), 8.04 (d, J = 5.4 Hz, 1H), 7.61-7.56 (m, 1H), 7.24 (t, J = 2.7 Hz, 1H), 6.86 (s, 1H), 4.61 (s, 1H), 4.20 (d, J = 13.0 Hz, 1H), 4.03 (d, J = 11.0 Hz, 1H), 3.83 (d, J = 14.5 Hz, 4H), 3.70 (d, J = 11.9 Hz, 1H), 3.55 (s, 1H), 3.29 (s, 1H), 2.57 (d, J = 2.5 Hz, 3H), 1.28 (d, J = 6.6 Hz, 3H). 41% |
| 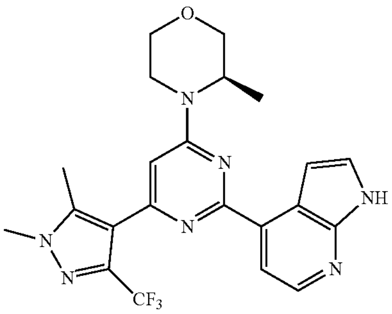 A8 | 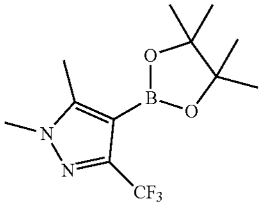 | 458 | 1H NMR (400 MHz, DMSO-$d_6$) δ 11.77 (s, 1H), 8.33 (d, J = 5.1 Hz, 1H), 8.01 (d, J = 5.0 Hz, 1H), 7.57 (t, J = 3.0 Hz, 1H), 7.23 (dd, J = 3.4, 1.9 Hz, 1H), 6.74 (s, 1H), 4.51 (s, 1H), 4.23 (d, J = 13.1 Hz 1H), 4.03 (d, J = 9.5 Hz, 1H), 3.92 (s, 3H), 3.81 (d, J = 11.5 Hz, 1H), 3.69 (d, J = 11.5 Hz, 1H), 3.55 (dd, J = 13.0, 9.9 Hz, 1H), 3.28 (s, 1H), 2.48 (s, 3H), 1.29 (d, J = 6.6 Hz, 3H). 36% |

-continued

| Structure | The structure of boronic ester | LC-MS/ [M + H]$^+$ | $^{1}$H NMR yield |
|---|---|---|---|
| 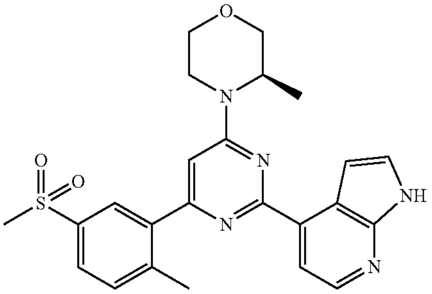 A9 | 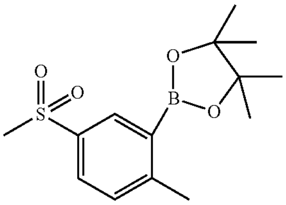 | 464 | $^{1}$H NMR (400 MHz, DMSO-$d_6$) δ 11.78 (s, 1H), 8.34 (d, J = 5.0 Hz, 1H), 8.05-8.00 (m, 2H), 7.93 (dd, J = 7.9, 2.1 Hz, 1H), 7.66 (d, J = 8.1 Hz, 1H), 7.57 (s. 1H), 7.22 (s, 1H), 6.99 (s, 1H), 4.67 (s, 1H), 4.01 (s, 1H), 3.82 (d, J = 11.4 Hz. 1H), 3.72 (s, 1H), 3.56 (s, 1H), 3.36 (d, J = 1.4 Hz, 2H), 3.27 (s, 3H), 2.55 (s, 3H), 1.31 (d, J = 6.7 Hz, 3H). 55% |
| 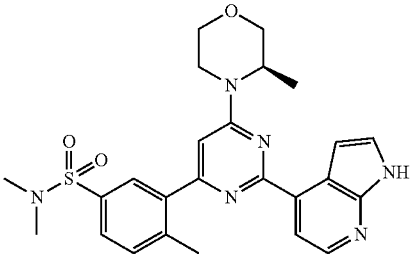 A10 | 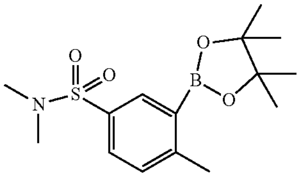 | 493 | $^{1}$H NMR (400 MHz, DMSO-$d_6$) δ 11.77 (s, 1H), 8.34 (d, J = 5.0 Hz, 1H), 8.01 (d, J = 5.1 Hz, 1H), 7.87 (d, J = 2.0 Hz, 1H), 7.78-7.73 (m, 1H), 7.66 (d, J = 8.1 Hz, 1H), 7.56 (t, J = 2.9 Hz, 1H), 7.24-7.21 (m, 1H), 6.98 (s, 1H), 4.67 (s, 1H), 4.29 (s, 1H), 4.02 (d, J = 9.1 Hz, 1H), 3.81 (d, J = 11.5 Hz, 1H), 3.70 (d, J = 10.8 Hz. 1H), 3.54 (d, J = 11.0 Hz, 1H), 3.35 (s, 1H), 2.67 (s, 6H), 2.56 (s, 3H), 1.31 (d, J = 6.8 Hz, 3H). 44% |
| 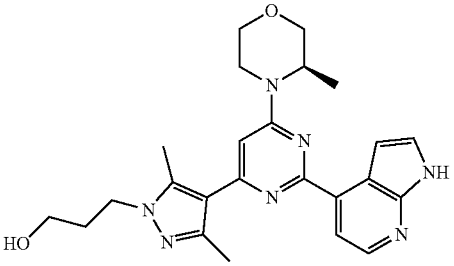 A11 | 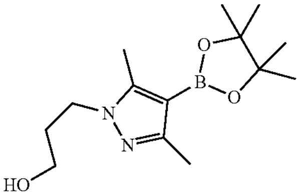 [SMILES: Cc1nn(CCCO)c(C)c1B1OC(C)(C)C(C)(C)O1] | 448 | $^{1}$H NMR (400 MHz, DMSO-$d_6$) δ 11.74 (s, 1H), 8.33 (d, J = 5.0 Hz, 1H), 8.01 (d, J = 5.1 Hz, 1H), 7.57 (t, J = 3.0 Hz, 1H), 7.24 (dd, J = 3.4, 1.9 Hz, 1H), 6.65 (s, 1H), 4.59 (t, J = 5.1 Hz, 2H), 4.22 (d, J = 13.3 Hz, 1H), 4.10 (t, J = 7.0 Hz, 2H), 4.02 (d, J = 11.8 Hz, 1H), 3.81 (d, J = 11.4 Hz, 1H), 3.70 (d, J = 10.3 Hz, 1H), 3.55 (dd, J = 13.1, 10.2 Hz,1H), 3.43 (q, J = 5.7 Hz, 2H), 2.53 (s, 3H), 2.38 (s, 3H), 2.00-1.86 (m, 3H), 1.29 (d, J = 6.7 Hz, 3H). 35% |
| 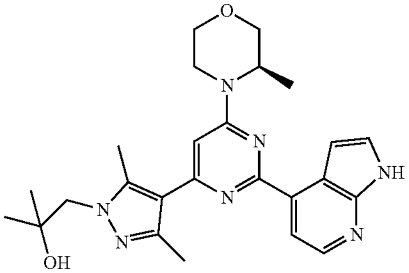 A12 | 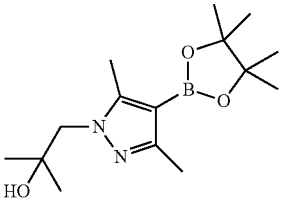 [SMILES: Cc1nn(CC(C)(C)O)c(C)c1B1OC(C)(C)C(C)(C)O1] | 462 | $^{1}$H NMR (400 MHz, DMSO-$d_6$) δ 11.75 (s, 1H), 8.33 (d, J = 5.0 Hz, 1H), 8.01 (d, J = 5.0 Hz, 1H), 7.57 (t, J = 3.0 Hz, 1H), 7.26-7.22 (m, 1H), 6.65 (s, 1H), 4.71 (s, 1H), 4.58 (s, 1H), 4.22 (d, J = 13.5 Hz, 1H), 4.02 (d, J = 11.9 Hz, 1H), 3.98 (s, 2H), 3.81 (d, J = 11.4 Hz, 1H), 3.70 (d, J = 9.9 Hz, 1H), 3.55 (t, J = 11.8 Hz, 1H), 3.27 (d, J = 12.9 Hz, 1H), 2.56 (s, 3H), 2.40 (s, 3H), 1.29 (d, J = 6.7 Hz, 3H), 1.16 (s, 6H). 33% |

-continued

| Structure | The structure of boronic ester | LC-MS/ [M + H]$^+$ | $^1$H NMR yield |
|---|---|---|---|
| 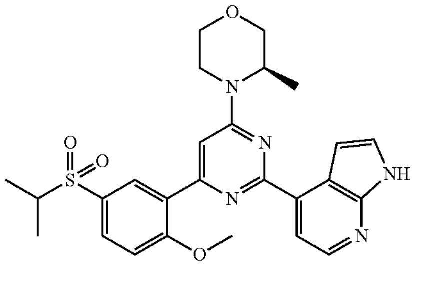 A13 | 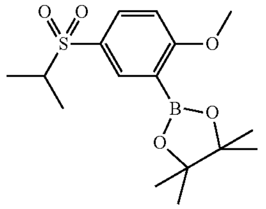 [SMILES: COc1ccc(S(=O)(=O)C(C)C)cc1B1OC(C)(C)C(C)(C)O1] | 508 | $^1$H NMR (400 MHz, DMSO-$d_6$) δ 11.84 (s, 1H), 8.45 (d, J = 2.5 Hz, 1H), 8.37 (d, J = 5.1 Hz, 1H), 8.03 (d, J = 5.0 Hz, 1H), 7.96 (dd, J = 8.8, 2.4 Hz, 1H), 7.59 (t, J = 3.0 Hz, 1H), 7.48 (d, J = 8.9 Hz, 1H), 7.32 (s, 1H), 7.28 (t, J = 2.7 Hz, 1H), 4.59 (s, 1H), 4.25 (s, 1H), 4.03 (s, 3H), 3.82 (d, J = 11.6 Hz, 1H), 3.71 (d, J = 10.4 Hz, 1H), 3.56 (t, J = 12.0 Hz, 1H), 3.45-3.39 (m, 1H), 3.32 (t, J = 11.8 Hz, 1H), 3.10 (dd, J = 7.3, 4.8 Hz, 1H), 1.31 (d, J = 6.7 Hz, 3H), 1.22 (d, J = 6.8 Hz, 6H). |

Example 2

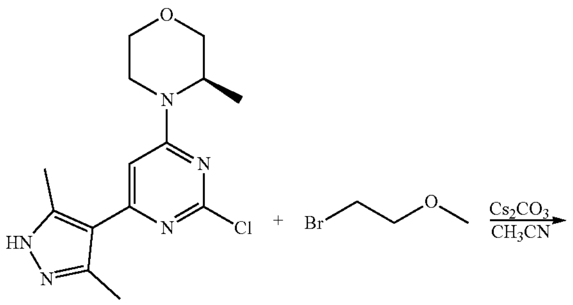

a7

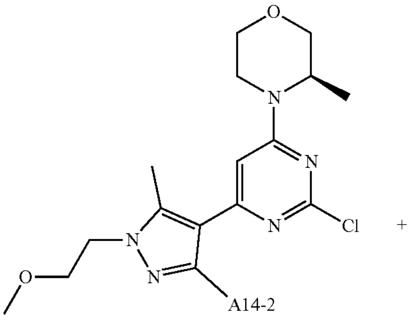

A14-2 +

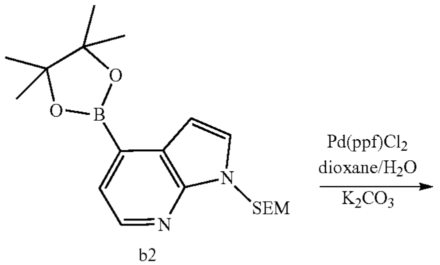

b2

-continued

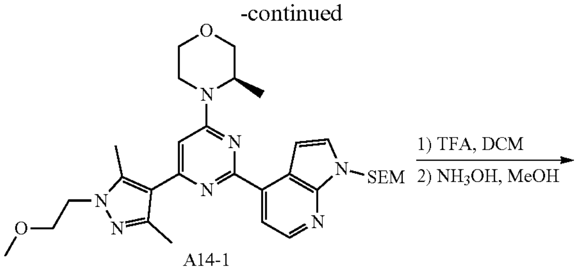

A14-1

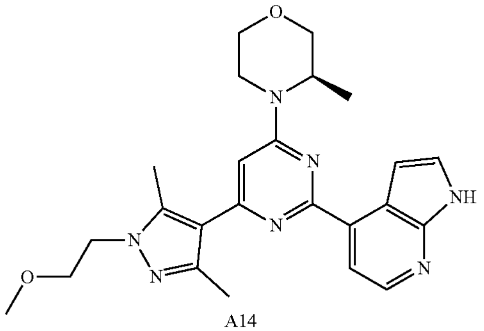

A14

Intermediate a7 (0.33 mmol, 100 mg), cesium carbonate (0.66 mmol, 215 mg) and 2-bromoethyl methyl ether (0.39 mmol, 59 mg) were added to a reaction flask, after dissolving in acetonitrile, the mixture was heated to reflux and reacted for 2 hours. The reaction was stopped, suction filtered, and separated by column chromatography to afford compound A14-2 (100 mg, yield: 83%), LC-MS: [M+H]$^+$: 366.

Under nitrogen protection, intermediate A14-2 (0.27 mmol, 100 mg) and intermediate b2 (0.33 mmol, 123 mg) were dissolved in 10 mL mixture of 1,4-dioxane and water (v/v: 9/1), potassium carbonate (0.54 mmol, 75 mg), Pd(dppf)$Cl_2$ (0.02 annul, 15 mg) were added, and the mixture was reacted at 90° C. for 12 hours. The reaction was stopped, filtered, the organic solvent was dried by rotary evaporation, water was added, extracted with ethyl acetate, and separated by column chromatography to afford compound A14-1 (120 mg, yield: 77%), LC-MS: $[M+H]^+$: 578.

Compound A14-1 (120 mg, 0.17 mmol) was dissolved in 5 mL of dichloromethane, 2 mL of trifluoroacetic acid was added dropwise, and after reacting at room temperature for 2 hours, the solvent was removed under reduced pressure. The mixture was dissolved in 5 mL of methanol again, 3 mL of ammonia was added, and the mixture was reacted at room temperature overnight. The solvent was removed under reduced pressure, and separated by preparative chromatography to afford the title compound A14 (50 mg, yield: 66%), LC-MS: $[M+H]^+$: 448.

The compounds synthesized by the route of example 2 are as follows:

-continued

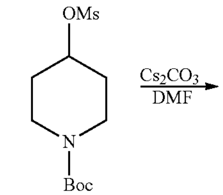

| Structure | The structure of the halide | LC-MS/ $[M + H]^+$ | $^1H$ NMR/yield |
|---|---|---|---|
| 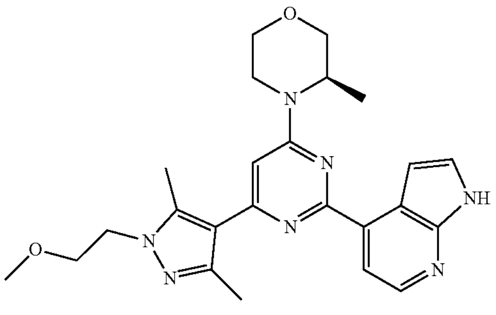 A14 | 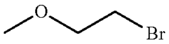 | 448 | $^1H$ NMR (400 MHz, DMSO-$d_6$) δ 11.86 (s, 1H), 8.35 (d, J = 4.9 Hz, 1H), 7.64 (d, J = 4.9 Hz, 1H), 7.60 (t, J = 2.9 Hz, 1H), 7.04 (s, 1H), 6.90 (dd, J = 3.4, 1.9 Hz, 1H), 4.58 (s, 1H), 4.21-4.10 (m, 3H), 3.99 (d, J = 11.4 Hz, 1H), 3.78 (d, J = 11.4 Hz, 1H), 3.69-3.65 (m, 3H), 3.57-3.49 (m, 1H), 3.23 (s, 4H), 2.65 (s, 3H), 2.48 (s, 3H), 1.26 (d, J = 6.5 Hz, 3H). 79% |
| 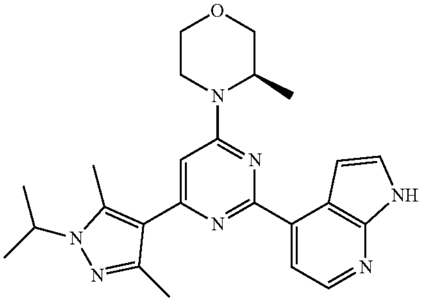 A15 | 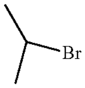 | 432 | $^1H$ NMR (400 MHz, DMSO-$d_6$) δ 11.74 (s, 1H), 8.33 (d, J = 5.0 Hz, 1H), 8.01 (d, J = 5.0 Hz, 1H), 7.57 (t, J = 2.9 Hz, 1H), 7.24 (dd, J = 3.4, 1.8 Hz, 1H), 6.66 (s, 1H), 4.56 (t, J = 6.4 Hz, 2H), 4.22 (d, J = 13.2 Hz, 1H), 4.02 (d, J = 10.4 Hz, 1H), 3.81 (d, J = 11.5 Hz, 1H), 3.69 (d, J = 11.7 Hz, 1H), 3.55 (t, J = 11.4 Hz, 1H), 3.26 (d, J = 11.7 Hz, 1H), 2.53 (s, 3H), 2.39 (s, 3H), 1.40 (d, J = 6.5 Hz, 6H), 1.29 (d, J = 6.7 Hz, 3H). 27% |

Example 3

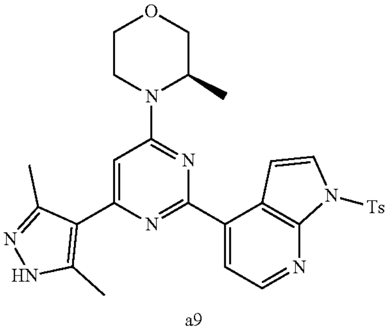

a9

+

-continued

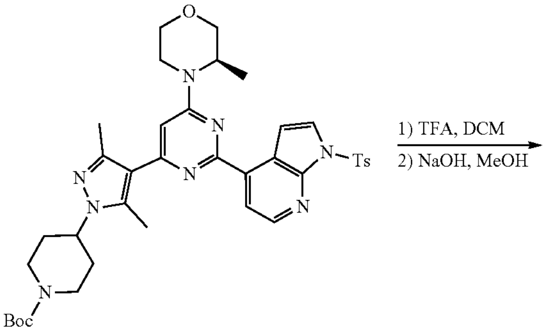

A16-1

-continued

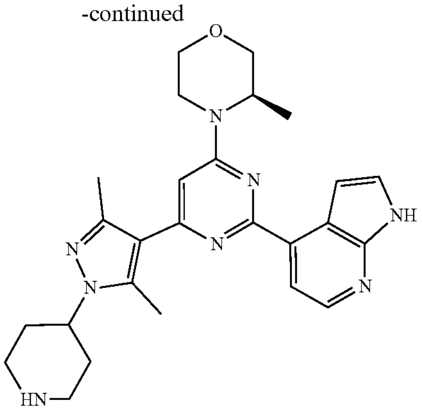

A16

Intermediate a9 (0.16 mmol, 85 mg), cesium carbonate (0.47 mmol, 153 mg) and N-Bile-piperidin-4-yl mesylate (0.19 mmol, 52 mg) were added to a reaction flask, after dissolving in DMF, the temperature of the mixture was raised to 80° C. and the reaction was continued for 12 hours. The reaction was stopped, filtered, water was added, extracted with ethyl acetate, and separated by column chromatography to afford compound A16-1 (70 mg, yield: 61%), LC-MS: $[M+H]^+$: 727.

Intermediate A16-1 (0.1 mmol, 70 mg) was dissolved in 6 mL of dichloromethane, 2 mL of trifluoroacetic acid was added dropwise, and the mixture reacted at room temperature for 2 hours. The reaction was stopped, the organic solvent was removed under reduced pressure. The mixture was dissolved in 10 mL of methanol again, 2 mL of 4N NaOH aqueous solution was added, and the mixture was reacted at 50° C. for 2 hours. The mixture was filtered, extracted with ethyl acetate, and separated by preparative chromatography to afford the title compound A16 (15 mg, yield: 30%), LC-MS: $[M+H]^+$: 473.

The compounds synthesized by the route of example 3 are as follows:

| Structure | The structure of mesylate or halide | LC-MS/ $[M + H]^+$ | $^1H$ NMR/yield |
|---|---|---|---|
| 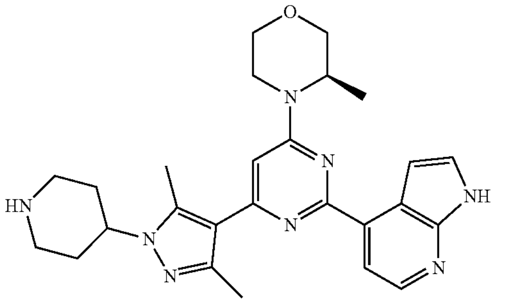 A16 | 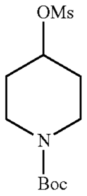 [SMILES: CC(C)(C)OC(=O)N1CCC(OS(C)(=O)=O)CC1] | 473 | $^1H$ NMR (400 MHz, DMSO-$d_6$) δ 11.74 (s, 1H), 8.33 (d, J = 5.0 Hz, 1H), 8.01 (d, J = 5.0 Hz, 1H), 7.56 (t, J = 2.9 Hz, 1H), 7.26-7.21 (m, 1H), 6.66 (s, 1H), 4.57 (s, 1H), 4.22 (d, J = 12.6 Hz, 2H), 4.02 (d, J = 10.8 Hz, 1H), 3.81 (d, J = 11.4 Hz, 1H), 3.69 (d, J = 11.2 Hz, 1H), 3.55 (t, J = 11.9 Hz, 1H), 3.28 (d, J = 3.5 Hz, 1H), 3.04 (d, J = 12.8 Hz, 2H), 2.61 (t, J = 12.3 Hz, 2H), 2.54 (s, 3H), 2.38 (s, 3H), 2.02-1.90 (m, 2H), 1.76 (d, J = 12.1 Hz, 2H), 1.29 (d, J = 6.6 Hz, 3H). 30% |
| 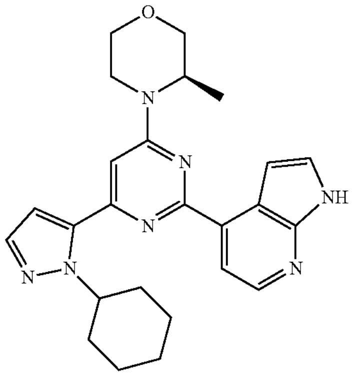 A17 | 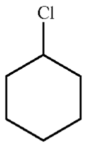 | 444 | $^1H$ NMR (400 MHz, DMSO-$d_6$) δ 11.80 (s, 1H), 8.35 (d, J = 5.1 Hz, 1H), 8.08 (d, J = 5.1 Hz, 1H), 7.94 (d, J = 2.4 Hz, 1H), 7.60 (t, J = 2.9 Hz, 1H), 7.38-7.33 (m, 1H), 7.15 (s, 1H), 7.00 (d, J = 2.3 Hz, 1H), 4.62 (s, 1H), 4.24 (d, J = 13.9 Hz, 2H), 4.02 (d, J = 11.0 Hz, 1H), 3.81 (d, J = 11.5 Hz, 1H), 3.70 (d, J = 10.0 Hz, 1H), 3.55 (s, 1H), 3.33 (d, J = 13.7 Hz, 1H), 2.09 (d, J = 12.3 Hz, 2H), 2.00 (d, J = 7.8 Hz, 1H), 1.88-1.68 (m, 5H), 1.44 (d, J = 12.8 Hz, 2H), 1.29 (d, J = 6.8 Hz, 3H). 22% |

-continued

| Structure | The structure of mesylate or halide | LC-MS/ [M + H]$^+$ | $^1$H NMR/yield |
|---|---|---|---|
| 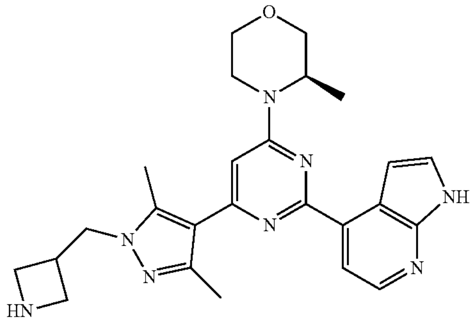 A18 | 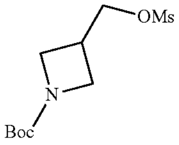 [SMILES: CC(C)(C)OC(=O)N1CC(COS(C)(=O)=O)C1] | 459 | $^1$H NMR (400 MHz, DMSO-$d_6$) δ 11.75 (s, 1H), 8.33 (d, J = 5.0 Hz, 1H), 8.00 (d, J = 5.0 Hz, 1H), 7.56 (d, J = 2.8 Hz, 1H), 7.24 (d, J = 3.2 Hz, 1H), 6.66 (s, 1H), 4.58 (s, 1H), 4.23 (t, J = 12.1 Hz, 3H), 4.02 (d, J = 11.1 Hz, 1H), 3.80 (d, J = 11.4 Hz, 2H), 3.69 (d, J = 11.0 Hz, 2H), 3.58-3.46 (m, 3H), 3.24 (d, J = 4.4 Hz, 1H), 3.03 (s, 1H), 2.54 (s, 3H), 2.37 (s, 3H), 1.29 (d, J = 6.7 Hz, 3H). 14% |
| 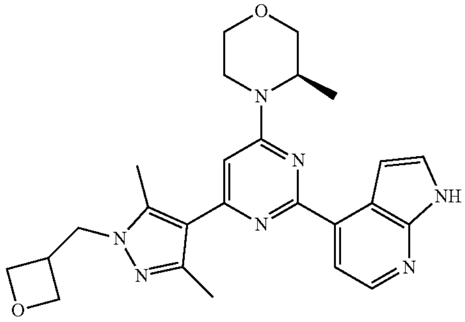 A19 | 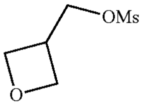 | 460 | $^1$H NMR (400 MHz, DMSO-$d_6$) δ 11.74 (s, 1H), 8.33 (d, J = 5.1 Hz, 1H), 8.00 (d, J = 5.0 Hz, 1H), 7.57 (t, J = 2.9 Hz, 1H), 7.26-7.21 (m, 1H), 6.66 (s, 1H), 4.67 (dd, J = 7.8, 6.1 Hz, 2H), 4.57 (s, 1H), 4.47 (t, J = 6.1 Hz, 2H), 4.36 (d, J = 7.4 Hz, 2H), 4.22 (d, J = 13.9 Hz, 1H), 4.02 (d, J = 11.0 Hz, 1H), 3.81 (d, J = 11.4 Hz, 1H), 3.69 (d, J = 9.7 Hz, 1H), 3.55 (t, J = 11.4 Hz, 1H), 3.44 (q, J = 7.1 Hz, 1H), 3.27 (d, J = 12.2 Hz, 1H), 2.54 (s, 3H), 2.37 (s, 3H), 1.29 (d, J = 6.7 Hz, 3H). 42% |
| 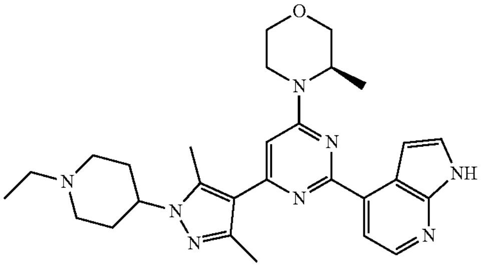 A20 | 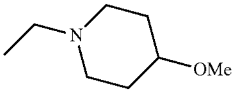 | 501 | $^1$H NMR (400 MHz, DMSO-$d_6$) δ 11.75 (s, 1H), 8.33 (d, J = 5.0 Hz, 1H), 8.01 (d, J = 5.0 Hz, 1H), 7.56 (t, J = 3.0 Hz, 1H), 7.26-7.22 (m, 1H), 6.66 (s, 1H), 4.56 (s, 1H), 4.22 (d, J = 13.1 Hz, 1H), 4.14 (s, 1H), 4.02 (d, J = 10.0 Hz, 1H), 3.81 (d, J = 11.5 Hz, 1H), 3.69 (d, J = 11.9 Hz, 1H), 3.53 (d, J = 12.6 Hz, 1H), 3.26 (d, J = 12.2 Hz, 1H), 2.98 (d, J = 7.0 Hz, 2H), 2.54 (s, 3H), 2.37 (d, J = 5.8 Hz, 5H), 2.07-1.98 (m, 4H), 1.82 (s, 2H), 1.29 (d, J = 6.7 Hz, 3H), 1.03 (t, J = 7.1 Hz, 3H). 30% |
| 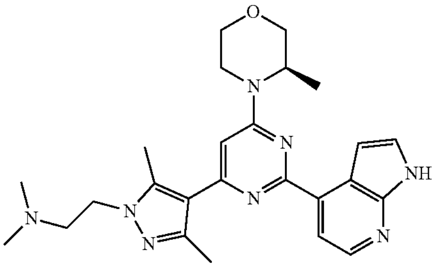 A21 | 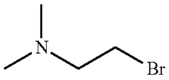 | 461 | $^1$H NMR (400 MHz, DMSO-$d_6$) δ 11.75 (s, 1H), 8.33 (d, J = 5.0 Hz, 1H), 8.01 (d, J = 5.0 Hz, 1H), 7.57 (d, J = 3.2 Hz, 1H), 7.24 (s, 1H), 6.65 (s, 1H), 4.58 (s, 1H), 4.22 (d, J = 13.2 Hz, 1H), 4.13 (t, J = 6.7 Hz, 2H), 4.02 (d, J = 11.6 Hz 1H), 3.81 (d, J = 11.4 Hz, 1H), 3.71 (s, 1H), 3.55 (t, J = 12.0 Hz, 1H), 3.28 (s, 1H), 2.62 (t, J = 6.7 Hz, 2H), 2.54 (s, 3H), 2.38 (s, 3H), 2.21 (s, 6H), 1.29 (d, J = 6.7 Hz, 3H). 20% |

-continued

| Structure | The structure of mesylate or halide | LC-MS/ [M + H]+ | 1H NMR/yield |
| --- | --- | --- | --- |
| 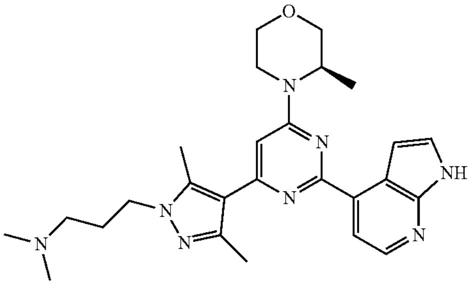 A22 | 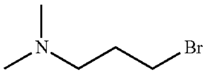 | 475 | $^1$H NMR (400 MHz, DMSO-$d_6$) δ 11.75 (s, 1H), 8.33 (d, J = 5.0 Hz, 1H), 8.01 (d, J = 5.0 Hz, 1H), 7.56 (t, J = 3.0 Hz, 1H), 7.24 (dd, J = 3.5, 2.0 Hz, 1H), 6.65 (s, 1H), 4.58 (s, 1H), 4.22 (d, J = 13.3 Hz, 1H), 4.08-4.00 (m, 3H), 3.81 (d, J = 11.5 Hz, 1H), 3.69 (d, J = 12.1 Hz, 1H), 3.53 (d, J = 11.5 Hz, 1H), 3.28 (s, 1H), 2.54 (s, 3H), 2.39 (s, 3H), 2.21 (t, J = 6.8 Hz, 2H), 2.14 (s, 6H), 1.89 (q, J = 6.9 Hz, 2H), 1.29 (d, J = 6.7 Hz, 3H). 32% |
| 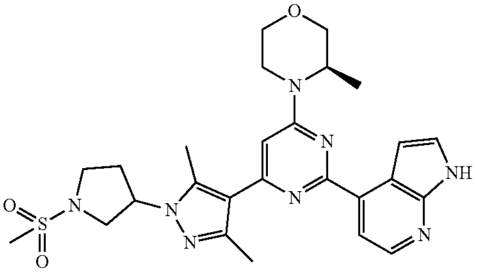 A23 | 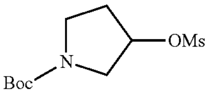 [SMILES: CC(C)(C)OC(=O)N1CCC(OS(C)(=O)=O)C1] | 537 | $^1$H NMR (400 MHz, DMSO-$d_6$) δ 11.76 (s, 1H), 8.33 (d, J = 5.0 Hz, 1H), 8.01 (d, J = 5.1 Hz, 1H), 7.57 (t, J = 2.9 Hz, 1H), 7.24 (dd, J = 3.4, 1.9 Hz, 1H), 6.68 (s, 1H), 5.16-5.06 (m, 1H), 4.57 (s, 1H), 4.23 (d, J = 13.2 Hz, 1H), 4.02 (d, J = 9.8 Hz, 1H), 3.84-3.75 (m, 2H), 3.69 (d, J = 10.2 Hz, 1H), 3.55 (td, J = 12.4, 10.3, 6.0 Hz, 3H), 3.42 (q, J = 7.4 Hz, 1H), 3.27 (d, J = 12.4 Hz, 1H), 3.00 (s, 3H), 2.57 (s, 3H), 2.40 (s, 3H), 2.34 (dt, J = 12.8, 6.8 Hz, 2H), 1.29 (d, J = 6.6 Hz, 3H). 49%. |
| 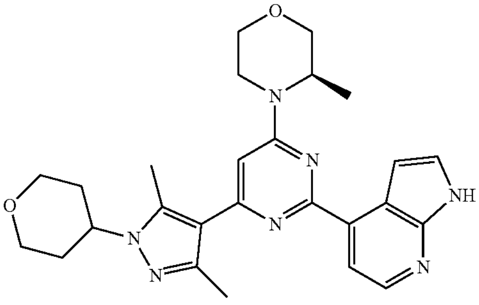 A24 | 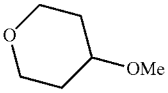 | 474 | $^1$H NMR (400 MHz, DMSO-$d_6$) δ 11.86 (s, 1H), 8.36 (d, J = 5.1 Hz, 1H), 7.99 (d, J = 5.0 Hz, 1H), 7.60 (d, J = 3.1 Hz, 1H), 7.23 (s, 1H), 6.72 (s, 1H), 4.59 (s, 1H), 4.45 (s, 1H), 4.25 (d, J = 13.5 Hz, 1H), 4.05-3.96 (m, 3H), 3.81 (d, J = 11.4 Hz, 1H), 3.70 (d, J = 10.3 Hz, 1H), 3.51 (t, J = 12.5 Hz, 3H), 3.32 (d, J = 12.8 Hz, 1H), 2.55 (s, 3H), 2.39 (s, 3H), 2.05 (ddd, J = 28.8, 14.0, 6.0 Hz, 2H), 1.80 (d, J = 12.3 Hz, 2H), 1.30 (d, J = 6.7 Hz, 3H). 23% |
| 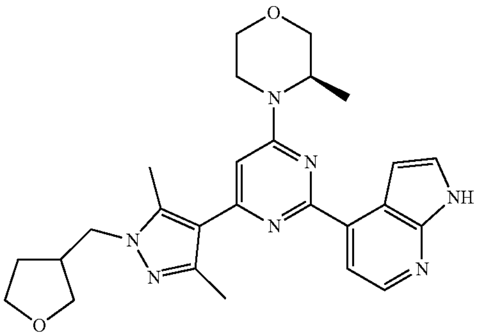 A28 | 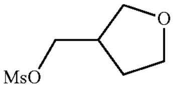 [SMILES: CS(=O)(=O)OCC1CCOC1] | 474 | $^1$H NMR (400 MHz, DMSO-$d_6$) δ 11.74 (s, 1H), 8.33 (d, J = 5.0 Hz, 1H), 8.01 (d, J = 5.0 Hz, 1H), 7.57 (t, J = 3.0 Hz, 1H), 7.24 (dd, J = 3.5, 1.9 Hz, 1H), 6.67 (s, 1H), 4.58 (s, 1H), 4.22 (d, J = 13.3 Hz, 1H), 4.08-3.99 (m, 3H), 3.86-3.77 (m, 2H), 3.68 (ddt, J = 15.1, 11.2, 5.5 Hz, 3H), 3.54 (ddd, J = 14.1, 10.2, 4.1 Hz, 2H), 3.29 (s, 1H), 2.74 (p, J = 6.7 Hz, 1H), 2.54 (s, 3H), 2.39 (s, 3H), 1.97 (dt, J = 12.7, 7.5 Hz, 1H), 1.67 (dq, J = 13.0, 6.7 Hz, 1H), 1.29 (d, J = 6.6 Hz, 3H). 30% |

Example 4

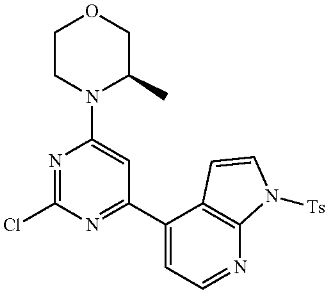

a5

+

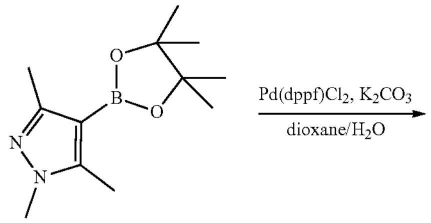

a10

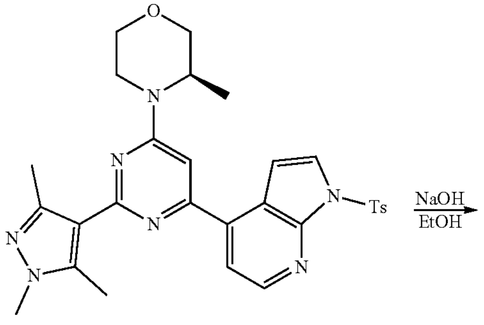

B1-1

-continued

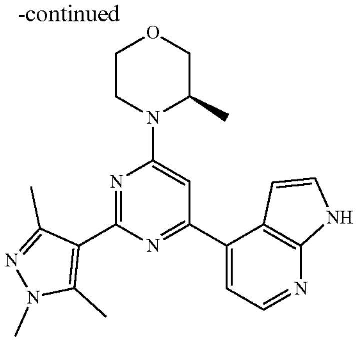

B1

Under nitrogen protection, intermediate a5 (0.21 mmol, 100 mg) and intermediate a10 (0.4 mmol, 94 mg) were dissolved in 10 mL mixture of 1,4-dioxane and water (v/v: 9/1), potassium carbonate (0.5 mmol, 848 mg) and Pd(dppf) $Cl_2$ (002 mmol, 15 mg) were added, and the mixture was reacted at 100° C. for 12 hours. The reaction was stopped, filtered, the organic solvent was dried by rotary evaporation water was added, extracted with ethyl acetate, and separated by column chromatography to afford compound B1-1 (80 mg, yield: 68%), LC-MS: $[M+H]^+$: 558.

Compound B1-1 (80 mg) was dissolved in 6 mL of ethanol, 3 mL of 4N NaOH aqueous solution was added, and the mixture was refluxed until the reaction was complete. The mixture was filtered, ethyl acetate was added for extraction, the solvent was removed under reduced pressure, and separated by preparative chromatography to afford the title compound B1 (quantitative yield), LC-MS: $[M+H]^+$: 404.

The compounds synthesized by the route of example 4 are as follows:

| Structure | The structure of boronic ester | LC-MS/ $[M + H]^+$ | $^1H$ NMR/yield |
|---|---|---|---|
| 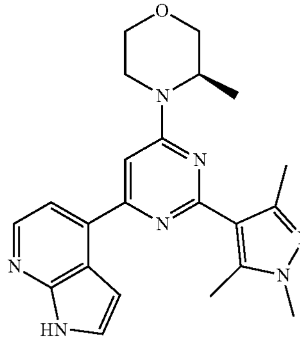 B1 | 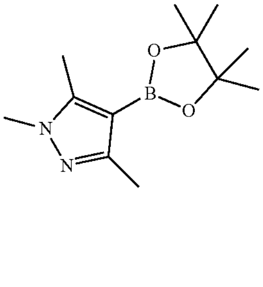 | 404 | $^1H$ NMR (400 MHz, DMSO-$d_6$) δ 11.86 (s, 1H), 8,35 (d, J = 4.9 Hz, 1H), 7.64 (d, J = 4.9 Hz, 1H), 7.62-7.57 (m, 1H), 7.03 (s, 1H), 6.91 (dd, J = 3.5, 1.8 Hz, 1H), 4.57 (s, 1H), 4.15 (d, J = 13.3 Hz, 1H), 3.99 (d, J = 9.8 Hz, 1H), 3.78 (d, J = 11.4 Hz, 1H), 3.72 (s, 3H), 3.67 (dd, J = 11.7, 3.1 Hz, 1H), 3.57-3.48 (m, 1H), 3.25 (td, J = 13.1, 3.9 Hz, 1H), 2.65 (s, 3H), 2.48 (s, 3H), 1.26 (d, J = 6.7 Hz, 3H). 56% |

-continued

| Structure | The structure of boronic ester | LC-MS/ [M + H]+ | $^1$H NMR/yield |
| --- | --- | --- | --- |
| 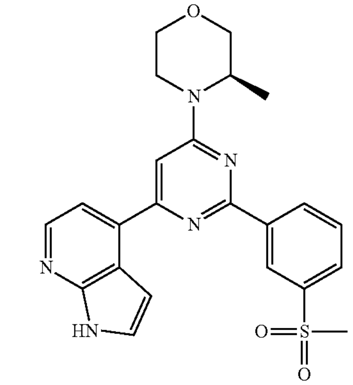 B2 | 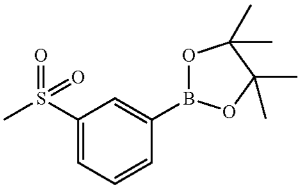 | 450 | $^1$H NMR (400 MHz, DMSO-d$_6$) δ 11.93 (s, 1H), 8.93 (t, J = 1.9 Hz, 1H), 8.78 (dt, J = 7.9, 1.5 Hz, 1H), 8.40 (d, J = 5.0 Hz, 1H), 8.16-8.05 (m, 1H), 7.84 (t, J = 7.8 Hz, 1H), 7.79 (d, J = 5.0 Hz, 1H), 7.66 (t, J = 3.0 Hz, 1H), 7.34 (s, 1H), 7.09 (dt, J = 2.2 Hz, 1H), 4.71 (s, 1H), 4.38 (d, J = 13.3 Hz, 1H), 4.04 (dd, J = 11.2, 3.7 Hz, 1H), 3.82 (d, J = 11.5 Hz, 1H), 3.71 (dd, J = 11.6, 3.1 Hz, 1H), 3.64-3.49 (m, 1H), 3.38-3.31 (m, 1H), 3.29 (d, J = 3.3 Hz, 3H), 1.31 (d, J = 6.7 Hz, 3H). 64% |
| 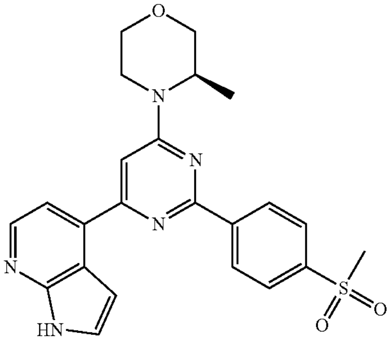 B3 | 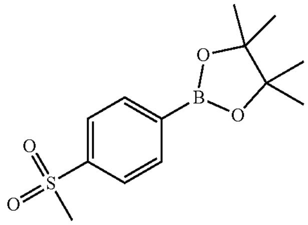 [SMILES: CC1(C)OB(c2ccc(S(C)(=O)=O)cc2)OC1(C)C] | 450 | $^1$H NMR (400 MHz, DMSO-d$_6$) δ 11.90 (s, 1H), 8.72-8.64 (m, 2H), 8.38 (d, J = 5.0 Hz, 1H), 8.12-8.04 (m, 2H), 7.78 (d, J = 5.0 Hz, 1H), 7.65 (t, J = 3.0 Hz, 1H), 7.34 (s, 1H), 7.09 (dd, J = 3.5, 1.8 Hz, 1H), 4.72 (s, 1H), 4.38 (d, J = 13.3 Hz, 1H), 4.05-3.98 (m, 1H), 3.81 (d, J = 11.5 Hz, 1H), 3.75-3.66 (m, 1H), 3.60-3.49 (m, 1H), 3.34 (s, 1H), 3.28 (s, 3H), 1.30 (d, J = 6.7 Hz, 3H). 34% |
| 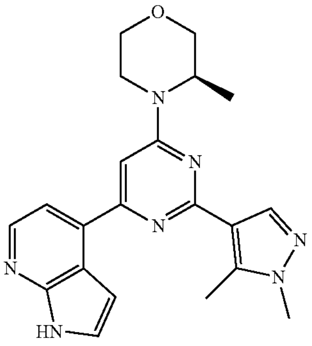 B4 | 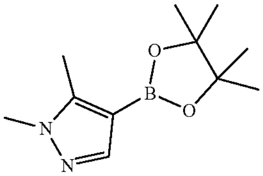 | 390 | $^1$H NMR (400 MHz, DMSO-d$_6$) δ 11.83 (s, 1H), 8.35 (d, J = 5.0 Hz, 1H), 8.02 (s, 1H), 7.68 (d, J = 5.1 Hz, 1H), 7.62-7.59 (m, 1H), 7.07 (s, 1H), 7.01 (s, 1H), 4.59 (s, 1H), 4.20 (s, 1H), 4.00 (d, J = 11.1 Hz, 1H), 3.81 (d, J = 2.6 Hz, 3H), 3.77 (s, 1H), 3.68 (d, J = 11.3 Hz, 1H), 3.53 (s, 1H), 3.26 (d, J = 15.5 Hz, 1H), 2.72 (s, 3H), 1.27 (s, 3H). 43% |
| 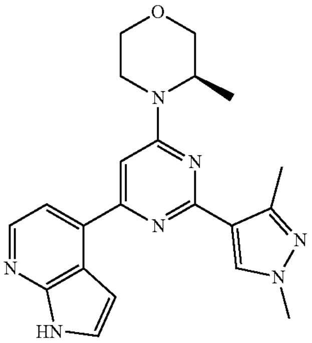 B5 | 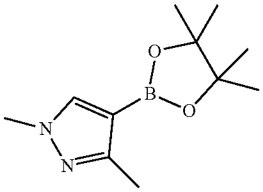 | 390 | $^1$H NMR (400 MHz, DMSO-d$_6$) δ 11.83 (s, 1H), 8.34 (d, J = 4.9 Hz, 1H), 8.28 (s, 1H), 7.68 (d, J = 5.0 Hz, 1H), 7.62-7.57 (m, 1H), 7.05 (s, 1H), 7.02-6.97 (m, 1H), 4.59 (s. 1H), 4.21 (d, J = 13.1 Hz, 1H), 3.99 (d, J = 11.6 Hz, 1H), 3.83 (s, 3H), 3.78 (d, J = 11.4 Hz, 1H), 3.68 (d, J = 11.7 Hz, 1H), 3.53 (s, 1H), 3.24 (s, 1H), 2,54 (s, 3H), 1.26 (d, J = 6.5 Hz, 3H). 17% |

-continued
| Structure | The structure of boronic ester | LC-MS/ [M + H]+ | 1H NMR/yield |
|---|---|---|---|
| 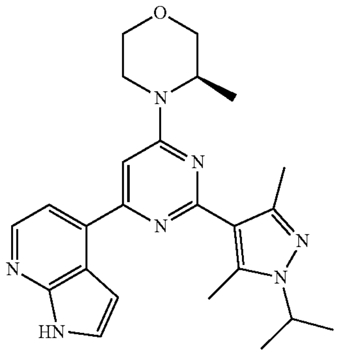 B6 | 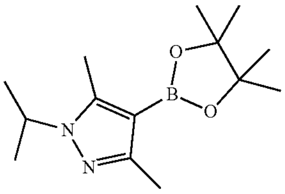 [SMILES: Cc1nn(C(C)C)c(C)c1B1OC(C)(C)C(C)(C)O1] | 432 | $^1$H NMR (400 MHz, DMSO-$d_6$) δ 11.85 (s, 1H), 8.35 (d, J = 5.0 Hz, 1H), 7.65 (d, J = 5.0 Hz, 1H), 7.59 (d, J = 3.0 Hz, 1H), 7.03 (s, 1H), 6.91 (dd, J = 3.5, 1.8 Hz, 1H), 4.55 (dt, J = 13.0, 6.6 Hz, 2H), 4.14 (d, J = 13.4 Hz, 1H), 3.99 (d, J = 10.6 Hz, 1H), 3.78 (d, J = 11.6 Hz, 1H), 3.67 (d, J = 10.8 Hz, 1H), 3.53 (dd, J = 12.4, 9.6 Hz, 1H), 3.24 (d, J = 12.1 Hz, 1H), 2.68 (s, 3H), 2.49 (s, 3H), 1.38 (d, J = 6.5 Hz, 6H), 1.27 (s, 3H). 15% |
| 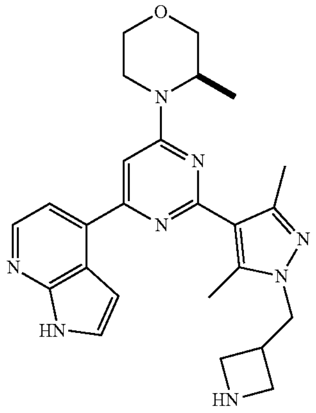 B7 | 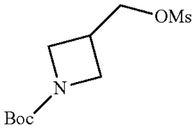 [SMILES: CC(C)(C)OC(=O)N1CC(COS(C)(=O)=O)C1] | 459 | $^1$H NMR (400 MHz, DMSO-$d_6$) δ 11.85 (s, 1H), 8.34 (dd, J = 5.0, 2.9 Hz, 1H), 7.64 (d, J = 4.8 Hz, 1H), 7.59 (d, J = 3.0 Hz, 1H), 7.02 (d, J = 3.7 Hz, 1H), 6.90 (d, J = 3.5 Hz, 1H), 4.57 (s, 1H), 4.19 (dd, J = 33.8, 10.3 Hz, 3H), 3.99 (d, J = 11.3 Hz, 1H), 3.78 (d, J = 11.6 Hz, 1H), 3.67 (d, J = 12.3 Hz, 1H), 3.58-3.40 (m, 3H), 2.99 (t, J = 11.3 Hz, 3H), 2.66 (s, 3H), 2.47 (s, 3H), 2.05-1.96 (m, 1H), 1.27 (s, 3H). 43% |
Example 5
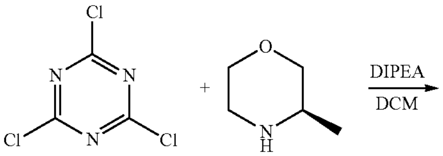
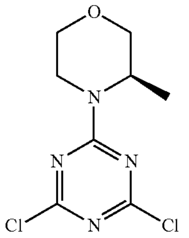
C1-3
-continued
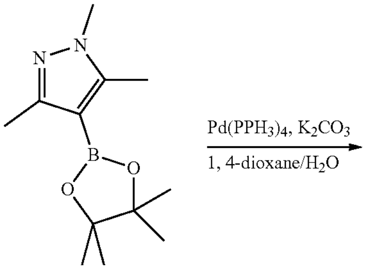
a10
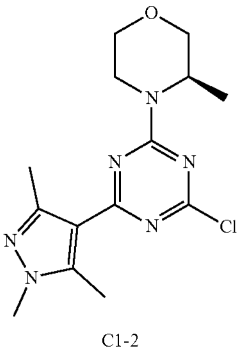
C1-2
TD107045-2 +

-continued

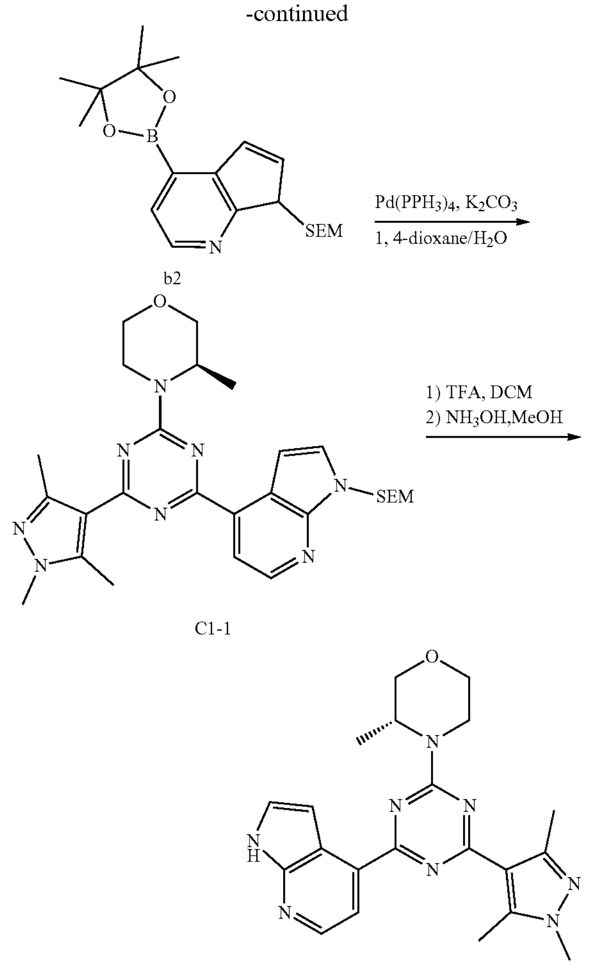

b2

C1-1

C1

At −50° C., cyanuric chloride (110 mmol, 1.97 g) and D1PEA (210 mmol, 2.76 g) were dissolved in 70 mL of dichloromethane, and (R)-2-methyl morpholine (110 mmol, 1.08 g) was slowly added dropwise. After the mixture was stirred at −50° C. for 1 hour, 50 mL of 1N HCl aqueous solution was added to quench the reaction, extracted with dichloromethane. The organic phase was dried over anhydrous sodium sulfate, filtered, and the solvent was dried by rotary evaporation to afford C1-3 (2.5 g, yield: 92%). LC-MS: $[M+H]^+$: 249.

Under nitrogen protection, C1-3 (0.4 mmol, 100 mg), intermediate a10 (0.4 mmol, 95 mg), potassium carbonate (1.2 mmol, 166 mg) and $Pd(PPh_3)_4$ (0.04 mmol, 46 mg) were dissolved in 5 mL mixture of 1,4-dioxane and water (v/v: 9/1), and the mixture was heated at 80° C. for 12 hours. The reaction was stopped, filtered, the organic solvent was removed under reduced pressure, water was added, extracted with ethyl acetate, and separated by column chromatography to afford compound C1-2 (80 mg, yield: 41%), LC-MS: $[M+H]^+$: 323.

Under nitrogen protection, C1-2 (0.25 mmol, 80 mg), intermediate b2 (0.3 mmol, 112 mg), potassium carbonate (0.75 mmol, 103 mg) and $Pd(dppf)Cl_2$ (0.025 mmol, 18 mg) were dissolved in 5 mL mixture of 1,4-dioxane and water (v/v: 9/1), and the mixture was reacted at 100° C. for 3 hours. The reaction was stopped, filtered, the organic solvent was dried by rotary evaporation, water was added, extracted with ethyl acetate, and separated by column chromatography to afford compound C1-1 (90 mg, yield: 68%), LC-MS: $[M+H]^+$: 535.

C1-1 (9.17 mmol, 90 mg) was dissolved in 5 mL of dichloromethane. 2 mL of trifluoroacetic acid was added dropwise, and the mixture was reacted at room temperature for 2 hours. The reaction was stopped, the organic solvent was removed under reduced pressure. The mixture was dissolved in 5 mi, of methanol again, 2 mL of ammonia was added dropwise, and the mixture was reacted at room temperature for 12 hours. The solvent was removed under reduced pressure, and separated by preparative chromatography to afford compound C1 (37 mg, yield: 53%), LC-MS: $[M+H]^+$: 405.

NMR (400 MHz, DMSO-$d_6$) δ 11.91 (s, 11H), 8.40 (d, J=5.0 Hz, 1H), 8.05 (d, J=4.9 Hz, 1H), 7.65 (t, J=2.9 Hz, 1H), 7.21 (d, J=2.6 Hz, 1H), 4.03 (d, J=11.0 Hz, 1H), 3.83 (d, J=12.7 Hz, 1H), 3.75 (s, 3H), 3.71-3.66 (m, 1H), 3.52 (d, J=11.4 Hz, 1H) 3.30 (d, J=6.7 Hz, 2H), 2.73 (s, 3H), 2.54 (s, 4H), 1.34 (s, 3H).

Example 6

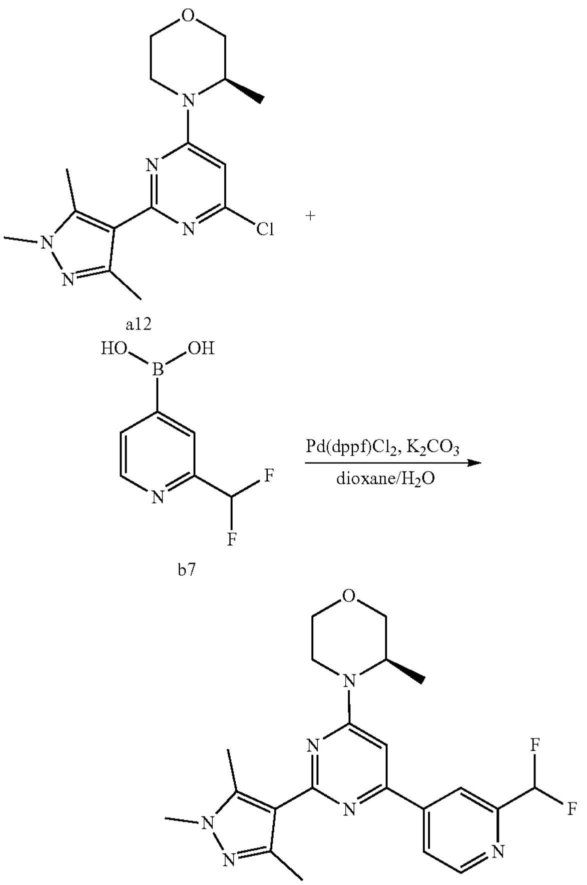

a12 b7

B8

Under nitrogen protection, intermediate a12 (0.19 mmol, 60 mg), intermediate b7 (0.37 mmol, 64 mg), potassium carbonate (0.57 mmol, 78 mg) and $Pd(dppf)Cl_2$ (0.02 mmol, 14 mg) were dissolved in 5 mL mixture of 1,4-dioxane and water (v/v: 9/1), and the mixture was reacted at 100° C. for 2 hours. The reaction was stopped, filtered, the organic solvent was dried by rotary evaporation, water was added, extracted with ethyl acetate, and separated by preparative chromatography to afford compound B8 (24 mg, yield: 31%), LC-MS: $[M+H]^+$: 415.

$^1$H NMR (400 MHz, DMSO-$d_6$) δ 8.85 (d, J=5.2 Hz, 1H), 8.47 (s, 1H), 8.35 (d, J=5.2 Hz, 1H), 7.33 (s, 1H), 7.05 (t, J=55.0 Hz, 1H), 4.66 (s, 1H), 4.24 (d, J=13.4 Hz, 1H), 4.00 (d, J=11.7 Hz, 1H), 3.79 (d, J=11.4 Hz, 1H), 3.73 (s, 3H), 3.69-3.63 (m, 1H), 3.50 (d, J=10.0 Hz, 1H), 3.30-3.24 (m, 1H), 2.66 (s, 3H), 2.49 (d, J=1.6 Hz, 3H), 1.25 (d, J=6.8 Hz, 3H).

Example 7

A25

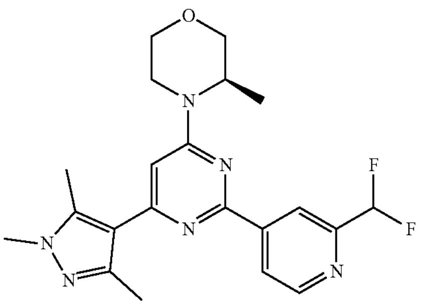

The title compound A25 was afforded by replacing intermediate a12 in Example 6 with intermediate all and referring to the route (17 mg, yield: 20%), LC-NIS: $[M+H]^+$: 415.

$^1$H NMR (400 MHz, DMSO-$d_6$) δ 8.84 (d, J=5.1 Hz, 1H), 8.49 (s, 1H), 8.43-8.38 (m, 1H), 7.08 (t, J=54.9 Hz, 1H), 6.69 (s, 1H), 4.56 (s, 1H), 4.26 (d, J=13.8 Hz, 1H), 4.00 (d, J=10.1 Hz, 1H), 3.79 (d, J=11.5 Hz, 1H), 3.74 (s, 3H), 3.70-3.64 (m, 1H), 3.52 (t, J=11.3 Hz, 1H), 3.29-3.20 (m, 1H), 2.52 (s, 3H), 2.38 (s, 3H), 1.26 (d, J=6.7 Hz, 3H).

Example 8

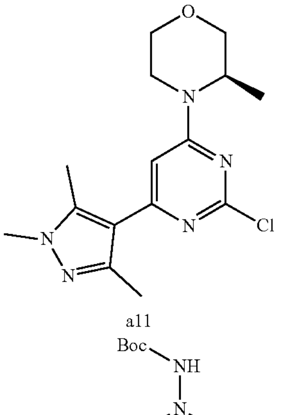

+ a11

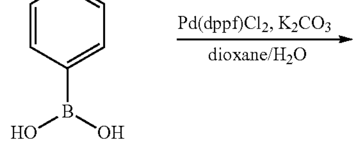

-continued

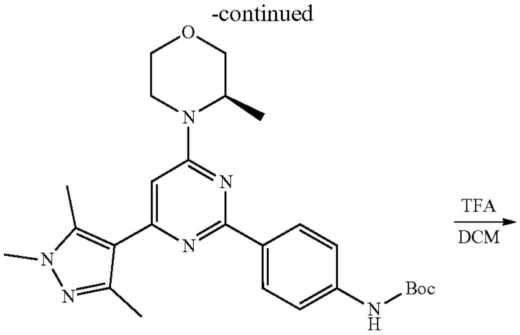

A26-2

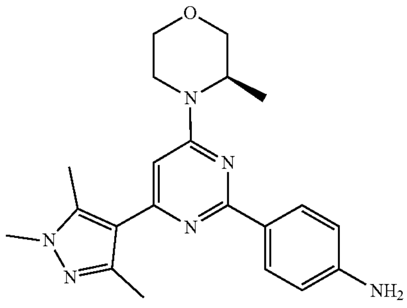

+

A26-1

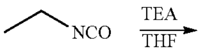

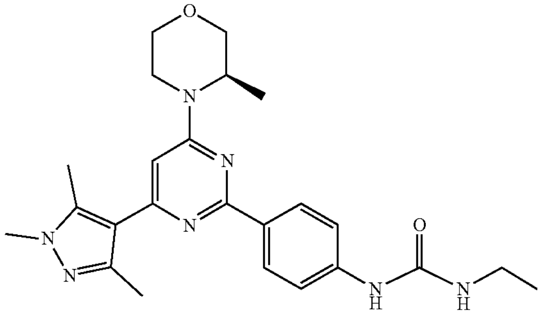

A26

Under nitrogen protection, intermediate all (0.31 mmol, 100 mg), 4-Bob-amino-phenylboronic acid (0.34 mmol, 81 mg), potassium carbonate (0.93 mmol, 129 mg) and Pd(dppf)$Cl_2$ (0.06 mmol, 45 mg) were dissolved in 5 mL mixture of 1,4-dioxane and water (v/v: 9/1), and the mixture was reacted at 90° C. for 12 hours. The reaction was stopped, filtered, the organic solvent was dried by rotary evaporation, water was added, extracted with ethyl acetate, and separated by column chromatography to afford compound A26-2 (124 mg, yield: 84%), LC-MS: $[M+H]^+$: 479.

Intermediate A26-2 (0.25 mmol, 124 mg) was dissolved in 5 mL of dichloromethane, 2 mL of trifluoroacetic acid was added dropwise, and the mixture was reacted at room temperature for 2 hours. The solvent was removed under reduced pressure to afford A26-1, LC-MS: $[M+H]^+$: 379.

In an ice bath, intermediate A26-1 (0.25 mmol) and triethylamine (1.4 mmol, 135 mg) were dissolved in 10 mL of anhydrous tetrahydrofuran, ethyl isocyanate (0.29 mmol, 20 mg) was added dropwise, after the mixture was stored and reacted for 1 hour, the reaction was quenched with 20 mL of saturated ammonium chloride aqueous solution, the solvent was removed under reduced pressure, and separated by preparative chromatography to afford compound A26 (40 mg, yield: 36%), LC-MS: $[M+H]^+$: 450.

Example 9
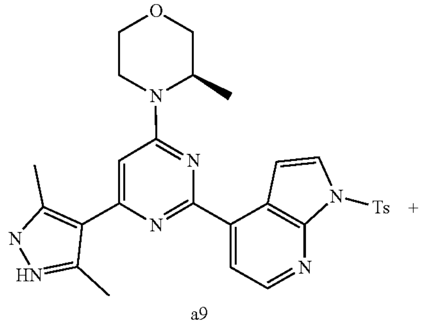
a9
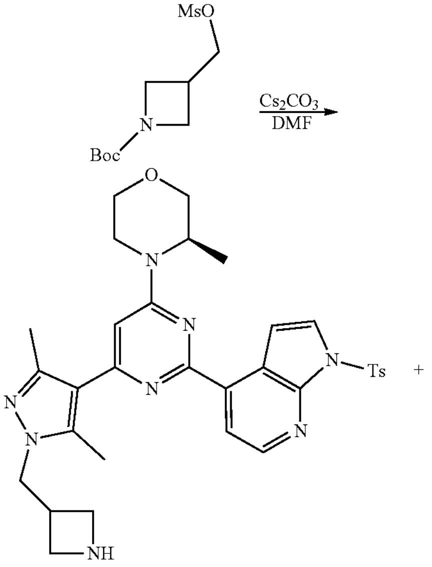
A18-1
-continued
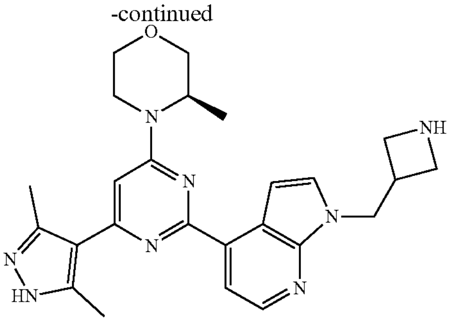
A27
Compound A27 was afforded at the same time by referring to the synthesis of compound A18, LC-MS: [M+H]+: 458.
$^1$H NMR (400 MHz, DMSO-$d_6$) δ 11.92 (s, 1H), 8.35 (d, J=5.0 Hz, 1H), 7.99 (d, J=5.1 Hz, 1H), 7.59 (d, J=3.4 Hz, 1H), 7.20 (s, 1H), 6.83 (s, 1H), 4.69-4.47 (m, 5H), 4.28 (s, 1H), 4.03 (d, J=11.2 Hz, 1H), 3.82 (d, J=12.0 Hz, 1H), 3.70 (d, J=11.1 Hz, 1H), 3.55 (t, J=12.4 Hz, 1H), 3.35 (s, 1H), 3.12 (s, 2H), 2.64 (s, 6H), 2.00 (d, J=8.3 Hz, 11H), 1.31 (d, J=6.7 Hz, 3H).
Example 10
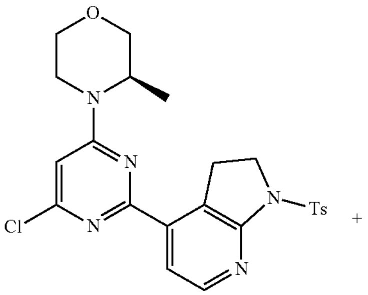
a4
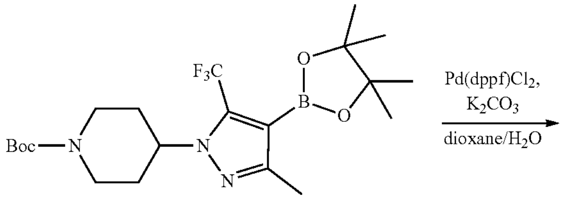
c3

-continued

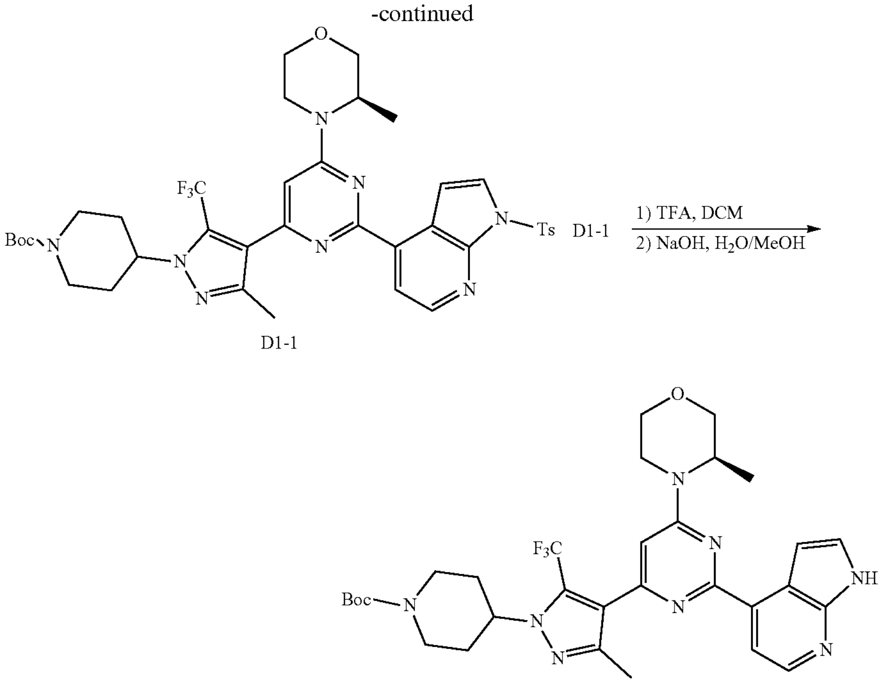

D1-1

D1

Under nitrogen protection, intermediate a4 (0.1 mmol, 48 mg) and intermediate c3 (0.15 mmol, 69 mg) was dissolved in 3 mL mixture of 1,4-dioxane and water (v/v: 9/1), potassium carbonate (0.3 mmol, 41 mg) and Pd(dppf)$Cl_2$ (0.01 mmol, 8 mg) were added, and the reaction was heated at 100° C., in microwave for 1 hour. The reaction was stopped, filtered, the organic solvent was evaporated under reduced pressure, 10 mL of water was added, extracted with ethyl acetate, and separated by column chromatography to afford compound D1-1 (77 mg, yield: 98%). LC-MS: $[M+H]^+$: 781.

Compound D1-1 (35 mg) was dissolved in 2 mL of dichloromethane, 0.5 mL of trifluoroacetic acid was added, after the mixture was reacted at room temperature for 2 hours, the solvent was removed under reduced pressure. Then the mixture was dissolved in mixture of water (0.5 mL) and methanol (3 mL), sodium hydroxide (0.45 mmol, 18 mg) was added, and the mixture was refluxed until the reaction was complete. The mixture was filtered, the solvent was removed under reduced pressure, and separated by preparative chromatography to afford the title compound D1 (6 mg, two-step yield: 26%), LC-MS, $[M+H]^+$: 527.

The following compounds were synthesized with reference to the route of Example 10:

| Structure | The structure of intermediate replacing c3 | LC-MS/ $[M + H]^+$ | $^1$H NMR |
|---|---|---|---|
| 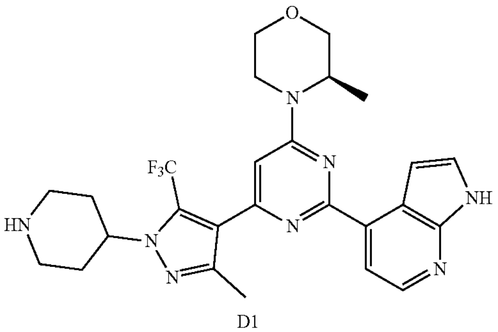 D1 | — | 527 | $^1$H NMR (400 MHz, DMSO-$d_6$) δ 11.76 (s, 1H), 8.32 (d, J = 5.0 Hz, 1H), 7.97 (d, J = 5.0 Hz, 1H), 7.56 (s, 1H), 7.20 (t, J = 2.6 Hz, 1H), 6.88 (s, 1H), 4.55 (s, 1H), 4.38-4.22 (m, 2H), 4.01 (d, J = 10.8 Hz, 1H), 3.79 (d, J = 11.5 Hz, 1H), 3.71-3.65 (m, 1H), 3.53 (d, J = 14.1 Hz, 1H), 3.09 (d, J = 12.4 Hz, 2H), 2.63 (t, J = 12.5 Hz, 2H), 2.27 (s, 3H), 2.11-1.95 (m, 3H), 1.87 (d, J = 12.0 Hz, 2H), 1.28 (d, J = 6.7 Hz, 3H). |

-continued

| Structure | The structure of intermediate replacing c3 | LC-MS/ [M + H]$^+$ | $^1$H NMR |
|---|---|---|---|
| 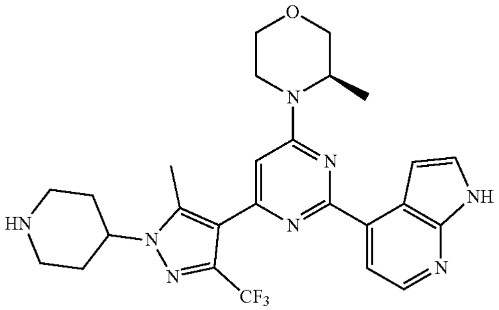 D2 | c4 | 527 | $^1$H NMR (400 MHz, DMSO-$d_6$) δ 11.76 (s, 1H), 8.32 (d, J = 5.0 Hz, 1H), 8.01 (d, J = 5.0 Hz, 1H), 7.57 (t, J = 2.9 Hz, 1H), 7.23 (dd, J = 3.4, 1.9 Hz, 1H), 6.77 (s, 1H), 4.52 (s, 1H), 4.44 (dt, J = 11.3, 6.0 Hz, 1H), 4.23 (d, J = 13.0 Hz, 1H), 4.06-3.99 (m, 1H), 3.81 (d, J = 11.5 Hz, 1H), 3.69 (dd, J = 11.1, 3.0 Hz, 1H), 3.59-3.49 (m, 1H), 3.34 (s, 1H), 3.07 (d, J = 12.5 Hz, 2H), 2.68-2.59 (m, 2H), 1.96-1.83 (m, 4H), 1.29 (d, J = 6.7 Hz, 3H). |
| 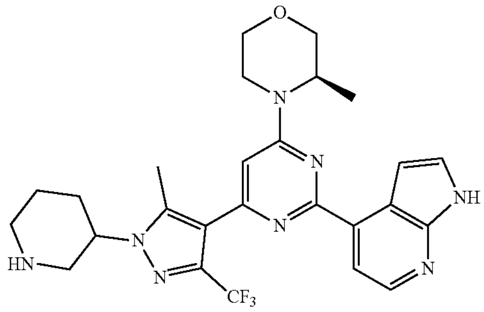 D12 (isomer 1) | c7 | 527 | $^1$H NMR (400 MHz, DMSO-$d_6$) δ 11.76 (s, 1H), 8.32 (d, J = 5.0 Hz, 1H), 8.01 (d, J = 5.0 Hz, 1H), 7.57 (s, 1H), 7.23 (s, 1H), 6.77 (s, 1H), 4.52 (s, 1H), 4.32 (s, 1H), 4.24 (d, J = 13.4 Hz, 1H), 4.02 (d, J = 11.3 Hz, 1H), 3.81 (d, J = 11.5 Hz, 1H), 3.69 (d, J = 11.2 Hz, 1H), 3.55 (t, J = 11.9 Hz, 1H), 3.29 (s, 1H), 3.12 (d, J = 11.4 Hz, 1H), 2.91 (d, J = 12.7 Hz, 1H), 2.80 (t, J = 11.2 Hz, 1H), 2.02 (d, J = 21.7 Hz, 3H), 1.76 (d, J = 13.3 Hz, 1H), 1.57 (s, 1H), 1.29 (d, J = 6.7 Hz, 3H). |
| 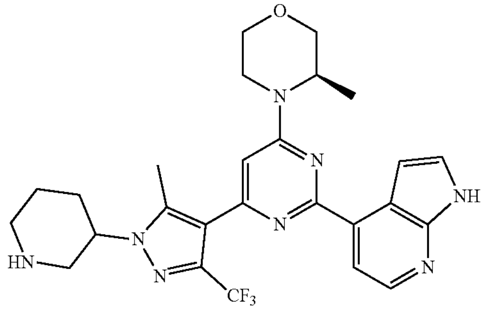 D13 (isomer 2) | c7 | 527 | $^1$H NMR (400 MHz, DMSO-$d_6$) δ 11.77 (s, 1H), 8.32 (d, J = 5.0 Hz, 1H), 8.01 (d, J = 5.0 Hz, 1H), 7.57 (t, J = 2.8 Hz, 1H), 7.23 (dd, J = 3.5, 1.9 Hz, 1H), 6.77 (s, 1H), 4.52 (s, 1H), 4.32 (s, 1H), 4.24 (d, J = 13.8 Hz, 1H), 4.03 (d, J = 10.8 Hz, 1H), 3.81 (d, J = 11.5 Hz, 1H), 3.69 (d, J = 11.0 Hz, 1H), 3.55 (t, J = 11.7 Hz, 1H), 3.29 (s, 1H), 3.11 (d, J = 13.0 Hz, 1H), 2.91 (d, J = 12.3 Hz, 1H), 2.79 (t, J = 11.1 Hz, 1H), 2.12-1.94 (m, 3H), 1.76 (d, J = 12.8 Hz, 1H), 1.58 (s, 1H), 1.29 (d, J = 6.7 Hz, 3H). |
| 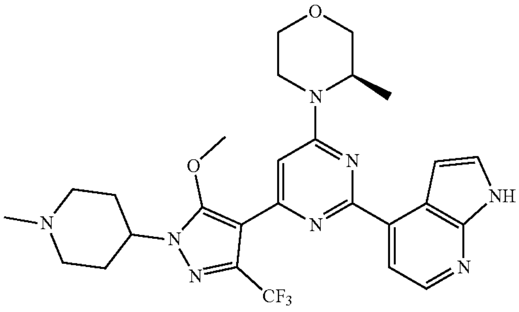 D14 | c8 | 557 | $^1$H NMR (400 MHz, DMSO-$d_6$) δ 11.77 (s, 1H), 8.33 (d, J = 5.1 Hz, 1H), 8.08-8.01 (m, 1H), 7.58 (t, J = 2.9 Hz, 1H), 7.25 (s, 1H), 6.85 (s, 1H), 4.49 (s, 1H), 4.35-4.18 (m, 2H), 4.03 (d, J = 10.2 Hz, 1H), 3.92 (s, 3H), 3.81 (d, J = 11.5 Hz, 1H), 3.70 (dd, J = 11.8, 2.9 Hz, 1H), 3.59-3.51 (m, 1H), 3.29 (s, 1H), 2.90 (d, J = 8.0 Hz, 2H), 2.22 (s, 3H), 2.06 (t, J = 10.7 Hz, 4H), 1.90 (d, J = 9.5 Hz, 2H), 1.30 (d, J = 6.7 Hz, 3H). |

-continued

| Structure | The structure of intermediate replacing c3 | LC-MS/ [M + H]+ | 1H NMR |
|---|---|---|---|
| 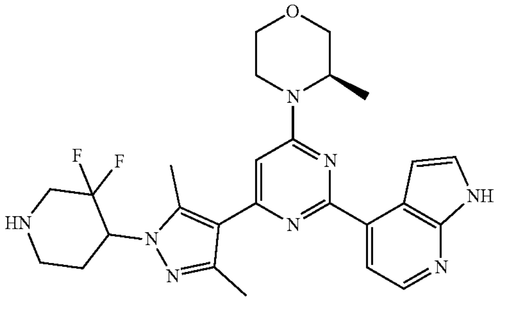 D57 | c14 | 509 | $^1$H NMR (400 MHz, DMSO-$d_6$) δ 11.77 (s, 1H), 8.33 (d, J = 5.0 Hz, 1H), 8.01 (d, J = 5.2 Hz, 1H), 7.59-7.55 (m, 1H), 7.24 (dd, J = 3.4, 2.0 Hz, 1H), 6.71 (s, 1H), 4.96-4.78 (m, 2H), 4.58 (s, 1H), 4.24 (d, J = 13.7 Hz, 1H), 4.05-3.98 (m, 1H), 3.81 (d, J = 12.3 Hz, 1H), 3.69 (d, J = 10.8 Hz, 1H), 3.59-3.50 (m, 1H), 3.07 (d, J = 13.4 Hz, 2H), 3.00 (d, J = 10.8 Hz, 1H), 2.92 (d, J = 14.9 Hz, 1H), 2.77-2.65 (m, 2H), 2.54 (s, 3H), 2.39 (s, 3H), 1.29 (d, J = 6.6 Hz, 3H). |

Example 11: D4

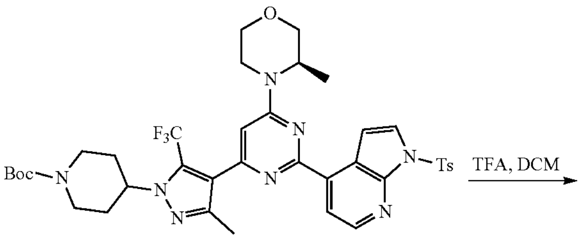

D1-1

-continued

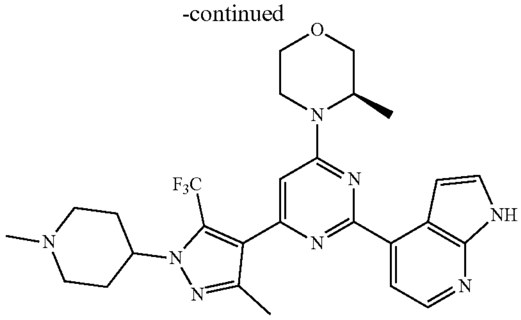

D4

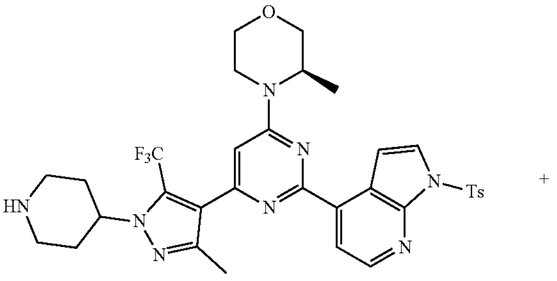

D4-1

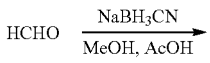

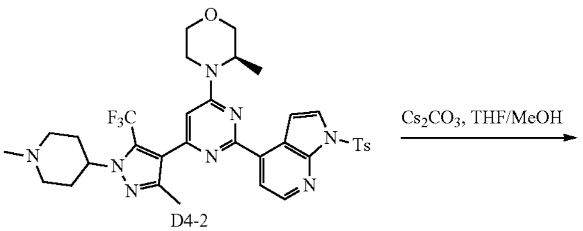

D4-2

Compound D1-1 (0.098 mmol, 77 mg) was dissolved in 3 mL of dichloromethane, 1 mL of trifluoroacetic acid was added dropwise, after the mixture was reacted at room temperature for 2 hours, the solvent was removed under reduced pressure to afford compound D4-1 (66 mg, quantitative yield). LC-MS: $[M+H]^+$: 682.

Compound D4-1 from the previous step was dissolved in 5 mL of methanol, 30% formaldehyde aqueous solution (0.2 mmol, 20 μL) and $NaBH_3CN$ (0.3 mmol, 20 mg) were added, after 1 drop of acetic acid was added dropwise, the mixture was reacted at room temperature for 3 hours. The solvent was removed under reduced pressure, and separated by TLC chromatography to afford compound D4-2 (40 mg, yield: 97%). LC-MS: $[M+H]^+$: 695.

Compound D4-2 (40 mg) was dissolved in mixture of tetrahydrofuran (1.5 mL) and methanol (2 mL), cesium carbonate (0.1 mmol, 33 mg) was added, and the mixture was refluxed until the reaction was complete. The mixture was filtered, the solvent was removed under reduced pressure, and separated by preparative chromatography to afford the title compound D4 (16 mg, yield: 93%), LC-MS: $[M+H]^+$: 541.

$^1$H NMR (400 MHz, DMSO-$d_6$) δ 11.76 (s, 1H), 8.32 (d, J=5.0 Hz, 1H), 7.97 (d, J=5.0 Hz, 1H), 7.56 (t, J=2.9 Hz, 1H), 7.20 (d, J=3.4, 2.0 Hz, 1H), 6.88 (s, 1H), 4.55 (s, 1H), 4.31-4.18 (m, 2H), 4.01 (d, J=10.2 Hz, 1H), 3.79 (d, J=11.4 Hz, 1H), 3.68 (d, 10.9 Hz, 1H), 3.54 (t, J=12.0 Hz, 1H), 2.92 (d, J=11.3 Hz, 2H), 2.27 (s, 3H), 2.21 (d, J=159 Hz, 5H) [Me, $CH_2$], 2.08 (d, J=11.9 Hz, 2H), 2.04-1.97 (m, 1H), 1.90 (d, J=11.8 Hz, 2H), 1.28 (d, J=6.7 Hz, 3H).

Example 12:133

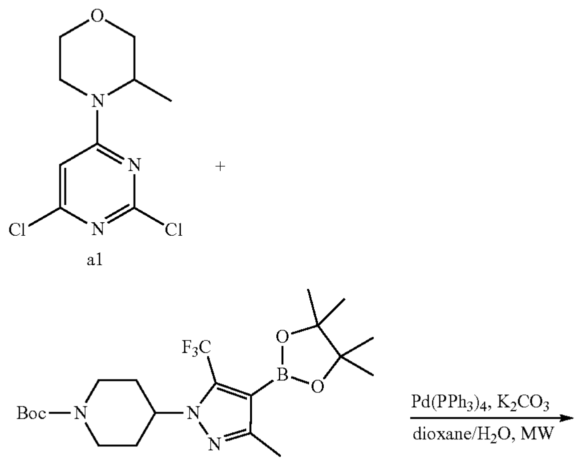

a1 c3

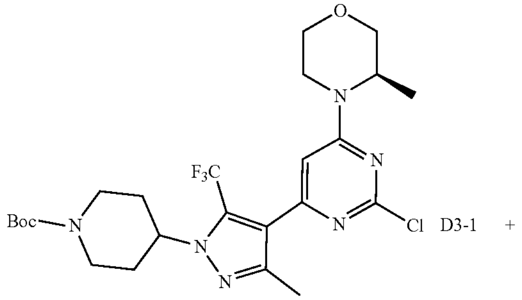

D3-1

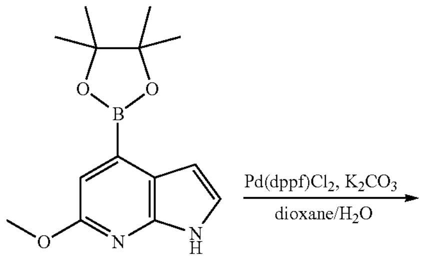

c5

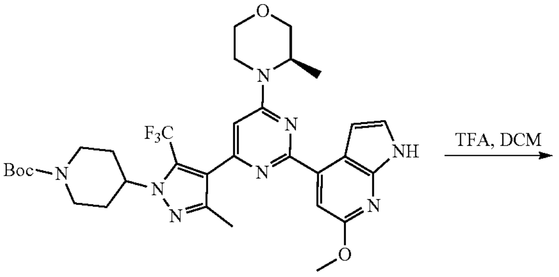

D3-2

-continued

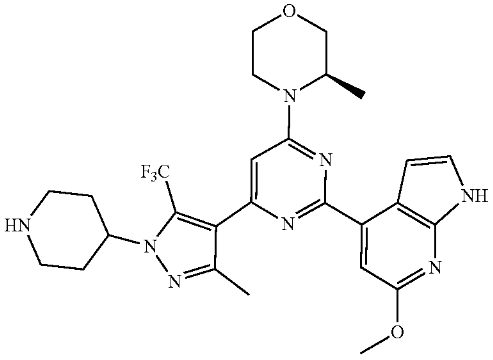

D3

Under nitrogen protection, intermediate a1 (1 mmol, 247 mg) and intermediate c3 (1.7 mmol, 780 mg) were dissolved in 10 mL mixture of 1,4-dioxane and water (v/v: 9/1), potassium carbonate (3 mmol, 414 mg) and $Pd(PPh_3)_4$ (0.1 mmol, 115 mg) were added, and the reaction was heated at 100° C. in microwave for 1 hour. The reaction was stopped, filtered, the organic solvent was dried by rotary evaporation, water was added, extracted with ethyl acetate, and separated by column chromatography to afford compound D3-1. LC-MS: $[M+H]^+$: 545.

Under nitrogen protection, compound D3-1 (0.11 mmol, 100 mg) and intermediate c5 (0.22 mmol, 60 mg) were dissolved in 3 mL mixture of 1,4-dioxane and water (v/v: 9/1), potassium carbonate (0.33 mmol, 45 mg) and Pd(dppf)$Cl_2$ (0.011 mmol, 8 mg) were added, and the mixture was reacted at 100° C. in microwave for 30 minutes. The reaction was stopped, filtered, the organic solvent was dried by rotary evaporation, water was added, extracted with ethyl acetate, and separated by column chromatography to afford compound 133-2 (20 mg, yield: 28%). LC-MS: $[M+H]^+$: 657.

Compound D3-2 (0.036 mmol, 24 mg) was dissolved in 2 mL of dichloromethane, 0.5 mL of trifluoroacetic acid was added, after the mixture was reacted at room temperature for 2 hours, the solvent was removed under reduced pressure, and separated by preparative chromatography to afford the title compound D3 (8 mg, yield: 40%), LC-MS: $[M+H]^+$: 557.

$^1H$ NMR (400 MHz, DMSO-$d_6$) 11.58 (s, 1H), 7.43 (s, 1H), 7.27 (t, J=2.9 Hz, 1H), 7.09-7.06 (m, 1H), 6.89 (s, 1H), 4.54 (s, 1H), 4.35-4.21 (m, 2H), 4.00 (d, J=9.4 Hz, 1H), 3.91 (s, 3H), 3.79 (d, J=11.6 Hz, 1H), 3.68 (d, J=10.4 Hz, 1H), 3.58-3.50 (m, 1H), 3.29 (s, 1H), 3.08 (d, J=12.6 Hz, 2H), 2.61 (t, J=12.4 Hz, 2H), 2.27 (s, 3H), 2.05-1.98 (m, 2H), 1.86 (d, J=12.0 Hz, 2H), 1.27 (d, J=6.7 Hz, 3H).

Example 13: D5

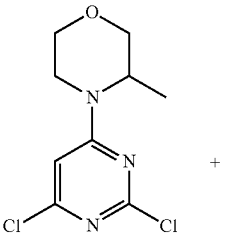

a1

-continued

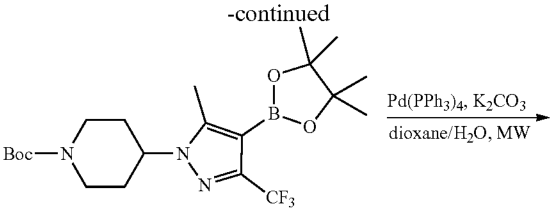

c4

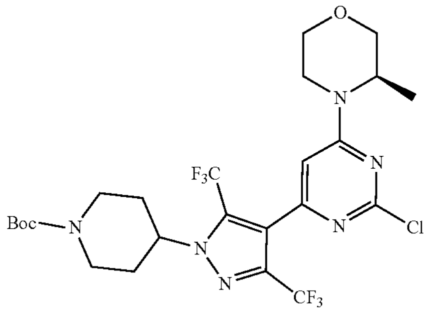

D5-1 +

D5-1

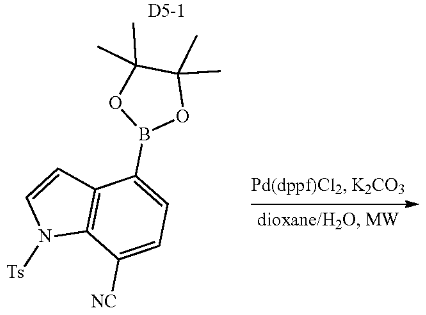

c2

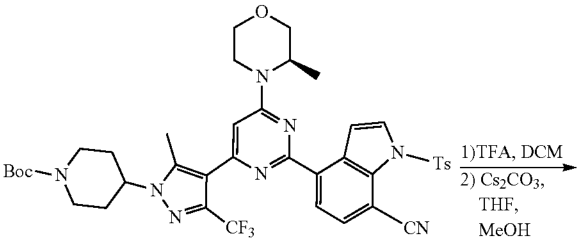

D5-2

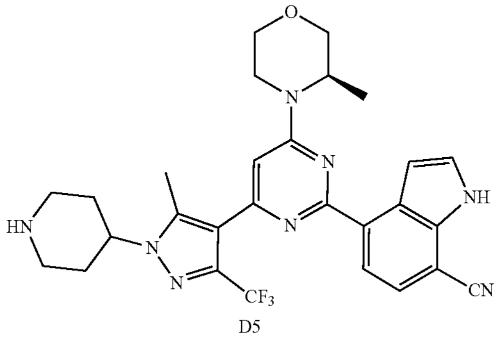

D5

Under nitrogen protection, intermediate a1 (1 mmol, 247 mg) and intermediate c4 (1.6 mmol, 734 mg) were dissolved in 10 mL mixture of 1,4-dioxane and water (v/v: 9/1), potassium carbonate (3 mmol, 414 mg), $Pd(PPh_3)_4$ (0.1 mmol, 115 mg) were added, and the mixture was reacted at 100° C. in microwave for 30 minutes. The reaction was stopped, filtered, the organic solvent was removed under reduced pressure, 10 ml, of water was added, extracted with ethyl acetate, and separated by column chromatography to afford compound D5-1 (150 mg, yield: 28%), LC-MS: $[M+H]^+$: 545.

Under nitrogen protection, compound D5-1 (0.18 mmol, 100 mg) and intermediate c2 (0.26 mmol, 109 mg) were dissolved in 5 mL mixture of 1,4-dioxane and water (v/v: 9/1), potassium carbonate (0.54 mmol, 74 mg), $Pd(dppf)Cl_2$ (0.018 mmol, 13 mg) were added, and the mixture was reacted at 100° C. in microwave for 30 minutes. The reaction was stopped, filtered, the organic solvent was removed under reduced pressure, 10 mL of water was added, extracted with ethyl acetate, and separated by TLC chromatography to afford compound D5-2 (110 mg, yield: 76%), LC-MS: $[M+H]^+$: 805.

Compound D5-2 (0.137 mmol, 110 mg) was dissolved in 4 mL of dichloromethane, 1 mL of trifluoroacetic acid was added dropwise, after the mixture was reacted at room temperature for 2 hours, the solvent was removed under reduced pressure. Then the mixture was dissolved in mixture of 5 mL methanol and 5 mL tetrahydrofuran again, cesium carbonate (1.37 mmol, 446 mg) was added, and the mixture was reacted at 70° C. for 1 hour. The solvent was removed under reduced pressure, and separated by preparative chromatography to afford the title compound D5 (24 mg, yield: 32%), LC-MS: $[M+H]^+$: 551.

$^1H$ NMR (400 MHz, DMSO-$d_6$) δ 12.11 (s, 1H), 8.21 (d, J=8.0 Hz, 1H), 7.70 (d, J=8.0 Hz, 1H), 7.58 (d, J=2.8 Hz, 1H), 7.47 (d, J=3.0 Hz, 1H), 6.75 (s, 1H), 4.56-4.38 (m, 2H), 4.22 (d, J=13.3 Hz, 1H), 4.06-3.98 (m, 1H), 3.80 (d, J=11.5 Hz, 1H), 3.72-3.65 (m, 1H), 3.58-3.50 (m, 1H), 3.29 (s, 1H), 3.06 (d, J=12.4 Hz, 2H), 2.68-2.60 (m, 2H), 1.87 (s, 4H), 1.29 (d, J=6.7 Hz, 3H).

Example 14: D6

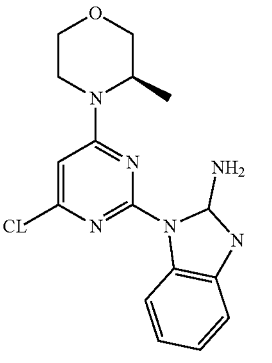

+ d1

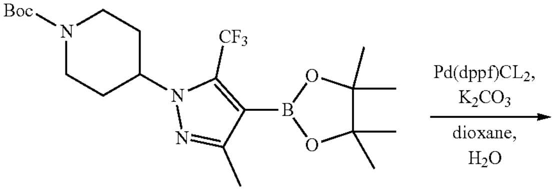

c3

-continued

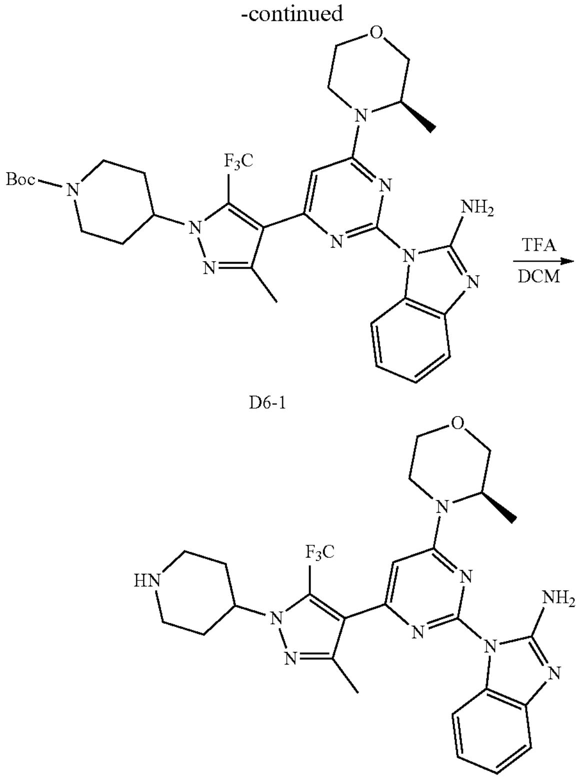

D6-1

D6

Under nitrogen protection, intermediate d1 (0.15 mmol, 50 mg) and intermediate c3 (0.17 mmol, 63 mg) were dissolved in 5 mL mixture of 1,4-dioxane and water (v/v: 9/1), potassium carbonate (0.29 mmol, 41 mg), Pd(dppf)$Cl_2$ (0.014 mmol, 11 mg) were added, and the mixture was reacted at 100° C. in microwave for 30 minutes. The reaction was stopped, filtered, the organic solvent was removed under reduced pressure, 10 mL of water was added, extracted with ethyl acetate, and separated by TLC chromatography to afford compound D6-1 (50 mg, yield: 52%), LC-MS: $[M+H]^+$: 642.

Compound D6-1 (0.078 mmol, 50 mg) was dissolved in 4 mL of dichloromethane, 1 mL of trifluoroacetic acid was added dropwise, after the mixture was reacted at room temperature for 2 hours, the solvent was removed under reduced pressure, and separated by preparative chromatography to afford the title compound D6 (14 mg, yield: 34%), LC-MS: $[M+H]^+$: 542.

The following compounds were synthesized with reference to the route of Example 14:

| Structure | The structure of intermediate replacing d1 | LC-MS/ $[M + H]^+$ | $^1H$ NMR |
|---|---|---|---|
| 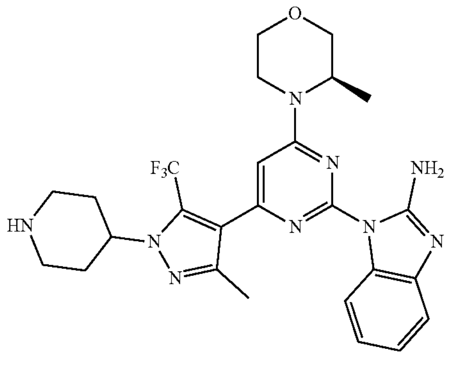 D6 | — | 542 | $^1H$ NMR (400 MHz, DMSO-$d_6$) δ 8.15 (d, J = 7.9 Hz, 1H), 7.66 (s, 2H), 7.19 (d, J = 7.6 Hz, 1H), 7.08 (t, J = 7.5 Hz, 1H), 6.96 (t, J = 7.7 Hz, 1H), 6.85 (s, 1H), 4.47 (s, 1H), 4.31 (s, 1H), 4.12 (d, J = 13.2 Hz, 1H), 4.01 (d, J = 11.3 Hz, 1H), 3.79 (d, J = 11.6 Hz, 1H), 3.69 (d, J = 10.9 Hz, 1H), 3.55 (t, J = 12.0 Hz, 1H), 3.36 (d, J = 11.9 Hz, 1H), 3.07 (d, J = 12.7 Hz, 2H), 2.61 (t, J = 12.4 Hz, 2H), 2.27 (s, 3H), 2.01 (t, J = 8.5 Hz, 2H), 1.86 (d, J = 11.5 Hz, 2H), 1.30 (d, J = 6.7 Hz, 3H). |

-continued

| Structure | The structure of intermediate replacing d1 | LC-MS/ $[M + H]^+$ | $^1H$ NMR |
|---|---|---|---|
| 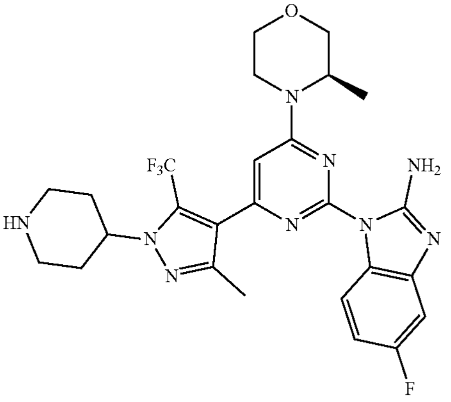 D7 | d2 | 560 | $^1H$ NMR (400 MHz, DMSO-$d_6$) δ 8.12 (dd, J = 8.8, 5.2 Hz, 1H), 7.84 (s, 2H), 6.97 (dd, J = 9.7, 2.6 Hz, 1H), 6.86 (s, 1H), 6.77 (td, J = 9.4, 2.7 Hz, 1H), 4.45 (s, 1H), 4.30 (s, 1H), 4.10 (d, J = 12.7 Hz, 1H), 4.01 (d, J = 10.3 Hz, 1H), 3.79 (d, J = 11.7 Hz, 1H), 3.72-3.66 (m, 1H), 3.55 (t, J = 11.3 Hz, 1H), 3.34 (d, J = 3.9 Hz, 1H), 3.06 (d, J = 12.8 Hz, 2H), 2.69-2.56 (m, 3H), 2.26 (s, 3H), 2.01 (dd, J = 12.6, 4.2 Hz, 2H), 1.85 (d, J = 11.4 Hz, 2H), 1.30 (d, J = 6.7 Hz, 3H). |

Example 15: D8

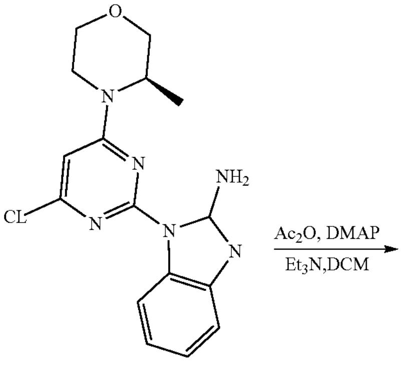

d1

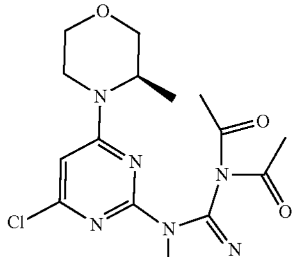

D8-1

+

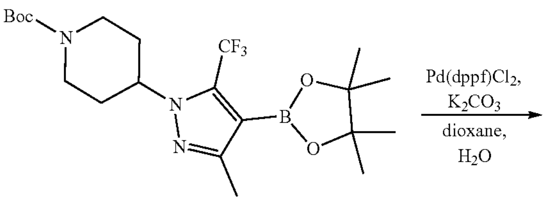

c3

-continued

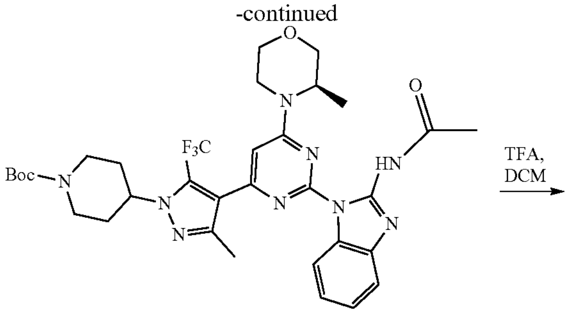

D8-2

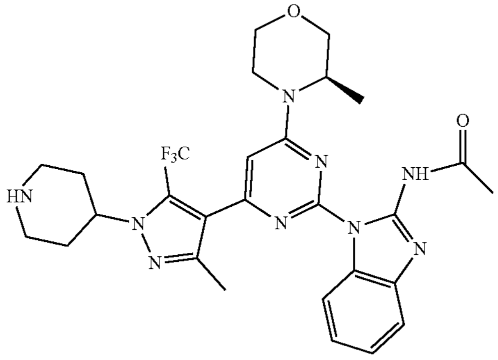

D8

Intermediate d1 (0.58 mmol, 200 mg) and 4-dimethylaminopyridine DMAP (0.029 mmol, 3.5 mg) were dissolved in 10 mL of dichloromethane, after triethylamine (2.9 mmol, 294 mg), acetic anhydride (261 mg, 4.4 mL) were added, the mixture was reacted at room temperature for 12 hours. The reaction was stopped, 30 mL of water was added, extracted with dichloromethane, dried over anhydrous sodium sulfate to afford compound D8-1 (200 mg, yield: 81%), LC-MS: $[M+H]^+$: 429.

Under nitrogen protection, compound D8-1 (0.16 mmol, 70 mg) and intermediate c3 (0.32 mmol, 150 rag) were dissolved in 5 mL mixture of 1,4-dioxane and water (v/v: 9/1), potassium carbonate (0.32 mmol, 44 mg), $Pd(dppf)Cl_2$ (0.016 mmol, 12 mg) were added, and the mixture was heated at 100° C. in microwave for 1 hour. The reaction was stopped, filtered, the organic solvent was removed under reduced pressure, 10 mL of water was added, extracted with ethyl acetate, and separated by TLC chromatography to afford compound D8-2 (40 mg, yield: 37%), LC-MS: $[M+H]^+$: 684.

Compound D8-2 (0.058 mmol, 40 mg) was dissolved in 4 mL of dichloromethane, 1 mL of trifluoroacetic acid was added dropwise, after the mixture was reacted at room temperature for 2 hours, the solvent was removed under reduced pressure, and separated by preparative chromatography to afford the title compound D8 (11 mg, yield: 33%), LC-MS: $[M+H]^+$: 584.

The following compounds were synthesized with reference to the route of Example 15:

| Structure | The structure replacing $Ac_2O$ | LC-MS/ $[M + H]^+$ | $^1H$ NMR |
|---|---|---|---|
| 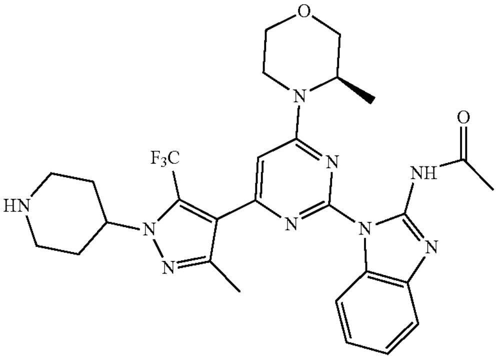 D8 | — | 584 | $^1H$ NMR (400 MHz, DMSO-$d_6$) δ 11.57 (s, 1H), 8.19 (d, J = 7.6 Hz, 1H), 7.59-7.54 (m, 1H), 7.29-7.21 (m, 2H), 6.91 (s, 1H), 4.48 (s, 1H), 4.33 (s, 1H), 4.14 (s, 1H), 4.00 (d, J = 11.4 Hz, 1H), 3.78 (d, J = 11.6 Hz, 1H), 3.68 (d, J = 11.5 Hz, 1H), 3.57-3.50 (m, 1H), 3.38 (d, J = 3.6 Hz, 1H), 3.10 (d, J = 12.5 Hz, 2H), 2.65 (s, 2H), 2.29 (s, 3H), 2.26 (s, 3H), 2.06-1.99 (m, 2H), 1.86 (d, J = 12.4 Hz, 2H), 1.30 (d, J = 4.5 Hz, 3H). |
| 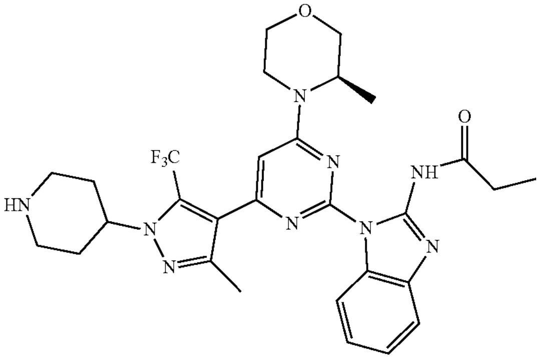 D21 | 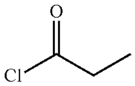 | 598 | $^1H$ NMR (400 MHz, DMSO-$d_6$) δ 11.66 (s, 1H), 8.79 (d, J = 11.3 Hz, 1H), 8.19 (d, J = 7.8 Hz, 1H), 7.61-7.55 (m, 1H), 7.31-7.23 (m, 2H), 6.92 (s, 1H), 4.73 (d, J = 4.3 Hz, 1H), 4.47 (s, 1H), 4.15 (s, 1H), 4.03 (s, 1H), 3.78 (s, 1H), 3.68 (d, J = 8.5 Hz, 1H), 3.58-3.50 (m, 2H), 3.44 (s, 1H), 3.37 (dd, J = 13.2, 3.8 Hz, 1H), 3.23 (t, J = 12.1 Hz, 2H), 2.63 (d, J = 7.5 Hz, 2H), 2.27 (s, 3H), 2.11 (d, J = 13.2 Hz, 3H), 2.04-1.95 (m, 1H), 1.30 (d, J = 6.5 Hz, 3H), 1.00 (t, J = 7.4 Hz, 3H). |
| 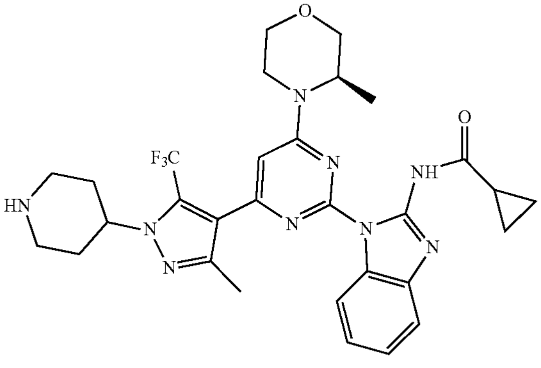 D38 | 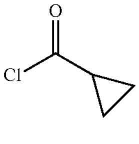 | 610 | $^1H$ NMR (400 MHz, DMSO-$d_6$) δ 11.62 (s, 1H), 8.13 (d, J = 7.2 Hz, 1H), 7.57 (dd, J = 6.8, 2.1 Hz, 1H), 7.25 (ddd, J = 7.6, 5.3, 1.7 Hz, 2H), 6.90 (s, 1H), 4.46 (s, 1H), 4.30 (t, J = 10.6 Hz, 1H), 4.16 (s, 1H), 4.03-3.95 (m, 1H), 3.78 (d, J = 11.6 Hz, 1H), 3.67 (dd, J = 11.3, 3.1 Hz, 1H), 3.35 (dd, J = 12.6, 9.6 Hz, 1H), 3.35 (s, 1H), 3.07 (d, J = 12.5 Hz, 2H), 2.61 (t, J = 12.2 Hz, 2H), 2.33 (s, 1H), 2.26 (s, 3H), 2.09-1.95 (m, 3H), 1.84 (d, J = 11.7 Hz, 2H), 1.29 (d, J = 6.7 Hz, 3H), 0.84 (dt, J = 6.5, 3.0 Hz, 2H), 0.77 (dd, J = 7.6, 4.1 Hz, 2H). |

Example 16: D10

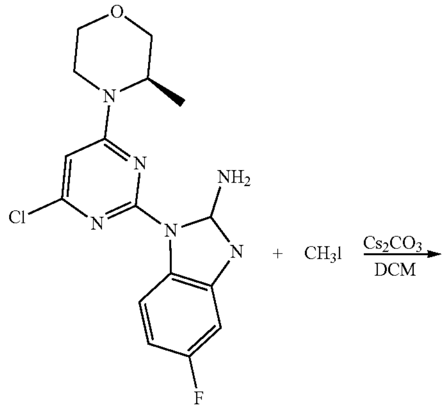

d2

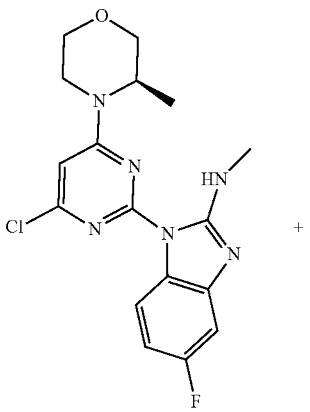

D10-1

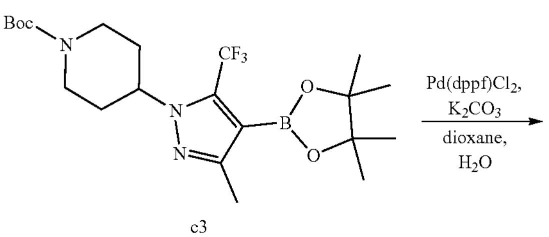

c3

-continued

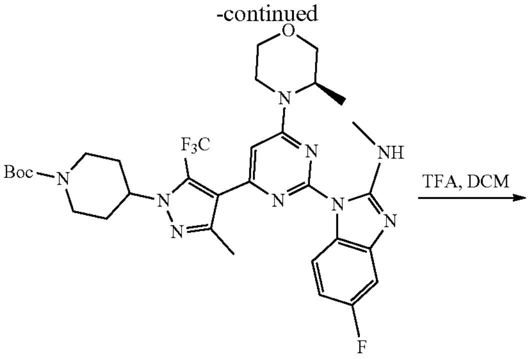

D10-2

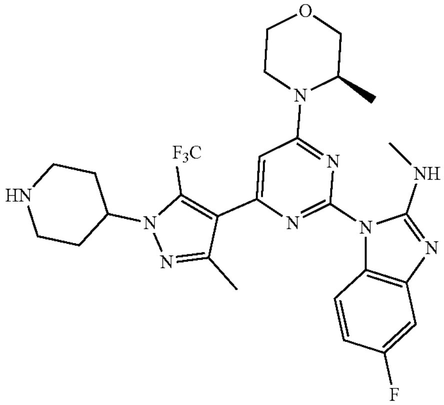

D10

Intermediate d2 (0.27 mmol, 100 mg) and cesium carbonate (0.69 mmol, 224 mc) were dissolved in 10 mL of DMF, methyl iodide (0.33 mmol, 47 mg) was added dropwise, and the mixture was reacted at 55° C. for 2 hours. The reaction was stopped, 30 mL of water was added, extracted with ethyl acetate, dried over anhydrous sodium sulfate, and separated by TLC chromatography to afford compound D10-1 (80 mg, yield: 82%), LC-MS: $[M+H]^+$: 363.

Under nitrogen protection, compound D101 (0.21 mmol, 80 mg) and intermediate c3 (0.42 mmol, 195 mg) were dissolved in 5 mL mixture of 1,4-dioxane and water (v/v: 9/1), potassium carbonate (0.42 mmol, 59 mg), $Pd(dppf)Cl_2$ (0.021 mmol, 16 mg) were added, and the mixture was heated at 100° C. in microwave for 1 hour. The reaction was stopped, filtered, the organic solvent was removed under reduced pressure, 10 mL of water was added, extracted with ethyl acetate, and separated by TLC chromatography to afford compound D10-2 (40 mg, yield: 30%), LC-MS: $[M+H]^+$: 674.

Compound D10-2 (0.06 mmol, 40 mg) was dissolved in 4 mL of dichloromethane. 1 mL of trifluoroacetic acid was added dropwise, after the mixture was reacted at room temperature for 2 hours, the solvent was removed under reduced pressure, and separated by preparative chromatography to afford the title compound D10 (10 mg, yield: 29%), LC-MS: $[M+H]^+$: 574.

The following compounds were synthesized with reference to the route of Example 16:

| Structure | The structure of intermediate replacing d2 | LC-MS/ [M + H]$^+$ | $^1$H NMR |
|---|---|---|---|
| 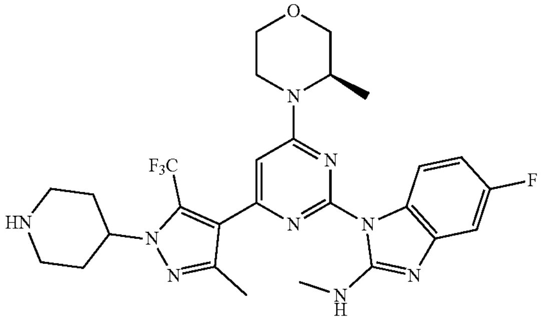 D10 | — | 574 | $^1$H NMR (400 MHz, DMSO-$d_6$) δ 8.58 (d, J = 5.6 Hz, 1H), 8.14 (dd, J = 8.8, 5.1 Hz, 1H), 7.06 (dd, J = 9.8, 2.7 Hz, 1H), 6.86 (s, 1H), 6.80 (d, J = 10.0 Hz, 1H), 4.45 (s, 1H), 4.36 (s, 1H), 4.11 (d, J = 13.9 Hz, 1H), 4.01 (d, J = 10.5 Hz, 1H), 3.79 (d, J = 11.8 Hz, 1H), 3.69 (d, J = 11.4 Hz, 1H), 3.53 (d, J = 12.6 Hz, 1H), 3.29 (s, 1H), 3.10 (d, J = 12.5 Hz, 2H), 3.03 (d, J = 4.8 Hz, 3H), 2.65 (t, J = 11.5 Hz, 2H), 2.28 (s, 3H), 2.02 (dd, J = 17.5, 9.7 Hz, 2H), 1.88 (d, J = 11.5 Hz, 2H), 1.30 (d, J = 6.7 Hz, 3H). |
| 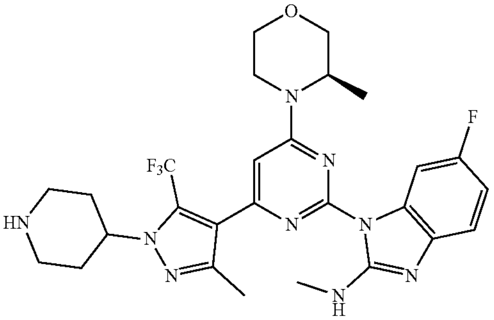 D22 | d6 | 574 | $^1$H NMR (400 MHz, DMSO-$d_6$) δ 8.38 (d, J = 5.4 Hz, 1H), 7.97 (dd, J = 10.3, 2.7 Hz, 1H), 7.23 (dd, J = 8.6, 5.1 Hz, 1H), 6.93 (dd, J = 8.8, 2.7 Hz, 1H), 6.89 (s, 1H), 4.46 (s, 1H), 4.32 (s, 1H), 4.05 (dd, J = 27.0, 12.2 Hz, 2H), 3.80 (d, J = 11.7 Hz, 1H), 3.73-3.66 (m, 1H), 3.55 (t, J = 11.5 Hz, 1H), 3.37 (s, 1H), 3.07 (d, J = 12.4 Hz, 2H), 3.02 (d, J = 4.9 Hz, 3H), 2.60 (t, J = 12.4 Hz, 2H), 2.28 (s, 3H), 2.02 (d, J = 8.4 Hz, 2H), 1.90-1.82 (m, 2H), 1.32 (d, J = 6.7 Hz, 3H). |
| 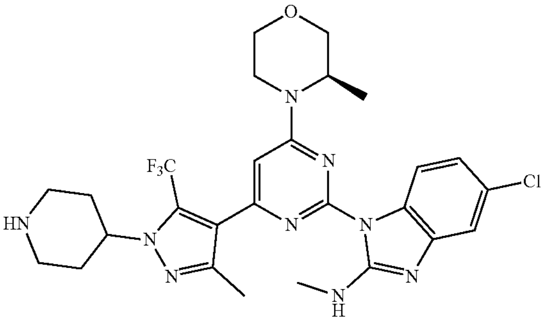 D25 | d8 | 591 | $^1$H NMR (400 MHz, DMSO-$d_6$) δ 8.58 (d, J = 5.2 Hz, 1H), 8.15 (d, J = 8.6 Hz, 1H), 7.28 (d, J = 2.1 Hz, 1H), 7.01 (dd, J = 8.6, 2.2 Hz, 1H), 6.87 (s, 1H), 4.45 (s, 1H), 4.33 (s, 1H), 4.10 (d, J = 13.0 Hz, 1H), 4.01 (d, J = 10.2 Hz, 1H), 3.79 (d, J = 11.6 Hz, 1H), 3.73-3.66 (m, 1H), 3.55 (t, J = 11.8 Hz, 1H), 3.39-3.34 (m, 1H), 3.09 (d, J = 3.7 Hz, 1H), 3.06 (d, J = 3.0 Hz, 1H), 3.03 (d, J = 4.8 Hz, 3H), 2.61 (t, J = 12.4 Hz, 2H), 2.28 (s, 3H), 2.02 (d, J = 9.8 Hz, 3H), 1.86 (d, J = 11.9 Hz, 2H), 1.30 (d, J = 6.7 Hz, 3H). |

Example 17: D11

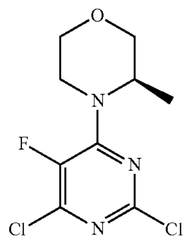

c6

+

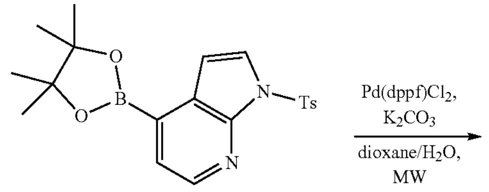

a3

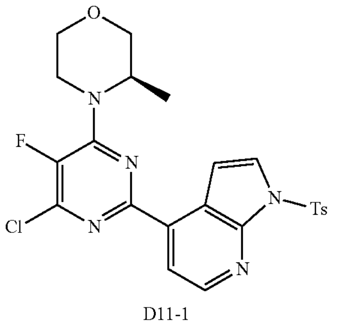

D11-1

+

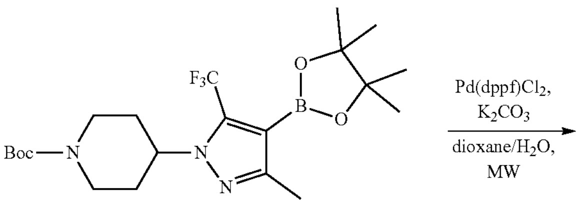

c3

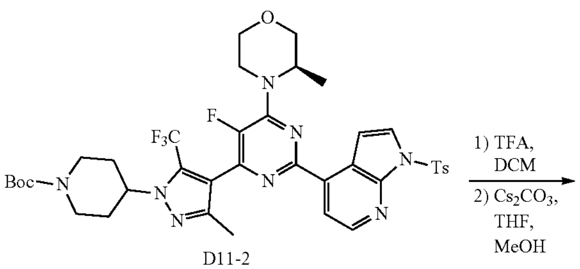

D11-2

-continued

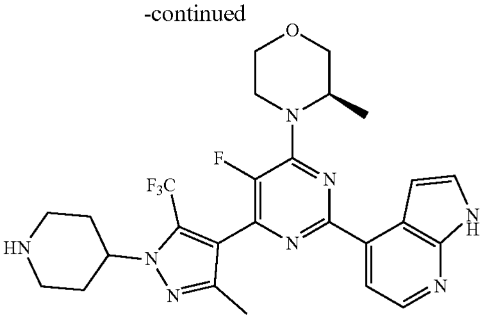

D11

Under nitrogen protection, intermediate c6 (1 mmol, 265 mg) and intermediate a3 (1 mmol, 398 mg) were dissolved in 12 mL mixture of 1,4-dioxane and water (v/v: 9/1), potassium carbonate (3 mmol, 414 mg), Pd(dppf)$Cl_2$ (0.1 mmol, 73 mg) were added, and the mixture was heated at 100° C. in microwave and reacted for 30 minutes. The reaction was stopped, filtered, the organic solvent was removed under reduced pressure, 10 mL of water was added, extracted with ethyl acetate, and separated by column chromatography to afford compound D11-1 (100 mg, yield: 20%), LC-MS: $[M+H]^+$: 502.

Under nitrogen protection, compound D11-1 (0.2 mmol, 100 mg) and intermediate c3 (0.24 mmol, 110 mg) were dissolved in 5 mL mixture of 1,4-dioxane and water (v/v: 9/1), potassium carbonate (0.6 mmol, 83 mg), Pd(dppf)$Cl_2$ (0.02 mmol, 16 mg) were added, and the mixture was heated at 100° C. in microwave and reacted for 30 minutes. The reaction was stopped, filtered, the organic solvent was removed under reduced pressure, 10 mL of water was added, extracted with ethyl acetate, and separated by flash column chromatography to afford compound D11-2 (30 mg, yield: 20%), LC-MS: $[M+H]^+$: 799.

Compound D11-2 (0.05 mmol, 40 mg) was dissolved in 4 mL of dichloromethane, 1 mL of trifluoroacetic acid was added dropwise, after the mixture was reacted at room temperature for 2 hours, the solvent was removed under reduced pressure. The mixture was dissolved in mixture of 3 mL methanol and 3 mL tetrahydrofuran again, cesium carbonate (0.3 mmol, 98 mg) was added, and the mixture was reacted at 70° C. for 2 hours. The mixture was filtered, the solvent was removed under reduced pressure, and separated by preparative chromatography to afford the title compound D11 (16 mg, two-step yield: 59%), LC-MS: $[M+H]^+$: 545.

$^1H$ NMR (400 MHz, DMSO-$d_6$) δ 11.80 (s, 1H), 8.32 (d, J=5.1 Hz, 1H), 7.90 (s, 1H), 7.58 (t, J=3.0 Hz, 1H), 7.16-7.11 (m, 1H), 4.59 (d, J=7.7 Hz, 1H), 4.25 (d, J=13.4 Hz, 2H), 4.03-3.96 (m, 1H), 3.76 (d, J=2.2 Hz, 2H), 3.67-3.46 (m, 3H), 3.08 (d, J=12.5 Hz, 2H), 2.61 (t, J=12.2 Hz, 2H), 2.26 (s, 3H), 2.02 (t, J=13.0 Hz, 2H), 1.87 (d, J=11.6 Hz, 2H), 1.38 (d, J=6.8 Hz, 3H).

Example 18: D15

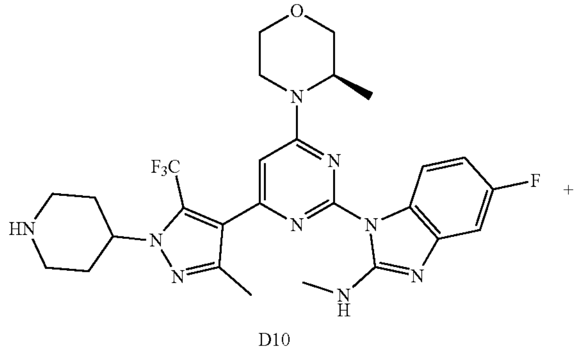

D10

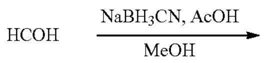

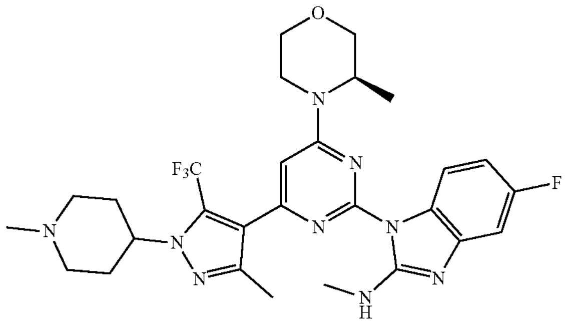

D15

Compound D10 (0.66 mmol, 380 mg) was dissolved in 10 mL of methanol, 30% formaldehyde aqueous solution (1.3 mmol, 140 μL) and $NaBH_3CN$ (1.95 mmol, 122 mg) were added, after 5 drops of acetic acid were added dropwise, the mixture was reacted at room temperature for 3 hours. The solvent was removed under reduced pressure, and separated by TLC chromatography to afford compound D15 (105 mg, yield: 28%) LC-MS: $[M+H]^+$: 588.

$^1H$ NMR (400 MHz, DMSO-$d_6$) δ 8.58 (d, J=5.1 Hz, 1H), 8.14 (dd, J=8.8, 5.2 Hz, 1H), 7.06 (dd, J=9.7, 2.7 Hz, 1H), 6.86 (s, 1H), 6.79 (td, J=9.4, 2.6 Hz, 1H), 4.45 (s, 1H), 4.23 (s, 1H), 4.10 (d, J=13.1 Hz, 1H), 4.01 (d, J=10.9 Hz, 1H), 3.79 (d, J=11.7 Hz, 1H), 3.69 (d, J=11.0 Hz, 1H), 3.55 (t, J=11.4 Hz, 1H), 3.37 (d, J=11.4 Hz, 1H), 3.03 (d, J=4.8 Hz, 3H), 2.92 (d, J=11.2 Hz, 2H), 2.28 (s, 3H), 2.22 (s, 3H), 2.20 (s, 1H), 2.16 (d, J=11.6 Hz, 1H), 2.11-2.03 (m, 2H), 1.90 (d, J=11.7 Hz, 2H), 1.30 (d, J=6.7 Hz, 3H).

Example 19: D16

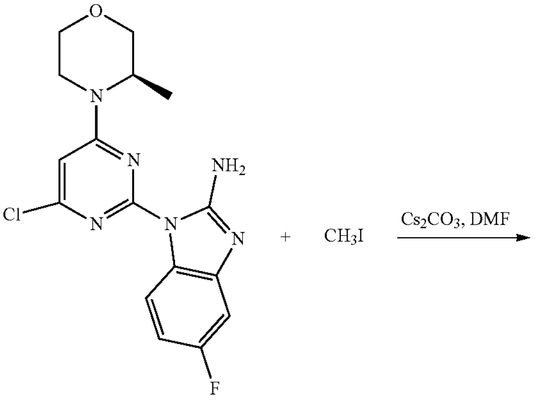

d2

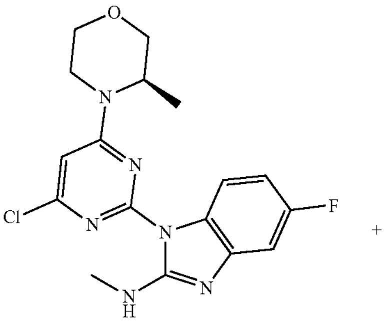

D16-1

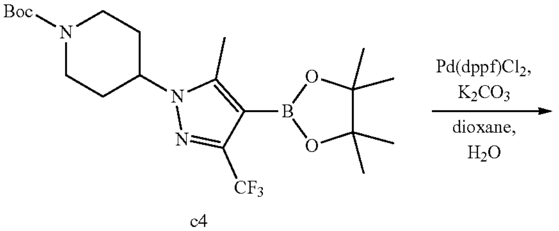

c4

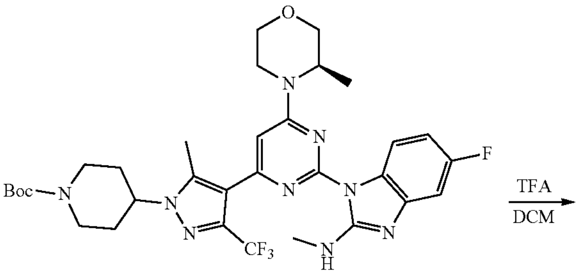

D16-2

-continued

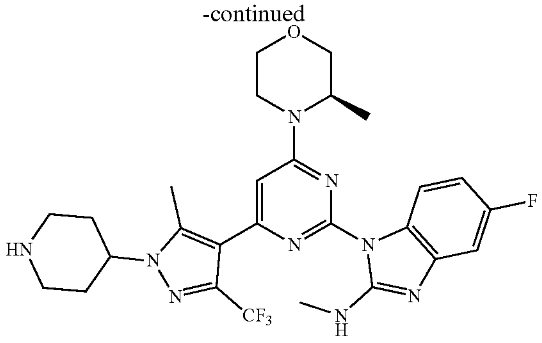

D16

Intermediate d2 (0.28 mmol, 100 mg) and cesium carbonate (0.83 mmol, 270 mg) were dissolved in 12 mL of DMF, methyl iodide (0.28 mmol, 40 mg) was added dropwise, and the mixture was reacted at 60° C. for 2 hours. The reaction was stopped, 30 ml of water was added, extracted with dichloromethane, dried over anhydrous sodium sulfate, and separated by TLC chromatography to afford compound D16-1 (50 mg, yield: 48%), LC-MS: $[M+H]^+$: 377.

Under nitrogen protection, compound D16-1 (0.14 mmol, 50 rug) and intermediate c4 (0.22 mmol, 102 mg) were dissolved in 0.5 mL, mixture of 1,4-dioxane and water (v/v: 9/1), potassium carbonate (0.22 mmol, 32 mg), Pd(dppf)$Cl_2$ (0.011 mmol, 8 mg) were added, and the mixture was heated at 100° C. in microwave and reacted for 1 hour. The reaction was stopped, filtered, the organic solvent was removed under reduced pressure, 15 mL of water was added, extracted with ethyl acetate, and separated by TLC chromatography to afford compound D16-2 (80 mg, yield: 85%), LC-MS: $[M+H]^+$: 674.

Compound D16-2 (80 mg) was dissolved in 14 mL of dichloromethane, 2 mL of trifluoroacetic acid was added dropwise, after the mixture was reacted at room temperature for 2 hours, the solvent was removed under reduced pressure, and separated by preparative chromatography to afford the title compound D16 (20 mg, yield: 30%), LC-MS: $[M+H]^+$: 574.

$^1$H NMR (400 MHz, DMSO-$d_6$) δ 8.65 (d, J=5.1 Hz, 1H), 8.16 (dd, J=8.8, 5.3 Hz, 1H), 7.06 (dd, J=9.6, 2.7 Hz, 1H), 6.79 (td, J=9.3, 2.7 Hz, 1H), 6.73 (s, 1H), 4.53-4.40 (m, 2H), 4.06 (dd, J=25.9, 11.4 Hz, 2H), 3.80 (d, J=11.6 Hz, 1H), 3.73-3.67 (m, 1H), 3.58-3.52 (m, 1H), 3.36 (s, 1H), 3.10 (d, J=12.5 Hz, 2H), 3.03 (d, J=4.8 Hz, 3H), 2.69 (t, J=10.6 Hz, 2H), 2.47 (s, 3H), 2.00 (q, J=6.4, 5.2 Hz, 1H), 1.93-1.88 (m, 3H), 1.3 (d, J=6.7 Hz, 3H).

Example 20:117

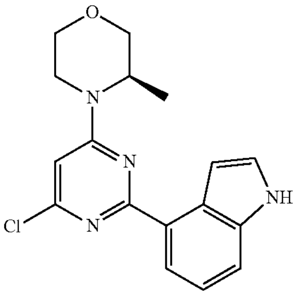

d4

+

-continued

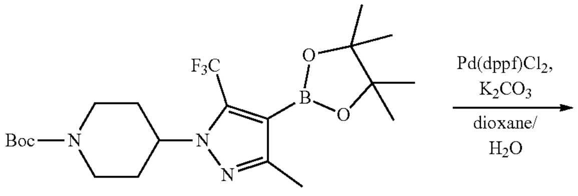

c3

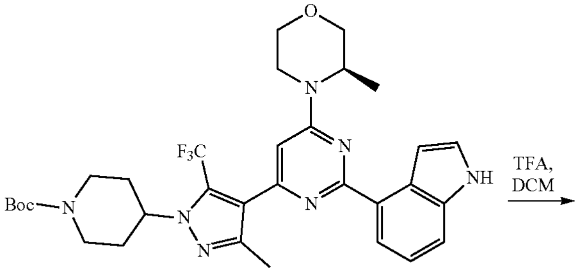

D17-1

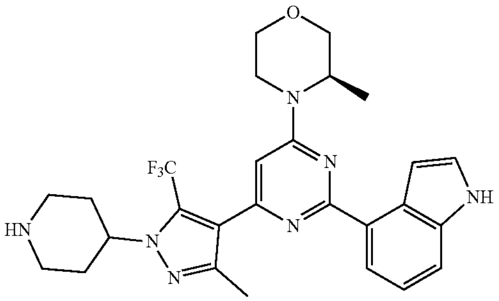

D17

Under nitrogen protection, intermediate d4 (0.14 mm 1, 45 mg) and intermediate c3 (0.25 mmol, 115 mg) were dissolved in 5 mL mixture of 1,4-dioxane and water (v/v: 9/1), potassium carbonate (0.3 mmol, 41 mg) and Pd(dppf) $Cl_2$ (0.014 mmol, 11 mg) were added, and the reaction was heated at 100° C. in microwave for 1 hour. The reaction was stopped, filtered, the organic solvent was evaporated under reduced pressure, 20 of water was added, extracted with ethyl acetate, and separated by TLC chromatography to afford compound D17-1 (50 mg, yield: 58%). LC-MS: $[M+H]^+$: 626.

Compound D1.7-1 (50 mg) was dissolved in 2 mL of dichloromethane, 0.5 mL of trifluoroacetic acid was added, after the mixture was reacted at room temperature for 2 hours, the solvent was removed under reduced pressure, and separated by preparative chromatography to afford the title compound D17 (31 mg, yield: 74%), LC-MS: $[M+H]^+$: 526.

The following compounds were synthesized with reference to the route of Example 20:

| Structure | The structure of intermediate replacing c3 | LC-MS/ [M + H]$^+$ | $^1$H NMR |
|---|---|---|---|
| 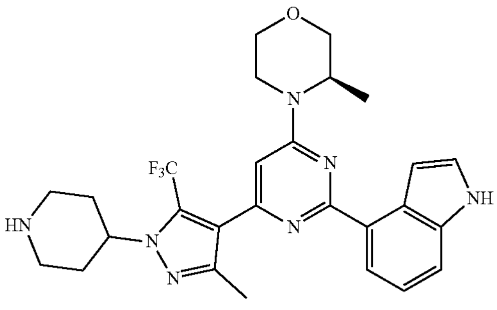 D17 | — | 526 | $^1$H NMR (400 MHz, DMSO-$d_6$) δ 11.22 (s, 1H), 8.09 (d, J = 7.5 Hz, 1H), 7.52 (d, J = 8.0 Hz, 1H), 7.42 (t, J = 2.8 Hz, 1H), 7.30 (t, J = 2.5 Hz, 1H), 7.17 (t, J = 7.8 Hz, 1H), 6.75 (s, 1H), 4.54 (s, 1H), 4.38-4.21 (m, 2H), 4.04-3.97 (m, 1H), 3.79 (d, J = 11.4 Hz, 1H), 3.68 (dd, J = 11.2, 3.1 Hz, 1H), 3.58-3.49 (m, 1H), 3.29-3.22 (m, 1H), 3.10 (d, J = 12.9 Hz, 2H), 2.64 (t, J = 12.0 Hz, 2H), 2.26 (s, 3H), 2.08-1.99 (m, 2H), 1.92-1.84 (m, 2H), 1.27 (d, J = 6.7 Hz, 3H). |
| 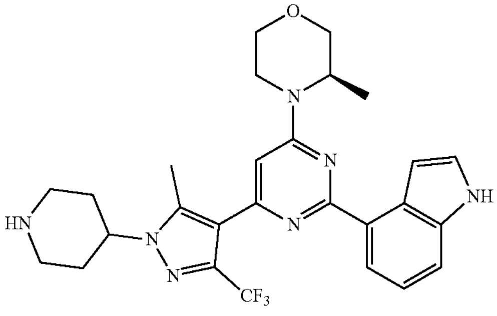 D18 | c4 | 526 | $^1$H NMR (400 MHz, DMSO-$d_6$) δ 11.22 (s, 1H), 8.14 (d, J = 7.4 Hz, 1H), 7.52 (d, J = 8.0 Hz, 1H), 7.42 (t, J = 2.7 Hz, 1H), 7.33 (t, J = 2.4 Hz, 1H), 7.18 (t, J = 7.8 Hz, 1H), 6.65 (s, 1H), 4.55-4.39 (m, 2H), 4.22 (d, J = 13.3 Hz, 1H), 4.06-3.98 (m, 1H), 3.80 (d, J = 11.4 Hz, 1H), 3.69 (dd, J = 11.5, 3.2 Hz, 1H), 3.59-3.50 (m, 1H), 3.25 (d, J = 2.0 Hz, 1H), 3.09 (d, J = 12.6 Hz, 2H), 2.71-2.62 (m, 2H), 2.00-1.86 (m, 4H), 1.28 (d, J = 6.7 Hz, 3H). |

Example 21: D19

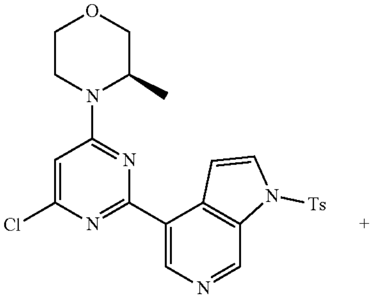
d5

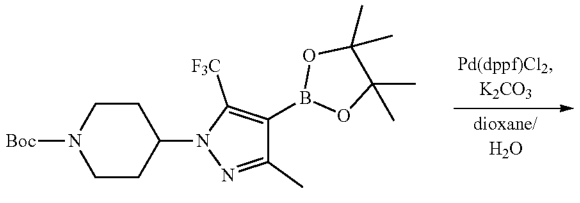

c3

-continued

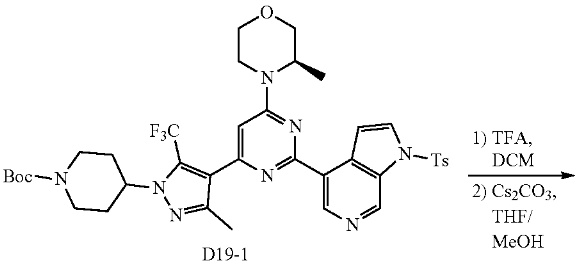

D19-1

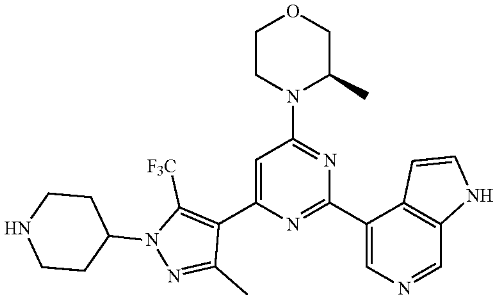
D19

Under nitrogen protection, intermediate d5 (0.31 mmol, 150 mg) and intermediate c3 (0.60 mmol, 275 mg) were dissolved in 15 mL mixture of 1,4-dioxane and water (v/v: 9/1), potassium carbonate (0.9 mmol, 124 mg) and Pd(dppf) $Cl_2$ (0.03 mmol, 25 mg) were added, and the reaction was heated at 100° C. in microwave for 1 hour. The reaction was stopped, filtered, the organic solvent was evaporated under reduced pressure, 10 mL of water was added, extracted with ethyl acetate, and separated by column chromatography to afford compound D19-1 (66 mg, yield: 28%). LC-MS: $[M+H]^+$: 781.

Compound D19-1 (66 mg) was dissolved in 5 mL of dichloromethane, 1 mL of trifluoroacetic acid was added, after the mixture was reacted at room temperature for 2 hours, the solvent was removed under reduced pressure. Then the mixture was dissolved in mixture of tetrahydrofuran (3 mL) and methanol (3 mL) again, cesium carbonate (0.2 mmol, 65 mg) was added, and the mixture was refluxed until the reaction was complete. The mixture was filtered, the solvent was removed under reduced pressure, and separated by preparative chromatography to afford the title compound D19 (20 mg, two-step yield: 46%), LC-MS: $[M+H]^+$: 527.

The following compounds were synthesized with reference to the route of Example 21:

| Structure | The structure of intermediate replacing c3 | LC-MS/ $[M + H]^+$ | $^1H$ NMR |
|---|---|---|---|
| 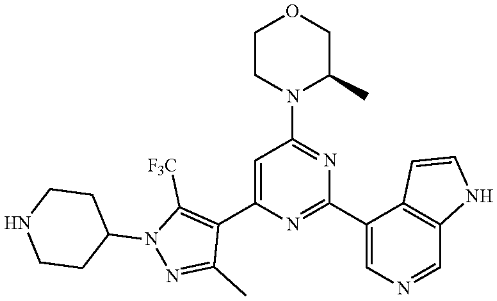 D19 | — | 527 | $^1H$ NMR (400 MHz, DMSO-$d_6$) δ 11.75 (s, 1H), 9.10 (s, 1H), 8.81 (s, 1H), 7.69 (t, J = 2.7 Hz, 1H), 7.25 (s, 1H), 6.81 (s, 1H), 4.54 (s, 1H), 4.39 (s, 1H), 4.26 (d, J = 13.9 Hz, 1H), 4.01 (d, J = 12.1 Hz, 1H), 3.79 (d, J = 11.5 Hz, 1H), 3.68 (d, J = 11.2 Hz, 1H), 3.59-3.50 (m, 1H), 3.29 (s, 1H), 3.14 (d, J = 12.7 Hz, 2H), 2.73 (d, J = 12.2 Hz, 2H), 2.28 (s, 3H), 2.11-2.07 (m, 1H), 2.03-1.97 (m, 1H), 1.91 (d, J = 12.1 Hz, 2H), 1.28 (d, J = 6.7 Hz, 3H). |
| 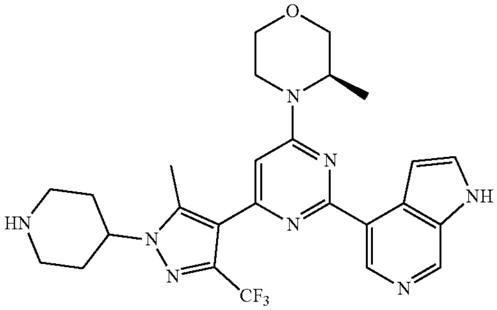 D20 | c4 | 527 | $^1H$ NMR (400 MHz, DMSO-$d_6$) δ 11.75 (s, 1H), 9.14 (s, 1H), 8.82 (s, 1H), 7.69 (t, J = 2.7 Hz, 1H), 7.28 (s, 1H), 6.70 (s, 1H), 4.48 (d, J = 14.6 Hz, 2H), 4.22 (d, J = 13.5 Hz, 1H), 4.02 (d, J = 10.2 Hz, 1H), 3.81 (d, J = 11.7 Hz, 1H), 3.69 (d, J = 10.5 Hz, 1H), 3.55 (t, J = 10.8 Hz, 1H), 3.29 (s, 1H), 3.09 (d, J = 12.6 Hz, 2H), 2.72-2.64 (m, 2H), 2.51 (s, 3H), 2.03-1.94 (m, 2H), 1.90 (s, 3H), 1.29 (d, J = 6.7 Hz, 3H). |

Example 22: D23

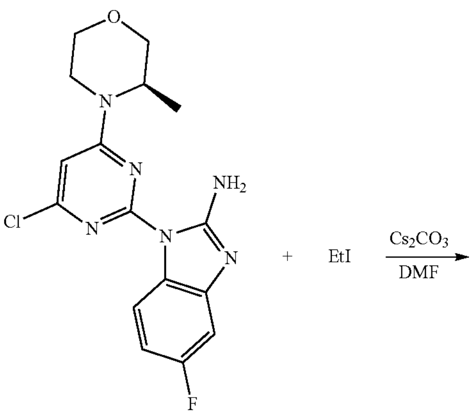

d2

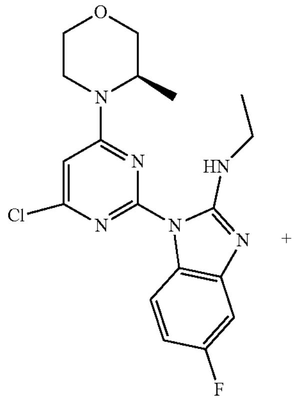

D23-1

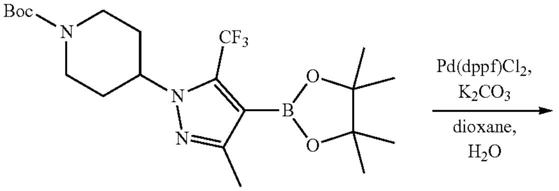

c3

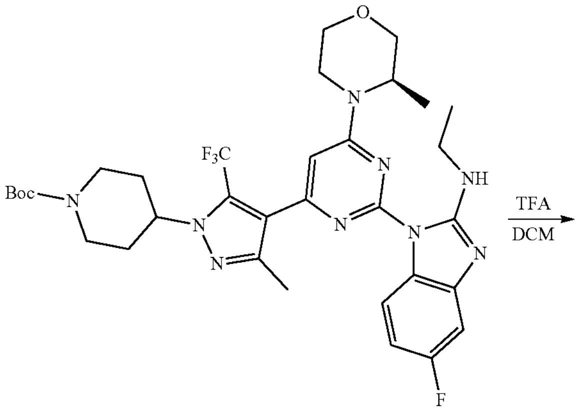

D23-2

-continued

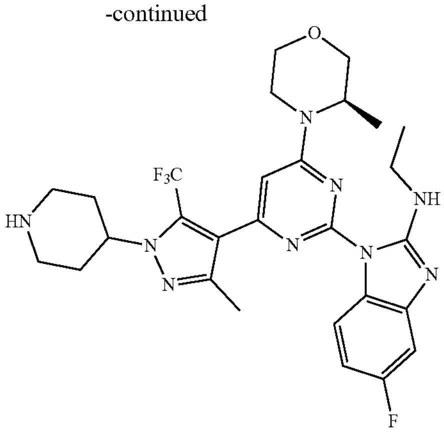

D23

Intermediate d2 (0.28 mmol, 100 mg) and cesium carbonate (0.69 mmol, 225 mg) were dissolved in 10 ml of DMF, iodoethane (0.33 mmol, 51 mg) was added dropwise, and the mixture was reacted at 60° C. for 1.5 hours. The reaction was stopped, 30 mL of water was added, extracted with dichloromethane, dried over anhydrous sodium sulfate, and separated by TLC chromatography to afford compound D23-1 (95 mg, yield: 87%), LC-MS: $[M+H]^+$: 391.

Under nitrogen protection, compound D23-1 (0.24 mmol, 95 mg) and intermediate c3 (0.48 mmol, 223 mg) were dissolved in 5 mL mixture of 1,4-dioxane and water (v/v: 9/1), potassium carbonate (0.48 mmol, 66 mg), Pd(dppf)$Cl_2$ (0.024 mmol, 18 mg) were added, then the mixture was heated at 100° C. in microwave and reacted for 1.5 hours. The reaction was stopped, filtered, the organic solvent was removed under reduced pressure, 15 mL of water was added, extracted with ethyl acetate, and separated by TLC chromatography to afford compound D23-2 (100 mg, yield: 61%), LC-MS: $[M+H]^+$: 688.

Compound D23-2 (100 mg) was dissolved in 15 mL of dichloromethane, 3 mL of trifluoroacetic acid was added dropwise, after the mixture was reacted at room temperature for 2 hours, the solvent was removed under reduced pressure, and separated by preparative chromatography to afford the title compound D23 (36 mg, yield: 44%), LC-MS: $[M+H]^+$: 588.

$^1$H NMR (400 MHz, DMSO-$d_6$) δ 8.65 (t, J=5.6 Hz, 1H), 8.15 (dd, J=8.9, 5.3 Hz, 1H), 7.05 (dd, J=9.7, 2.7 Hz, 1H), 6.87 (s, 1H), 6.78 (id, J=9.4, 2.7 Hz, 1H), 4.44 (s, 1H), 4.32 (s, 1H), 4.09 (d, J=12.9 Hz, 1H), 4.05-3.98 (m, 1H), 3.79 (d, J=11.7 Hz, 1H), 3.69 (d, J=11.4 Hz, 1H), 3.56 (d, J=12.2 Hz, 1H), 3.50 (dd, J=13.3, 6.7 Hz, 2H), 3.40-3.35 (m, 1H), 3.07 (d, J=12.7 Hz, 2H), 2.60 (t, J=12.3 Hz, 2H), 2.27 (s, 3H), 2.01 (t, J=9.0 Hz, 2H), 1.85 (d, J=11.6 Hz, 2H), 1.30 (d, J=6.7 Hz, 3H), 1.19 (d, J=7.1 Hz, 3H).

Example 23: A29

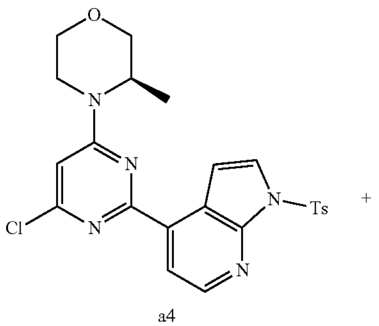

a4

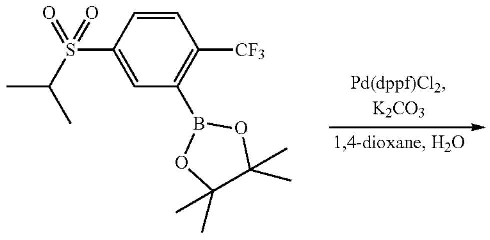

b10

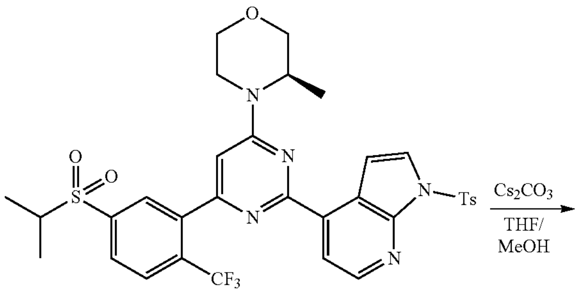

A29-1

-continued

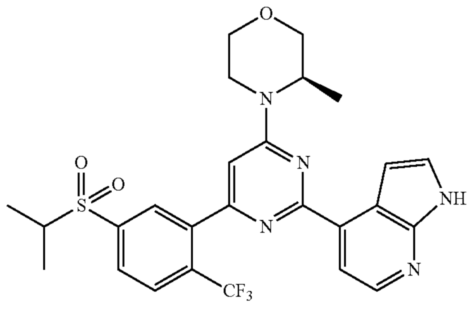

A29

Under nitrogen protection, intermediate a4 (0.41 mmol, 200 mg) and intermediate b10 (0.49 mmol, 190 mg) were dissolved in 10 mL mixture of 1,4-dioxane and water (v/v, 9/1), potassium carbonate (1.24 mmol, 170 mg) and Pd(dppf)$Cl_2$ (0.08 mmol, 60 mg) were added, the reaction was heated to 90° C. and stirred for 3 hours. The reaction was stopped, filtered, 30 mL of water was added, extracted with ethyl acetate, dried over anhydrous sodium sulfate, and separated by flash column chromatography to afford compound A29-1 (240 mg, yield: 69%), LC-MS: $[M+H]^+$: 700.

Compound A29-1 (0.286 mmol, 200 mg) was dissolved in 8 mL mixture of tetrahydrofuran and methanol (v/v, 1/1), cesium carbonate (0.86 mmol, 280 mg) was added, and the mixture was refluxed until the reaction was complete. The mixture was filtered, the solvent was removed under reduced pressure, and separated by preparative chromatography to afford the title compound A29 (yield: 42%), LC-MS: $[M+H]^+$: 546.

$^1$H NMR (400 MHz, DMSO-$d_6$) δ 11.77 (s, 1H), 8.32 (d, 5.0 Hz, 1H), 8.22 (q, =8.4 Hz, 2H), 8.12 (s, 1H), 7.98 (d, J=5.0 Hz, 1H), 7.56 (t, J=3.0 Hz, 1H), 7.18 (dd, J=3.4, 1.9 Hz, 1H), 7.03 (s, 4.63 (s, 1H), 4.26 (d, J=13.1 Hz, 1H), 4.08-3.97 (m, 1H), 3.81 (d, J=11.6 Hz, 1H), 3.74-3.62 (m, 2H), 3.61-3.48 (m, 1H), 3.35 (dd, J=12.9, 3.8 Hz, 1H), 1.31 (d, J=6.7 Hz, 3H), 1.24 (d, J=2.1 Hz, 6H).

The following compounds were synthesized with reference to the route of Example 23:

| Structure | The structure of intermediate replacing b10 | LC-MS/ [M + H]$^+$ | $^1$H NMR |
|---|---|---|---|
| 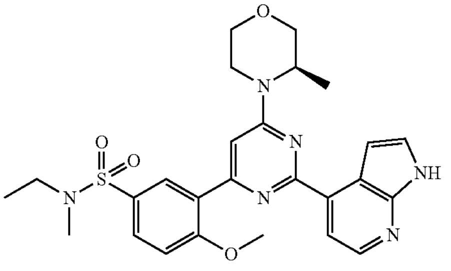 A30 | 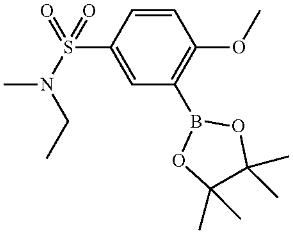 b11 | 523 | $^1$H NMR (400 MHz, DMSO-$d_6$) δ 11.78 (s, 1H), 8.42 (d, J = 2.5 Hz, 1H), 8.35 (d, J = 5.0 Hz, 1H), 8.02 (d, J = 5.0 Hz, 1H), 7.89 (dd, J = 8.7, 2.5 Hz, 1H), 7.57 (t, J = 2.9 Hz, 1H), 7.44 (d, J = 8.8 Hz, 1H), 7.33 (s, 1H), 7.30-7.26 (m, 1H), 4.58 (s, 1H), 4.23 (d, J = 13.1 Hz, 1H), 4.01 (s, 4H), 3.82 (d, J = 11.4 Hz, 1H), 3.71 (dd, J = 11.4, 3.0 Hz, 1H), 3.56 (dd, J = 13.2, 10.2 Hz, 1H), 3.34 (d, J = 3.8 Hz, 1H), 3.08 (q, J = 7.1 Hz, 2H), 2.71 (s, 3H), 1.31 (d, J = 6.7 Hz, 3H), 1.08 (t, J = 7.1 Hz, 3H). |
| 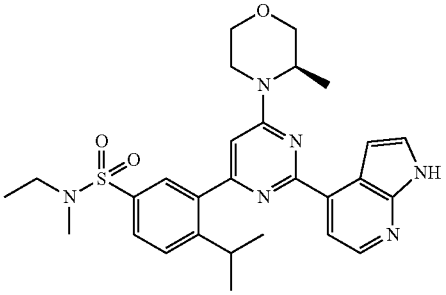 A33 | 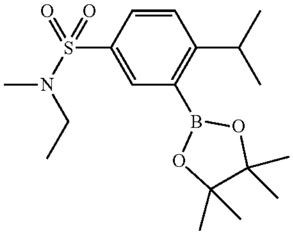 b12 | 535 | $^1$H NMR (400 MHz, DMSO-$d_6$) δ 11.77 (s, 1H), 8.33 (d, J = 5.0 Hz, 1H), 7.98 (d, J = 5.0 Hz, 1H), 7.84 (dd, J = 8.3, 2.1 Hz, 1H), 7.79-7.70 (m, 2H), 7.56 (t, J = 2.9 Hz, 1H), 7.19 (dd, J = 3.5, 1.9 Hz, 1H), 6.90 (s, 1H), 4.65 (s, 1H), 4.28 (d, J = 13.1 Hz, 1H), 4.01 (dd, J = 11.5, 3.6 Hz, 1H), 3.80 (d, J = 11.4 Hz, 1H), 3.70 (dd, J = 11.5, 3.2 Hz, 1H), 3.62-3.49 (m, 1H), 3.44-3.31 (m, 2H), 3.08 (q, J = 7.1 Hz, 2H), 2.71 (s, 3H), 1.31 (d, J = 6.9 Hz, 3H), 1.26-1.23 (m, 6H), 1.07 (t, J = 7.1 Hz, 3H). |
| 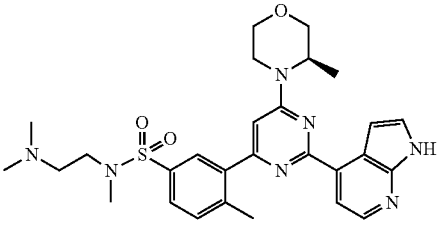 A34 | 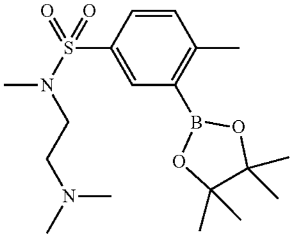 b13 | 550 | $^1$H NMR (300 MHz, DMSO-$d_6$) δ 11.80 (s, 1H), 8.33 (d, J = 5.0 Hz, 1H), 8.01 (d, J = 5.0 Hz, 1H), 7.91 (d, J = 2.1 Hz, 1H), 7.80 (dd, J = 8.0, 2.1 Hz, 1H), 7.69-7.53 (m, 2H), 7.23 (dd, J = 3.5, 1.7 Hz, 1H), 6.98 (s, 1H), 4.66 (s, 1H), 4.30 (d, J = 12.9 Hz, 1H), 4.02 (d, J = 10.2 Hz, 1H), 3.81 (d, J = 11.4 Hz, 1H), 3.70 (d, J = 10.7 Hz, 1H), 3.53 (d, J = 11.9 Hz, 1H), 3.31 (s, 4H), 3.12 (d, J = 6.9 Hz, 2H), 2.74 (s, 3H), 2.55 (s, 3H), 2.50 (s, 6H) [in DMSO-$d_6$], 2.25 (s, 2H), 1.28 (m, 3H). |
| 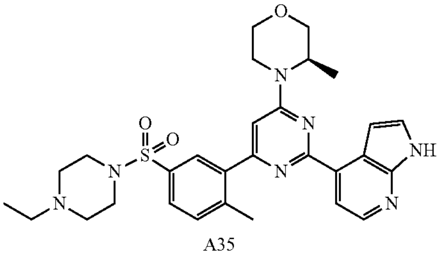 A35 | 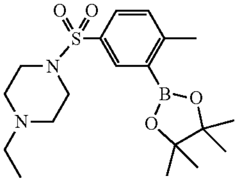 b14 | 562 | $^1$H NMR (400 MHz, DMSO-$d_6$) δ 11.77 (s, 1H), 8.34 (d, J = 5.0 Hz, 1H), 8.01 (d, J = 5.0 Hz, 1H), 7.85 (s, 1H), 7.74 (d, J = 8.2 Hz, 1H), 7.66 (d, J = 8.1 Hz, 1H), 7.56 (s, 1H), 7.22 (d, J = 2.9 Hz, 1H), 7.00 (s, 1H), 4.66 (s, 1H), 4.30 (d, J = 12.8 Hz, 1H), 4.02 (d, J = 10.3 Hz, 1H), 3.81 (d, J = 11.5 Hz, 1H), 3.70 (d, J = 10.5 Hz, 1H), 3.55 (t, J = 11.9 Hz, 1H), 3.28 (s, 1H), 2.93 (s, 4H), 2.56 (s, 3H), 2.42 (s, 4H), 2.30 (d, J = 7.2 Hz, 2H), 1.31 (d, J = 6.8 Hz, 3H), 0.92 (t, J = 7.1 Hz, 3H). |

-continued

| Structure | The structure of intermediate replacing b10 | LC-MS/ [M + H]+ | $^1$H NMR |
| --- | --- | --- | --- |
| 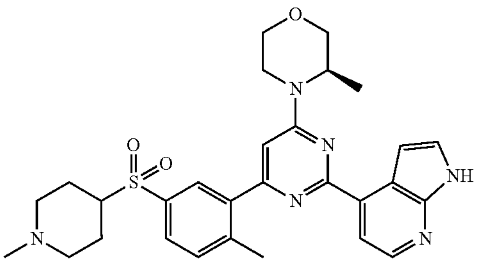 A36 | 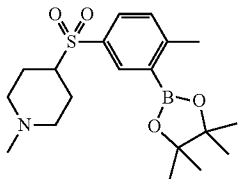 b15 | 547 | $^1$H NMR (400 MHz, DMSO-$d_6$) δ 11.79 (s, 1H), 8.34 (d, J = 5.0 Hz, 1H), 8.02 (d, J = 5.0 Hz, 1H), 7.96 (d, J = 2.1 Hz, 1H), 7.84 (dd, J = 8.0, 2.0 Hz, 1H), 7.68 (d, J = 8.1 Hz, 1H), 7.56 (t, J = 3.0 Hz, 1H), 7.22 (dd, J = 3.3, 2.0 Hz, 1H), 7.00 (s, 1H), 4.68 (s, 1H), 4.28 (s, 1H), 4.02 (d, J = 10.1 Hz, 1H), 3.81 (d, J = 11.5 Hz, 1H), 3.70 (d, J = 9.8 Hz, 1H), 3.56 (t, J = 11.3 Hz, 1H), 3.34 (d, J = 10.1 Hz, 1H), 3.27-3.20 (m, 1H), 2.81 (d, J = 10.9 Hz, 2H), 2.57 (s, 3H), 2.11 (s, 3H), 1.83 (s, 4H), 1.56 (s, 2H), 1.31 (d, J = 6.7 Hz, 3H). |
| 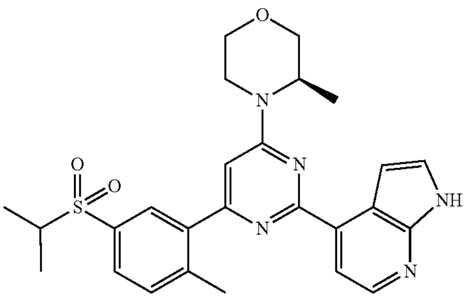 A39 | 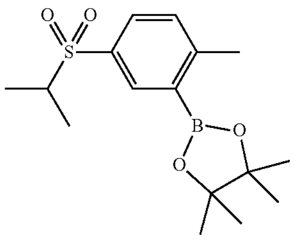 b16 | 492 | $^1$H NMR (400 MHz, DMSO-$d_6$) δ 11.78 (s, 1H), 8.34 (d, J = 5.0 Hz, 1H), 8.01 (d, J = 5.0 Hz, 1H), 7.97 (d, J = 2.0 Hz, 1H), 7.86 (dd, J = 8.0, 2.0 Hz, 1H), 7.67 (d, J = 8.1 Hz, 1H), 7.57 (t, J = 3.0 Hz, 1H), 7.26-7.16 (m, 1H), 6.99 (s, 1H), 4.68 (s, 1H), 4.30 (d, J = 13.6 Hz, 1H), 4.02 (d, J = 10.6 Hz, 1H), 3.81 (d, J = 11.5 Hz, 1H), 3.71 (d, J = 11.6 Hz, 1H), 3.58-3.46 (m, 2H), 3.29 (s, 1H), 2.57 (s, 3H), 1.31 (d, J = 6.7 Hz, 3H), 1.20 (dd, J = 6.9, 1.5 Hz, 6H). |
| 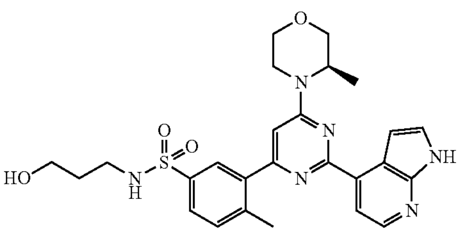 A40 | 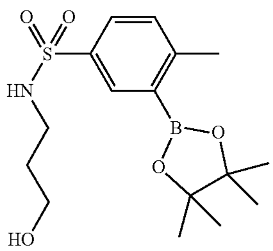 b17 | 523 | $^1$H NMR (400 MHz, DMSO-$d_6$) δ 11.78 (s, 1H), 8.34 (d, J = 5.0 Hz, 1H). 8.02 (d, J = 5.0 Hz, 1H), 7.93 (d, J = 2.1 Hz, 1H), 7.78 (dd, J = 8.0, 2.1 Hz, 1H), 7.62-7.52 (m, 3H), 7.23 (dd, J = 3.4, 1.9 Hz, 1H), 6.95 (s, 1H), 4.66 (s, 1H), 4.41 (t, J = 5.1 Hz, 1H), 4.29 (d, J = 13.1 Hz, 1H), 4.02 (d, J = 10.5 Hz, 1H), 3.81 (d, J = 11.3 Hz, 1H), 3.70 (d, J = 10.9 Hz, 1H), 3.59-3.50 (m, 1H), 3.39 (t, J = 5.8 Hz, 2H), 3.29 (s, 1H), 2.83 (q, J = 6.8 Hz, 2H), 2.53 (s, 3H), 1.55 (t, J = 6.9 Hz, 2H), 1.31 (d, J = 6.7 Hz, 3H). |

Example 24: A31

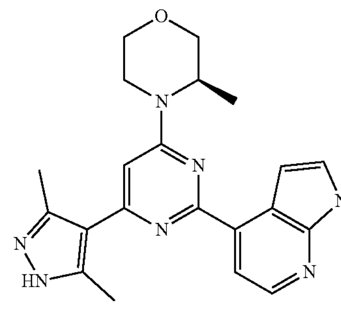

a9

+

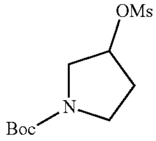

$Cs_2CO_3$

DMF

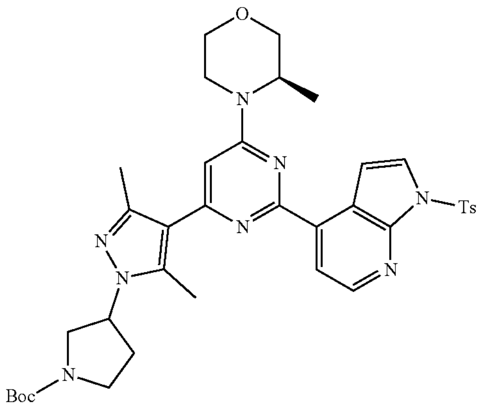

A31-1

TFA

DCM

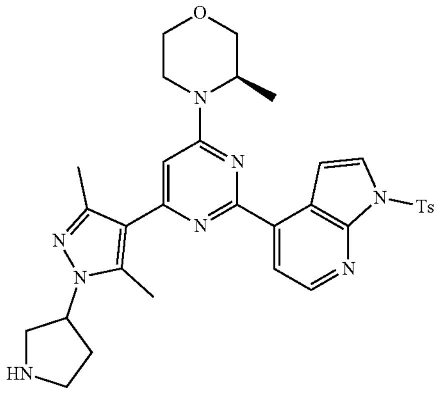

A31-2

+

-continued $CH_3CHO$ $NaCNBH_3$

MeOH, AcOH

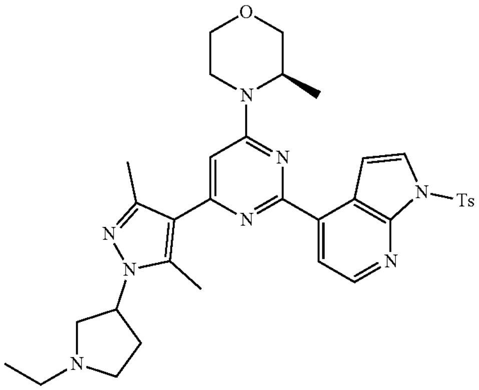

A31-3

$Cs_2CO_3$

THF/MeOH

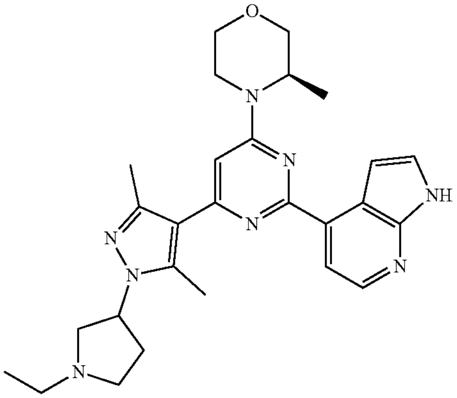

A31

Intermediate a9 (0.78 mmol, 425 mg), cesium carbonate (2.35 mmol, 765 mg) and tert-butyl 3-((methylsulfonyl)oxy) pyrrolidine-1-carboxylate (0.94 mmol, 249 mg) were added to a reaction flask, and dissolved in 10 mL of DMF. The reaction was heated to 80° C. and reacted for 2 hours. The reaction was stopped, 40 mL of water was added to the reaction, extracted with ethyl acetate, and separated by flash column chromatography to afford compound A31-1 (380 mg, yield: 69%), LC-MS: $[M+H]^+$: 713.

Intermediate A31-1 (380 mg) was dissolved in 6 mL of dichloromethane, 2 mL of trifluoroacetic acid was added dropwise, and the mixture was reacted at room temperature for 2 hours. The reaction was stopped, the solvent was removed under reduced pressure. 20 mL of saturated sodium bicarbonate aqueous solution was added to the reaction, extracted with dichloromethane to afford crude intermediate A31-2, which was directly proceeded in the next step. LC-MS: $[M+H]^+$: 613.

In an ice bath, crude intermediate A31-2 and 10 drops of 40% acetaldehyde aqueous solution was dissolved in 5 mL of methanol, 4 drops of glacial acetic acid were added dropwise. After the mixture was stirred for 5 minutes, $NaCNBH_3$ (0.82 mmol, 51 mg) was slowly added, the mixture was stirred for 2 hours, then the reaction was stopped. 40 mL of 4M ammonium chloride aqueous solution was added to the mixture, extracted with ethyl acetate, and separated by flash column chromatography to afford intermediate A31-3, two-step total yield: 73%. LC-MS: $[M+H]^+$: 641.

Intermediate A31-3 (9.125 mmol, 80 mg) was dissolved in 8 mL mixture of methanol and THF (v/v, 1/1), cesium carbonate (0.375 mmol, 122 tug) was added, and the mixture was reacted at 60° C. for 2 hours. The mixture was filtered, the solvent was removed under reduced pressure, and separated by preparative chromatography to afford the title compound A31 (45 mug, yield: 74%), LC-MS: $[M+H]^+$: 487.

$^1H$ NMR (400 MHz, DMSO-$d_6$) δ 11.75 (s, 1H), 8.33 (d, 5.0 Hz, 1H), 8.01 (d, J=5.0 Hz, 1H), 7.57 (t, J=3.0 Hz, 1H), 7.24 (dd, =3.4, 1.9 Hz, 1H), 6.65 (s, 1H), 4.92 (p, J=7.2 Hz, 1H), 4.57 (s, 1H), 4.22 (d, J=13.2 Hz, 1H), 4.02 (d, J=9.1 Hz, 1H), 3.81 (d, J=11.5 Hz, 1H), 3.69 (d, J=10.7 Hz, 1H), 3.59-3.50 (m, 1H), 3.29 (s, 1H), 3.09 (t, J=8.4 Hz, 1H), 2.78 (q, J=7.0 Hz, 1H), 2.65-2.58 (m, 2H), 2.54 (s, 3H), 2.46 (dd, J=7.1, 3.1 Hz, 2H), 2.39 (s, 3H), 2.23 (s, 2H), 11.29 (d, J=6.7 Hz, 3H), 1.05 (t, J=7.2 Hz, 3H).

Example 25: A32

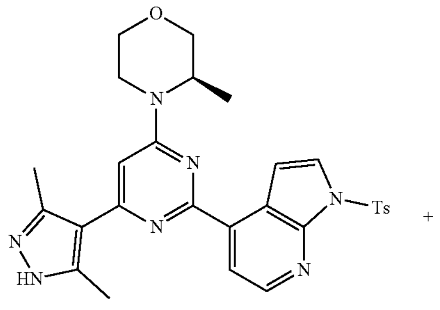

a9

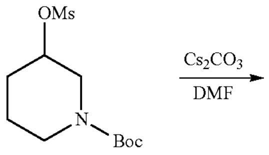

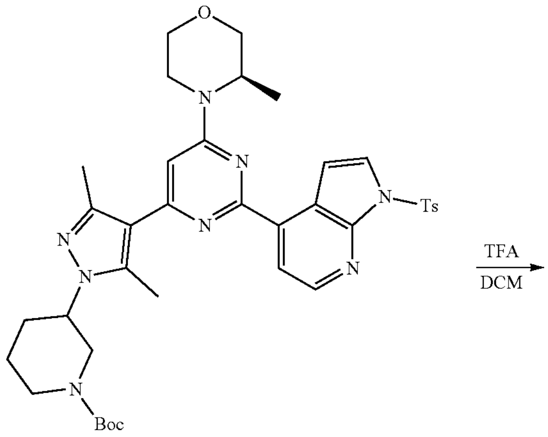

A32-1

-continued

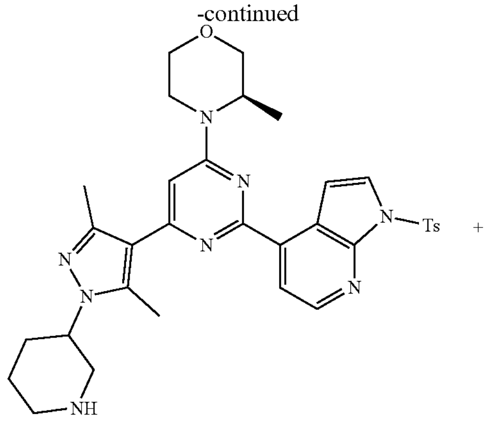

A32-2

HCHO $NaCNBH_3$

MeOH, AcOH

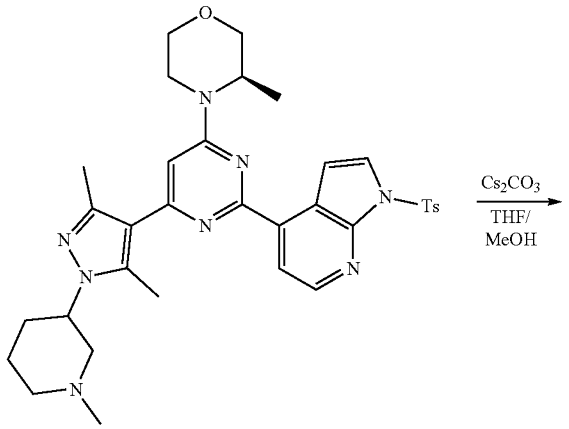

A32-3

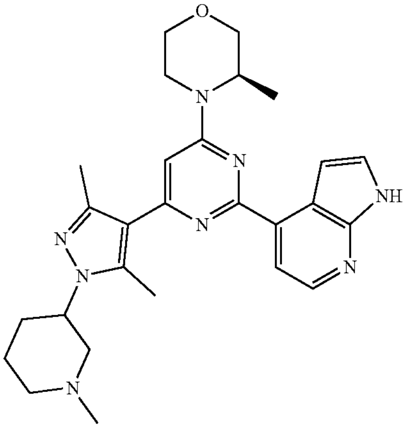

A32

Intermediate a9 (0.27 mmol, 140 mg), cesium carbonate (0.81 mmol, 263 mg) and Cert-butyl 3-((methylsulfonyl)oxy)piperidine-1-carboxylate (0.32 mmol, 90 mg) were added to a reaction flask, and dissolved in 8 mL of DMF. The mixture was heated up to 100° C. and reacted for 4 hours. The reaction was stopped, 40 mL of water was added to the reaction, extracted with ethyl acetate, and separated by flash column chromatography to afford compound A32-1 (yield: 55%), LC-MS: $[M+H]^+$: 727.

Intermediate A32-1 (75 mg) was dissolved in 4 mL of dichloromethane, 1 mL of trifluoroacetic acid was added dropwise, and the mixture was reacted at room temperature for 2 hours. The reaction was stopped, and the solvent was removed under reduced pressure. 20 mL of saturated sodium bicarbonate aqueous solution was added to the reaction, extracted with dichloromethane to Word crude intermediate A32-2, which was directly proceeded in the next step. LC-MS: $[M+H]^+$: 627.

In an ice bath, crude intermediate A32-2 and 1 mL of 40% formaldehyde aqueous solution were dissolved in 3 mL of methanol, 2 drops of glacial acetic acid were added drop-wise. After the mixture was stirred for 5 minutes, $NaCNBH_3$ (0.5 mmol, 33 mg) was slowly added, and after the mixture was continued to stir for 2 hours, the reaction was stopped. 20 mL of 4M ammonium chloride aqueous solution was added to the reaction, extracted with ethyl acetate, and separated by TLC chromatography to afford intermediate A32-3, two-step total yield: 54%. LC-MS: $[M+H]^+$: 641.

Intermediate A32-3 (0.05 mmol, 33 mg) was dissolved in 4 mL mixture of methanol and THF (v/v, 1/1), cesium carbonate (0.2 mmol, 65 mg) was added, and the mixture was reacted at 60° C. for 2 hours. The mixture was filtered, the solvent was removed under reduced pressure, and separated by preparative chromatography to afford the title compound A32 (22 mg, yield: 91%), LC-MS: $[M+H]^+$: 487.

$^1H$ NMR (400 MHz, DMSO-$d_6$) δ 11.75 (s, 1H), 8.33 (d, J=5.1 Hz, 1H), 8.01 (d, J=5.1 Hz, 1H), 7.56 (t, J=3.0 Hz, 1H), 7.24 (t, =2.7 Hz, 1H), 6.66 (s, 1H), 4.56 (s, 1H), 4.22 (d, J=14.7 Hz, 2H), 4.02 (d, J=10.8 Hz, 11H), 3.81 (d, J=11.4 Hz, 1H), 3.69 (d, J=9.7 Hz, 1H), 3.53 (d, J=14.3 Hz, 1H), 2.89 (s, 1H), 2.81 (s, 2H), 2.54 (s, 3H), 2.37 (s, 3H), 2.23 (s, 3H), 1.99 (s, 1H), 1.85 (d, J=30.5 Hz, 3H), 1.77 (d, J=12.5 Hz, 1H), 1.67 (s, 1H), 1.30 (s, 3H).

Example 26: A37

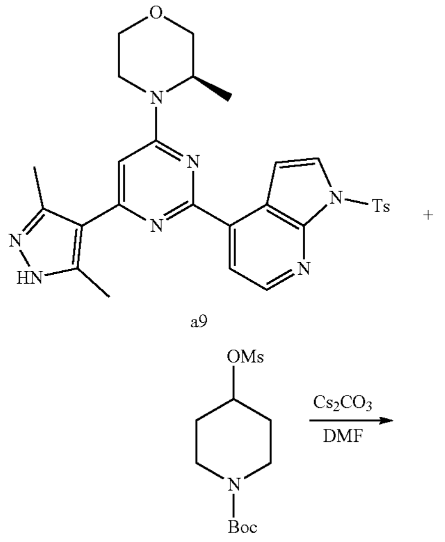

a9

-continued

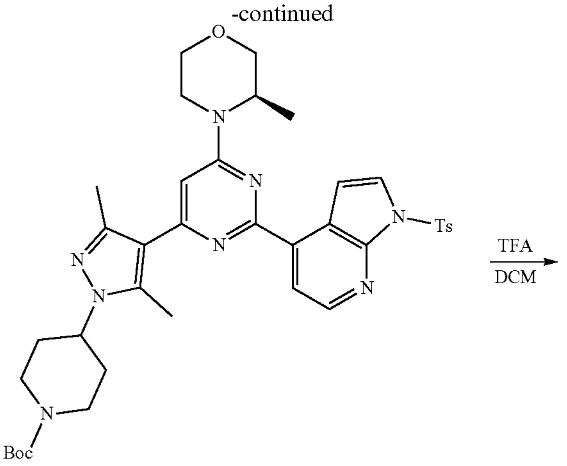

A37-1

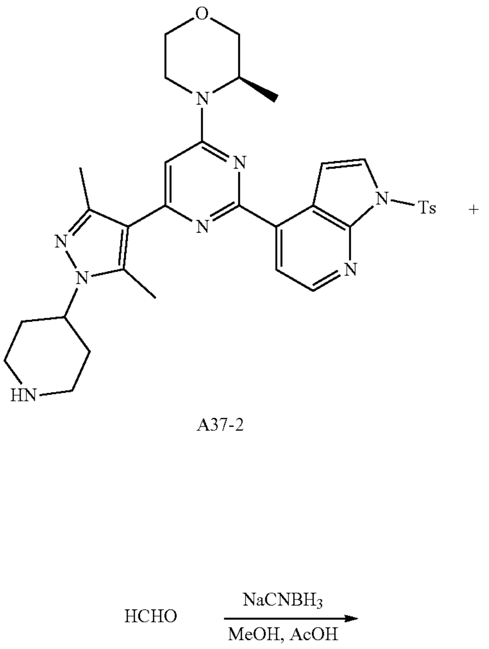

A37-2

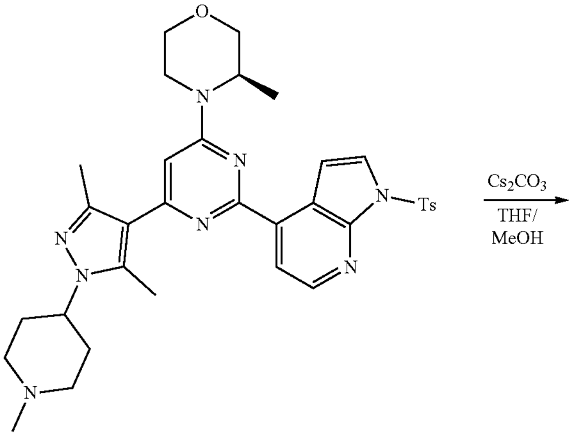

A37-3

-continued

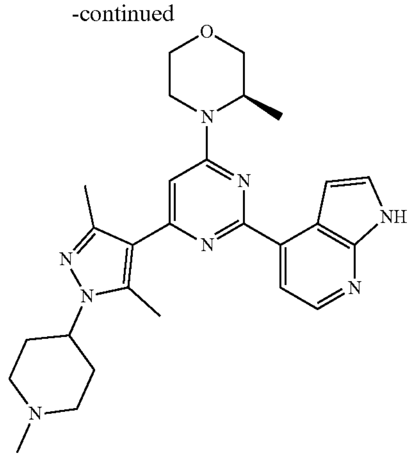

A37

Intermediate a9 (0.38 mmol, 210 mg), cesium carbonate (1.16 mmol, 378 mg) and tert-butyl 4-((methylsulfonyl)oxy) piperidine-1-carboxylate (0.46 mmol, 129 mg) were added to a reaction flask, after dissolving in 8 mL of DMF, the mixture was heated up to 90° C. and reacted for 5 hours. The reaction was stopped, 30 mL of water was added to the reaction, extracted with ethyl acetate, and separated by flash column chromatography to afford intermediate A37-1 (yield: 41%), LC-MS: $[M+H]^+$: 727.

Intermediate A37-1 (115 mg) was dissolved in 3 mL of dichloromethane, 1 mL of trifluoroacetic acid was added dropwise, and the mixture was reacted at room temperature for 2 hours. The reaction was stopped, the organic solvent was removed under reduced pressure. 20 mL of saturated sodium bicarbonate aqueous solution was added to the reaction, extracted with dichloromethane to afford crude intermediate A37-2, which was directly proceeded in the next step. LC-MS: $[M+H]^+$: 627.

In an ice bath, crude intermediate A37-2 and 1 mL of 40% formaldehyde aqueous solution was dissolved in 2 mL of methanol, 2 drops of glacial acetic acid were added dropwise. After the mixture was stirred for 5 minutes, $NaCNBH_3$ (0.72 mmol, 45 mg) was slowly added, the mixture was stirred for 2 hours, then the reaction was stopped. 20 mL of 4M ammonium chloride aqueous solution was added to the reaction, extracted with ethyl acetate, and separated by TLC chromatography to afford intermediate A37-3, two-step total yield: 51%. LC-MS: $[M+H]^+$: 641.

Intermediate A37-3 (0.08 mmol, 50 mg) was dissolved in 4 mL mixture of methanol and THF(v/v, 1/1), cesium carbonate (0.23 mmol, 76 mg) was added, and the mixture was reacted at 60° C. for 2 hours. The mixture was filtered, the solvent was removed under reduced pressure, and separated by preparative chromatography to afford the title compound A37 (9 mg, yield: 22%), LC-MS: $[M+H]^+$: 487.

Example 27: A38

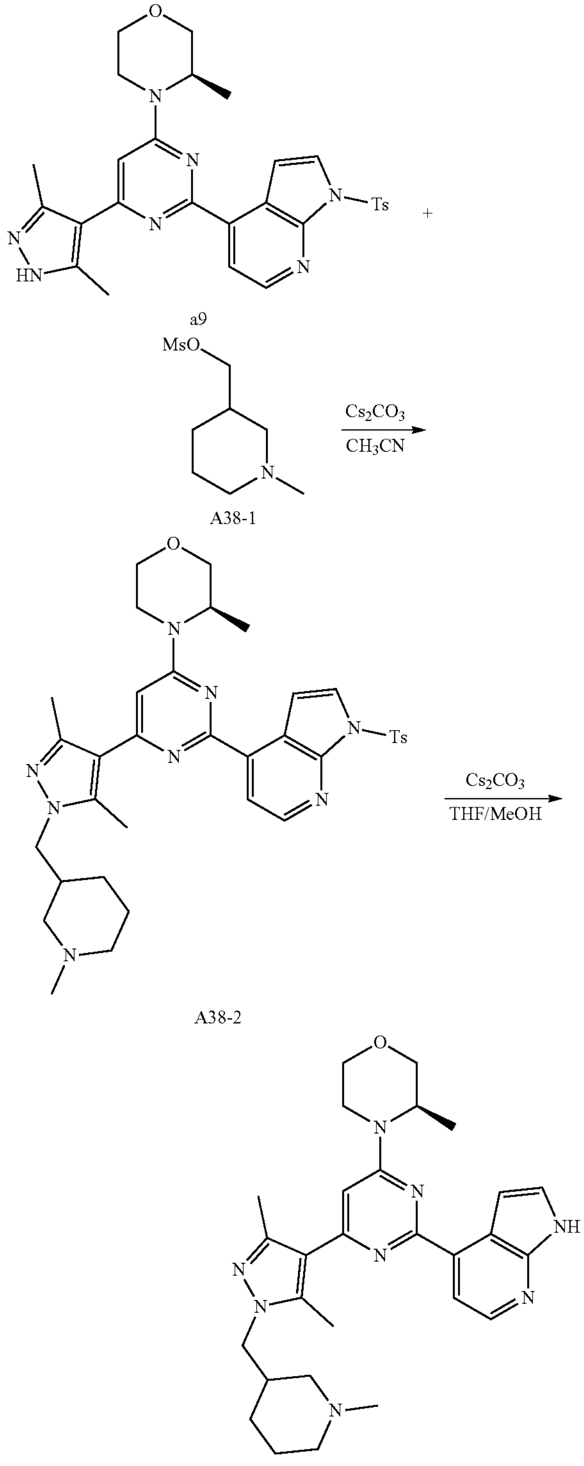

a9

A38-1

A38-2

A38

Intermediate a9 (0.12 mmol, 66 mg), cesium carbonate (0.24 mmol, 79 mg) and the raw material A38-1 (0.24 mmol, 50 mg) were added to a reaction flask, after dissolving in 5 mL of acetonitrile, the mixture was heated up to 80° C. and reacted for 2 hours. The reaction was stopped, 40 mL of water was added to the reaction, extracted with ethyl acetate, and separated by flash column chromatography to afford intermediate A38-2 (80 mg, yield: 99%), LC-MS: $[M+H]^+$: 655.

Intermediate A38-2 (0.12 mmol, 80 mg) was dissolved in 4 mL mixture of methanol and THF(v/v, 1/1), cesium carbonate (0.24 mmol, 79 mg) was added, and the mixture was reacted at 80° C. for 2 hours. The mixture was filtered, the solvent was removed under reduced pressure, and separated by preparative chromatography to afford the title compound A38 (15 mg, yield: 25%), LC-MS: $[M+H]^+$: 501.

$^1$H NMR (400 MHz, DMSO-$d_6$) δ 11.75 (s, 1H), 8.33 (d, J=5.0 Hz, 1H), 8.01 (d, J=4.9 Hz, 1H), 7.56 (t, J=2.9 Hz, 1H), 7.23 (dd, J=3.5, 1.9 Hz, 1H), 6.67 (s, 1H), 4.59 (s, 1H), 4.22 (d, J=12.8 Hz, 1H), 4.06-3.92 (m, 3H), 3.81 (d, J=11.5 Hz, 1H), 3.69 (d, J=11.3 Hz, 1H), 3.55 (t, J=11.4 Hz, 1H), 3.28 (s, 1H), 2.96 (dt, J=50.5, 23.5 Hz, 4H), 2.39 (s, 3H), 2.16 (s, 1H), 2.13 (s, 3H), 2.08 (d, J=11.3 Hz, 4H), 1.46 (s, 2H), 1.29 (d, J=6.7 Hz, 3H).

Example 28: A41

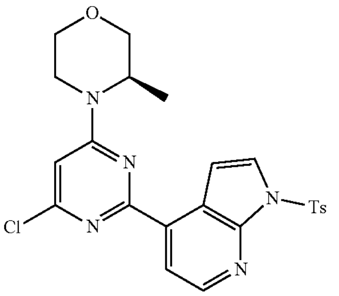

+ a4

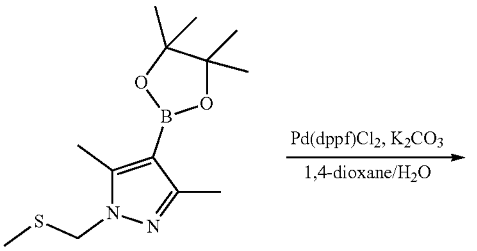

b18

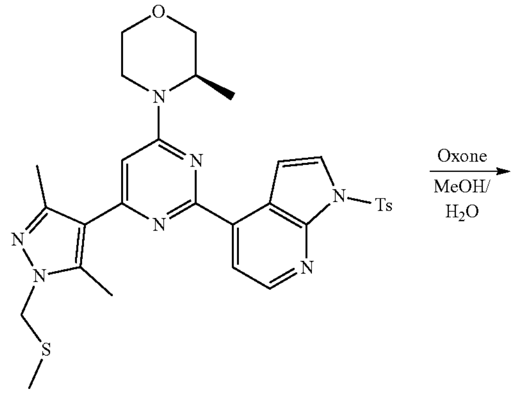

A41-1

-continued

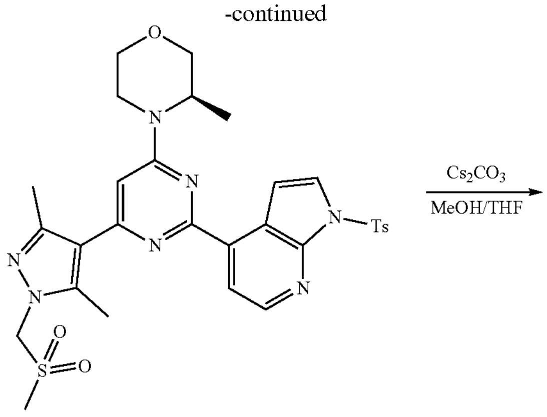

A41-2

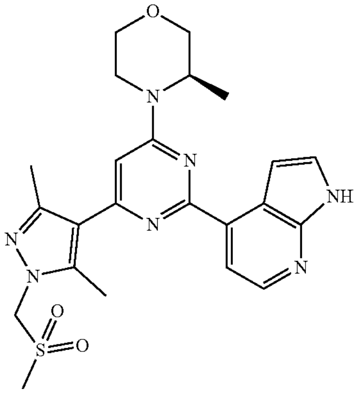

A41

Under nitrogen protection, intermediate a4 (0.18 mmol, 85 mg) and intermediate b18 (0.18 mmol, 50 mg) were dissolved in 5 mL mixture of 1,4-dioxane and water (v/v: 9/1), potassium carbonate (0.53 mmol, 73 mg) and Pd(dppf)$Cl_2$ (0.02 mmol, 15 mg) were added, and the mixture was reacted at 100° C. in microwave for 30 minutes. The reaction was stopped, filtered, 20 mL of water was added, extracted with ethyl acetate, and separated by flash column chromatography to afford compound A41-1 (77 mg, yield: 73%), LC-MS: $[M+H]^+$: 604.

Compound A41-1 (0.127 mmol, 77 mg) was dissolved in 6 mL mixture of methanol and water (v/v, 5/1) in a reaction flask, potassium monopersulfate (Oxone, 0.38 mmol, 233 mg) was slowly added, after the mixture was reacted at room temperature for 3 hours, the reaction was stopped. 30 mL of water was added and extracted with dichloromethane to afford crude compound A41-2 (70 mg), LC-MS: $[M+H]^+$: 636.

Crude compound A41-2 (0.03 mmol, 15 mg) was dissolved in 3 mL mixture of methanol and tetrahydrofuran (v/v, 1/1) cesium carbonate (0.07 mmol, 23 rag) was added, the reaction was heated to 60° C. and reacted for 3 hours, and the reaction was stopped. 20 mL of water was added, extracted with dichloromethane, and separated by preparative chromatography to afford the title compound A41 (3 mg, yield: 27%), LC-MS: $[M+H]^+$: 482.

$^1$H NMR (400 MHz, DMSO-$d_6$) δ 11.76 (s, 1H), 8.34 (d, J=5.0 Hz, 1H), 8.01 (d, J=5.0 Hz, 1H), 7.58 (t, 3.0 Hz, 1H), 7.23 (dd, J=3.4, 1.9 Hz, 1H), 6.72 (s, 1H), 5.73 (s, 2H), 4.61 (s, 1H), 4.25 (d, =13.3 Hz, 1H), 4.06-3.98 (m, 1H), 3.81 (d,

J=11.4 Hz, 1H), 3.70 (d, J=9.9 Hz, 1H), 3.58-3.50 (m, 1H), 3.28 (d, J=9.7 Hz, 1H), 3.09 (s, 3H), 2.59 (s, 3H), 2.43 (s, 3H), 1.30 (d, J=6.6 Hz, 3H).

Example 29: D24

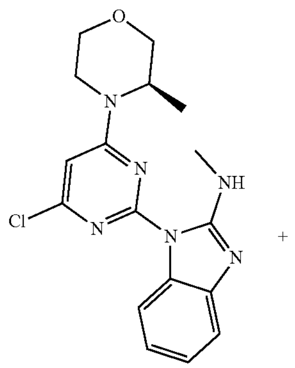

d7

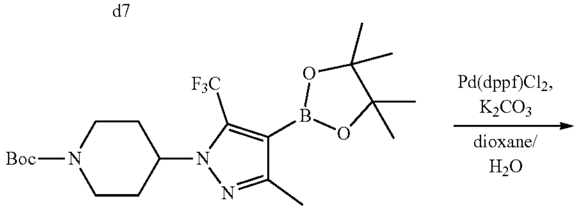

c3

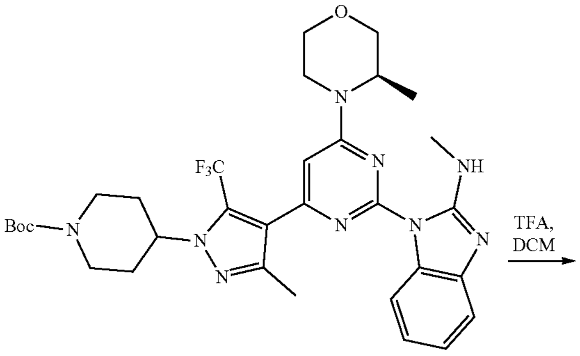

D24-1

-continued

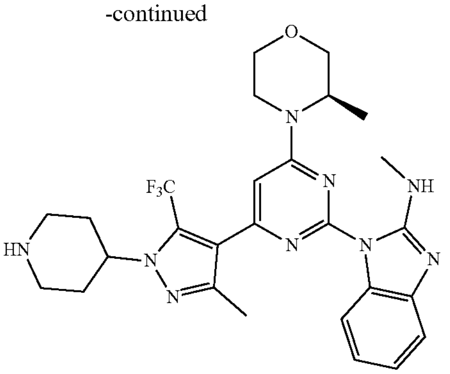

D24

Under nitrogen protection, intermediate d7 (0.92 mmol, 330 mg) and intermediate c3 (1.8 mmol, 845 mg) were dissolved in 15 mL mixture of 1,4-dioxane and water (v/v: 9/1), potassium carbonate (1.83 mmol, 254 mg) and $Pd(dppf)Cl_2$ (0.09 mmol, 67 mg) were added, and the mixture was reacted at 101° C. for 2 hours. The reaction was stopped, filtered, 40 mL of water was added, extracted with ethyl acetate, and separated by flash column chromatography to afford compound D24-1 (400 mg, yield: 67%), LC-MS: $[M+H]^+$: 656.

Compound D24-1 (0.6 mmol, 400 mg) was dissolved in 6 mL of dichloromethane, 2 mL of trifluoroacetic acid was added, the mixture was reacted at room temperature for 3 hours, and the reaction was stopped. 30 mL of saturated sodium bicarbonate aqueous solution was slowly added, extracted with dichloromethane, and separated by preparative chromatography to afford the title compound D24 (yield: 55%), LC-MS: $[M+H]^+$: 556.

The following compounds were synthesized with reference to the route, of Example 29:

| Structure | The structure replacing c3 | LC-MS/ $[M + H]^+$ | $^1H$ NMR |
|---|---|---|---|
| 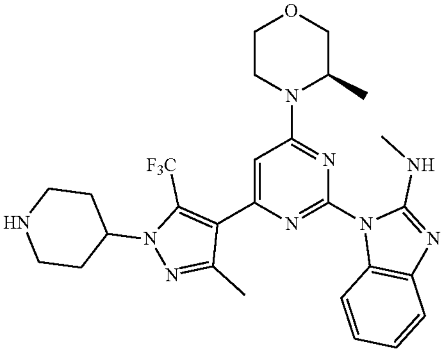 D24 | — | 588 | $^1H$ NMR (400 MHz, DMSO-$d_6$) δ 8.46 (t, J = 4.9 Hz, 1H), 8.18 (d, J = 8.0 Hz, 1H), 7.26 (d, J = 7.7 Hz, 1H), 7.10 (t, J = 7.6 Hz, 1H), 6.98 (t, J = 7.7 Hz, 1H), 6.85 (s, 1H), 4.47 (s, 1H), 4.31 (d, J = 12.3 Hz, 1H), 4.13 (d, J = 13.2 Hz, 1H), 4.02 (d, J = 11.9 Hz, 1H), 3.80 (d, J = 11.6 Hz, 1H), 3.69 (d, J = 10.7 Hz, 1H), 3.55 (dd, J = 13.2, 10.4 Hz, 1H), 3.38 (d, J = 8.6 Hz, 1H), 3.08 (d, J = 12.5 Hz, 2H), 3.03 (d, J = 4.8 Hz, 3H), 2.61 (t, J = 12.3 Hz, 2H), 2.28 (s, 3H), 2.08-1.96 (m, 2H), 1.87 (d, J = 12.0 Hz, 2H), 1.31 (d, J = 6.8 Hz, 3H). |

-continued

| Structure | The structure replacing c3 | LC-MS/ [M + H]+ | $^1$H NMR |
|---|---|---|---|
| 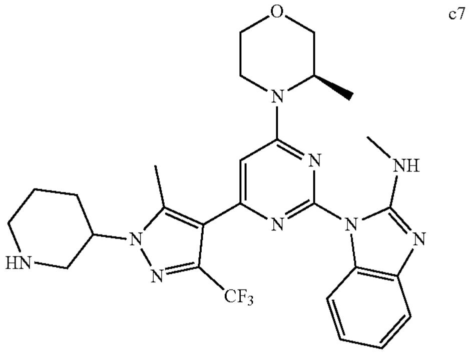 D45 | c7 | 556 | $^1$H NMR (400 MHz, DMSO-$d_6$) δ 8.52 (d, J = 5.0 Hz, 1H), 8.20 (d, J = 8.0 Hz, 1H), 7.29-7.23 (m, 1H), 7.10 (dd, J = 8.0, 6.8 Hz, 1H), 7.02-6.96 (m, 1H), 6.71 (s, 1H), 4.46 (s, 1H), 4.32 (t, J = 10.2 Hz, 1H), 4.11 (d, J = 12.8 Hz, 1H), 4.06-4.00 (m, 1H), 3.81 (d, J = 11.6 Hz, 1H), 3.70 (dd, J = 11.4, 3.2 Hz, 1H), 3.60-3.52 (m, 1H), 3.37 (td, J = 12.9, 3.9 Hz, 2H), 3.13 (d, J = 12.3 Hz, 1H), 3.03 (d, J = 4.8 Hz, 3H), 2.91 (d, J = 12.5 Hz, 1H), 2.79 (t, J = 11.1 Hz, 1H), 2.47 (s, 3H), 2.05 (s, 1H), 2.00 (d, J = 8.0 Hz, 1H), 1.76 (d, J = 13.3 Hz, 1H), 1.65-1.50 (m, 1H), 1.32 (d, J = 6.7 Hz, 3H). |
| 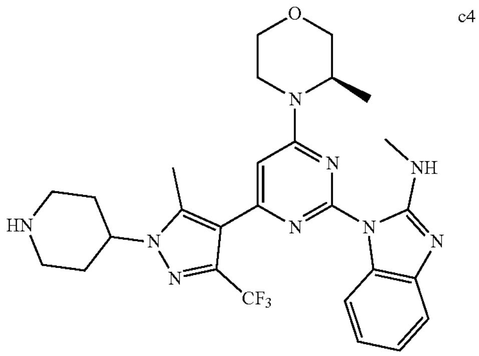 D56 | c4 | 556 | $^1$H NMR (400 MHz, DMSO-$d_6$) δ 8.58-8.51 (m, 1H), 8.20 (d, J = 7.3 Hz, 1H), 7.28-7.24 (m, 1H), 7.10 (td, J = 7.6, 1.2 Hz, 1H), 7.02-6.96 (m, 1H), 6.73 (s, 1H), 4.53-4.41 (m, 2H), 4.11 (d, J = 14.1 Hz, 1H), 4.03 (dd, J = 11.7, 4.6 Hz, 1H), 3.81 (d, J = 11.7 Hz, 1H), 3.69 (dd, J = 11.9, 2.7 Hz, 1H), 3.55 (td, J = 11.7, 3.5 Hz, 1H), 3.38 (dd, J = 13.2, 4.5 Hz, 1H), 3.08 (d, J = 13.0 Hz, 2H), 3.02 (d, J = 4.8 Hz, 3H), 2.71-2.61 (m, 2H), 2.47 (s, 3H), 1.95-1.85 (m, 4H), 1.32 (d, J = 6.7 Hz, 3H). |

Example 30: D26

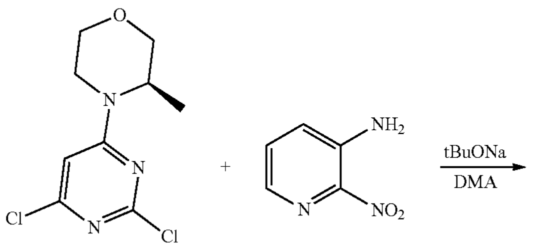

a1

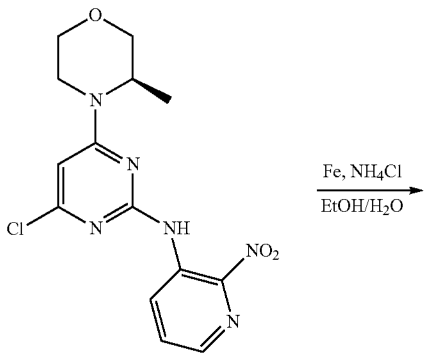

D26-1

-continued

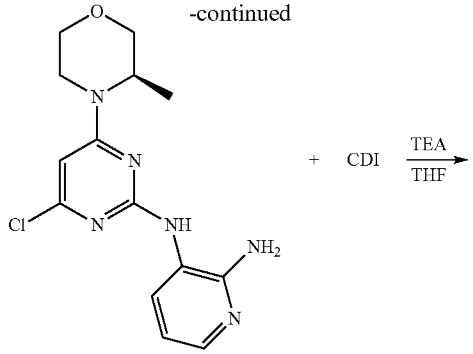

D26-2

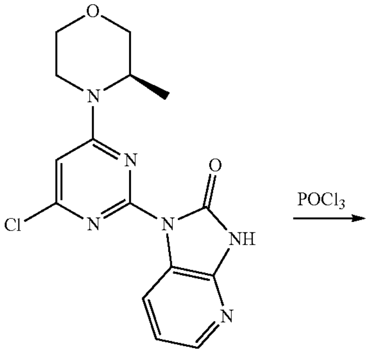

D26-3

-continued

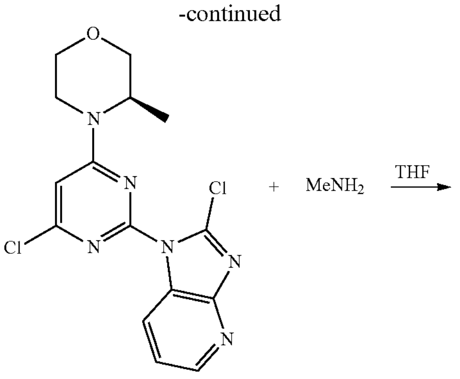

D26-4

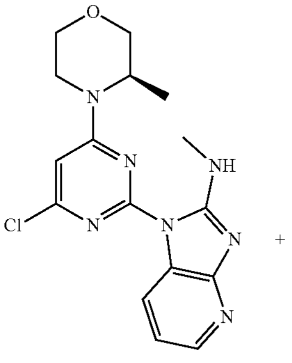

D26-5

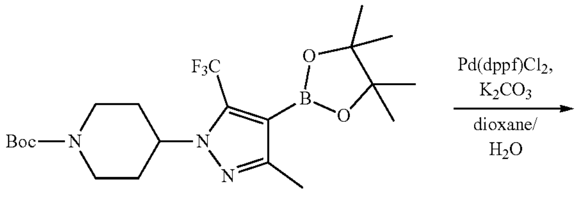

c3

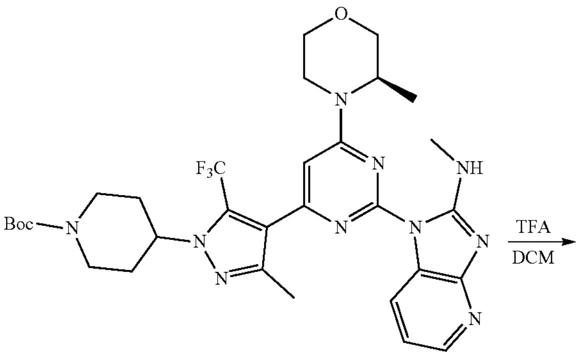

D26-6

-continued

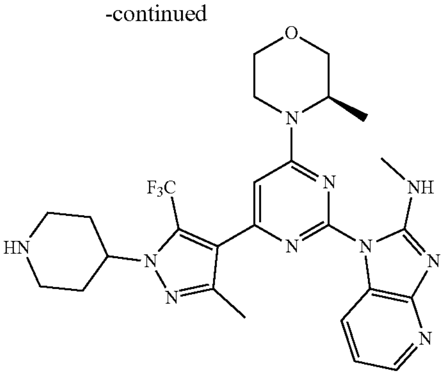

D26

Intermediate a1 (2.02 mmol, 500 mg) and 2-nitro-3-amino-pyridine (2.4 mmol, 337 mg) were added to a microwave reaction flask, and dissolved in 8 mL of DMA. After sodium tort-butoxide (4 mmol, 384 mg) was added, the reaction was reacted at 100° C. in microwave for 1.5 hours. The reaction was stopped, 30 mL of water was added, extracted with ethyl acetate, and dried over anhydrous sodium sulfate to afford crude intermediate D26-1, LC-MS: $[M+H]^+$: 351.

Intermediate D26-1 (crude) from the previous step, reduced iron powder (12 mmol, 672 mg) and ammonium chloride (12 mmol, 642 mg) were added to a reaction flask, 22 mL of ethanol and 4 mL of water were added to dissolve. The mixture was reacted at 80° C. for 2 hours. The reaction was stopped, suction filtered, 60 mL of water was added, extracted with ethyl acetate, dried over anhydrous sodium sulfate, and separated by flash column chromatography to afford intermediate D26-2 (two-step yield: 91%), LC-MS: $[M+H]^+$: 321.

Intermediate D26-2 (0.65 mmol, 210 mg), triethylamine (3.3 mmol, 331 mg) and carbonyl diimidazole (3.3 mmol, 530 mg) were added to a reaction flask, and dissolved in 10 mil, of tetrahydrofuran. The reaction was heated to 50° C. and reacted for 10 hours. The reaction was stopped, 40 mL of water was added, extracted with ethyl acetate, dried over anhydrous sodium sulfate, and separated by flash column chromatography to afford intermediate D26-3 (200 mg, yield: 89%), LC-MS: $[M+H]^+$: 347.

Intermediate D26-3 (0.35 mmol, 120 mg) was dissolved in 5 mL of phosphorus oxychloride, the mixture was heated up to 100° C. and reacted for 10 hours. The reaction was stopped, the mixture was placed in an ice bath, 20 mL of ice water was slowly added, and the pH of the mixture was adjusted to about 10 with saturated sodium carbonate aqueous solution. The mixture was extracted with ethyl acetate, dried over anhydrous sodium sulfate, and separated by flash column chromatography to afford intermediate 1726-4 (70 mg, yield: 55%), LC-MS: $[M+H]^+$: 366.

Intermediate D26-4 (0.16 mmol, 60 mg) was dissolved in 10 mL of tetrahydrofuran, methylamine solution (1 mL, 2.5 M) was slowly added, and the reaction was heated to 70° C. and reacted for 4 hours. The reaction was stopped, and separated by flash column chromatography to afford intermediate 1726-5 (30 mg, yield: 53%), LC-MS: $[M+H]^+$: 360.

Under nitrogen protection, intermediate D26-5 (0,083 mmol, 30 mg) and intermediate c3 (0.15 mmol, 69 mg) were dissolved in 3 mL mixture of 1,4-dioxane and water (v/v: 9/1), potassium carbonate (0.17 mmol, 23 mg) and Pd(dppf) $Cl_2$ (0.008 mmol, 7 mg) were added, and the mixture was heated at 100° C. and reacted for 2 hours. The reaction was stopped, filtered, 10 mL of water was added, extracted with ethyl acetate, and separated by TLC chromatography to afford compound D26-6 (50 mg, yield: 67%), LC-MS: $[M+H]^+$: 657.

Compound D26-6 (0.076 mmol, 50 mg) was dissolved in 3 mL of dichloromethane, 1.0 mL of trifluoroacetic acid was added, after the mixture was reacted at room temperature for 3 hours, the reaction was stopped. 20 of saturated sodium bicarbonate aqueous solution was slowly added, extracted with dichloromethane, and separated by preparative chromatography to afford the title compound D26 (14 mg, yield: 34%), LC-MS: $[M+H]^+$: 557.

$^1H$ NMR (400 MHz, DMSO-$d_6$) δ 8.88 (d, J=26.7 Hz, 1H), 8.40 (d, J=7.9 Hz, 1H), 8.13 (dd, J=5.3, 1.6 Hz, 1H), 7.03 (dd, J=7.9, 5.1 Hz, 1H), 6.89 (s, 1H), 4.74 (s, 1H), 4.45 (s, 1H), 4.07 (dd, J=33.0, 11.6 Hz, 2H), 3.80 (d, J=11.6 Hz, 1H), 3.72-3.67 (m, 1H), 3.59-3.53 (m, 1H), 151 (s, 1H), 3.21 (d, J=9.7 Hz, 2H), 3.10 (d, 4.8 Hz, 3H), 2.36 (s, 2H), 2.30 (s, 3H), 2.17-1.98 (m, 4H), 1.31 (d, 6.8 Hz, 3H).

Example 31: D27

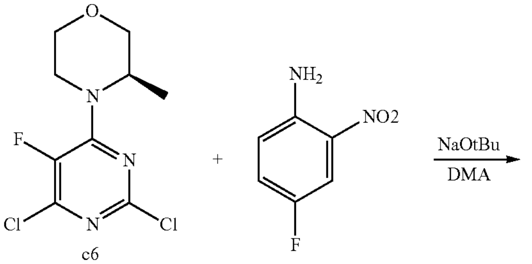

c6 d2-1

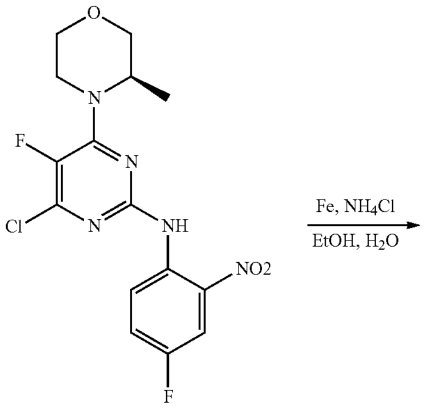

D27-1

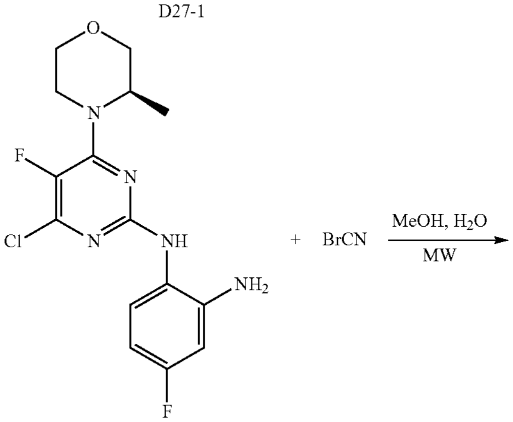

D27-2

-continued

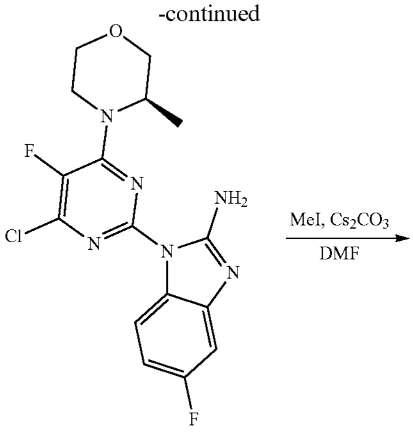

D27-3

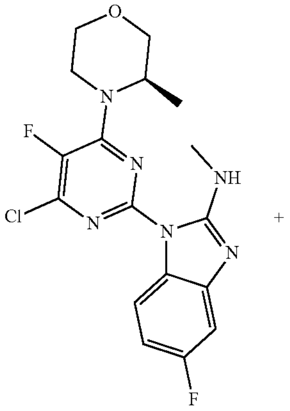

D27-4

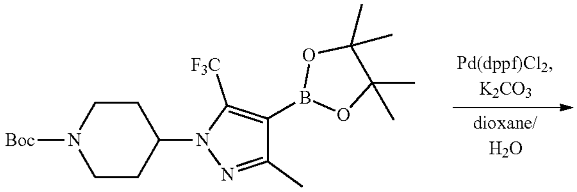

c3

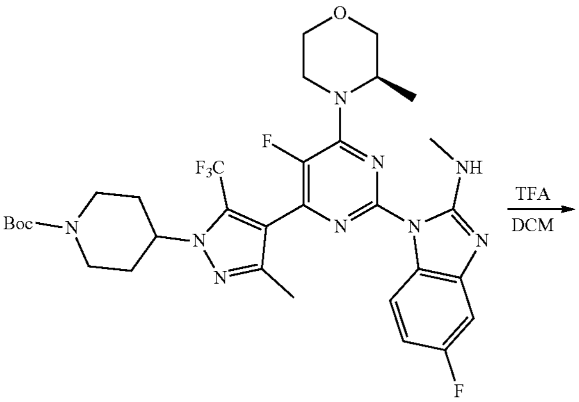

D27-5

-continued

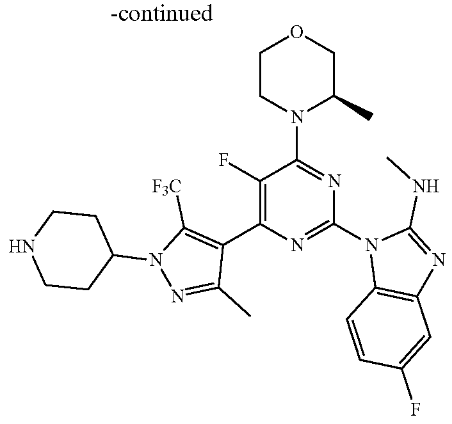

D27

Intermediate c6 (1 mmol, 265 mg) and 2-nitro-4-fluoroaniline d2-1 (1 mmol, 171 mg) were added to a microwave reaction flask, and dissolved in 8 mL of DMA. After sodium Cert-butoxide (2 mmol, 192 mg) was added, the reaction was reacted at 100° C. in microwave for 1 hour. The reaction was stopped, 30 mL of water was added, extracted with ethyl acetate, dried over anhydrous sodium sulphate, and separated by flash column chromatography to afford intermediate D27-1 (150 mg, yield: 39%), LC-MS: $[M+H]^+$: 386.

Intermediate D27-1 (0.39 mmol, 150 mg), reduced iron powder (1.95 mmol, 1109 mg) and ammonium chloride (3.9 mmol, 206 mg) were added to a reaction flask, the mixture was dissolved in 10 mL ethanol and 2 mL water. The mixture was reacted at 100° C. for 2 hours. The reaction was stopped, suction filtered, 30 mL of water was added, extracted with ethyl acetate, dried over anhydrous sodium sulfate to afford crude intermediate D27-2 (70 mg), LC-MS: $[M+H]^+$: 356.

Intermediate D27-2 (0.2 mmol, 70 mg), bromonitrile (0.4 mmol, 42 mg) were added to a reaction flask, and dissolved in 4 mL methanol and 1 mL water. The mixture was heated up to 80° C. and reacted for 2 hours. The reaction was stopped, 40 mL of water was added, extracted with ethyl acetate, dried over anhydrous sodium sulfate, and separated by flash column chromatography to afford intermediate D27-3 (60 mg, yield: 79%), LC-MS: $[M+H]^+$: 381.

Intermediate D27-3 (0.47 mmol, 180 mg) and cesium carbonate (1.42 mmol, 462 mg) were dissolved in 6 mL of DMF, methyl iodide (0.47 mmol, 0.029 mL) was added dropwise, and the mixture was reacted at 50° C. for 3 hours. The reaction was stopped, 20 mL of water was added, extracted with dichloromethane, dried over anhydrous sodium sulfate, and separated by TLC chromatography to afford compound D274 (150 mg, yield: 81%), LC-MS: $[M+H]^+$: 395.

Under nitrogen protection compound D274 (0.38 mmol, 150 mg) and intermediate c3 (0.76 mmol, 348 mg) were dissolved in 5 mL mixture of 1,4-dioxane and water (v/v: 9/1), potassium carbonate (1.14 mmol, 157 mg), Pd(dppf) $Cl_2$ (0.04 mmol, 28 mg) were added, and the mixture was reacted at 100° C. in microwave for 1 hour. The reaction was stopped, filtered, the solvent was removed under reduced pressure, 15 mL of water was added, extracted with ethyl acetate, and separated by TLC chromatography to afford compound D27-5 (112 mg, yield: 43%), LC-MS: $[M+H]^+$: 692.

Compound D27-5 (112 mg) was dissolved in 5 mL of dichloromethane, 2 mL of trifluoroacetic acid was added dropwise, after the mixture was reacted at room temperature for 2 hours, the solvent was removed under reduced pressure, and separated by preparative chromatography to afford the title compound D27 (30 mg, yield: 32%), LC-MS: $[M+H]^+$: 592.

$^1H$ NMR (400 MHz, DMSO-$d_6$) δ 8.19 (d, J=5.2 Hz, 1H), 8.05 (dd, J=8.8, 5.2 Hz, 1H), 7.07 (dd, J=9.6, 2.7 Hz, 1H), 6.80 (td, J=9.3, 2.7 Hz, 1H), 4.49 (d, J=7.3 Hz, 1H), 4.30 (d, J=11.5 Hz, 1H), 4.10 (d, J=11.9 Hz, 1H), 4.03-3.97 (m, 1H), 3.76 (d, J=2.2 Hz, 2H), 3.67-3.55 (m, 2H), 3.09 (s, 1H), 3.06 (s, 1H), 3.04 (d, J=5.0 Hz, 3H), 2.61 (t, J=12.1 Hz, 2H), 2.25 (s, 3H), 2.04 (dd, J=13.0, 8.9 Hz, 2H), 1.87 (d, J=11.8 Hz, 2H), 1.40 (d, J=6.8 Hz, 3H).

Example 32: D28

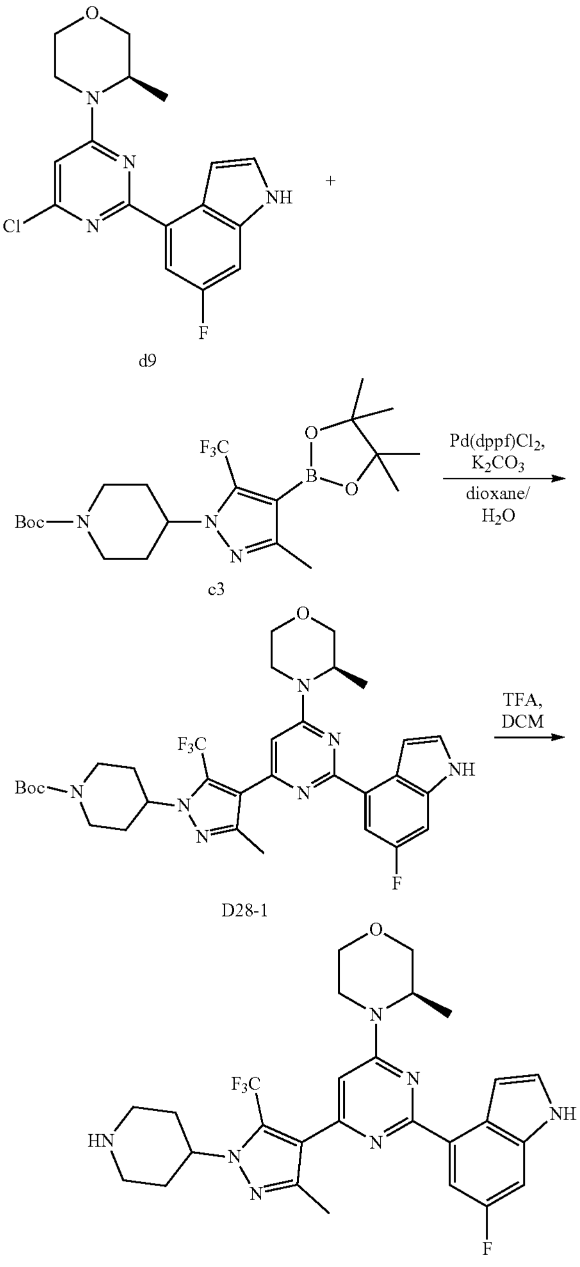

d9 c3

D28-1

D28

Under nitrogen protection, intermediate d9 (4.0 mmol, 1.4 g) and intermediate c3 (4.0 mmol, 3.7 g) was dissolved in 50 mL mixture of 1,4-dioxane and water (v/v: 9/1), potassium carbonate (12 mmol, 1.67 g) and $Pd(dppf)Cl_2$ (0.4 mmol, 296 mg) were added, then the mixture was heated up to 100° C. and reacted for 2 hours. The reaction was stopped, filtered, the solvent was removed under reduced pressure, 80 mL of water was added, extracted with ethyl acetate, and separated by column chromatography to afford compound D28-1 (2.4 g, yield: 93%). LC-MS: $[M+H]^+$: 644.

Compound D28-1 (2.4 g) was dissolved in 30 mL of dichloromethane, 10 mL of trifluoroacetic acid was added, after the mixture was reacted at room temperature for 2 hours, the solvent was removed under reduced pressure. 80 mL of saturated sodium carbonate aqueous solution was slowly added, extracted with dichloromethane, and separated by column chromatography to afford the title compound D28 (yield: 90%), LC-MS: $[M+H]^+$: 544.

The following compounds were synthesized with reference to the route of Example 42:

| Structure | The structure replacing c3 | LC-MS/ $[M + H]^+$ | $^1$H NMR |
|---|---|---|---|
| 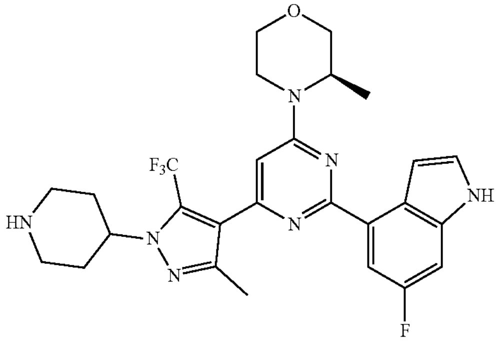 D28 | — | 544 | $^1$H NMR (400 MHz, DMSO-$d_6$) δ 11.32 (s, 1H), 8.78 (d, J = 10.7 Hz, 1H), 8.39 (d, J = 11.7 Hz, 1H), 7.86 (dd, J = 11.5, 2.5 Hz, 1H), 7.44 (t, J = 2.7 Hz, 1H), 7.36-7.27 (m, 2H), 6.81 (s, 1H), 4.71 (d, J = 11.9 Hz, 1H), 4.53 (s, 1H), 4.26 (d, J = 13.4 Hz, 1H), 4.02 (d, J = 9.0 Hz, 1H), 3.81 (s, 1H), 3.69 (dd, J = 11.6, 3.1 Hz, 1H), 3.57-3.51 (m, 1H), 3.46 (d, J = 12.5 Hz, 1H), 3.25 (m, 4H), 2.35 (d, J = 13.5 Hz, 2H), 2.29 (s, 3H), 2.14 (d, J = 13.3 Hz, 2H), 2.00 (q, J = 7.3 Hz, 1H), 1.28 (d, J = 6.7 Hz, 3H). |
| 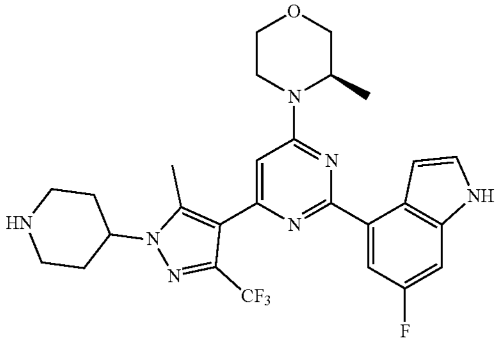 D47 | c4 | 544 | $^1$H NMR (400 MHz, DMSO-$d_6$) δ 11.28 (s, 1H), 7.92 (dd, J = 11.7, 2.4 Hz, 1H), 7.43 (t, J = 2.8 Hz, 1H), 7.34-7.28 (m, 2H), 6.70 (s, 1H), 4.55-4.38 (m, 2H), 4.21 (d, J = 13.1 Hz, 1H), 4.02 (dd, J = 11.9, 3.5 Hz, 1H), 3.80 (d, J = 11.5 Hz, 1H), 3.69 (dd, J = 11.6, 3.1 Hz, 1H), 3.55 (td, J = 11.8, 2.9 Hz, 1H), 3.29-3.33 (m, 4H), 3.07 (d, J = 12.6 Hz, 2H), 2.69-2.60 (m, 2H), 1.95-1.84 (m, 4H), 1.29 (d, J = 6.7 Hz, 3H). |
| 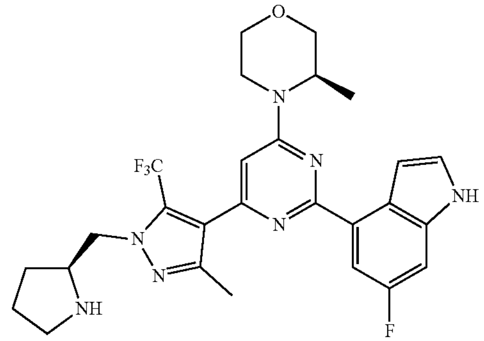 D52 | c12 | 544 | $^1$H NMR (600 MHz, DMSO-$d_6$) δ 11.34 (s, 1H), 7.89 (dd, J = 11.6, 2.5 Hz, 1H), 7.45 (t, J = 2.8 Hz, 1H), 7.34-7.30 (m, 2H), 6.75 (s, 1H), 4.67-4.63 (m, 1H), 4.59-4.53 (m, 2H), 4.03 (m, 2H), 3.81 (d, J = 11.3 Hz, 1H), 3.71-3.68 (m, 1H), 3.57-3.53 (m, 1H), 3.29 (m, 2H), 3.22 (m, 1H), 2.33 (s, 3H), 2.19 (m, 2H), 1.96 (m, 2H), 1.78-1.70 (m, 2H), 1.28 (d, J = 6.8 Hz, 3H). |

-continued

| Structure | The structure replacing c3 | LC-MS/ [M + H]+ | 1H NMR |
|---|---|---|---|
| 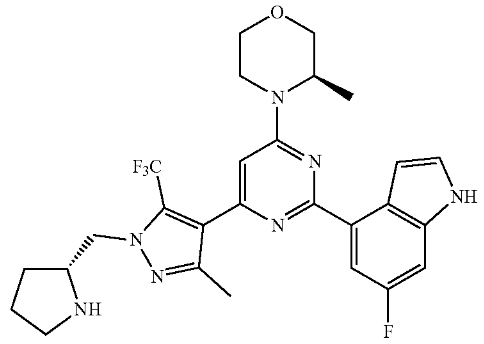 D53 | c13 | 544 | NT |
| 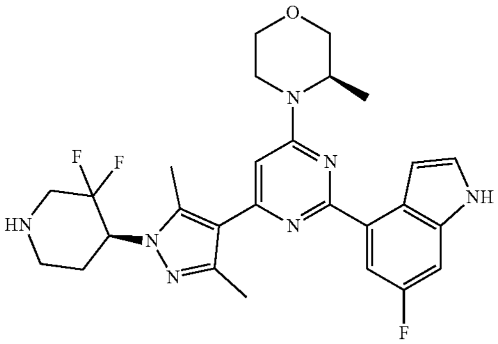 D54a | c14 | 526 | $^1$H NMR (400 MHz, DMSO-$d_6$) δ 11.30 (s, 1H), 7.90 (dd, J = 11.6, 2.4 Hz, 1H), 7.46-7.43 (m, 1H), 7.36-7.33 (m, 1H), 7.31 (dd, J = 9.2, 1.9 Hz, 1H), 6.64 (s, 1H), 4.96-4.78 (m, 2H), 4.57 (d, J = 4.7 Hz, 1H), 4.23 (d, J = 13.5 Hz, 1H), 4.01 (dd, J = 11.5, 3.4 Hz, 1H), 3.80 (d, J = 12.0 Hz, 1H), 3.69 (dd, J = 11.6, 3.4 Hz, 1H), 3.58-3.50 (m, 1H), 3.13-3.00 (m, 2H), 2.81-2.68 (m, 2H), 2.53 (s, 3H), 2.38 (s, 3H), 2.03-1.89 (m, 2H), 1.28 (d, J = 6.7 Hz, 3H). |
| 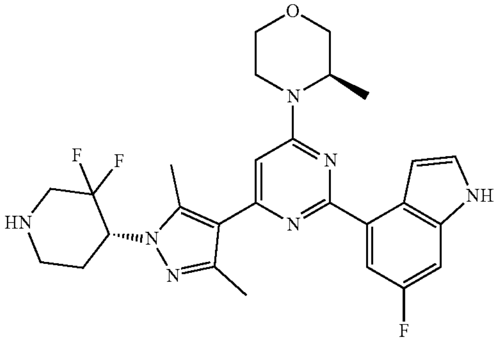 D54b | c14 | 526 | $^1$H NMR (400 MHz, DMSO-$d_6$) δ 11.31 (s, 1H), 7.90 (dd, J = 11.6, 2.5 Hz, 1H), 7.45-7.43 (m, 1H), 7.36-7.33 (m, 1H), 7.31 (m, 1H), 6.65 (s, 1H), 4.94-4.79 (m, 2H), 4.56 (s, 1H), 4.23 (d, J = 12.2 Hz, 1H), 4.01 (dd, J = 12.1, 3.4 Hz, 1H), 3.80 (d, J = 10.0 Hz, 1H), 3.69 (dd, J = 11.8, 2.6 Hz, 1H), 3.58-3.49 (m, 1H), 3.12-3.00 (m, 2H), 2.79-2.64 (m, 2H), 2.53 (s, 3H), 2.38 (s, 3H), 1.97-1.88 (m, 2H), 1.28 (d, J = 6.7 Hz, 3H). |
| 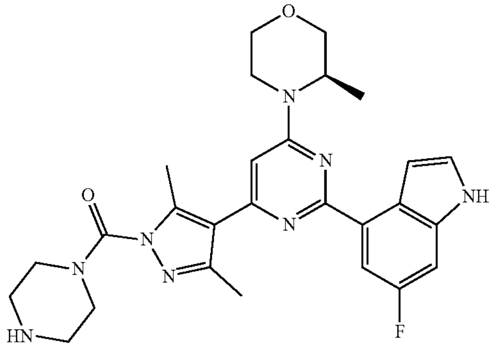 D55 | c15 | 519 | $^1$H NMR (400 MHz, DMSO-$d_6$) δ 11.33 (s, 1H), 7.90 (dd, J = 11.5, 2.4 Hz, 1H), 7.48-7.43 (m, 1H), 7.36-7.29 (m, 2H), 6.72 (s, 1H), 4.58 (s, 1H), 4.24 (d, J = 13.2 Hz, 1H), 4.02 (d, J = 12.6 Hz, 1H), 3.80 (d, J = 14.3 Hz, 1H), 3.69 (d, J = 13.2 Hz, 1H), 3.60-3.48 (m, 3H), 3.34 (s, 1H), 3.31-3.23 (m, 2H), 2.76 (s, 4H), 2.55 (s, 3H), 2.42 (s, 3H), 1.29 (s, 3H). |

Example 33: D29

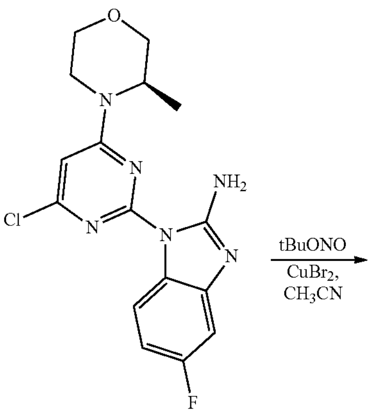

d2

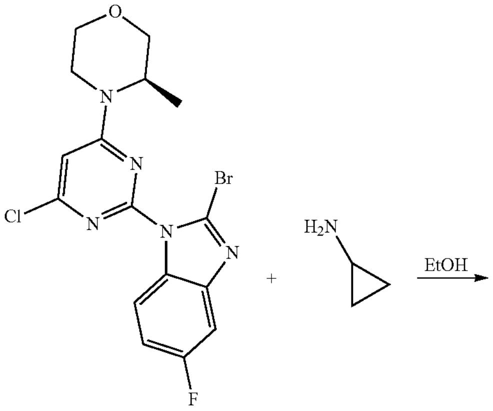

D29-1

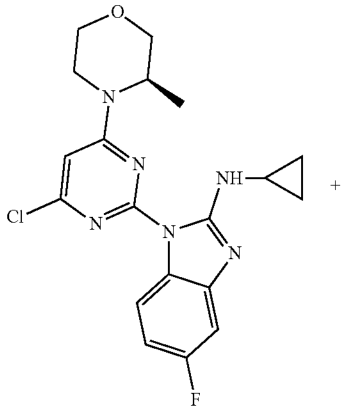

D29-2

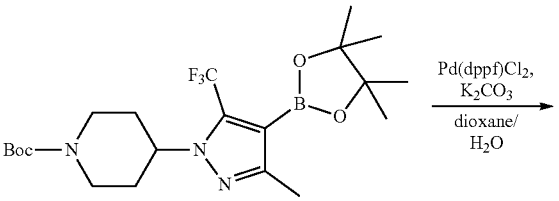

c3

-continued

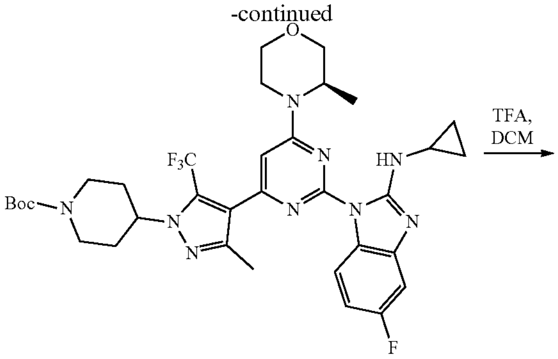

D29-3

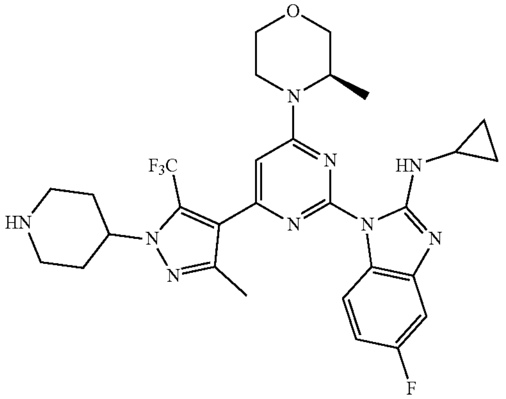

D29

In an ice bath, intermediate d2 (0.55 mmol, 200 mg) and copper bromide (0.82 mmol, 184 mg) were dissolved in 10 mL of acetonitrile. Tert-butyl nitrite (0.83 mina 85 mg) was slowly added, after the mixture was stirred in an ice bath continuously for 5 hours, the reaction was stopped. The mixture was filtered, and separated by flash column chromatography to afford intermediate D29-1 (30 mg, yield: 1:3%), LC-MS: $[M+H]^+$: 427.

Under nitrogen protection, intermediate D29-1 (0.13 mmol, 56 mg) and cyclopropylamine (1.3 mmol, 74 mg) were dissolved in 5 mL of ethanol, then the mixture was heated up to 80° C. and reacted for 10 hours. The reaction was stopped, and separated by flash column chromatography to afford intermediate D29-2 (35 mg, yield: 67%). LC-MS: $[M+H]^+$: 403.

Under nitrogen protection, intermediate D29-2 (0.087 mmol, 35 mg) and intermediate c3 (0.10 mmol, 48 mg) were dissolved in 5 mL mixture of 1,4-dioxane and water (v/v: 9/1), potassium carbonate (0.26 mmol, 36 mg) and Pd(dppf) $Cl_2$ (0.01 mmol, 13 mg) were added, the mixture was heated up to 100° C. and reacted for 2 hours. The reaction was stopped, filtered, the solvent was removed under reduced pressure. 20 mL of water was added, extracted with ethyl acetate, and separated by column chromatography to afford compound D29-3 (40 mg, yield: 66%). LC-MS: $[M+H]^+$: 682.

Compound D29-3 (40 mg) was dissolved in 6 mL of dichloromethane, 1.5 mL of trifluoroacetic acid was added, after the mixture was reacted at room temperature for 2 hours, the solvent was removed under reduced pressure. 20 mL of saturated sodium bicarbonate aqueous solution was slowly added, extracted with dichloromethane, and separated by preparative chromatography to afford the title compound D29 (23 mg, yield: 68%), LC-MS: $[M+H]^+$: 582.

$^1$H NMR (400 MHz, DMSO-$d_6$) δ 8.77 (d, J=2.8 Hz, 1H), 8.15 (dd, J=8.8, 5.3 Hz, 1H), 7.12 (dd, J=9.7, 2.6 Hz, 1H), 6.86 (s, 1H), 6.84-6.76 (m, 1H), 4.43 (s, 1H), 4.34 (d, J=12.2 Hz, 1H), 4.04 (dd, J=24.4, 11.8 Hz, 2H), 3.79 (d, J=11.6 Hz, 1H), 3.69 (d, J=11.9 Hz, 1H), 3.55 (t, J=11.8 Hz, 1H), 3.37 (d, J=11.8 Hz, 1H), 3.08 (d, J=12.5 Hz, 2H), 2.86 (s, 1H), 2.62 (t, J=12.4 Hz, 2H), 2.26 (s, 3H), 2.06-1.97 (m, 2H), 1.85 (d, J=12.2 Hz, 2H), 1.30 (d, J=6.6 Hz, 3H), 0.79 (d, J=5.7 Hz, 2H), 0.54-0.46 (m, 2H).

Example 34: D30a-1-D30b

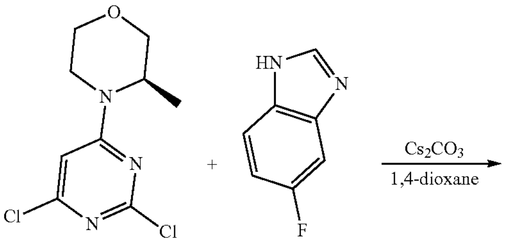

a1 D30a-3

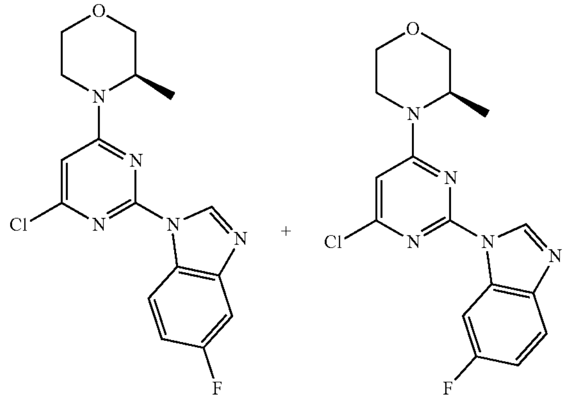

D30a-1 D30b-1

D30a-1 +

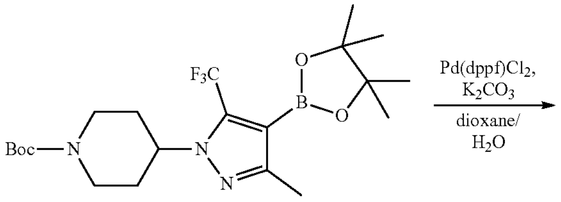

c3

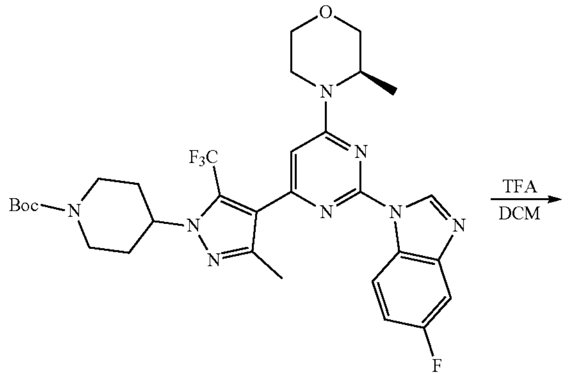

D30a-2

-continued

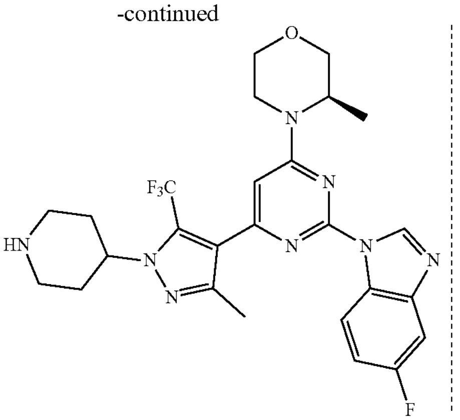

D30a

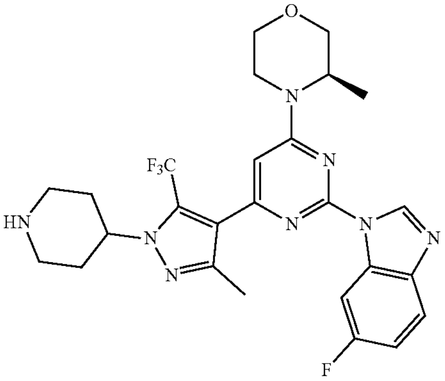 [SMILES: CNc1nc2ncccc2n1-c1nc(-c2c(C)nn(C3CCNCC3)c2C(F)(F)F)cc(N2CCOC[C@H]2C)n1 ; "D26"]

D30b

Intermediate a1 (0.811 mmol, 200 mg) and 5-fluorobenzimidazole (0.88 mmol, 121 mg) were dissolved in 6 mL of 1,4-dioxane, and cesium carbonate (11.61 mmol, 525 mg) was added. The mixture was heated up to 100° C. and reacted for 4 hours. The reaction was stopped, the solvent was removed under reduced pressure, and separated by flash column chromatography to afford intermediate D30a-1 (70 mg, yield: 25%) and D30b-11 (100 mg, yield: 36%). LC-MS: [M+H]$^+$: 348.

Under nitrogen protection, intermediate D30a-1 (0.2 mmol, 70 mg) and intermediate c3 (0.24 mmol, 111 mg) were dissolved in 5 mL, mixture of 1,4-dioxane and water (v/v: 9/1), potassium carbonate (0.6 mmol, 84 mg) and Pd(dppf)$Cl_2$ (0.04 mmol, 29 mg) were added, and the mixture was heated up to 100° C. and reacted for 2 hours. The reaction was stopped, filtered, 30 mL of water was added, extracted with ethyl acetate, and separated by flash column chromatography to afford compound D30a-2 (30 mg, yield: 24%). LC-MS: [M+H]$^+$: 645.

Compound 1330a-2 (30 mg) was dissolved in 6 mL of dichloromethane, 1.5 mL of trifluoroacetic acid was added, after the mixture was reacted at room temperature for 2 hours, the solvent was removed under reduced pressure. 20 mL of saturated sodium bicarbonate aqueous solution was slowly added, extracted with dichloromethane, and separated by preparative chromatography to afford the title compound D30a (20 mg, yield: 79%), LC-MS: [M+H]$^+$: 545.

$^1$H NMR (400 MHz, DMSO-$d_6$) δ 9.15 (s, 1H), 8.411 (dd, J=8.9, 5.1 Hz, 1H), 7.59 (dd, J=9.2, 2.5 Hz, 1H), 7.25 (td, J=9.4, 2.5 Hz, 1H), 6.87 (s, 1H), 4.54 (s, 1H), 4.38-424 (m, 2H), 1.03-3.95 (m, 1H), 3.78 (d, J=11.6 Hz, 1H), 3.68 (dd, J=11.7, 3.1 Hz, 1H), 3.53 (dd, J=12.7, 9.7 Hz, 1.14), 3.27 (d,

J=5.0 Hz, 1H), 3.08 (d, J=12.7 Hz, 2H), 2.62 (t, J=12.2 Hz, 2H), 2.29 (s, 3H), 2.02 (dd, J=14.0, 9.0 Hz, 3H), 1.86 (d, J=11.3 Hz, 2H), 1.29 (d, J=6.8 Hz, 3H).

The title compound D30b was synthesized by referring to the synthesis route of compound D30a and intermediate D30a-1 was replaced with D30b-1 in the second step.

$^1$H NMR (400 MHz, DMSO-$d_6$) δ 9.11 (s, 1H), 8.16 (dd, J=9.9, 2.7 Hz, 1H), 7.78 (dd, J=8.8, 5.0 Hz, 1H), 7.20 (td, J=9.1, 2.6 Hz, 1H), 6.89 (s, 1H), 4.54 (s, J=13.0 Hz, 2H), 4.04-3.96 (m, 1H), 3.78 (d, J=11.6 Hz, 1H), 3.71-3.64 (m, 1H), 1.58-3.49 (m, 1H), 3.33-3.35 (m, 1H), 3.08 (d, 12.7 Hz, 2H), 2.62 (t, J=12.4 Hz, 2H), 2.29 (s, 3H), 2.07-1.97 (m, 2H), 1.87 (d, J=12.1 Hz, 2H), 1.29 (d, 6.7 Hz, 3H).

The following compound was synthesized with reference to the route of Example 34:

-continued

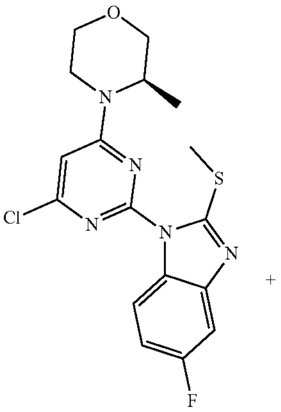

D31-1

| Structure | The structure replacing D30a-3 | LC-MS/ [M + H]$^+$ | $^1$H NMR |
|---|---|---|---|
| 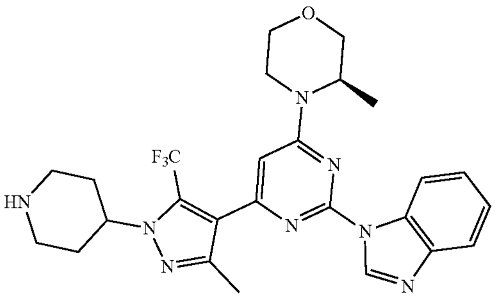 D46 | 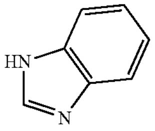 | 527 | $^1$H NMR (400 MHz, DMSO-$d_6$) δ 9.08 (s, 1H), 8.43 (d, J = 7.9 Hz, 1H), 7.76 (d, J = 7.7 Hz, 1H), 7.41-7.28 (m, 2H), 6.85 (s, 1H), 4.51 (t, J = 11.3 Hz, 2H), 4.28 (s, 1H), 4.01 (dd, J = 11.6, 3.6 Hz, 1H), 3.79 (d, J = 11.6 Hz, 1H), 3.68 (dd, J = 11.6, 3.1 Hz, 1H), 3.58-3.51 (m, 1H), 3.32 (d, J = 13.1 Hz, 2H), 3.23 (m, 2H), 2.88 (dd, J = 13.5, 10.9 Hz, 2H), 2.30 (s, 3H), 2.18 (q, J = 11.0 Hz, 2H), 1.99 (d, J = 11.5 Hz, 2H), 1.30 (d, J = 6.7 Hz, 3H). |

Example 35: D31

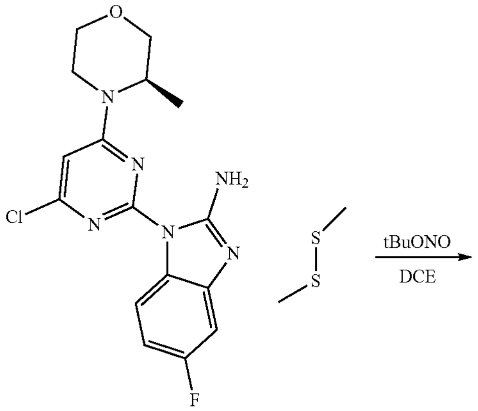

d2

-continued

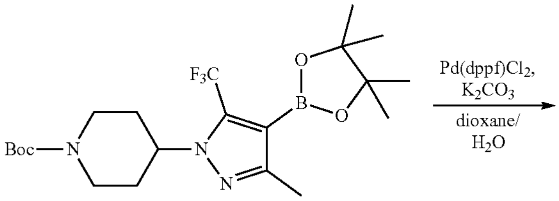

c3

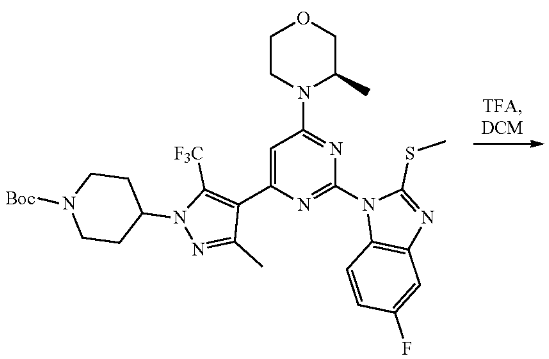

D31-2

-continued

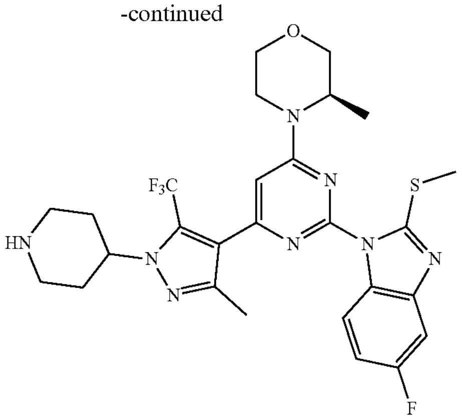

D31

Under nitrogen protection, intermediate d2 (0.55 mmol, 200 mg) and dimethyl sulfide (0.72 mmol, 68 mg) were dissolved in 8 mL of dichloroethane. After the mixture was heated up to 60° C., tert-butyl nitrite (0.72 mmol, 74 mg) was dissolved in 1 mL of dichloroethane and slowly added to the mixture, and continuously stirred for 5 hours. The reaction was stopped, and separated by flash column chromatography to afford intermediate D31-1 (210 mg, yield: 78%). LC-MS: $[M+H]^+$: 394.

Under nitrogen protection, intermediate D31-1 (0.25 mmol, 100 mg) and intermediate c3 (0.31 mmol, 140 mg) were dissolved in 8 mL mixture of 1,4-dioxane and water (v/v: 7/1), potassium carbonate (0.76 mmol, 105 mg) and $Pd(dppf)Cl_2$ (0.05 mmol, 37 rag) were added, the mixture was heated up to 100° C. and reacted for 2 hours. The reaction was stopped, filtered, the solvent was removed under reduced pressure, 20 mL of water was added, extracted with ethyl acetate, and separated by flash column chromatography to afford compound D31-2 (30 mg, yield: 18%). LC-MS: $[M+H]^+$: 691.

Compound D31-2 (30 mg) was dissolved in 3 mL of dichloromethane, 1.0 mL of trifluoroacetic acid was added, after the mixture was reacted at room temperature for 2 hours, the solvent was removed under reduced pressure. 20 mL of saturated sodium bicarbonate aqueous solution was slowly added, extracted with dichloromethane, and separated by preparative chromatography to afford the title compound D31 (11 mg, yield: 47%), LC-MS: $[M+H]^+$: 591. HPLC purity: 94.73%.

Example 36: D32

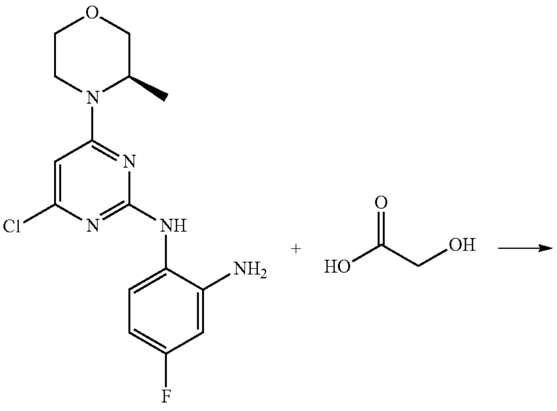

d2-3

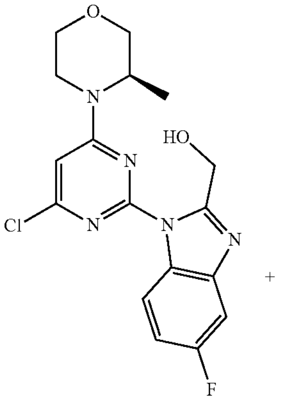

D32-1

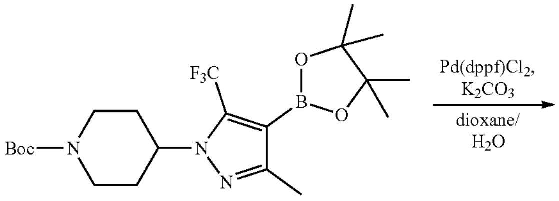

c3

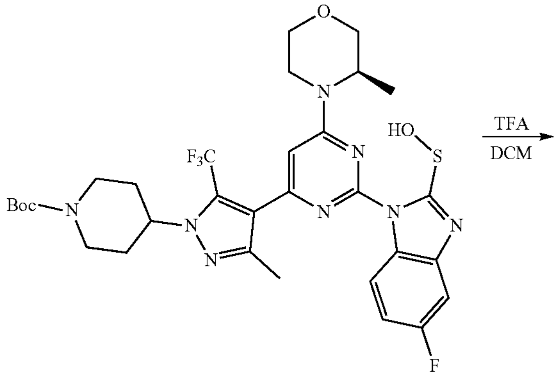

D32-2

-continued

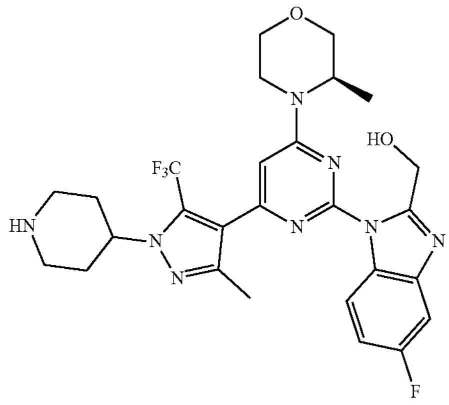

D32

Intermediate d2-3 (2.96 mmol, 1.0 g) was dissolved in 5 g glycolic acid, the reaction was heated to 140° C. and stirred for 4 hours. The reaction was stopped, 30 mL of saturated sodium carbonate aqueous solution was slowly added to the reaction, extracted with dichloromethane, and separated by flash column chromatography to afford intermediate D32-1 (80 mg, yield: 7%), LC-MS: $[M+H]^+$: 378.

Under nitrogen protection, intermediate D32-1 (0.21 mmol, 80 mg) and intermediate c3 (0.25 mmol, 232 mg) were dissolved in 8 mL mixture of 1,4-dioxane and water (v/v: 7/1), potassium carbonate (0.63 mmol, 87 rag) and $Pd(dppf)Cl_2$ (0.04 mmol, 31 mg) were added, and the mixture was heated up to 90° C. and reacted at for 3 hours. The reaction was stopped, filtered, the solvent was removed under reduced pressure, 20 mL of water was added, extracted with ethyl acetate, and separated by flash column chromatography to afford compound D32-2 (35 mg, yield: 25%). LC-MS: $[M+H]^+$: 675.

Compound D32-2 (25 mg) was dissolved in 3 mL of dichloromethane, 1.0 mL of trifluoroacetic acid was added, after the mixture was reacted at room temperature for 2 hours, the solvent was removed under reduced pressure. 20 mL of saturated sodium bicarbonate aqueous solution was slowly added, extracted with dichloromethane, and separated by preparative chromatography to afford the title compound D32 (17 mg, yield: 57%), LC-MS: $[M+H]^+$: 575, HPLC purity: 99.71%.

Example 37: D33-1-D34

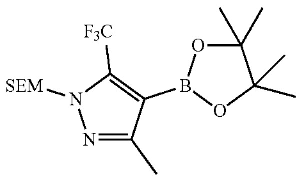

c9a

+

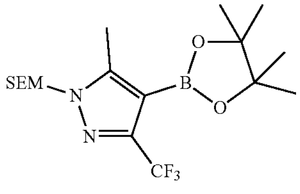

c9b

+

-continued
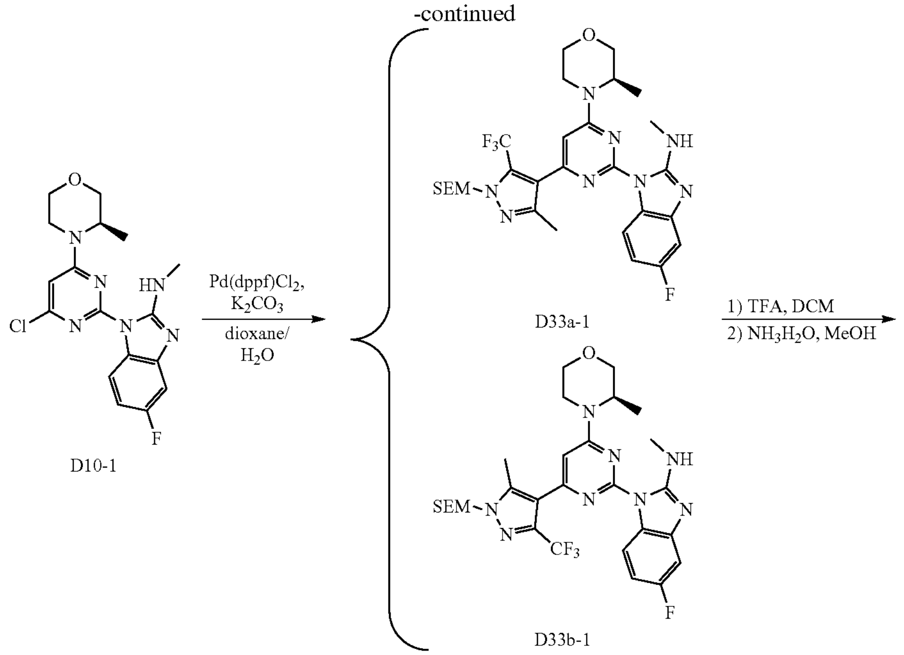
D10-1 D33a-1 D33b-1
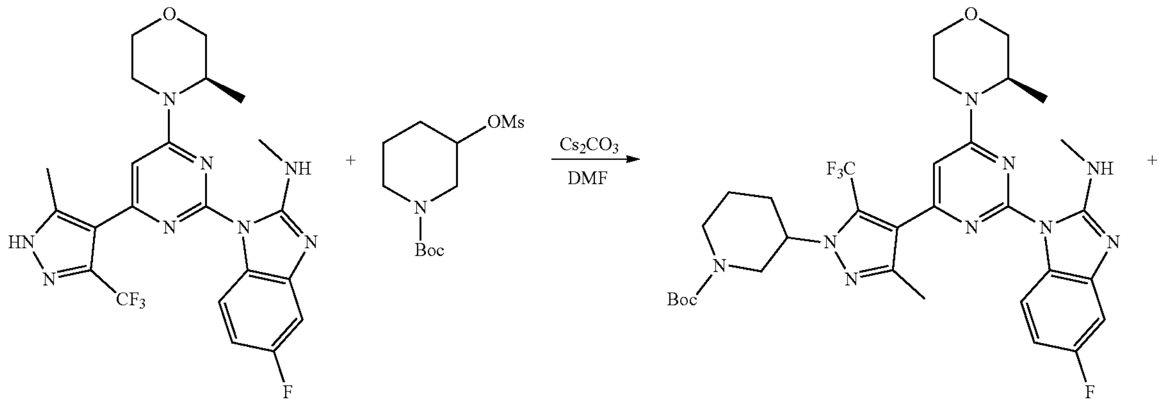
D33-2 D33-3
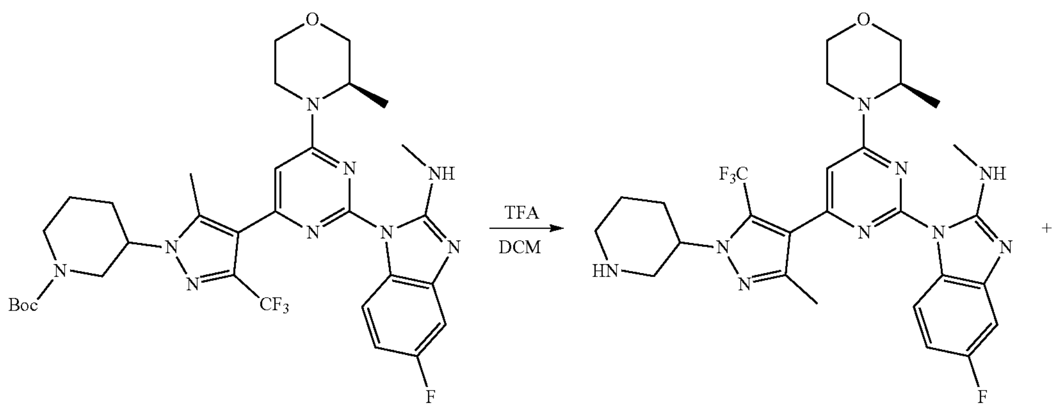
D34-1 D33

-continued

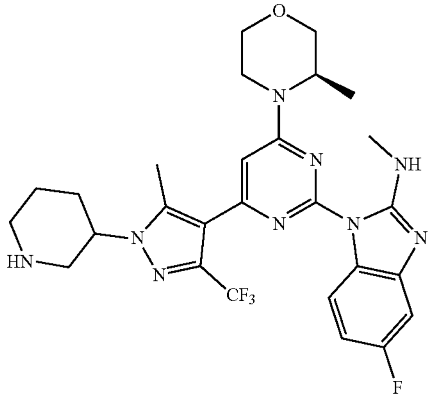

D34

Under nitrogen protection intermediate D10-1 (0.53 mmol, 200 mg) and mixture of intermediate c9a/c9b (1.06 mmol, 432 mg) were dissolved in 10 mL mixture of 1,4-dioxane and water (v/v: 9/1), potassium carbonate (1.59 mmol, 219 mg) and Pd(dppf)$Cl_2$ (0.05 mmol, 39 mg) were added, and the mixture was heated to 105° C. in microwave and reacted for 1 hour. The reaction was stopped, filtered, the solvent was removed under reduced pressure, 20 mL of water was added, extracted with ethyl acetate, and separated by flash column chromatography to afford mixture of D33a-1 and D33b-1 (200 mg, yield: 61%). LC-MS: $[M+H]^+$: 621.

The mixture of D33a-1 and D33b-1 (0.32 mmol, 200 mg) was dissolved in 5 mL of dichloromethane, 2.0 mL of trifluoroacetic acid was added, after the mixture was reacted at room temperature for 2 hours, the solvent was removed under reduced pressure. The mixture was dissolved in 3 mL of methanol, 3 mL of 7M ammonia solution was slowly added, the mixture was stirred at room temperature for 2 hours, and the reaction was stopped. The mixture was extracted with dichloromethane, and separated by TLC chromatography to afford intermediate 1333-2 (130 mg, yield: 83%), LC-MS: $[M+H]^+$: 491.

Intermediate D33-2 (0.26 mmol, 130 mg), tert-butyl 3-((methylsulfonyl)oxy)piperidine-1-carboxylate (0.29 mmol, 81 mg) and cesium carbonate (0.80 mmol, 259 mg) were dissolved in 5 mL of DMF, after the mixture was heated up to 80° C. and reacted for 1 hour, tert-butyl 3-((methylsulfonyl)oxy)piperidine-1-carboxylate (0.29 mmol, 81 mg) vas added to the reaction again and continued to stir for 5 hours. The reaction was stopped, 40 ml of water was added, extracted with dichloromethane, and separated by TLC chromatography to afford mixture of D33-3 and D34-1 (150 mg, yield: 86%), LC-MS: $[M+H]^+$: 674.

The mixture of D33-3 and D34-1 (0.148 mmol, 100 mg) was dissolved in 3 mL of dichloromethane, 1.0 mL of trifluoroacetic acid was added, after the mixture was reacted at room temperature for 2 hours, the solvent was removed under reduced pressure. 20 mL of saturated sodium bicarbonate aqueous solution was slowly added, extracted with dichloromethane, and separated by preparative chromatography to afford the title compound D33 (15 mg, yield: 18%), and the title compound D34 (60 mg, yield: 71%), LC-MS: $[M+H]^+$: 574.

D33: $^1$H NMR (400 MHz, DMSO-$d_6$) δ 9.24 (s, 1H), 9.12 (s, 1H), 8.84 (s, 1H), 8.26 (dd, J=8.9, 5.1 Hz, 1H), 7.20 (dd, J=9.1, 2.6 Hz), 6.98 (dt, J=10.4, 5.3 Hz, 1H), 6.78 (5, 1H), 4.76 (d, J=10.1 Hz, 1H), 4.42 (s, 1H), 4.14-3.99 (m, 2H), 3.82 (d, J=11.6 Hz, 1H), 3.70 (dd, J=11.7, 3.1 Hz, 1H), 3.60-3.52 (m, 2H), 3.43-3.24 (m, 3H), 3.10 (d, 4.8 Hz, 3H), 2.48 (s, 3H), 2.14 (s, 2H), 2.05-1.93 (m, 2H), 1.85 (t, 13.0 Hz, 1H), 1.32 (d, J 6.7 Hz, 3H).

D34: $^1$H NMR (400 MHz, DMSO-$d_6$) δ 9.02 (d, J=15.1 Hz, 2H), 8.83 (s, 1H), 8.22 (dd, J=8.9, 5.0 Hz, 1H), 7.17 (dd, J=9.1, 2.6 Hz, 1H), 6.92 (d, J=10.8 Hz, 2H), 4.75 (s, 1H), 4.45 (s, 1H), 4.11 (d, J=13.0 Hz, 1H), 4.05-4.00 (m, 1H), 3.81 (d, J=11.6 Hz, 1H), 3.72-3.67 (m, 1H), 3.55 (m, 2H), 3.45 (dd, J=21.6, 10.7 Hz, 2H), 3.38-3.29 (m, 2H), 3.09 (d, J=4.9 Hz, 3H), 2.31 (s, 3H), 2.13 (s, 2H), 2.00 (dd, J=15.0, 7.5 Hz, 2H), 1.82 (s, 1H), 1.31 (d, J=6.7 Hz, 3H).

Example 38: D35

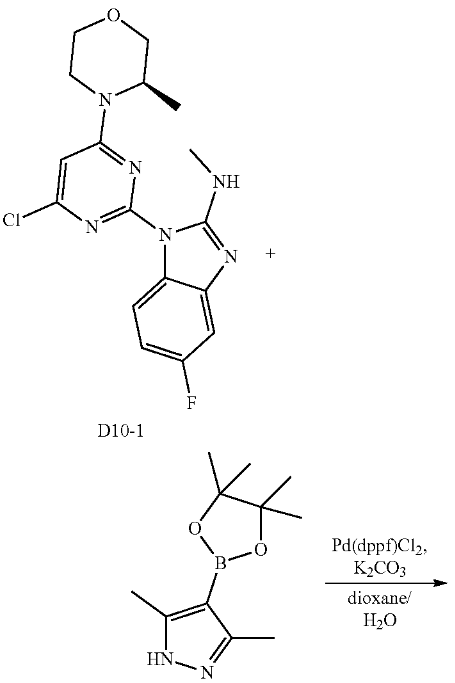

D10-1 a6

-continued

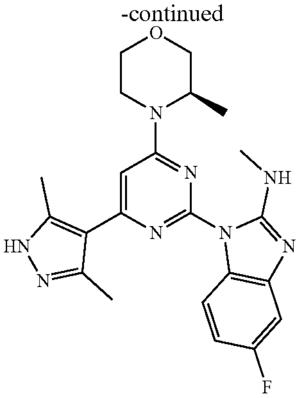

D35-1

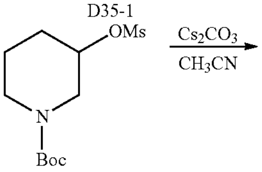

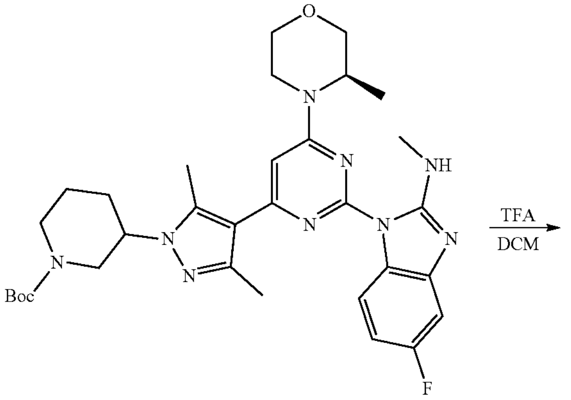

D35-2

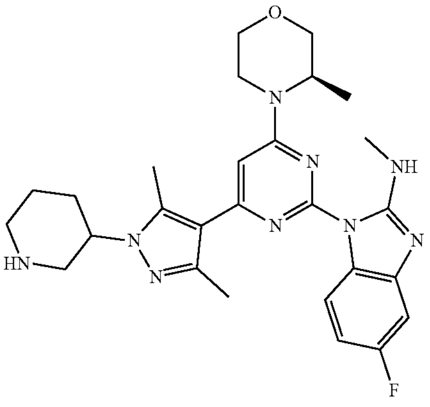

D35

Under nitrogen protection, intermediate D10-1 (0.39 mmol, 150 mg) and intermediate a6 (0.48 mmol, 106 mg) were dissolved in 10 mL mixture of 1,4-dioxane and water (v/v: 9/1), potassium carbonate (0.80 mmol, 110 mg) and $Pd(dppf)Cl_2$ (0.04 mmol, 30 mg) were added, and the mixture was heated to 105° C. in microwave and reacted for 1 hour. The reaction was stopped, filtered, the solvent was removed under reduced pressure, 20 mL of water was added, extracted with ethyl acetate, and separated by flash column chromatography to afford compound D35-1 (150 mg, yield: 86%). LC-MS: $[M+H]^+$: 437.

Intermediate D35-1 (0.34 mmol, 150 mg), tert-butyl 3-((methylsulfonyl)oxy)piperidine-1-carboxylate (0.52 mmol, 145 mg) and cesium carbonate (0.68 mmol, 221 mg) were dissolved in 10 mL of acetonitrile, after the mixture was heated up to 80° C. and reacted for 1 hour, tert-butyl 3-((methylsulfonyl)oxy)piperidine-1-carboxylate (0.52 mmol, 145 mg) was added to the reaction again and continued to stir for 5 hours. The reaction was stopped, 40 mL of water was added, extracted with dichloromethane, and separated by TLC chromatography to afford compound D35-2 (30 mg, yield: 15%), LC-MS: $[M+H]^+$: 619.

Compound D35-2 (0.048 mmol, 30 mg) was dissolved in 2 mL of dichloromethane, 0.5 mL of trifluoroacetic acid was added, after the mixture was reacted at room temperature for 2 hours, the solvent was removed under reduced pressure. 10 mL of saturated sodium bicarbonate aqueous solution was slowly added, extracted with dichloromethane, and separated by preparative chromatography to afford the title compound D35 (7 mg, yield: 28%), LC-MS: $[M+H]^+$: 519.

$^1$H NMR (400 MHz, DMSO-$d_6$) δ 8.84-8.75 (n), 1H), 8.17 (dd, J=8.9, 5.3 Hz, 1H), 7.06 (dd, J=9.7, 2.6 Hz, 1H), 6.80 (td, J=9.5, 2.6 Hz, 1H), 6.59 (s, 1H), 4.45 (s, 1H), 4.17-3.98 (m, 3H), 3.80 (d, J=11.6 Hz, 1H), 3.69 (d, J=10.9 Hz, 1H), 3.56 (d, J=11.2 Hz, 1H), 3.08 (d, J=4.8 Hz, 3H), 3.02 (d, J=11.8 Hz, 1H), 2.90 (d, J=12.5 Hz, 1H), 2.81 (t, J=11.2 Hz, 1H), 2.47 (s, 3H), 2.33 (s, 3H), 2.00 (dd, J=14.7, 7.0 Hz, 3H), 1.73 (d, J=13.3 Hz, 1H), 1.50 (d, J=38.4 Hz, 2H), 1.30 (d, J=6.6 Hz, 3H).

Example 39: D36

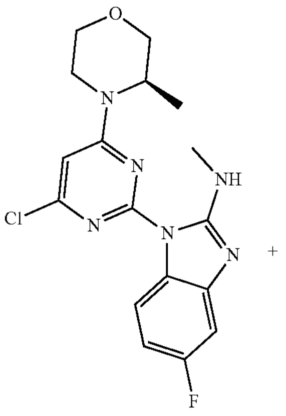

D10-1

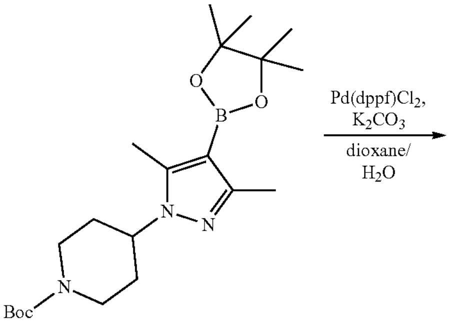

c10

-continued

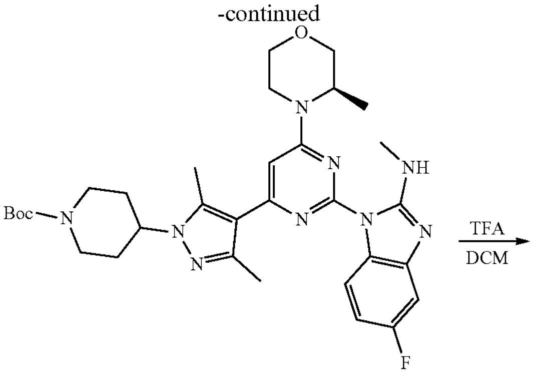

D36-1

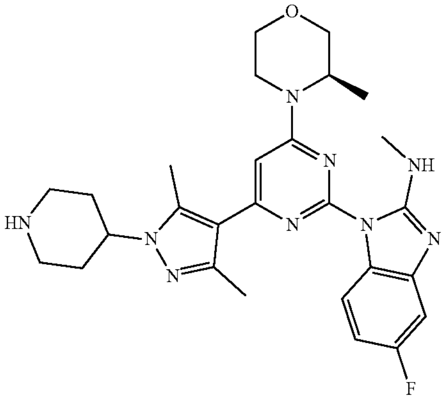

D36

Under nitrogen protection, intermediate D10-1 (0.27 mmol, 100 mg) and intermediate c10 (0.35 mmol 140 mg) were dissolved in 10 mL mixture of 1,4-dioxane and water (v/v: 9/1), potassium carbonate (0.53 mmol, 73 mg) and Pd(dppf)$Cl_2$ (0.03 mmol, 20 mg) were added, and the mixture was heated to 110° C. in microwave and reacted for 1 hour. The reaction was stopped, filtered, the solvent was removed under reduced pressure, 20 mL of water was added, extracted with ethyl acetate, and separated by TLC chromatography to afford compound D36-1 (120 mg, yield: 72%). LC-MS: $[M+H]^+$: 619.

Compound D36-1 (0.19 mmol, 120 mg) was dissolved in 5 mL of dichloromethane, 2 mL of trifluoroacetic acid was added, after the mixture was reacted at room temperature for 2 hours, the solvent was removed under reduced pressure. 20 ml of saturated sodium bicarbonate aqueous solution was slowly added, extracted with dichloromethane, and separated by preparative chromatography to afford the title compound D36 (74 mg, yield: 76%), LC-MS: $[M+H]^+$: 519.

$^1$H NMR (400 MHz, DMSO-$d_6$) δ 8.79 (d, J=5.1 Hz, 1H), 8.17 (dd, J=8.8, 5.3 Hz, 1H), 7.06 (dd, J=9.7, 2.6 Hz, 1H), 6.79 (td, J=9.4, 2.7 Hz, 1H), 6.59 (s, 1H), 4.45 (s, 1H), 4.27 (d, J=11.6 Hz, 1H), 4.10-3.99 (m, 2H), 3.80 (d, 11.5 Hz, 1H), 3.69 (dd, J=11.8, 3.1 Hz, 1H), 3.59-3.50 (m, 1H), 3.36 (d, =4.0 Hz, 1H), 3.13 (d, J=12.4 Hz, 2H), 3.08 (d, J=4.8 Hz, 3H), 2.72 (d, J=12.3 Hz, 2H), 2.48 (s, 3H), 2.33 (s, 3H), 1.97 (td, 13.3, 10.5, 6.8 Hz, 3H), 1.82 (d, 10.7 Hz, 2H), 1.30 (d, J=6.7 Hz, 3H).

Example 40: D37

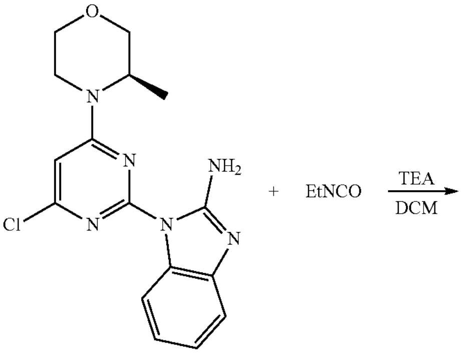

d1

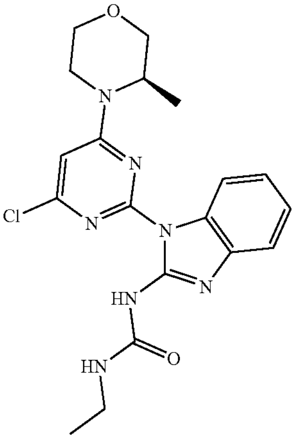

+

D37-1

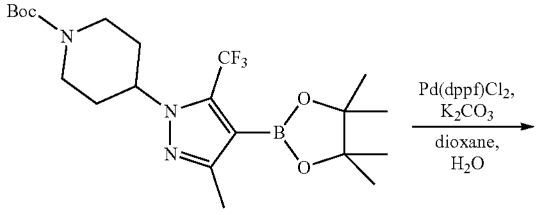

c3

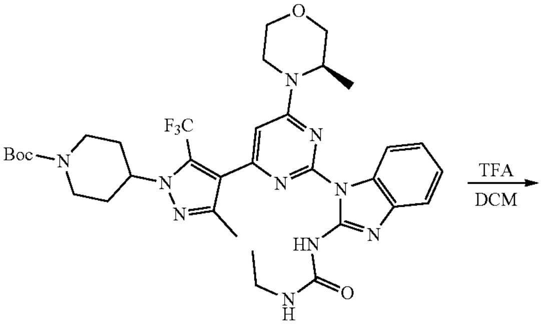

D37-2

-continued

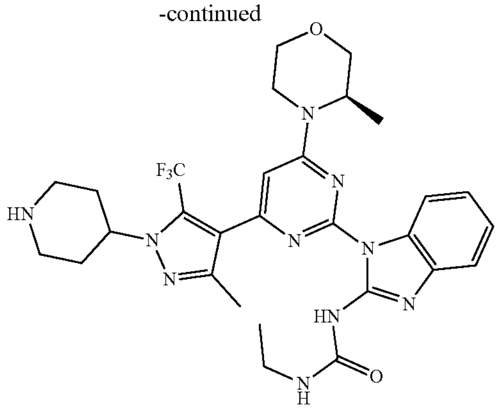

D37

Intermediate d1 (0.35 mmol, 120 mg) and triethylamine (1.75 mmol, 177 mg) were dissolved in 8 mL of dichloromethane, ethyl isocyanate (1.75 mmol, 124 mg) was slowly added, the mixture was reacted at room temperature for 10 hours, and the reaction was stopped. The solvent was removed under reduced pressure, 20 mL of water was slowly added, extracted with dichloromethane, and separated by TLC chromatography to afford intermediate D37-1 (120 mg, yield: 83%), LC-MS: $[M+H]^+$: 416.

Under nitrogen protection, intermediate D37-1 (0.22 mmol, 90 mg) and intermediate c3 (0.66 mmol, 298 mg) were dissolved in 10 mL mixture of 1,4-dioxane and water (v/v, 9/1), potassium carbonate (0.44 mmol, 61 mg) and $Pd(dppf)Cl_2$ (0.02 mmol, 16 mg) were added, and the mixture was heated to 120° C. in microwave and reacted for 1 hour. The reaction was stopped, filtered, the solvent was removed under reduced pressure, 20 mL of water was added, extracted with ethyl acetate, and separated by TLC chromatography to afford compound D37-2 (100 mg, yield: 64%). LC-MS: $[M+H]^+$: 713.

Compound D37-2 (0.14 mmol, 100 mg) was dissolved in 5 mL of dichloromethane, 2 mL of trifluoroacetic acid was added, after the mixture was reacted at room temperature for 2 hours, the solvent was removed under reduced pressure, 20 mL of saturated sodium bicarbonate aqueous solution was slowly added, extracted with dichloromethane, and separated by preparative chromatography to afford the title compound D37 (48 mg, yield: 56%), LC-MS: $[M+H]^+$: 613.

Example 41: D39

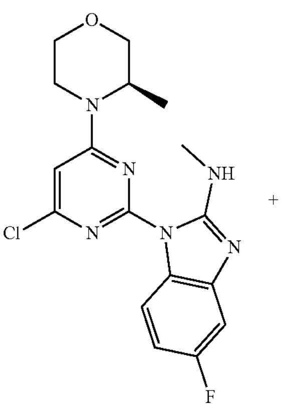

D10-1

-continued

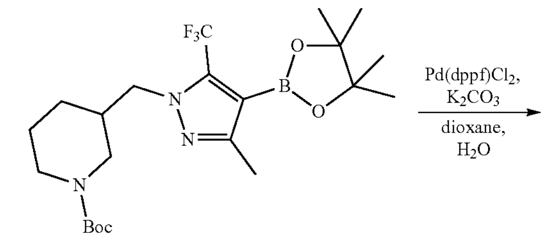

c11

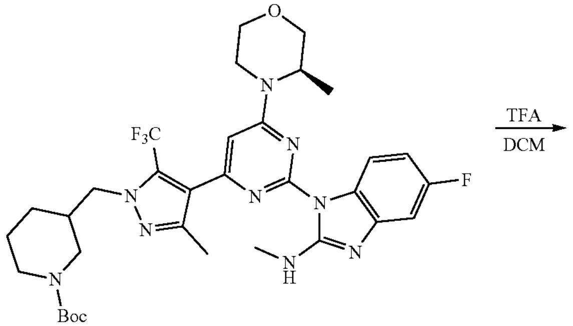

D39-1

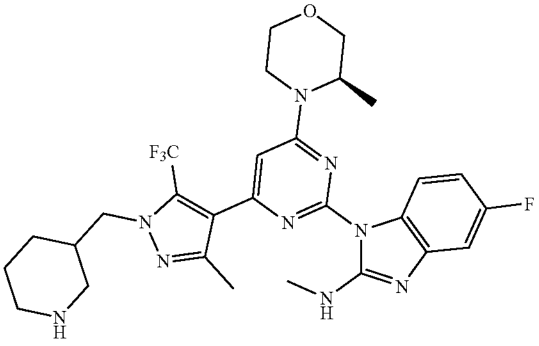

D39

Under nitrogen protection, intermediate D10-1 (0.26 mmol, 100 mg) and intermediate c11 (0.48 mmol, 226 mg) were dissolved in 10 mL mixture of 1,4-dioxane and water (v/v, 9/1), potassium carbonate (0.53 mmol, 73 mg) and $Pd(dppf)Cl_2$ (0.03 mmol, 19 mg) were added, and the mixture was heated to 110° C. in microwave and reacted for 1 hour. The reaction was stopped, filtered, the solvent was removed under reduced pressure, 20 mL of water was added, extracted with ethyl acetate, and separated by TLC chromatography to afford compound D39-1 (100 mg, yield: 56%). LC-MS: $[M+H]^+$: 688.

Compound D39-1 (0.14 mmol, 100 mg) was dissolved in 5 mL of dichloromethane, 2 mL of trifluoroacetic acid was added, after the mixture was reacted at room temperature for 2 hours, the solvent was removed under reduced pressure. 20 mL of saturated sodium bicarbonate aqueous solution was slowly added, extracted with dichloromethane, and separated by preparative chromatography to afford the title compound D39 (17 mg, yield: 21%). LC-MS: $[M+H]^+$: 588.

The following compounds were synthesized with reference to the route of Example 41:

| Structure | The structure replacing D10-1 | LC-MS/ [M + H]$^+$ | $^1$H NMR |
|---|---|---|---|
| 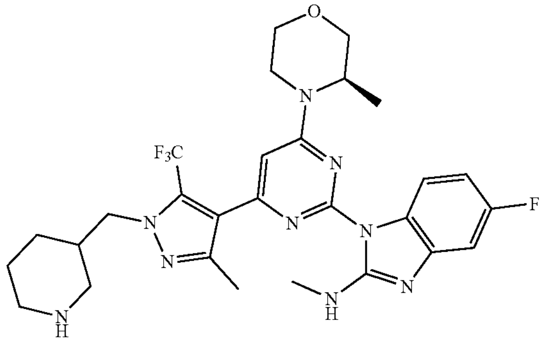 D39 | — | 588 | $^1$H NMR (400 MHz, DMSO-d$_6$) δ 8.59 (d, J = 5.1 Hz, 1H), 8.14 (dd, J = 8.8, 5.3 Hz, 1H), 7.06 (dd, J = 9.6, 2.7 Hz, 1H), 6.84 (s, 1H), 6.79 (td, J = 9.4, 2.7 Hz, 1H), 4.46 (s, 1H), 4.16-4.08 (m, 3H), 4.01 (d, J = 10.2 Hz, 1H), 3.79 (d, J = 11.7 Hz, 1H), 3.69 (dd, J = 11.6, 3.1 Hz, 1H), 3.53 (dd, J = 14.3, 4.8 Hz, 1H), 3.37 (dd, J = 12.9, 3.8 Hz, 1H), 3.28 (s, 1H), 3.03 (d, J = 4.8 Hz, 3H), 2.82 (d, J = 9.7 Hz, 2H), 2.32 (t, J = 10.8 Hz, 2H), 2.27 (s, 3H), 2.05-1.96 (m, 2H), 1.62 (dd, J = 27.6, 12.7 Hz, 2H), 1.30 (d, J = 6.6 Hz, 3H). |
| 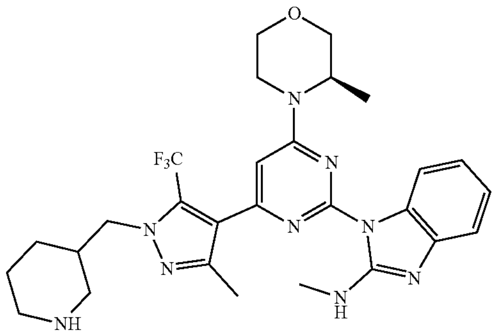 D40 | d7 | 570 | $^1$H NMR (400 MHz, DMSO-d$_6$) δ 8.66 (s, 1H), 8.36 (s, 1H), 8.23 (d, J = 8.1 Hz, 1H), 7.33 (d, J = 7.4 Hz, 1H), 7.20 (d, J = 13.6 Hz, 2H), 7.09 (s, 1H), 6.85 (s, 1H), 4.47 (s, 1H), 4.24 (d, J = 7.1 Hz, 2H), 4.12 (d, J = 12.9 Hz, 1H), 4.04 (d, J = 11.2 Hz, 1H), 3.82 (d, J = 11.6 Hz, 1H), 3.70 (d, J = 11.6 Hz, 1H), 3.54 (d, J = 12.2 Hz, 2H), 3.25 (s, 1H), 3.07 (d, J = 4.8 Hz, 3H), 2.80-2.86 (m, 2H), 2.69-2.65 (m, 1H), 2.30 (s, 3H), 2.03-1.97 (m, 2H), 1.84 (d, J = 13.7 Hz, 1H), 1.65 (dd, J = 34.3, 13.8 Hz, 2H), 1.31 (s, 3H). |

Example 42: D41+D42

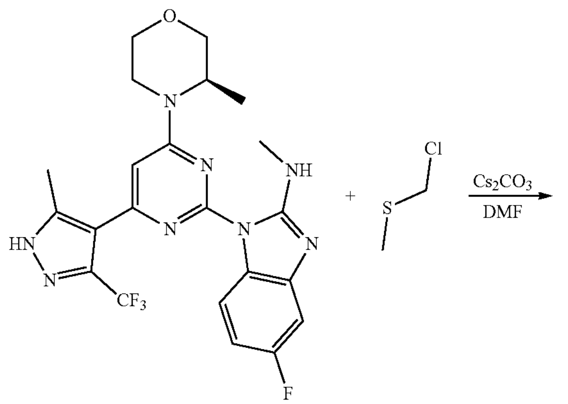

D33-2

-continued

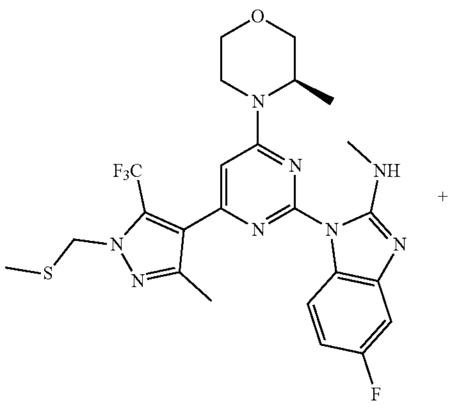

D41-1

-continued

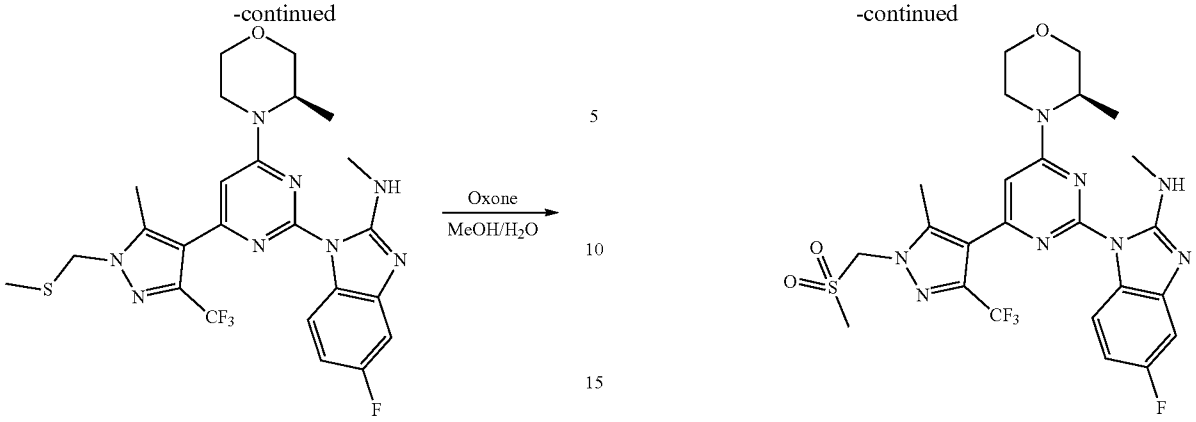

D42-1

D42

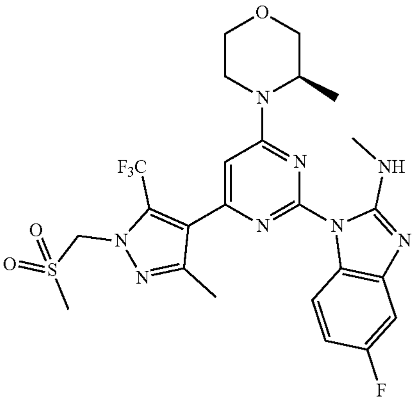

D41

+

Intermediate D3:3-2 (0.61 mmol, 300 mg), (chloromethyl)(methyl)sulfane (1.83 mmol, 176 ng) and cesium carbonate (1.83 mmol, 596 mg) were dissolved in 10 mL of DMF, and the mixture was heated up to 80° C. and reacted for 2 hours. The reaction was stopped, filtered, 40 mL of water was added, extracted with dichloromethane, and separated by flash column chromatography to afford mixture of D41-1 and D42-1 (170 mg, total yield: 51%), LC-MS: $[M+H]^+$: 551.

The mixture of D41-1 and D42-1 (0.148 mmol, 100 mg) was dissolved in 12 mL mixture of methanol and water (v/v, 5/1), potassium monopersulfate (Oxone, 0.93 mmol, 569 mg) was slowly added, and the mixture was reacted at room temperature for 2 hours. The mixture was filtered, 30 mL of saturated sodium thiosulfate solution was added, extracted with dichloromethane, and separated by preparative chromatography to afford the title compound D41 (20 mg, yield: 23%) and the title compound D42 (40 mg, yield: 47%), LC-MS: $[M+H]^+$: 583.

The following compounds were synthesized with reference to the route of Example 42:

| Structure | The structure replacing D33-2 | LC-MS/ $[M + H]^+$ | $^1H$ NMR |
|---|---|---|---|
| 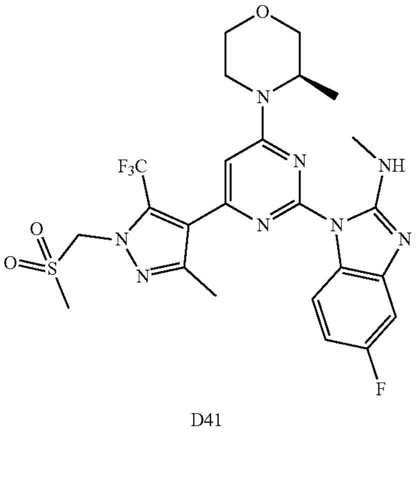 D41 | — | 583 | $^1H$ NMR (400 MHz, DMSO-$d_6$) δ 8.56 (d, J = 5.3 Hz, 1H), 8.14 (dd, J = 8.8, 5.2 Hz, 1H), 7.10-7.03 (m, 1H), 6.88 (s, 1H), 6.79 (dd, J = 10.1, 7.9 Hz, 1H), 5.86 (s, 2H), 4.47 (s, 1H), 4.13 (d, J = 13.3 Hz, 1H), 4.02 (d, J = 10.4 Hz, 1H), 3.78 (s, 1H), 3.70 (d, J = 10.7 Hz, 1H), 3.56 (t, J = 11.8 Hz, 1H), 3.39 (d, J = 13.3 Hz, 1H), 3.19 (s, 3H), 3.02 (d, J = 4.7 Hz, 3H), 2.34 (s, 3H), 1.31 (d, J = 6.7 Hz, 3H). |

-continued

| Structure | The structure replacing D33-2 | LC-MS/ [M + H]+ | 1H NMR |
|---|---|---|---|
| 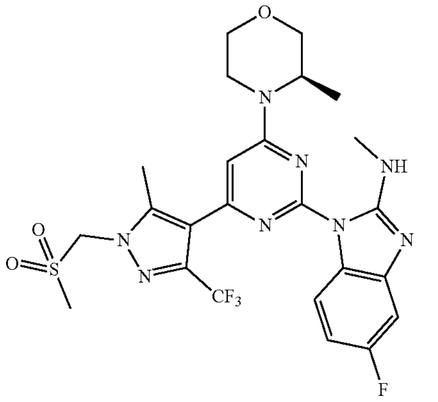 D42 | — | 583 | $^1H$ NMR (400 MHz, DMSO-$d_6$) δ 8.60 (d, J = 5.1 Hz, 1H), 8.15 (dd, J = 8.8, 5.3 Hz, 1H), 7.06 (dd, J = 9.7, 2.6 Hz, 1H), 6.78 (d, J = 8.9 Hz, 2H), 6.00 (s, 2H), 4.48 (s, 1H), 4.12 (d, J = 13.1 Hz, 1H), 4.06-3.99 (m, 1H), 3.80 (d, J = 11.6 Hz, 1H), 3.74-3.67 (m, 1H), 3.60-3.51 (m, 1H), 3.37 (td, J = 12.8, 4.0 Hz, 1H), 3.16 (s, 3H), 3.03 (d, J = 4.8 Hz, 3H), 2.53 (s, 3H), 1.32 (d, J = 6.7 Hz, 3H). |
| 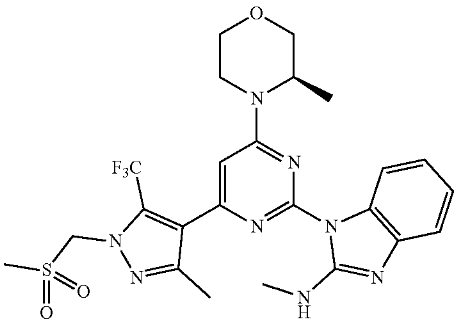 D43 | D43-2 | 565 | $^1H$ NMR (400 MHz, DMSO-$d_6$) δ 8.32 (d, J = 8.1 Hz, 1H), 7.45 (d, J = 7.7 Hz, 1H), 7.33 (dt, J = 15.0, 7.7 Hz, 2H), 7.01 (s, 1H), 5.88 (s, 2H), 4.50 (s, 1H), 4.14 (s, 1H), 4.03 (d, J = 10.8 Hz, 1H), 3.81 (d, J = 11.6 Hz, 1H), 3.72-3.69 (m, 1H), 3.60-3.51 (m, 1H), 3.44-3.37 (m, 1H), 3.20 (s, 3H), 3.14 (d, J = 4.9 Hz, 3H), 2.35 (s, 3H), 1.33 (d, J = 6.7 Hz, 3H). |
| 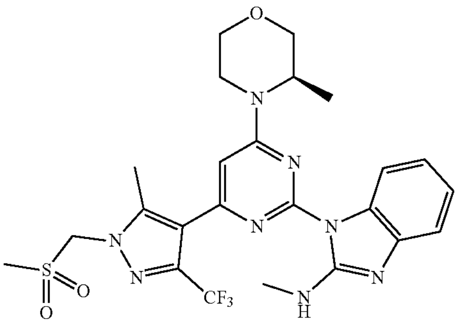 D44 | D43-2 | 565 | $^1H$ NMR (400 MHz, DMSO-$d_6$) δ 8.33 (d, J = 7.9 Hz, 1H), 7.45 (d, J = 7.7 Hz, 1H), 7.33 (dt, J = 14.9, 7.7 Hz, 2H), 6.89 (s, 1H), 6.02 (s, 2H), 4.50 (s, 1H), 4.19-4.10 (m, 1H), 4.03 (d, J = 11.4 Hz, 1H), 3.80 (s, 1H), 3.59-3.53 (m, 1H), 3.42 (d, J = 13.7 Hz, 1H), 3.16 (s, 1H), 3.14 (d, J = 4.9 Hz, 3H), 2.54 (s, 3H), 1.33 (d, J = 6.7 Hz, 3H). |

Wherein: the synthesis of D43-2 was as follow:
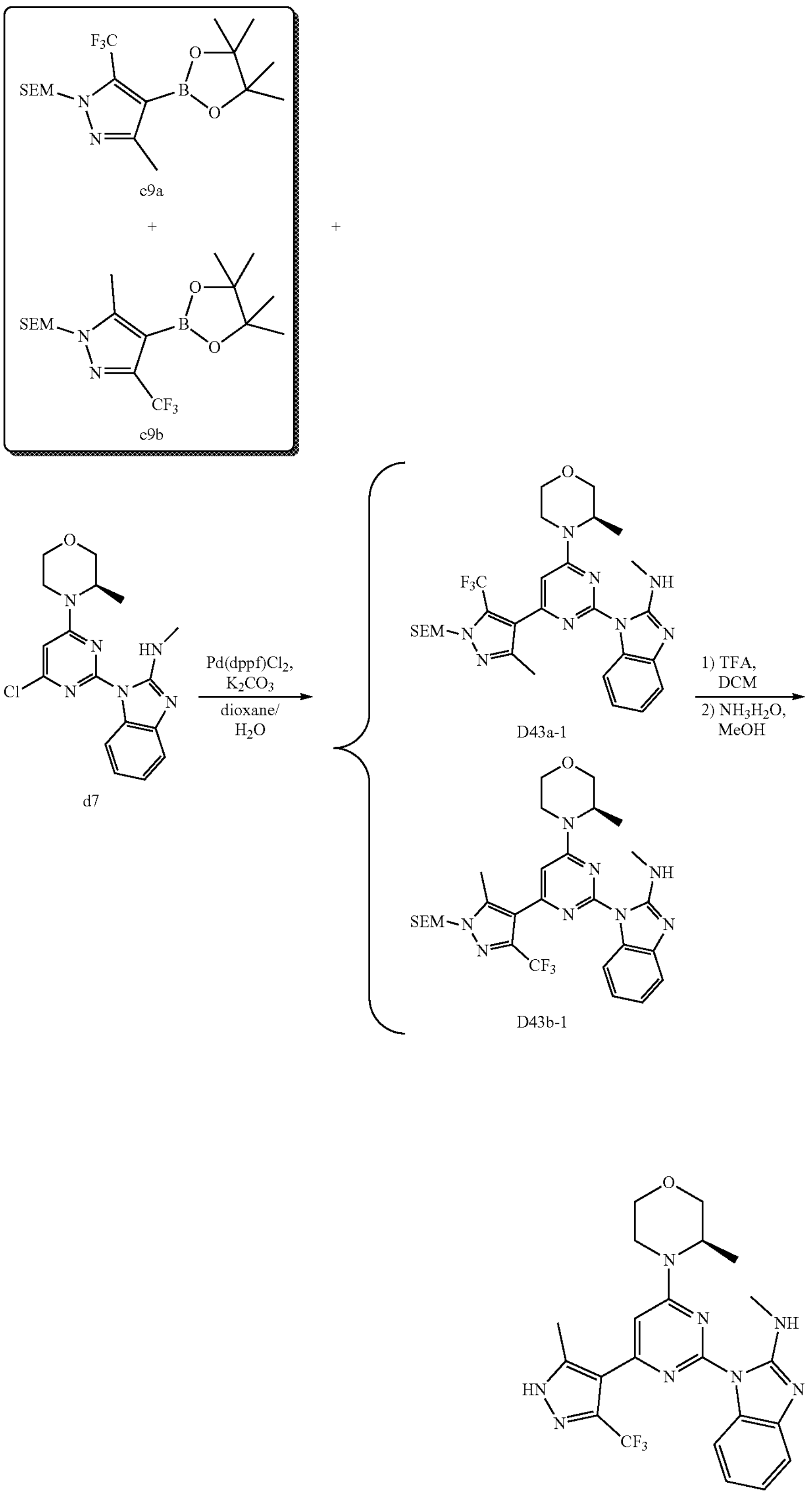
c9a
c9b
d7
D43a-1
D43b-1
D43-2

Under nitrogen protection, intermediate d7 (0.28 mmol, 100 mg) and mixture of intermediate c9a/c9h (0.56 mmol, 227 mg) were dissolved in 10 mL mixture of 1,4-dioxane and water (v/v, 9/1), potassium carbonate (0.84 mmol, 116 mg) and Pd(dppf)$Cl_2$ (0.03 mmol, 20 mg) were added, and the mixture was heated to 105° C. in microwave and reacted for 1 hour. The reaction was stopped, filtered, the solvent was removed under reduced pressure, 20 mL of water was added, extracted with ethyl acetate, and separated by flash column chromatography to afford mixture of D43a-1 and D43b-1 (300 mg, yield: 89%). LC-MS: $[M+H]^+$: 603.

The mixture of D43a-1 and D43b-1 (0.5 mmol, 300 mg) was dissolved in 8 mL of dichloromethane, 2.0 mL of trifluoroacetic acid was added, after the mixture was reacted at room temperature for 2 hours, the solvent was removed under reduced pressure. The mixture was dissolved in 4 mL of methanol again, 3 mL of 7 M ammonia solution was slowly added, the mixture was stirred at room temperature for 2 hours, and the reaction was stopped. The mixture was extracted with dichloromethane, and separated by flash column chromatography to afford compound D43-2 (220 mg, yield: 93%), LC-MS: $[M+H]^+$: 473.

Example 43: D48

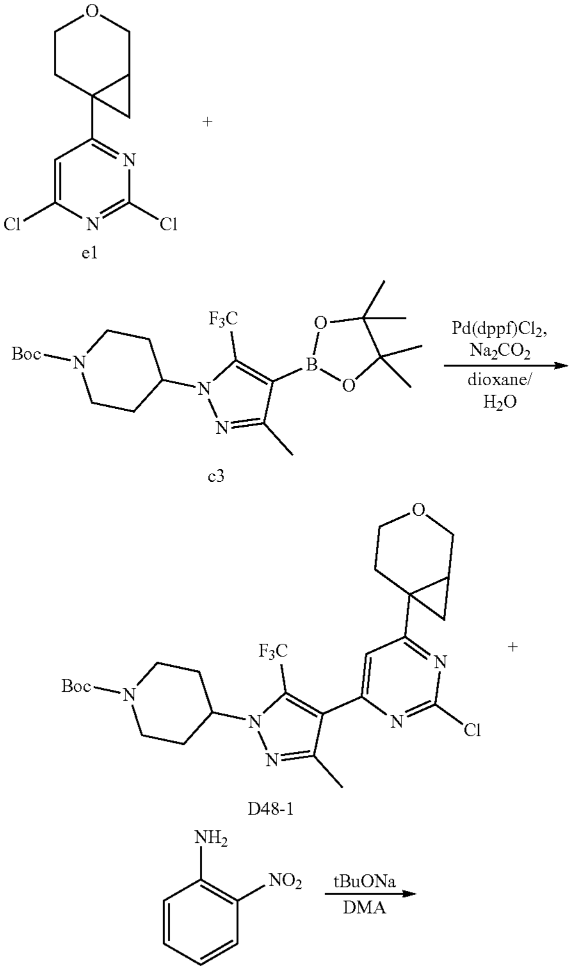

e1 c3

D48-1

-continued

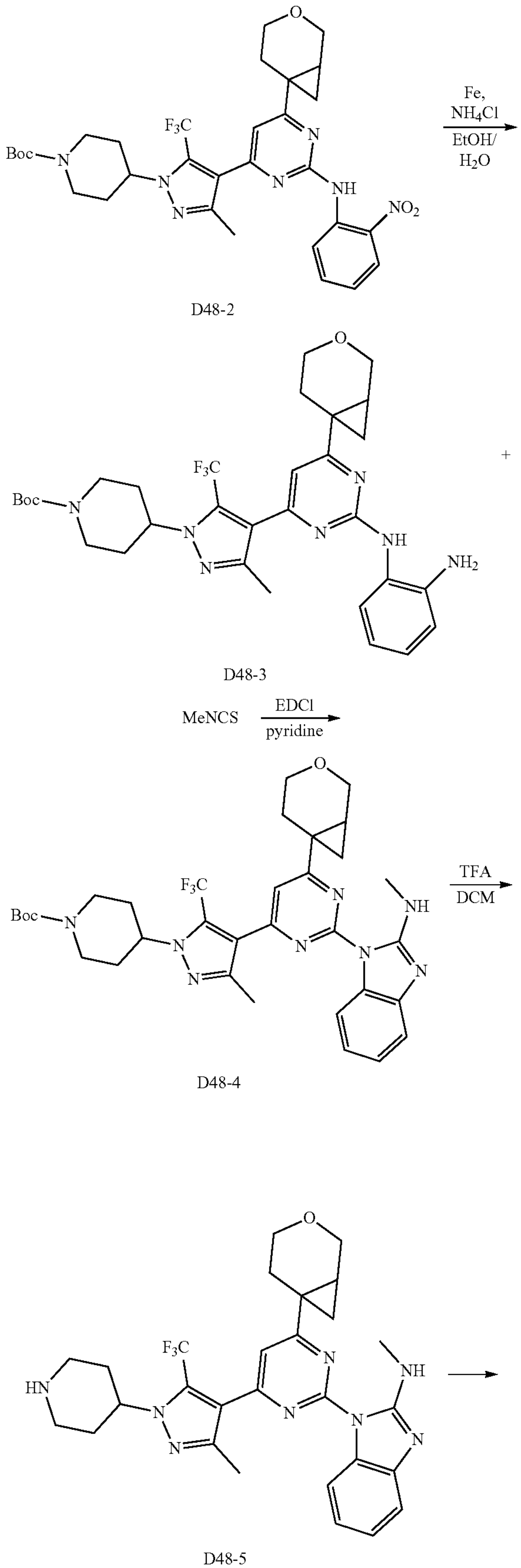

D48-2

D48-3

D48-4

D48-5

-continued

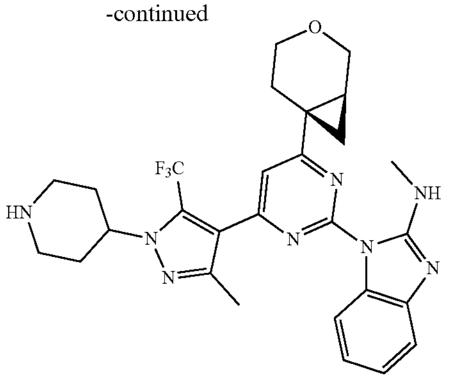

D48

Under nitrogen protection, intermediate e1 (1.39 mmol, 340 mg) and intermediate c3 (1.53 mmol, 703 mg) were dissolved in 10 mL mixture of 1,4-dioxane and water (v/v: 9/1), sodium carbonate (4.17 mmol, 442 mg) and Pd(dppf)$Cl_2$ (0.14 mmol, 103 mg) were added, the mixture was heated up to 110° C. and reacted for 2 hours. The reaction was stopped, filtered, the solvent was removed under reduced pressure, 20 mL of water was added, extracted with ethyl acetate, and separated by flash column chromatography to afford intermediate D48-1 (450 mg, yield: 60%). LC-MS: $[M+H]^+$: 543.

Intermediate D48-1 (0.83 mmol, 450 mg) and 2-nitroaniline (0.99 mmol, 138 mg) were added to a reaction flask, and dissolved in 8 mL of DMA. After sodium test-butoxide (1.66 mmol, 159 was added, the mixture was heated up to 100° C. and reacted for 2 hours. The reaction was stopped, 30 mL of water was added, extracted with ethyl acetate, and washed with saturated sodium chloride aqueous solution to afford crude intermediate D48-2, LC-MS: $[M+H]^+$: 644.

Intermediate D48-2 (500 rag, crude), reduced iron powder (3.89 mmol, 218 mg) and ammonium chloride (7.8 mmol, 413 mg) were added to a reaction flask, and dissolved in 30 mL ethanol and 5 n L water, and the mixture was reacted at 80° C. for 2 hours. The reaction was stopped, suction filtered, 100 mL of water was added, extracted with ethyl acetate, dried over anhydrous sodium sulfate, and separated by flash column chromatography to afford intermediate D48-3 (260 mg, two-step yield: 52%), LC-MS: $[M+H]^+$: 614.

Intermediate D48-3 (0.42 mmol, 260 mg) was dissolved in 8 mL of pyridine, methyl isothiocyanate (0.5 mmol, 37 mg) was slowly added, and the mixture was reacted at 90° C. for 0.5 hours. The reaction was cooled to room temperature, EDCI (0.63 mmol, 120 mg) was added, the mixture was continued to heat up to 90° C. and stirred for 4 hours continuously, then the reaction was stopped. 50 mL of water was added to the reaction, extracted with ethyl acetate, dried over anhydrous sodium sulfate, and separated by flash column chromatography to afford intermediate D48-4 (130 mg, yield: 48%), LC-MS: $[M+H]^+$: 653.

Intermediate D48-4 (0.38 mmol, 250 mg) was dissolved in 8 mL of dichloromethane, 2.0 mL of trifluoroacetic acid was added, after the mixture was reacted at room temperature for 2 hours, the solvent was removed under reduced pressure, and separated by preparative chromatography to afford compound D48-5 (130 mg, yield: 62%). LC-MS: $[M+H]^+$: 553.

Compound D48-5 was separated by chiral chromatography to afford the title compound D48.

$^1$H NMR (400 MHz, DMSO-$d_6$) δ 8.34 (q, J=5.7, 5.1 Hz, 1H), 8.22 (d, J=8.4 Hz, 1H), 7.43 (s, 1H), 7.29 (dd, 7.7, 0.9 Hz, 1H), 7.13 (td, J=7.8, 1.3 Hz, 1H), 7.03-6.98 (m, 1H), 4.40-4.32 (m, 1H), 3.99 (dd, J=11.6, 4.5 Hz, 1H), 3.90 (d, J=12.5 Hz, 1H), 3.62 (dt, J=11.2, 5.6 Hz, 1H), 3.48-3.41 (m, 1H), 3.09 (s, 1H), 3.06 (d, J=4.8 Hz, 3H), 2.71-2.66 (m, 1H), 2.63-2.57 (m, 2H), 2.04-1.96 (m, 2H), 1.88 (d, J=13.9 Hz, 2H), 1.60 (dd, J=9.2, 3.9 Hz, 1H), 1.35 (dd, J=5.9, 4.8 Hz, 1H).

Example 44: D49

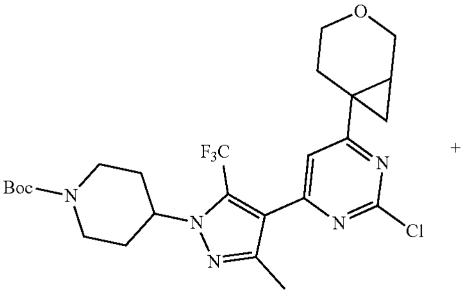

D48-1

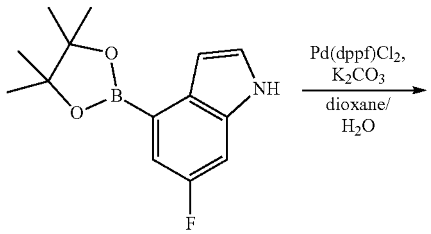

d9-1

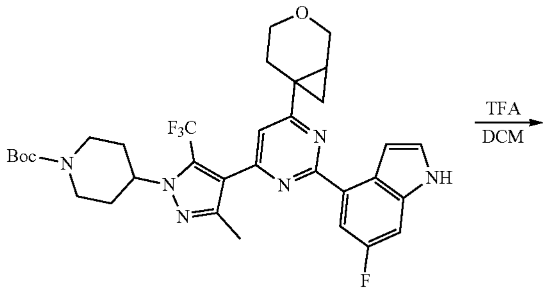

D49-1

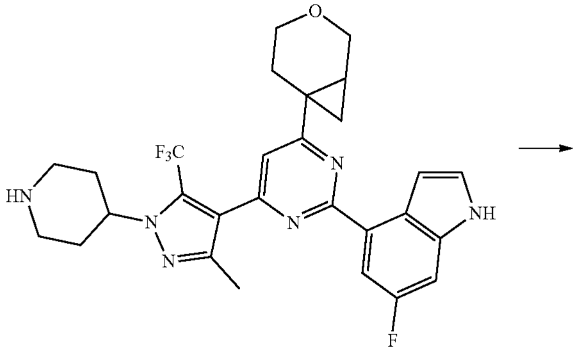

D49-2

-continued

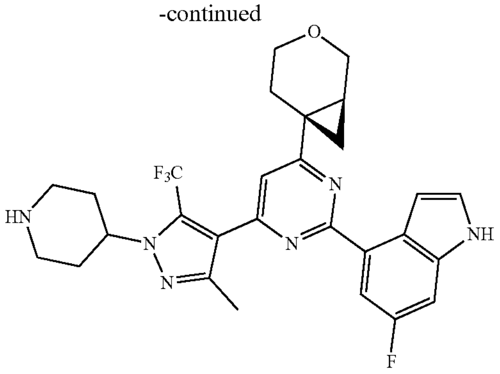

D49

Under nitrogen protection, intermediate D48-1 (0.35 mmol, 190 mg) and intermediate d9-1 (0.52 mmol, 137 mg) were dissolved in 5 mL mixture of 1,4-dioxane and water (v/v, 9/1), potassium carbonate (1.05 mmol, 145 mg) and Pd(dppf)$Cl_2$ (0.04 mmol, 23 mg) were added, and the mixture was heated up to 110° C. and reacted for 2 hours. The reaction was stopped, filtered, the solvent was removed under reduced pressure, 20 mL of water was added, extracted with ethyl acetate, and separated by flash column chromatography to afford intermediate D49-1 (200 mg, yield: 89%). LC-MS: $[M+H]^+$: 641.

Intermediate D49-1 (0.31 mmol, 200 mg) was dissolved in 6 mL of dichloromethane, 2.0 mL of trifluoroacetic acid was added, after the mixture was reacted at room temperature for 2 hours, the solvent was removed under reduced pressure. The residue was separated by preparative chromatography to afford compound D49-2 (100 mg, yield: 60%). LC-MS: $[M+H]^+$: 541.

Compound D49-2 was separated by chiral chromatography to afford the title compound D49.

$^{1}H$ NMR (400 MHz, DMSO-$d_6$) δ 11.40 (s, 1H), 7.94 (dd, =11.6, 2.6 Hz, 1H), 7.50 (t, J=2.2 Hz, 1H), 7.42 (s, 1H), 7.37 (dd, J=9.2, 2.3 Hz, 1H), 7.35-7.29 (m, 1H), 4.54-4.43 (m, 1H), 3.99 (dd, J=11.4, 4.6 Hz, 1H), 3.90 (d, 11.4 Hz, 1H), 3.68-3.57 (m, 1H), 3.49-3.39 (m, 1H), 3.34 (s, 2H), 3.20 (d, J=12.6 Hz, 2H), 2.86-2.73 (m, 2H), 2.30 (s, 3H), 2.18-1.93 (m, 5H), 1.60 (dd, J=9.8, 2.9 Hz, 1H), 1.31-1.24 (m, 1H).

Example 45: D50

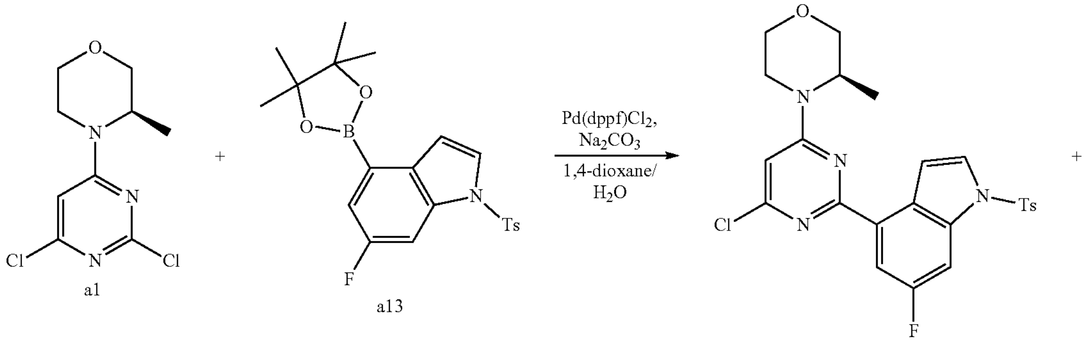

al a13

D50-1

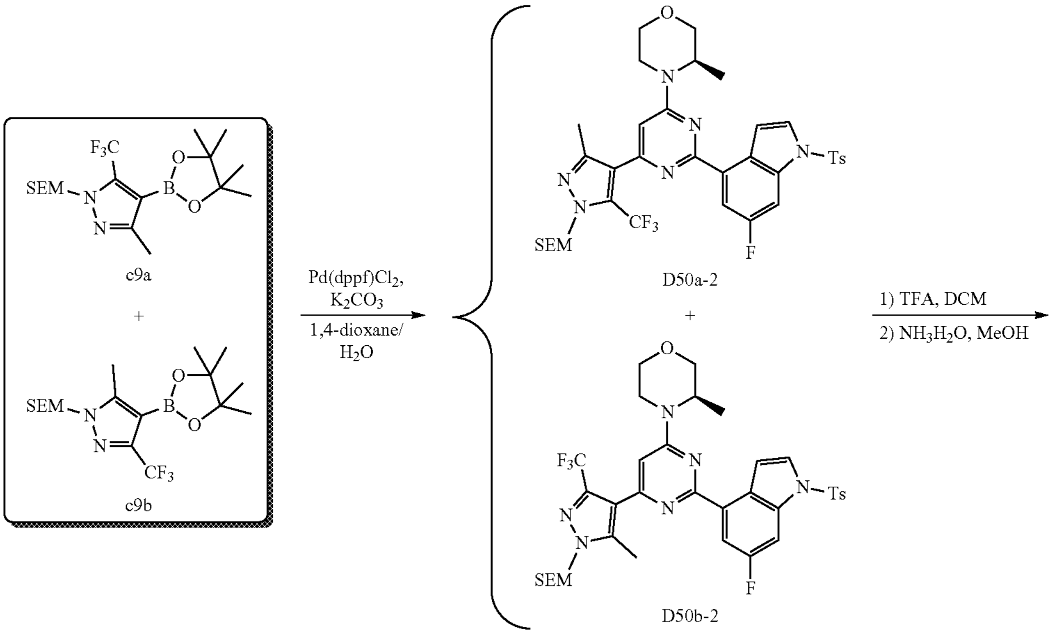

-continued

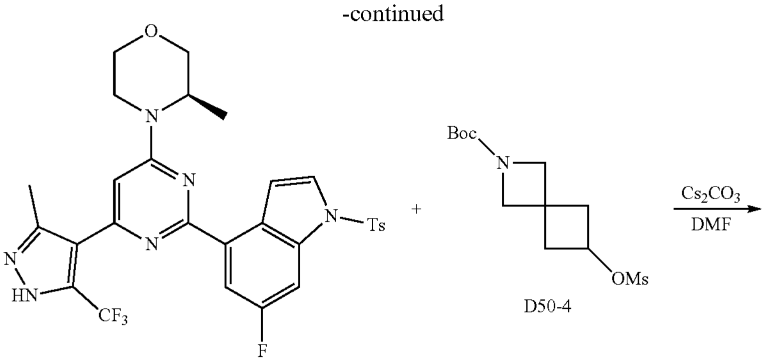

D50-3 D50-4

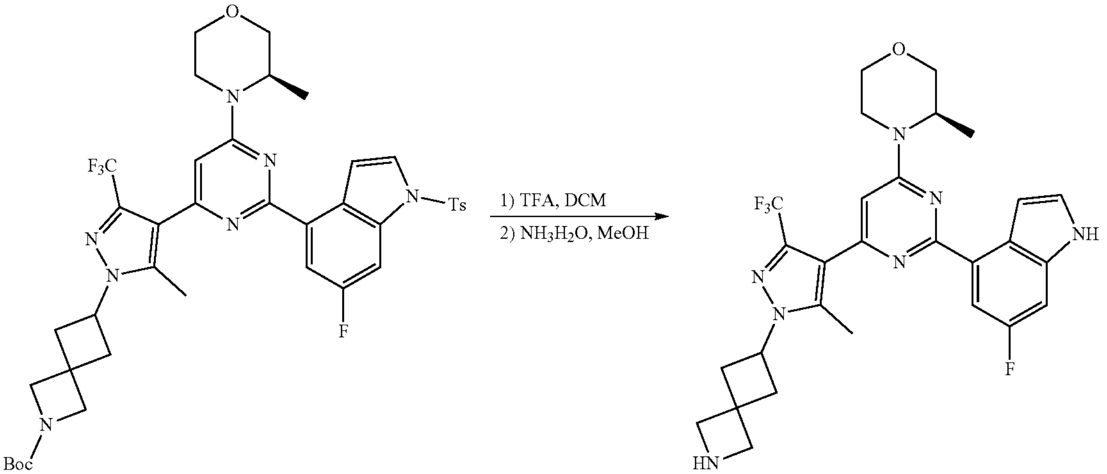

D50-5 D50

Under nitrogen protection, intermediate a1 (1.0 mmol, 247 mg) and intermediate a13 (7.0 mmol, 415 mg) were dissolved in 10 mL mixture of 1,4-dioxane and water (v/v, 9/1), sodium carbonate (3 mmol, 318 mg) and $Pd(dppf)Cl_2$ (0.1 mmol, 73 mg) were added, the mixture was heated up to 100° C. and reacted for 10 hours. The reaction was stopped, filtered, the solvent was removed under reduced pressure. 30 mL of water was added, extracted with ethyl acetate, and separated by flash column chromatography to afford intermediate D50-1 (124 mg, yield: 25%). LC-MS: $[M+H]^+$: 501.

Under nitrogen protection, intermediate D50-1 (0.64 mmol, 320 mg) and mixture of intermediate e9a and c9b (1.28 mmol, 520 mg) were dissolved in 10 mL mixture of 1,4-dioxane and water (v/v, 9/1), potassium carbonate (7.9 mmol, 265 mg) and $Pd(dppf)Cl_2$ (0.06 mmol, 47 mg) were added, and the mixture was heated up to 110° C. and reacted for 5 hours. The reaction was stopped, filtered, the solvent was removed under reduced pressure, 30 mL of water was added, extracted with ethyl acetate, and separated by flash column chromatography to afford mixture of D50a-2 and D50b-2 (yield: 99%). LC-MS: $[M+H]^+$: 745.

The mixture of D50a-2 and D50b-2 (0.71 mmol, 530 mg) was dissolved in 12 mL of dichloromethane, 4.0 mL of trifluoroacetic acid was added, after the mixture was reacted at room temperature for 2 hours, the solvent was removed under reduced pressure. The mixture was dissolved in 10 mL of methanol again, 5 mL of 7 M ammonia solution was slowly added, the reaction was stirred at room temperature for 2 hours, and the reaction was stopped. The mixture was extracted with dichloromethane, and separated by flash column chromatography to afford intermediate D50-3 (400 mg, yield: 91%), LC-MS: $[M+H]^+$: 615.

Intermediate D50-3 (0.16 mmol, 100 mg) and the raw material D50-4 (0.33 mmol, 71 mg) were added to a reaction flask, and dissolved in 5 mL of DMF. After cesium carbonate (0.49 mmol, 159 mg) was added, the mixture was reacted at 80° C. for 10 hours. The reaction was stopped, filtered, the solvent was removed under reduced pressure, and separated by flash column chromatography to afford intermediate D50-5 (60 mg, yield: 47%), LC-MS: $[M+H\text{-}tBu]^+$: 810.

Intermediate D50-5 (55 mg) was dissolved in 3 mL of dichloromethane, 0.5 mL of trifluoroacetic acid was added, after the mixture was reacted at room temperature for 2 hours, the solvent was removed under reduced pressure. The mixture was dissolved in 3 mL mixture of methanol and tetrahydrofuran (v/v, 1/1) again, cesium carbonate (0.3 mmol, 93 mg) was added, the mixture was heated up to 80° C. and stirred for 2 hours, then the reaction was stopped. The mixture was extracted with dichloromethane, and separated by preparative chromatography to afford the title compound D50 (11 mg, yield: 30%, containing trace amounts of isomers), LC-MS: $[M+H]^+$: 556, HPLC purity: 93.2%.

The following compound was synthesized with reference to the route of Example 45:

| Structure | The structure replacing D50-4 | LC-MS/ [M + H]+ | $^{1}$H NMR |
|---|---|---|---|
| 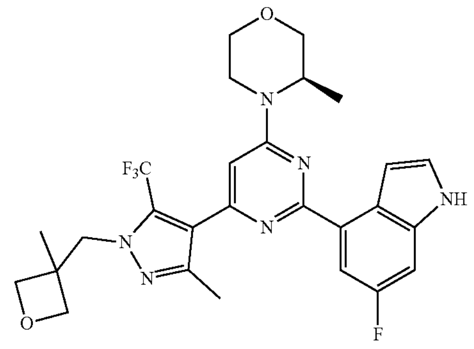 D51 | 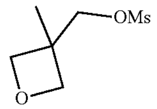 | 545 | $^{1}$H NMR (300 MHz, DMSO-$d_6$) δ 11.31 (s, 1H), 7.87 (dd, J = 11.6, 2.4 Hz, 1H), 7.43 (t, J = 2.7 Hz, 1H), 7.37-7.26 (m, 2H), 6.80 (s, 1H), 4.72 (dd, J = 6.1, 2.6 Hz, 2H), 4.55 (s, 1H), 4.48 (s, 1H), 4.28 (d, J = 6.1 Hz, 2H), 4.01 (d, J = 11.2 Hz, 1H), 3.79 (d, J = 11.3 Hz, 1H), 3.67-3.70 (m, 1H), 3.54 (t, J = 10.7 Hz, 1H), 3.32-3.31 (s, 2H), 3.27-3.29 (m, 1H), 2.26 (s, 3H), 1.28 (d, J = 6.7 Hz, 3H), 1.24 (s, 3H). |

Example 46: ATR Kinase Activity Assay

Biotinylated protein derived from p53 (Eurofins, art. No.: 14-952) was phosphorylated with ATR kinase. The amount of phosphorylated protein was determined by time-resolved fluorescence in this assay. The amount of phosphorylated protein was detected by anti-p53-phospho-(serine 15)-K-specific antibody (Cisbio, art. No.: 61GSTDLA) and d2 labeled anti-GST antibody (Cisbio, art. No. 61P08KAE). Before the experiment, the following working solution was prepared as required: 1× reaction buffer (20 mM HEPES PH8.0, 1% glycerol, 0.01% Brij-35), dilution buffer (20 mM HEPES PH8.0, 1% glycerol, 0.01% Brij-35, 5 mM DTT and 1% BSA), stop solution (20 mM HEPES PH8.0, 1% glycerol, 0.01% Brij-35, 250 mM EDTA), detection buffer (50 mM HEPES pH7.0, 150 mM NaCl, 267 mM KF, 0.1% sodium cholate, 0.01% Tween-20, 0.0125% sodium azide). The reagents used above are purchased from Sigma or Invitrogen, except for those where the manufacturer was mentioned.

Operations are as follows:

4× gradient dilution of compound solutions was prepared with 1× reaction buffer to obtain 9 compound solutions of different concentrations, and 2.5 μL 4× gradient dilution of compound solutions was added to a 384-well analysis plate (784075, Greiner). 4× p53 substrate working solution (40 nM) was prepared with 1× reaction buffer, and 2.5 μL 4× p53 substrate working solution was added to the 384-well analysis plate. 4×ATR/ATRIP working solution (12.8 ng/μL) was prepared with dilution buffer, and 2.5 μL 4×pATR/ATRIP working solution was added to the 384-well analysis plate. 4×ATP working solution (2 mM) was prepared with deionized water, 2.5 μL 4×ATP working solution was added to the 384-well analysis plate, and incubated at room temperature in dark for 30 minutes. 5 μL stop solution was added to the 384 analysis plate. Finally, 5 μL test mixture (0.084 ng/μL Anti-phospho-p53(ser15)-K and 5 ng/μL Anti-GST-d2) was added to the 384 well analysis plate, incubated overnight at room temperature, and the fluorescence signal was detected with ENVISION (Perkinelmer) instrument (excitation wavelength: 320 nm, emission wavelength: 665 nm and 615 nm). The inhibition rate in each well was calculated by the fluorescence intensity value of each hole: ER (Emission Ratio)=(Fluorescence intensity at 665 nm/Fluorescence intensity at 615 nm); inhibition rate=(ER positive-ER test compound)/(ER positive-ER negative)×100%, the $IC_{50}$ value of compounds were calculated by standard parameter fitting software (GraphPad Prism 6.0).

The kinase inhibitory activity of the Examples:

| No. | ATR/ $IC_{50}$/nM | No. | ATR/ $IC_{50}$/nM | No. | ATR/ $IC_{50}$/nM |
|---|---|---|---|---|---|
| A4 | 179 | B1 | 255 | D29 | 5 |
| A5 | >10000 | B2 | 4305 | D30a | 16 |
| A8 | 21 | B3 | >10000 | D30b | 54 |
| A9 | 31 | B4 | 1720 | D31 | 2698 |
| A10 | 25 | B5 | 1612 | D32 | 1774 |
| A11 | 15 | B6 | 979 | D33 | 13 |
| A12 | 44 | B7 | 340 | D34 | 73 |
| A13 | 66 | B8 | >10000 | D35 | 5 |
| A14 | 571 | C1 | 41 | D36 | 15 |
| A15 | 21 | D1 | 5 | D37 | 71 |
| A16 | 4 | D2 | 6 | D38 | 5 |
| A17 | 2274 | D3 | 31 | D39 | 3 |
| A18 | 47 | D4 | 6 | D40 | 5 |
| A19 | 18 | D5 | 108 | D41 | 29 |
| A20 | 98 | D6 | <1 | D42 | 97 |
| A21 | 56 | D7 | 1 | D43 | 19 |
| A22 | 81 | D8 | 3 | D44 | 34 |
| A23 | 14 | D10 | 3 | D45 | 10 |
| A24 | 57 | D11 | 8 | D46 | 6 |
| A25 | 2323 | D12 | 3 | D47 | 5 |
| A26 | 2171 | D13 | <1 | D48 | 2 |
| A27 | 47 | D14 | 28 | D49 | 2 |
| A28 | 25 | D15 | 17 | D50 | 3 |
| A29 | 631 | D16 | 82 | D51 | 32 |
| A30 | 110 | D17 | 1 | D52 | 2 |
| A31 | 48 | D18 | <1 | D53 | 4 |
| A32 | 27 | D19 | 1 | D54a | 4 |
| A33 | 936 | D20 | <1 | D54b | 13 |
| A34 | 282 | D21 | 2 | D55 | 3 |
| A35 | 63 | D22 | 16 | D56 | 9 |
| A36 | 91 | D23 | 8 | D57 | 16 |
| A37 | 37 | D24 | 3 | | |
| A38 | 30 | D25 | 83 | | |
| A39 | 121 | D26 | 12 | | |
| A40 | 50 | D27 | 8 | | |
| A41 | 11 | D28 | <1 | | |

Example 47: In Vitro Cell Proliferation Inhibition Assay

By detecting the effect of compound on cell activity in vitro in the tumor cell lines TOV21G (ovarian cancer) and MV4-11 (leukemia), the effect of compound inhibiting cell proliferation was studied in this assay.

TOV21G cells and MV4-11 cells were purchased from American Type Culture Collection (ATCC).

TOV21G cells were cultured in MCDB105/M199 medium (containing 15% PBS), and used for testing when the cell confluence reaches 85% or more. Each well of a 96-well culture plate was inoculated with about 1000 cells, cultured for 24 hours, and treated with different concentrations (0-10 μM) of compound solution to be tested in triplex. Blank wells (contains medium only) and control wells (seeded cells was not treated with drug) were set. Cells were cultured for 120 hours, 40 μL Cell Titer-Glo solution (Promega, #G7573) were added to each well, incubated with shaking for 20 min in the dark, 100 μL solution was transferred from each well to a 96-well white plate (Corning, #3917), and the luminescence value was read by Biotek Synergy H1 multifunctional microplate reader.

MV-4-11 cells were cultured in IMDM medium (containing 20% FBS), each well of a 96-well culture plate was inoculated with about 10000 cells, and treated with different concentrations (0-10 μM) of compounds to be tested in triplex. Blank wells (containing medium only) and control wells (inoculated with cells but not treated with drug) were set. Cells were cultured for 120 hours, 40 μL Cell Titer-Glo solution was added to each well, incubated with shaking for 20 min in the dark, 100 μL solution was transferred from each well to a 96-well white plate, and the luminescence value was read by Biotek Synergy H1 multifunctional microplate reader.

Inhibition rate (%)=100%×(control well−test well)/(control well−blank well)

The proliferation test results showed that the test compounds were effective in the studied human tumor cells, which was reflected by the $IC_{50}$ value ($IC_{50}$ is the inhibitory concentration at 50% of the maximum effect).

Cell activity test results of CellTiter-Glo luminescence method:

| No. | TOV21G/$IC_{50}$/μM | MV4-11/$IC_{50}$/μM |
|---|---|---|
| D1 | 0.26 | 0.12 |
| D2 | 0.92 | 0.78 |
| D3 | 0.28 | 0.29 |
| D4 | 0.33 | 0.19 |
| D6 | 0.24 | 0.17 |
| D7 | 0.46 | 0.31 |
| D8 | 0.43 | 0.22 |
| D10 | 0.38 | 0.33 |
| D11 | 0.64 | 0.37 |
| D12 | 0.28 | 0.29 |
| D13 | 0.80 | 0.25 |
| D14 | 1.20 | 0.81 |
| D15 | 0.77 | 0.25 |
| D16 | 1.05 | 1.36 |
| D17 | 0.23 | 0.14 |
| D18 | 0.51 | 0.28 |
| D19 | 0.11 | 0.08 |
| D20 | 0.16 | 0.07 |
| D21 | 0.14 | 0.19 |
| D22 | 0.85 | 0.92 |
| D23 | 0.58 | 0.69 |
| D24 | 0.12 | 0.08 |
| D25 | 1.03 | 0.99 |
| D26 | 3.58 | 3.09 |
| D27 | 0.72 | 0.97 |
| D28 | 0.28 | 0.23 |
| D29 | 0.71 | 0.50 |
| D30a | 2.09 | 0.41 |
| D30b | 2.22 | 0.33 |
| D31 | NT | NT |
| D32 | NT | NT |
| D33 | 1.45 | 1.31 |
| D34 | NT | NT |
| D35 | 0.74 | 0.84 |

-continued

| No. | TOV21G/$IC_{50}$/μM | MV4-11/$IC_{50}$/μM |
|---|---|---|
| D36 | 0.66 | 0.64 |
| D37 | NT | NT |
| D38 | 0.14 | 0.23 |
| D39 | 0.86 | 1.23 |
| D40 | 0.72 | 0.58 |
| D41 | 0.94 | 0.57 |
| D42 | 2.01 | 1.73 |
| D43 | 0.21 | 0.54 |
| D44 | 0.79 | 0.68 |
| D45 | 0.92 | 0.64 |
| D46 | 1.33 | 0.53 |
| D47 | 0.60 | 0.55 |
| D48 | 0.55 | 0.20 |
| D49 | 0.50 | 0.55 |
| D50 | NT | 0.81 |
| D51 | 0.68 | 0.66 |
| D52 | 0.37 | 0.59 |
| D53 | 0.71 | 0.62 |
| D54a | 0.18 | 0.09 |
| D54b | 0.44 | 0.26 |
| D55 | 0.19 | 0.22 |
| D56 | 0.44 | 0.32 |
| D57 | 0.41 | 0.22 |

Example 48: In Vitro Liver Microsomal Stability Assay of the Compounds

Experiments on the stability of the compound of the present disclosure in liver microsomes were performed. The compounds to be tested (final concentration: 2.0 nM) were co-incubated with human/mouse liver microsomes with or without NADPH, and the concentration of compounds in the incubation supernatant was detected within 60 minutes. The results of representative compounds are as follows:

| Compound | Human liver microsomes $t_{1/2}$ (min) | Mouse liver microsomes $t_{1/2}$ (min) |
|---|---|---|
| D1 | 338 | 62 |
| D17 | 303 | 170 |
| D24 | 203 | 110 |

Example 49: In Vivo Pharmacokinetics Assay of the Compounds

The in vivo pharmacokinetics of the compounds was studied.

Experimental Method

Male ICR mice (3 in each group) were orally administered by gavage with a dose of 10 mg/kg. Plasma samples were collected before (0 h) and after administration (0.25, 0.5, 1, 2, 4, 6, 8, 24 h), and the collected samples were analyzed by LC/MS and data were collected. The collected analytical data were used to calculate the relevant pharmacokinetic parameters by Analyst v1.6.2 (AB Applied Biosystems Company, USA).

The results of representative compounds are as follows:

| Compound | $t_{1/2}$ (h) | $T_{max}$ (h) | Cmax (ng/mL) | AUC (h*ng/mL) |
|---|---|---|---|---|
| D24 | 3.1 | 5.3 | 467 | 5452 |
| D28 | 3.9 | 4.7 | 199 | 2162 |

The above is a further detailed description of the present disclosure in connection with the specific preferred embodiments, and the specific embodiments of the present disclosure are not limited to the description it will be apparent to those skilled in the art that the present disclosure may be practiced by making various simple deduction and replacement, without departing from the spirit and scope of the invention.

The invention claimed is:

1. A compound of formula (I), or a pharmaceutically acceptable salt, enantiomer, diastereomer, racemate, solvate, hydrate, polymorph, prodrug, or isotopic variant thereof, or mixture thereof:

(I)

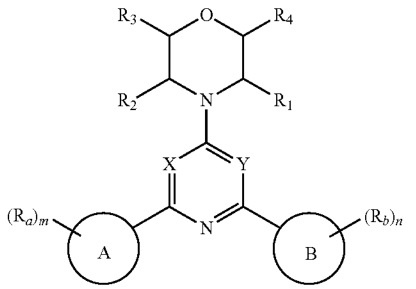

wherein,

X is CH or N; Y is CH or N; and wherein at least one of X and Y is N;

$R_1$, $R_2$, $R_3$ and $R_4$ are independently selected from H, $C_{1-6}$ alkyl and $C_{1-6}$ haloalkyl; or $R_1$ and $R_2$, $R_3$ and $R_4$ are connected to form bond, $C_{1-6}$ alkylene, $C_{2-6}$ alkenylene or $C_{2-6}$ alkynylene; at least one of $R_1$ and $R_2$ is $C_{1-6}$ alkyl;

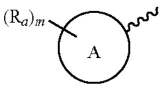

is

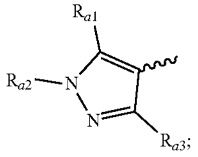

ring B is 5- to 10-membered heteroaryl;

$R_{a1}$ and $R_{a3}$ are independently selected from H, halogen, —CN, -L-NRR', -L-OR, —C(O)R, —C(O)OR, —C(O)NRR', —OC(O)R', —NRC(O)R', —OC(O)NRR', —NRC(O)NRR', $C_{1-6}$ alkyl, $C_{1-6}$ haloalkyl, $C_{1-6}$ alkoxy, $C_{1-6}$ haloalkoxy, -L-S(O)$_p$R*, -L-S(=O)(=NR)R*, -L-$C_{3-7}$ cycloalkyl and -L-4- to 8-membered heterocyclyl, each of which is optionally substituted with R** group;

$R_{a2}$ is selected from -L-$C_{3-7}$ cycloalkyl and -L-4- to 8-membered heterocyclyl, which is optionally substituted with R** group;

wherein L is independently selected from bond, —O—, —S—, —NR—, —C(O)—, $C_{1-6}$ alkylene, $C_{2-6}$ alkenylene and $C_{2-6}$ alkynylene; p=1 or 2;

R*is selected from $C_{1-6}$ alkyl, $C_{1-6}$ haloalkyl, -L'-NRR', -L'-OR, -L'-$C_{3-7}$ cycloalkyl and -L'-4- to 8-membered heterocyclyl; wherein L' is independently selected from bond, $C_{1-6}$ alkylene, $C_{2-6}$ alkenylene, $C_{2-6}$ alkynylene, —O—$C_{1-6}$ alkylene and —NH—$C_{1-6}$ alkylene;

$R_b$ is independently selected from H, halogen, —CN, —OH, $C_{1-6}$ alkyl, $C_{1-6}$ alkoxy, -L-$C_{3-7}$ cycloalkyl, -L-3- to 8-membered heterocyclyl, —NRR', —C(O)R, —C(O)OR, —C(O)NRR', —OC(O)R', —NRC(O)R', —OC(O)NRR' and —NRC(O)NRR';

R** is independently selected from H, halogen, —CN, —C(=O)R, $C_{1-6}$ alkyl, $C_{1-6}$ haloalkyl, $C_{1-6}$ alkoxy, $C_{1-6}$ haloalkoxy, 4- to 8-membered heterocyclyl, —S(O)$_p$—$C_{1-6}$ alkyl, —S(O)$_p$—$C_{1-6}$ haloalkyl and —NRR';

R and R' are independently selected from H, $C_{1-6}$ alkyl and $C_{1-6}$ haloalkyl, or R, R' are taken together with the nitrogen atoms to which they are attached to form 4- to 8-membered heterocyclyl;

n=0, 1, 2, 3, 4 or 5.

2. The compound, or the pharmaceutically acceptable salt, enantiomer, diastereomer, racemate, solvate, hydrate, polymorph, prodrug, or isotopic variant thereof, or mixture thereof according to claim 1, which has the structure of formula (II):

(II)

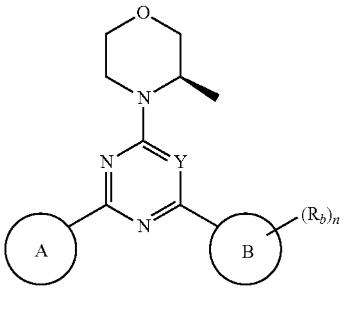

wherein, Y, ring A, ring B, $R_b$ and n are as defined in claim 1;

alternatively, $R_{a1}$ is selected from H, $C_{1-6}$ alkyl and $C_{1-6}$ haloalkyl; alternatively is H or methyl;

$R_{a2}$ is as defined in claim 1; alternatively, $R_{a2}$ is -L-4- to 8-membered heterocyclyl, which is optionally substituted with R group; wherein L is selected from bond, $C_{1-6}$ alkylene, $C_{2-6}$ alkenylene and $C_{2-6}$ alkynylene, p=1 or 2; R is selected from H, halogen, —OR, —C(O)R, $C_{1-6}$ alkyl, $C_{1-6}$ haloalkyl, 4- to 8-membered heterocyclyl, —S(O)$_p$—$C_{1-6}$ alkyl, —S(O)$_p$—$C_{1-6}$ haloalkyl and —NRR', wherein R and R' are independently selected from H, $C_{1-6}$ alkyl and $C_{1-6}$ haloalkyl;

$R_{a3}$ is selected from H, $C_{1-6}$ alkyl and $C_{1-6}$ haloalkyl; alternatively is H or methyl;

ring B is selected from

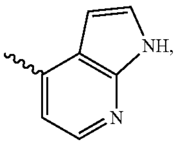, 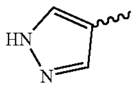 and 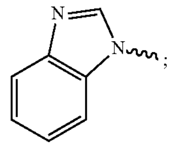;

$R_b$ is selected from H, halogen, $C_{1-6}$ alkyl and $C_{1-6}$ haloalkyl; alternatively is methyl, halogen or methylamino;

n=0, 1, 2, 3 or 4; alternatively, n=0, 1 or 2.

3. The compound, or the pharmaceutically acceptable salt, enantiomer, diastereomer, racemate, solvate, hydrate, polymorph, prodrug, or isotopic variant thereof, or mixture thereof according to claim 1, which has the structure of formula (III):

(III)

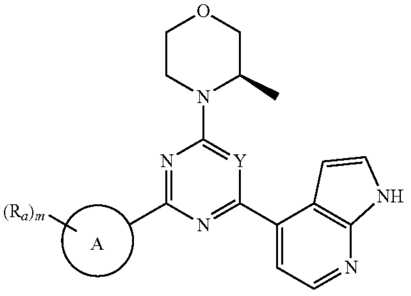

wherein, Y, ring A, $R_a$ and m are as defined in claim 2;

$R_{a1}$ is selected from $C_{1-6}$ alkyl and $C_{1-6}$ haloalkyl; alternatively is methyl;

$R_{a2}$ is as defined in claim 2; alternatively, $R_{a2}$ is -L-4- to 8-membered heterocyclyl, which is optionally substituted with R group; wherein L is selected from bond, $C_{1-6}$ alkylene, $C_{2-6}$ alkenylene and $C_{2-6}$ alkynylene, p=1 or 2; R is selected from H, halogen, —OR, —C(O)R, $C_{1-6}$ alkyl, $C_{1-6}$ haloalkyl, 4- to 8-membered heterocyclyl, —$S(O)_p$—$C_{1-6}$ alkyl, —$S(O)_p$—$C_{1-6}$ haloalkyl and —NRR', wherein R and R' are independently selected from H, $C_{1-6}$ alkyl and $C_{1-6}$ haloalkyl;

$R_{a3}$ is selected from $C_{1-6}$ alkyl and $C_{1-6}$ haloalkyl; alternatively is methyl.

4. The compound, or the pharmaceutically acceptable salt, enantiomer, diastereomer, racemate, solvate, hydrate, polymorph, prodrug, or isotopic variant thereof, or mixture thereof according to claim 1, which has the structure of formula (IV):

(IV)

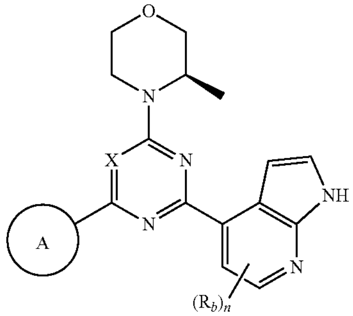

wherein,

X is CH or N;

ring A is:

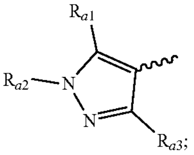

$R_{a1}$ is selected from H, $C_{1-6}$ alkyl and $C_{1-6}$ haloalkyl; alternatively is H or methyl;

$R_{a2}$ is -L-4- to 8-membered heterocyclyl, which is optionally substituted with R group; wherein L is selected from bond, $C_{1-6}$ alkylene, $C_{2-6}$ alkenylene and $C_{2-6}$ alkynylene, p=1 or 2; R is selected from H, halogen, —OR, —C(O)R, $C_{1-6}$ alkyl, $C_{1-6}$ haloalkyl, 4- to 8-membered heterocyclyl, —$S(O)_p$—$C_{1-6}$ alkyl, —$S(O)_p$—$C_{1-6}$ haloalkyl and —NRR', wherein R and R' are independently selected from H, $C_{1-6}$ alkyl and $C_{1-6}$ haloalkyl;

alternatively, $R_{a2}$ is -L-4- to 8-membered heterocyclyl, wherein L is bond or $C_{1-6}$ alkylene; alternatively is azetidin-3-ylmethyl, oxetan-3-ylmethyl, pyran-4-yl, tetrahydropyrrolyl or piperidinyl;

$R_{a3}$ is selected from H, $C_{1-6}$ alkyl and $C_{1-6}$ haloalkyl; alternatively is H, methyl, $CF_3$;

$R_b$ is selected from H, halogen, —CN, —OH, $C_{1-6}$ alkyl, $C_{1-6}$ alkoxy, -L-$C_{3-7}$ cycloalkyl, -L-3- to 8-membered heterocyclyl, —NRR', —C(O)R; alternatively is H, halogen, methoxy or —$CH_2$-azetidin-3-yl;

n=0, 1, 2 or 3.

5. The compound, or the pharmaceutically acceptable salt, enantiomer, diastereomer, racemate, solvate, hydrate, polymorph, prodrug, or isotopic variant thereof, or mixture thereof according to claim 1, which has the structure of formula (IV):

(IV)

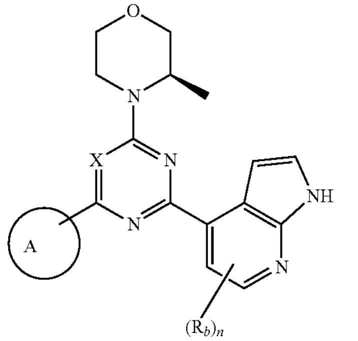

wherein,

X is CH or N;

ring A is:

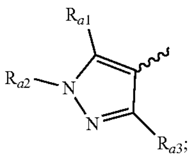

$R_{a1}$ is selected from $C_{1-6}$ alkyl and $C_{1-6}$ haloalkyl; alternatively is methyl;

$R_{a2}$ is -L-4- to 8-membered heterocyclyl, which is optionally substituted with R group, wherein L is selected from bond, $C_{1-6}$ alkylene, $C_{2-6}$ alkenylene and $C_{2-6}$ alkynylene; R is selected from halogen, $C_{1-6}$ alkyl, $C_{1-6}$ haloalkyl, —S(O)$_p$—$C_{1-6}$ alkyl and —S(O)$_p$—$C_{1-6}$ haloalkyl, wherein p=1 or 2;

alternatively, $R_{a2}$ is selected from -L-4- to 8-membered heterocyclyl, pyran-4-yl, tetrahydropyrrolyl or piperidinyl;

$R_{a3}$ is selected from H, $C_{1-6}$ alkyl and $C_{1-6}$ haloalkyl; alternatively is methyl, $CF_3$;

$R_b$ is selected from H, halogen, —CN, —OH, $C_{1-6}$ alkyl, $C_{1-6}$ alkoxy, -L-$C_{3-7}$ cycloalkyl, -L-3- to 8-membered heterocyclyl, —NRR', —C(O)R; alternatively is H, halogen, methoxy or —$CH_2$-azetidin-3-yl, and wherein R and R' are independently selected from H, $C_{1-6}$ alkyl and $C_{1-6}$ haloalkyl, or R, R' are taken together with the nitrogen atoms to which they are attached to form 4- to 8-membered heterocyclyl;

n=0, 1, 2 or 3.

6. The compound, or the pharmaceutically acceptable salt, enantiomer, diastereomer, racemate, solvate, hydrate, polymorph, prodrug, or isotopic variant thereof, or mixture thereof according to claim 1, which has the structure of formula (V):

(V)

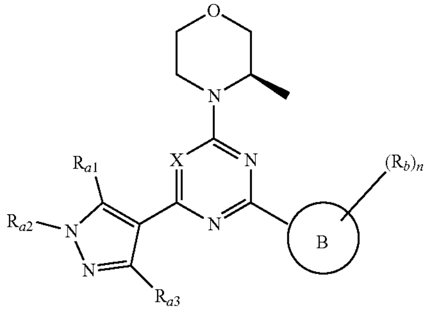

wherein,

X is CH or N;

$R_{a1}$ is selected from $C_{1-6}$ alkyl and $C_{1-6}$ haloalkyl; alternatively is methyl;

$R_{a2}$ is L-4- to 8-membered heterocyclyl; alternatively is piperidinyl;

$R_{a3}$ is selected from $C_{1-6}$ alkyl and $C_{1-6}$ haloalkyl; alternatively is methyl or trifluoromethyl;

ring B is selected from:

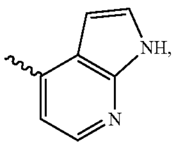 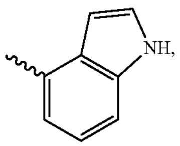

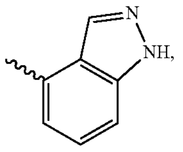 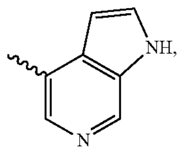

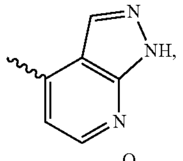 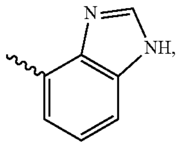

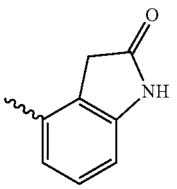 and 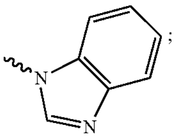

$R_b$ is selected from H, halogen, —CN, —OH, $C_{1-6}$ alkyl, $C_{1-6}$ alkoxy, -L-$C_{3-7}$ cycloalkyl, -L-3- to 8-membered heterocyclyl, —NRR' and —NRC(O)R', wherein R and R' are independently selected from H, $C_{1-6}$ alkyl and $C_{1-6}$ haloalkyl;

L is selected from bond and $C_{1-6}$ alkylene;

n=0, 1, 2, 3, 4 or 5; alternatively, n=0, 1 or 2.

7. A compound, or a pharmaceutically acceptable salt, enantiomer, diastereomer, racemate, solvate, hydrate, polymorph, prodrug, or isotopic variant thereof, or mixture thereof, which has the structure of formula (VI):

(VI)

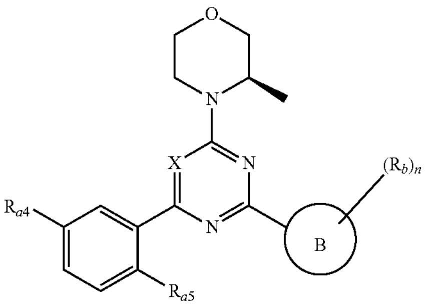

wherein,

X is CH or N;

$R_{a4}$ is -L-$S(O)_2R^*$, which is optionally substituted with $R^{**}$ group; wherein, L is selected from bond and $C_{1-6}$ alkylene, $R^*$ is selected from $C_{1-6}$ alkyl, $C_{1-6}$ haloalkyl, -L'-NRR' and -L'-4- to 8-membered heterocyclyl; and wherein L' is selected from bond and $C_{1-6}$ alkylene, R and R' are independently selected from H, $C_{1-6}$ alkyl, or R, R' are taken together with the nitrogen atoms to which they are attached to form 4- to 8-membered heterocyclyl; $R^{**}$ is selected from H, —CN, C(═O)R, $C_{1-6}$ alkyl, $C_{1-6}$ haloalkyl, —$S(O)_p$—$C_{1-6}$ alkyl, —$S(O)_p$—$C_{1-6}$ haloalkyl and —NRR', wherein p=1 or 2;

alternatively, $R_{a4}$ is —$S(O)_2R^*$, wherein, $R^*$ is selected from $C_{1-6}$ alkyl, -L'-NRR' and 4- to 8-membered heterocyclyl, and wherein R and R' are independently selected from H, $C_{1-6}$ alkyl and $C_{1-6}$ haloalkyl, or R, R' are taken together with the nitrogen atoms to which they are attached to form 4- to 8-membered heterocyclyl; L' is selected from bond and $C_{1-6}$ alkylene; alternatively is —$SO_2N(Me)_2$, —$SO_2Me$, -$SO_2$iPr or —$SO_2$-piperidin-4-yl;

$R_{a5}$ is selected from methyl, methoxy, isopropyl or trifluoromethyl;

ring B is selected from:

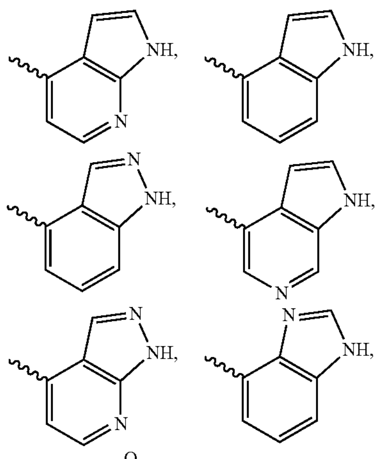

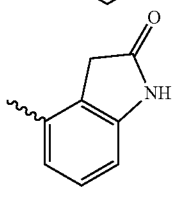

and

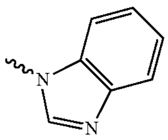

;

$R_b$ is selected from H, halogen, —CN, —OH, $C_{1-6}$ alkyl, $C_{1-6}$ alkoxy, -L-$C_{3-7}$ cycloalkyl, -L-3- to 8-membered heterocyclyl, —NRR' and —NRC(O)R', wherein R and R' are independently selected from H, $C_{1-6}$ alkyl and $C_{1-6}$ haloalkyl;

n=0, 1, 2, 3, 4 or 5; alternatively, n=0, 1 or 2.

8. The compound, or the pharmaceutically acceptable salt, enantiomer, diastereomer, racemate, solvate, hydrate, polymorph, prodrug, or isotopic variant thereof, or mixture thereof according to claim 1, which has the structure of formula (VII):

(VII)

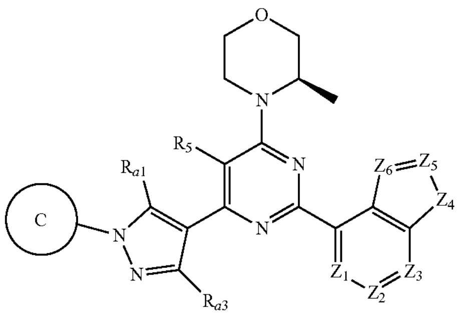

wherein, ring C is $C_{3-7}$ cycloalkyl or 4- to 8-membered heterocyclyl, each of which is substituted with $R_{a12}$ (alternatively 5- to 6-membered heterocyclyl substituted with $R_{a12}$, alternatively 5- to 6-membered heterocyclyl containing N atom(s) substituted with $R_{a12}$);

$R_{a1}$ is $C_{1-6}$ alkyl, $C_{1-6}$ haloalkyl, $C_{1-6}$ alkoxy or $C_{1-6}$ haloalkoxy (alternatively methyl, trifluoromethyl or methoxy);

$R_{a3}$ is $C_{1-6}$ alkyl or $C_{1-6}$ haloalkyl (alternatively methyl or trifluoromethyl);

$R_{a12}$ is H, $C_{1-6}$ alkyl or $C_{1-6}$ haloalkyl;

$R_5$ is H, halogen, $C_{1-6}$ alkyl or $C_{1-6}$ haloalkyl;

$Z_1$ is N or $CR_{b1}$;

$Z_2$ is N or $CR_{b2}$;

$Z_3$ is N or $CR_{b3}$;

$Z_4$ is $NR_{b4}$ or $C(R_{b4})_2$;

$Z_5$ is N or $CR_{b5}$;

$Z_6$ is N or $CR_{b6}$;

$R_{b1}$, $R_{b2}$, $R_{b3}$, $R_{b4}$, $R_{b5}$ and $R_{b6}$ are independently selected from H, halogen, $C_{1-6}$ alkyl, $C_{1-6}$ haloalkyl, $C_{1-6}$ alkoxy and $C_{1-6}$ haloalkoxy (alternatively selected from H, halogen and methoxy);

alternatively, $R_{a1}$ is $C_{1-6}$ alkyl or $C_{1-6}$ haloalkyl (alternatively methyl or trifluoromethyl);

$R_{b2}$ is H or halogen (alternatively H or F);

$R_{b3}$ is alternatively H;

alternatively, at least one of $R_{a1}$ and $R_{a3}$ is $C_{1-6}$ haloalkyl.

9. The compound, or the pharmaceutically acceptable salt, enantiomer, diastereomer, racemate, solvate, hydrate, polymorph, prodrug, or isotopic variant thereof, or mixture thereof according to claim 1, which has the structure of formula (VIII):

(VIII)

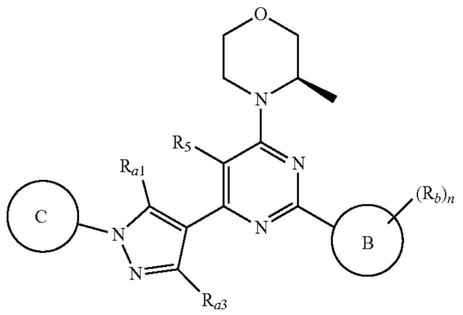

wherein, ring C is

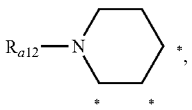

wherein the point of attachment with the rest of the molecule is at one of the positions shown by *;

$R_{a1}$ is $C_{1-6}$ alkyl or $C_{1-6}$ haloalkyl (alternatively is methyl or trifluoromethyl);

$R_{a3}$ is $C_{1-6}$ alkyl or $C_{1-6}$ haloalkyl (alternatively is methyl or trifluoromethyl);

$R_{a12}$ is H or $C_{1-6}$ alkyl (alternatively is H or methyl);

$R_5$ is H or halogen (alternatively is H or F);

ring B is selected from

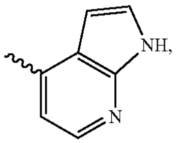

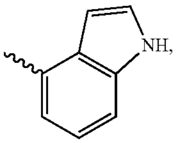

and

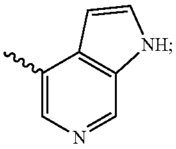

$R_b$ is H, methoxy or halogen (alternatively is H or halogen);

n is 0, 1, 2 or 3;

alternatively, at least one of $R_{a1}$ and $R_{a3}$ is $C_{1-6}$ haloalkyl.

10. The compound, or the pharmaceutically acceptable salt, enantiomer, diastereomer, racemate, solvate, hydrate, polymorph, prodrug, or isotopic variant thereof, or mixture thereof according to claim 1, which has the structure of formula (IX):

(IX)

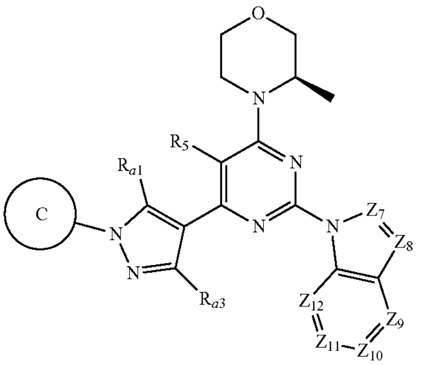

wherein, ring C is $C_{3-7}$ cycloalkyl or 4- to 8-membered heterocyclyl, each of which is substituted with $R_{a12}$ (alternatively 5- to 6-membered heterocyclyl substituted with $R_{a12}$, alternatively 5- to 6-membered heterocyclyl containing N atom(s) substituted with $R_{a12}$);

$R_{a1}$ is $C_{1-6}$ alkyl or $C_{1-6}$ haloalkyl;

$R_{a3}$ is $C_{1-6}$ alkyl or $C_{1-6}$ haloalkyl;

$R_{a12}$ is H, $C_{1-6}$ alkyl or $C_{1-6}$ haloalkyl;

$R_5$ is H, halogen, $C_{1-6}$ alkyl or $C_{1-6}$ haloalkyl;

$Z_7$ is N or $CR_{b7}$;

$Z_8$ is N or $CR_{b8}$;

$Z_9$ is N or $CR_{b9}$;

$Z_{10}$ is N or $CR_{b10}$;

$Z_{11}$ is N or $CR_{b11}$;

$Z_{12}$ is N or $CR_{b12}$;

wherein, $R_{b7}$ is H, -L-OR, -L-$C_{1-6}$ alkyl, -L-$C_{3-7}$ cycloalkyl, —NRR', —NRC(O)R' or —NRC(O)NRR';

$R_{b8}$, $R_{b9}$, $R_{b10}$, $R_{b11}$ and $R_{b12}$ are independently selected from H, halogen, —CN, $C_{1-6}$ alkyl, $C_{1-6}$ haloalkyl, $C_{1-6}$ alkoxy and $C_{1-6}$ haloalkoxy (alternatively selected from H, halogen, —CN and methoxy);

L is independently selected from bond, —O—, —S—, —NR—, —C(O)—, $C_{1-6}$ alkylene, $C_{2-6}$ alkenylene and $C_{2-6}$ alkynylene;

R and R' are independently selected from H, $C_{1-6}$ alkyl and $C_{1-6}$ haloalkyl.

11. The compound, or the pharmaceutically acceptable salt, enantiomer, diastereomer, racemate, solvate, hydrate, polymorph, prodrug, or isotopic variant thereof, or mixture thereof according to claim 10, wherein $Z_7$ is N or $CR_{b7}$;

wherein, $R_{b7}$ is selected from —NRR', —NRC(O)R' or —NRC(O)NRR';

wherein, R and R' are independently selected from H, $C_{1-6}$ alkyl and $C_{1-6}$ haloalkyl.

12. The compound, or the pharmaceutically acceptable salt, enantiomer, diastereomer, racemate, solvate, hydrate, polymorph, prodrug, or isotopic variant thereof, or mixture thereof according to claim 1, which has the structure of formula (X):

(X)

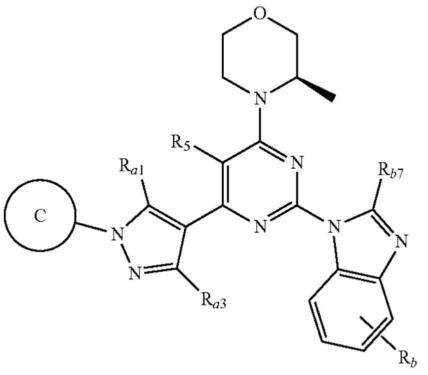

wherein,
ring C is

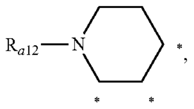

wherein the point of attachment with the rest of the molecule is at one of the positions shown by *;

$R_{a1}$ is $C_{1-6}$ alkyl or $C_{1-6}$ haloalkyl (alternatively is methyl or trifluoromethyl);

$R_{a3}$ is $C_{1-6}$ alkyl or $C_{1-6}$ haloalkyl (alternatively is methyl or trifluoromethyl);

$R_{a12}$ is H or $C_{1-6}$ alkyl (alternatively is H or methyl);

$R_5$ is H;

$R_{b7}$ is selected from —NRR', —SR, —NRC(O)R' or —NRC(O)NRR'; wherein, R and R' are independently selected from H, $C_{1-6}$ alkyl and $C_{1-6}$ haloalkyl (alternatively, $R_{b7}$ is selected from $NH_2$, NHMe, NHEt, NHC(O)Me or NHC(O)Et);

$R_b$ is H or halogen (alternatively is H or F).

13. A compound, or a pharmaceutically acceptable salt, enantiomer, diastereomer, racemate, solvate, hydrate, polymorph, prodrug, or isotopic variant thereof, or mixture thereof, which has the structure of formula (XI):

(XI)

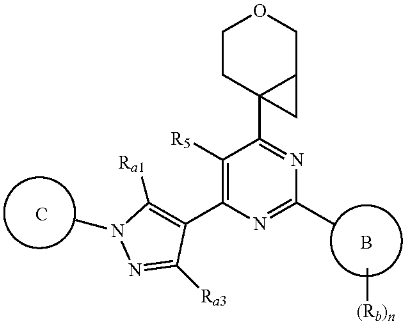

wherein, ring C is $C_{3-7}$ cycloalkyl or 4- to 8-membered heterocyclyl, each of which is substituted with $R_{a12}$ (alternatively 5- to 6-membered heterocyclyl substituted with $R_a$12, alternatively 5- to 6-membered heterocyclyl containing N atom(s) substituted with $R_{a12}$);

$R_{a1}$ is $C_{1-6}$ alkyl or $C_{1-6}$ haloalkyl (alternatively is methyl or trifluoromethyl);

$R_{a3}$ is $C_{1-6}$ alkyl or $C_{1-6}$ haloalkyl (alternatively is methyl or trifluoromethyl);

$R_{a12}$ is H, $C_{1-6}$ alkyl or $C_{1-6}$ haloalkyl (alternatively is H or methyl);

$R_5$ is H, halogen, $C_{1-6}$ alkyl or $C_{1-6}$ haloalkyl (alternatively is H or F);

ring B is selected from:

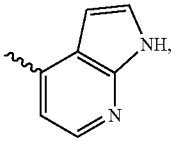

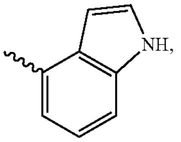

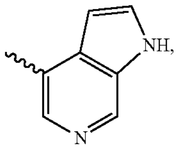

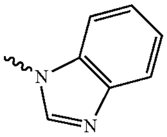

or

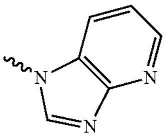

;

$R_b$ is selected from H, halogen, —CN, -L-$C_{1-6}$ alkyl, $C_{1-6}$ alkoxy, -L-$C_{3-7}$ cycloalkyl, -L-3- to 8-membered heterocyclyl, —NRR', —NRC(O)R' and —NRC(O)NRR', wherein R and R' are independently selected from H, $C_{1-6}$ alkyl and $C_{1-6}$ haloalkyl.

14. A compound, which is selected from:

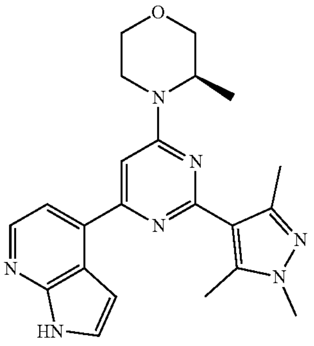

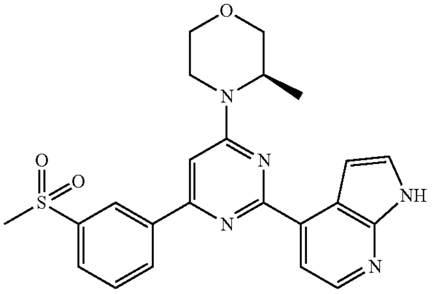

-continued
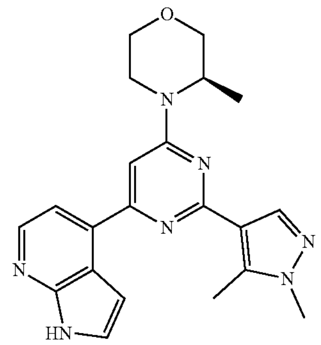
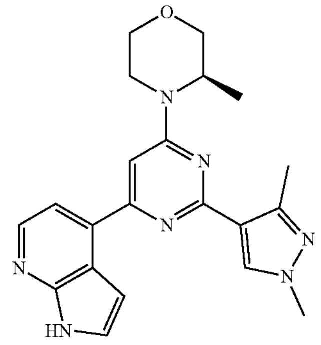
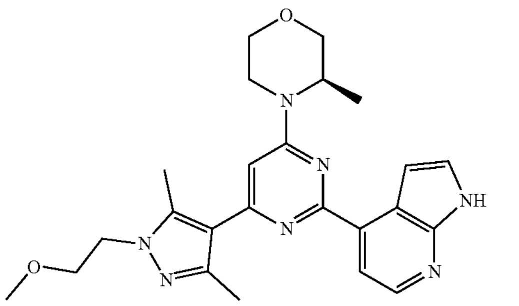
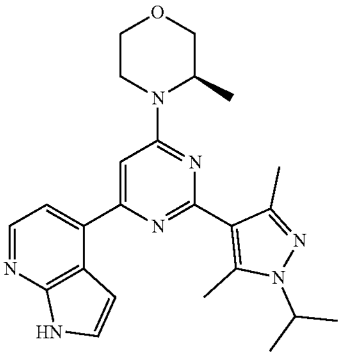
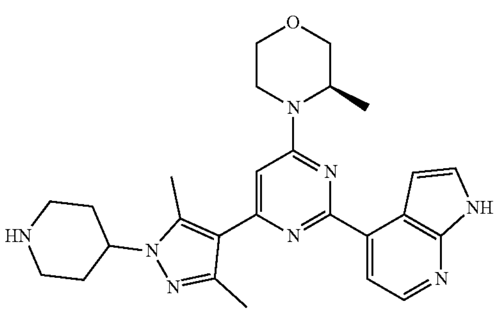
-continued
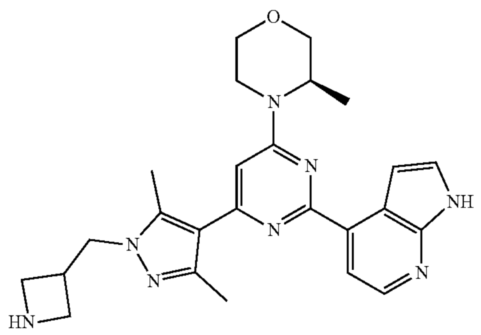
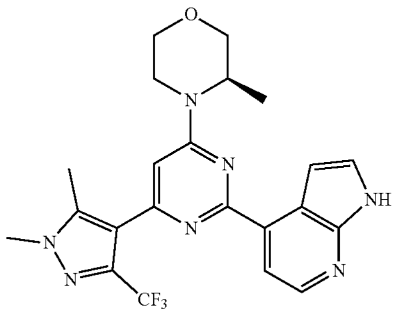
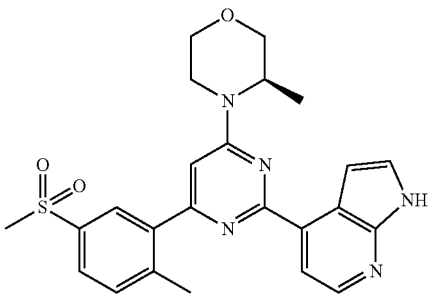
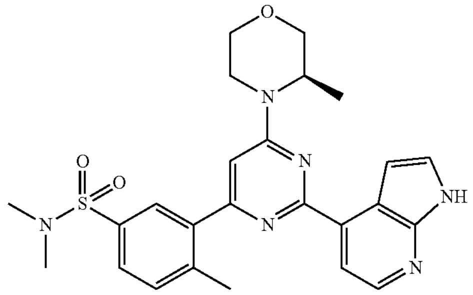
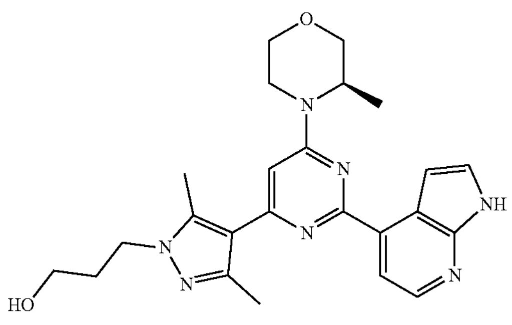

-continued
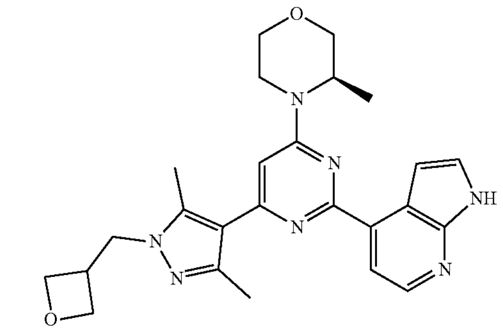
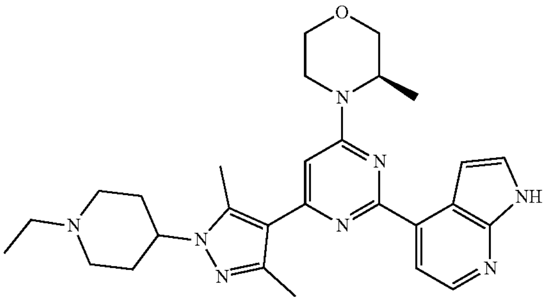
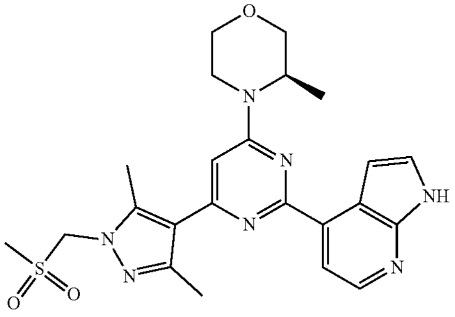
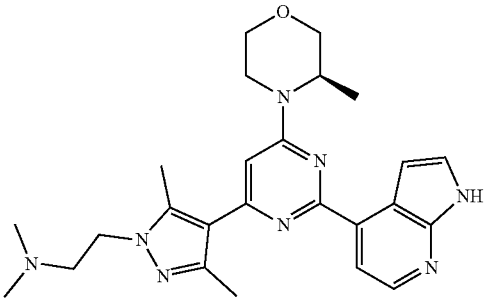
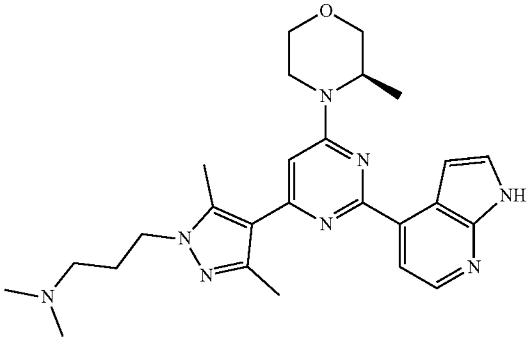
-continued
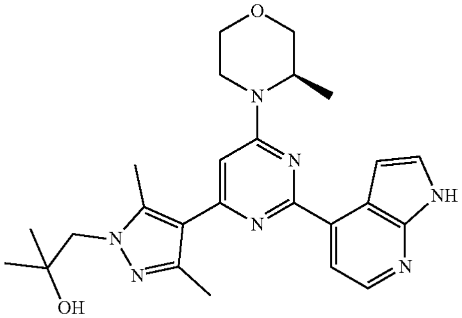
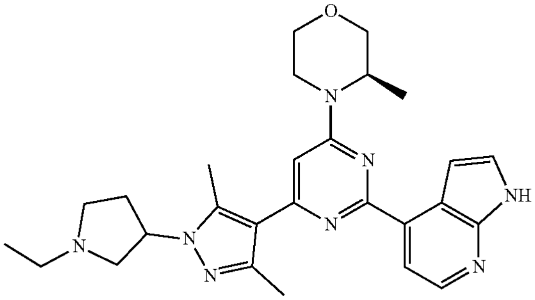
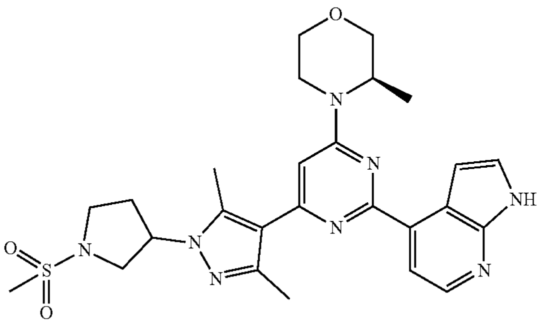
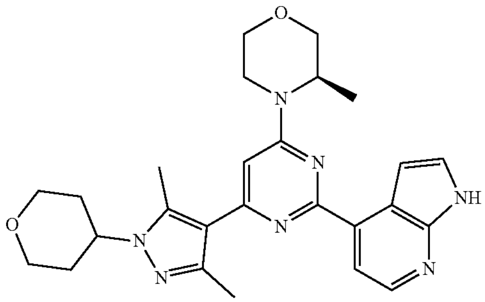
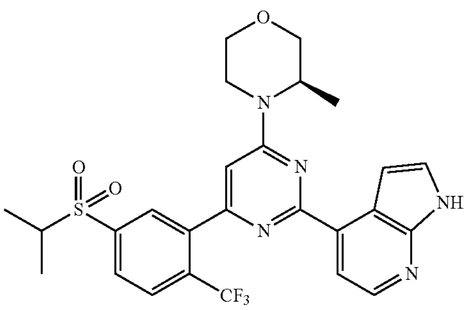

-continued
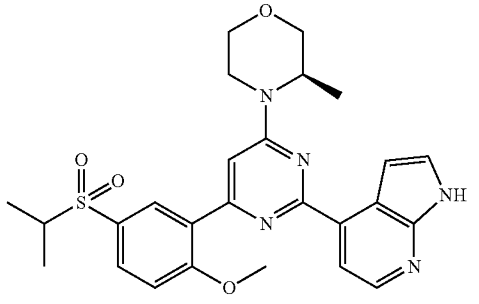
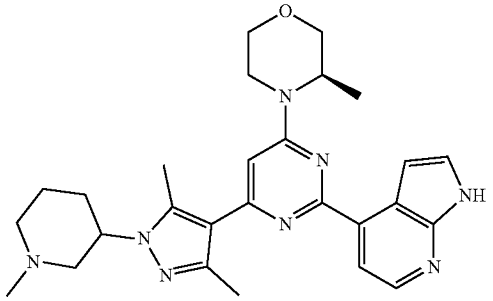
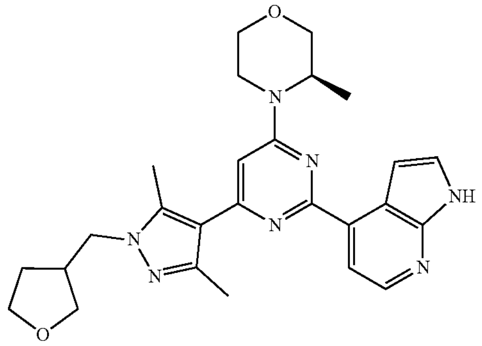
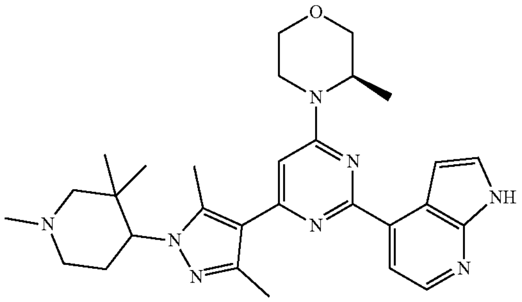
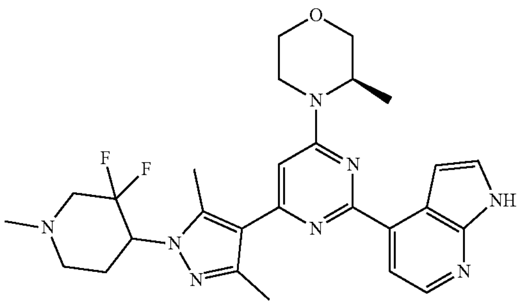
-continued
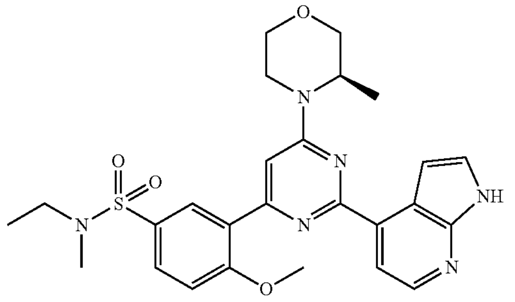
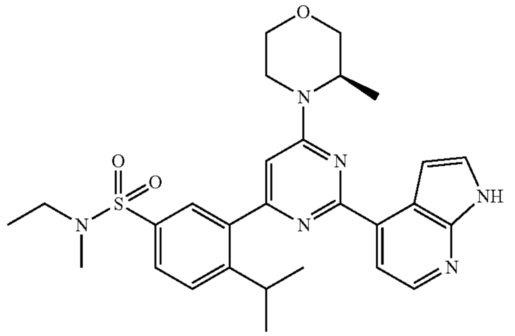
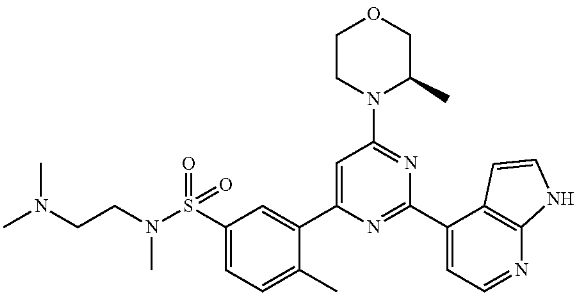
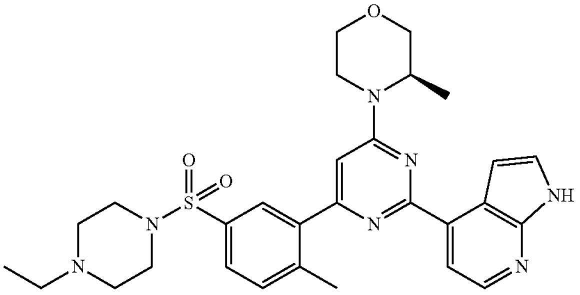
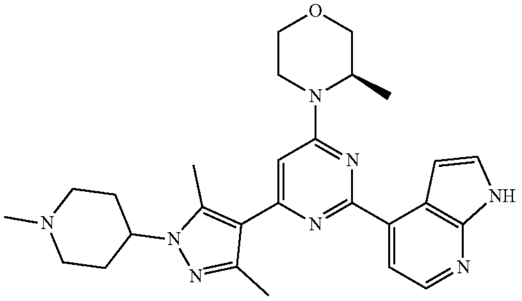

-continued
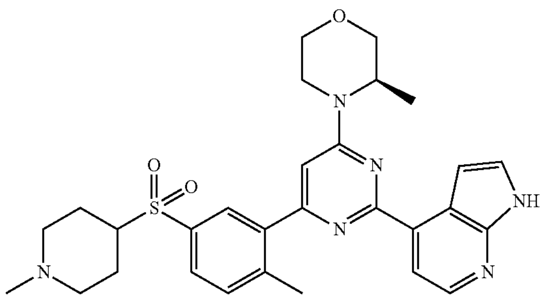
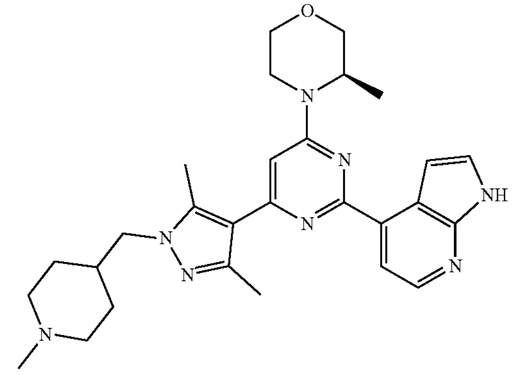
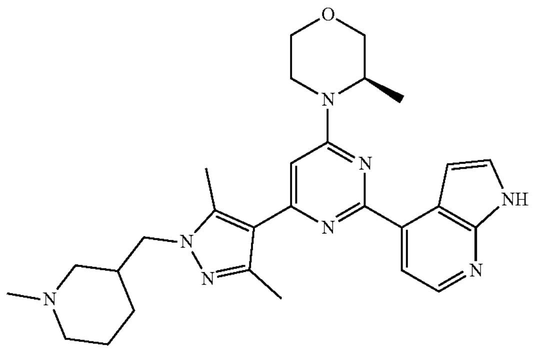
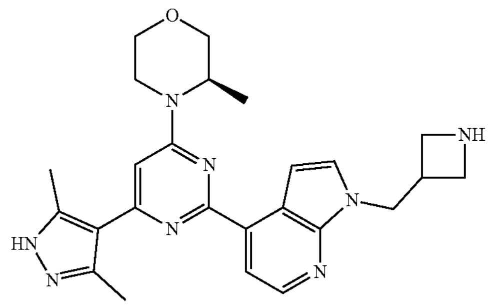 [SMILES: Cc1n[nH]c(C)c1-c1cc(N2CCOC[C@H]2C)nc(-c2ccnc3c2ccn3CC2CNC2)n1]
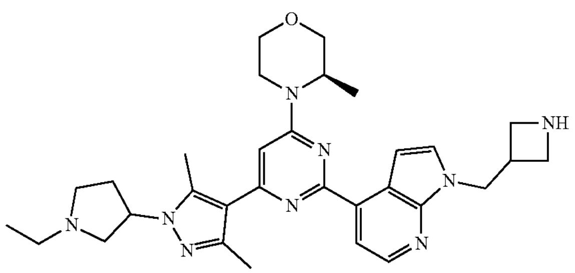 [SMILES: CCN1CCC(n2nc(C)c(-c3cc(N4CCOC[C@H]4C)nc(-c4ccnc5c4ccn5CC4CNC4)n3)c2C)C1]
-continued
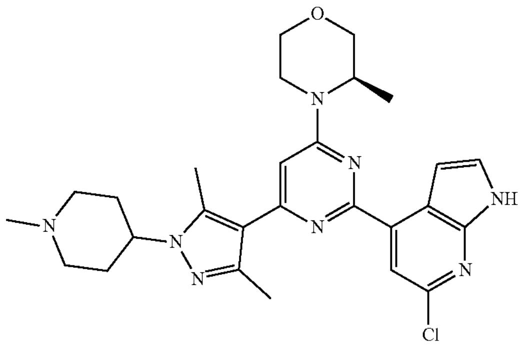
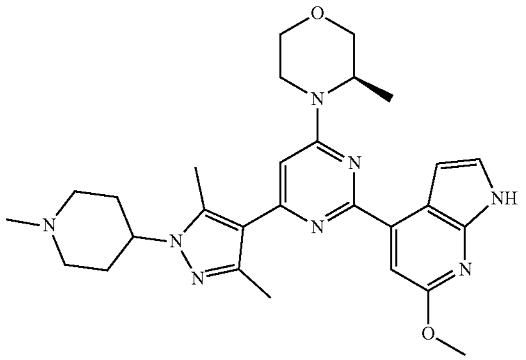
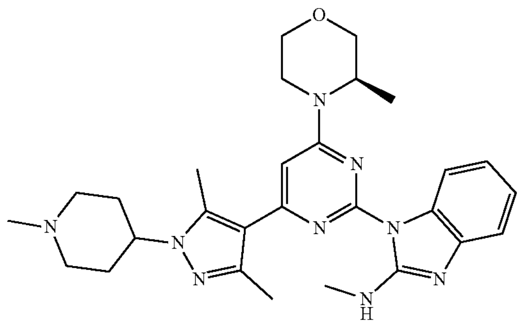 [SMILES: CNc1nc2ccccc2n1-c1nc(-c2c(C)nn(C3CCN(C)CC3)c2C)cc(N2CCOC[C@H]2C)n1]
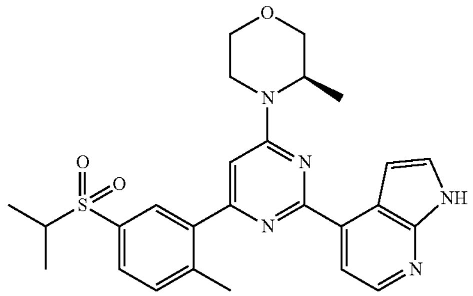
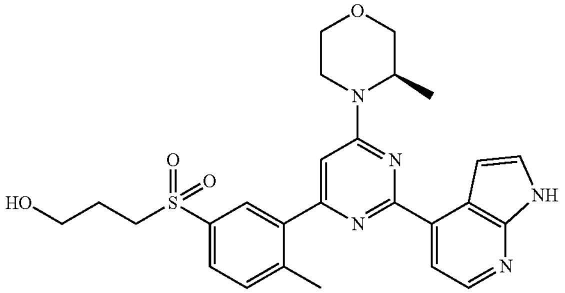

-continued
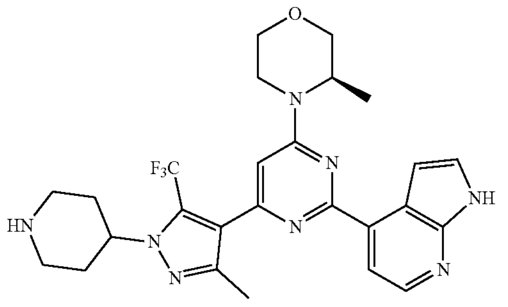
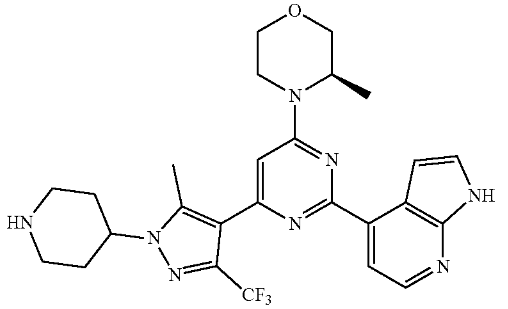
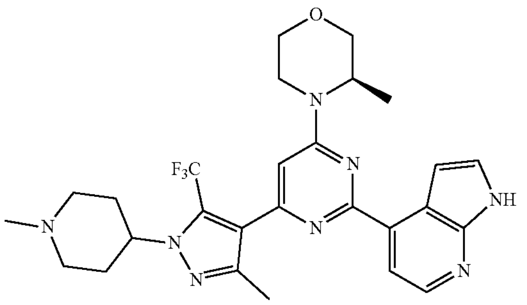
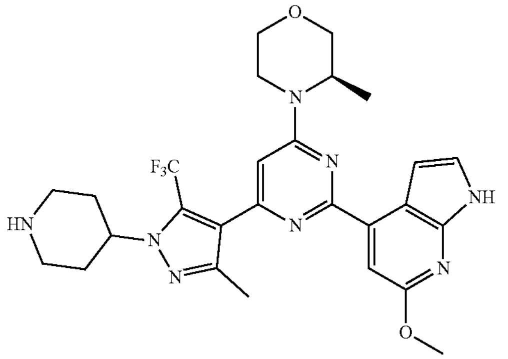
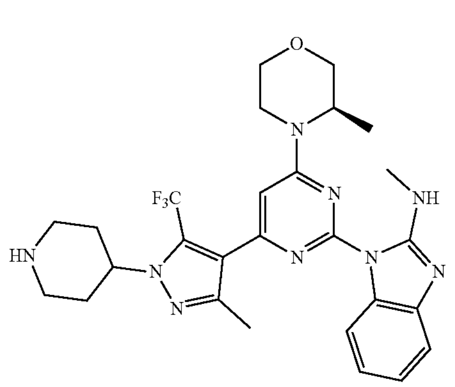
-continued
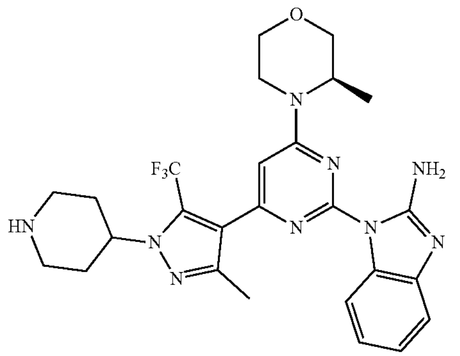
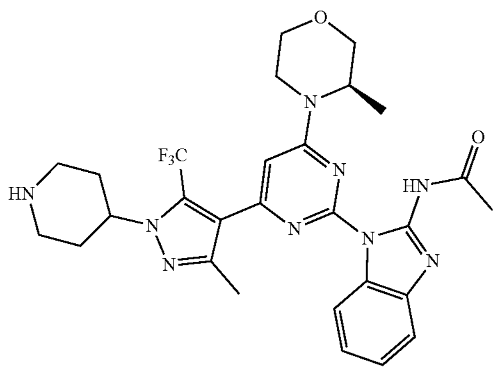
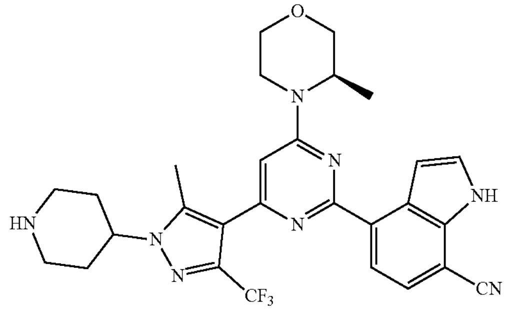
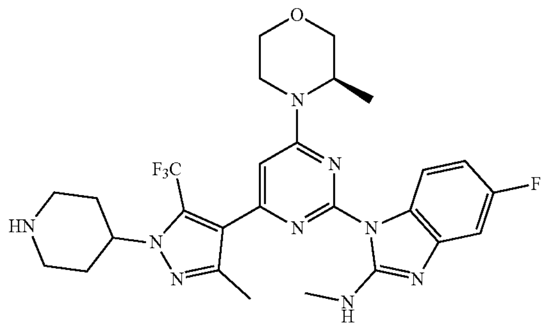
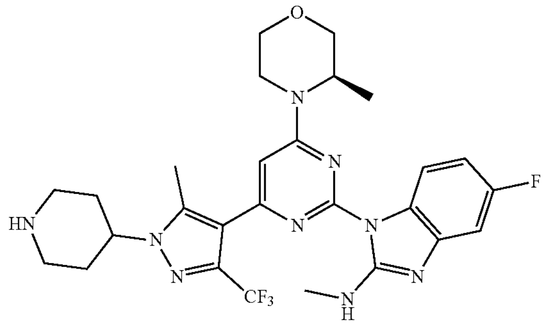

-continued
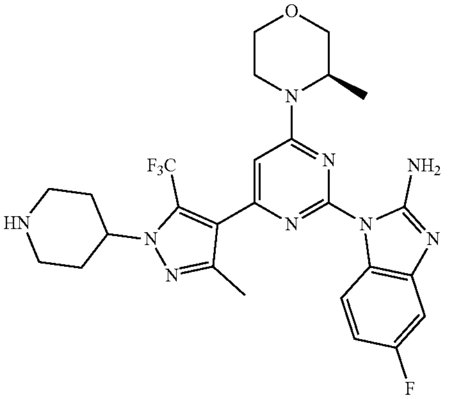
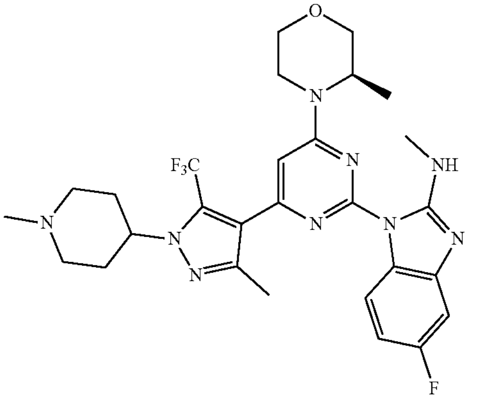
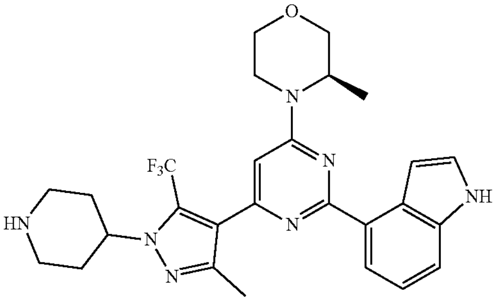
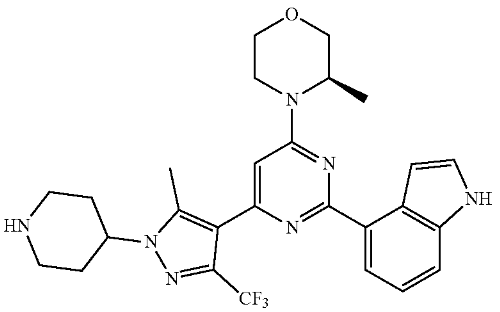
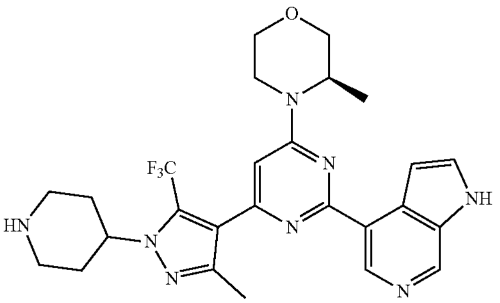
-continued
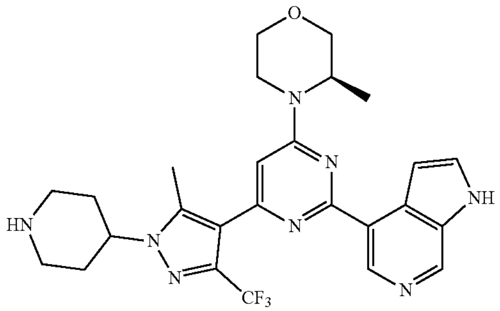
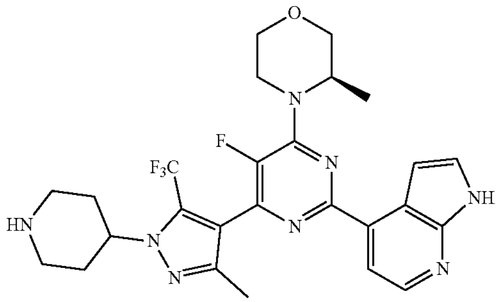
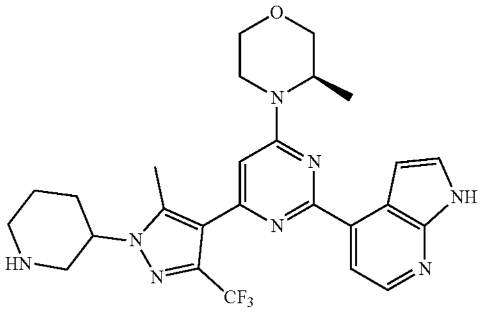
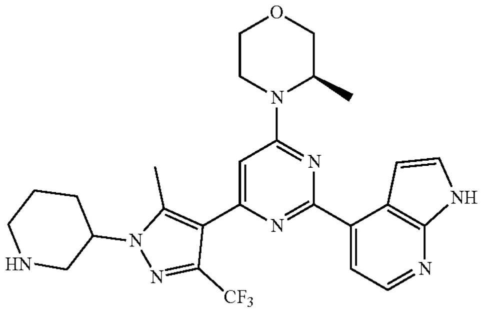
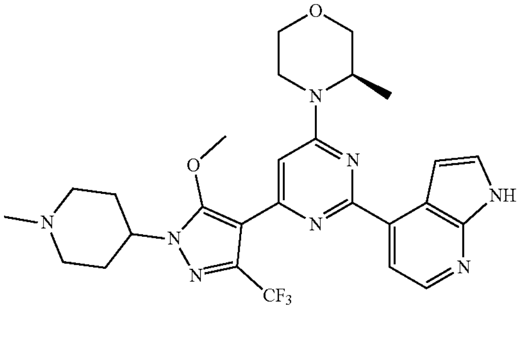

-continued
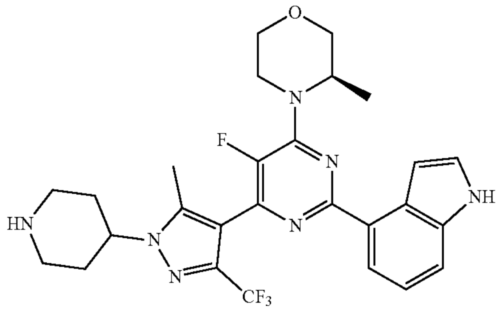
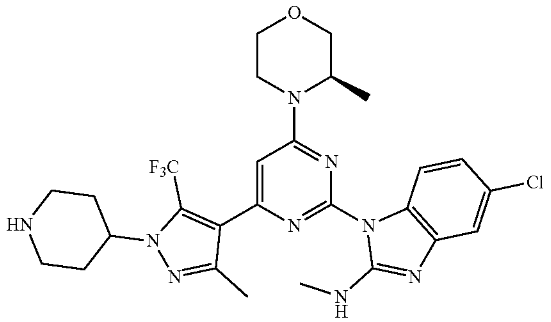
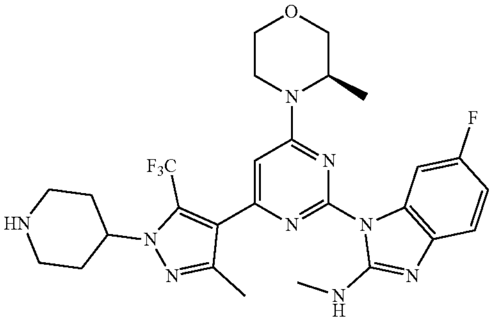
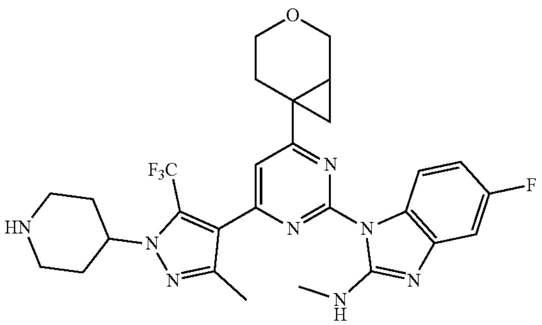
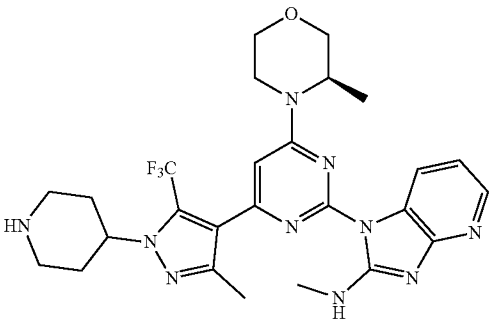
-continued
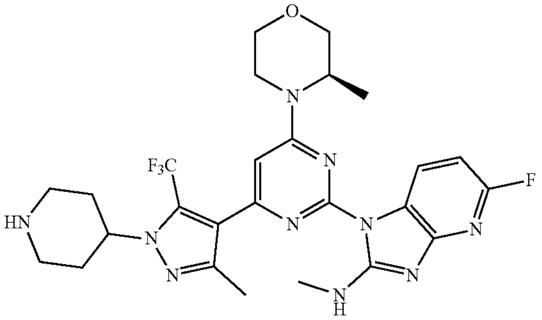
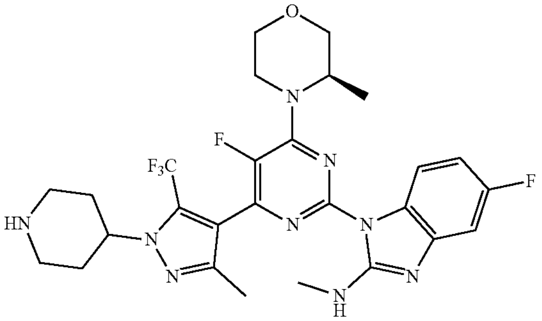
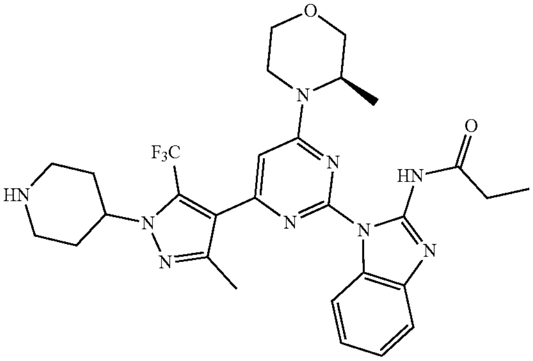
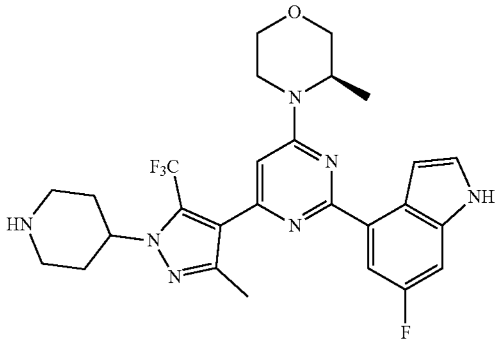
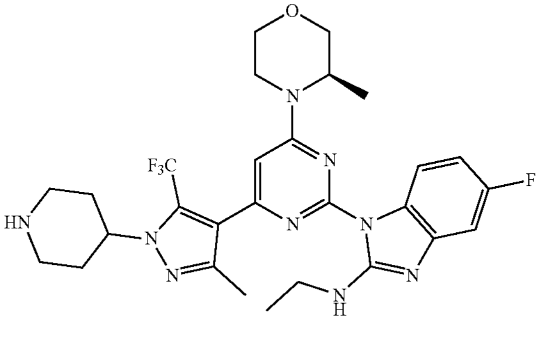

-continued
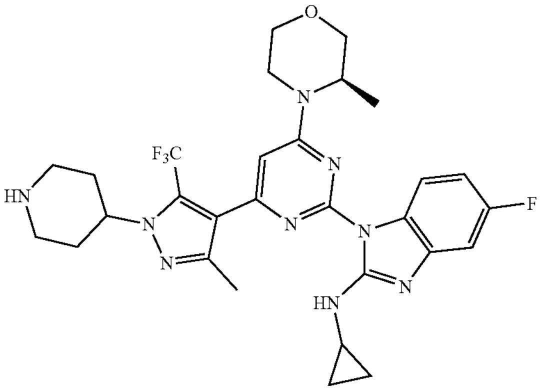
-continued
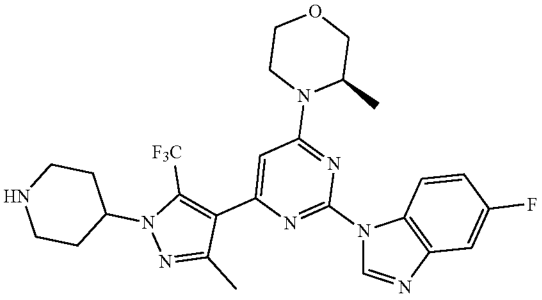
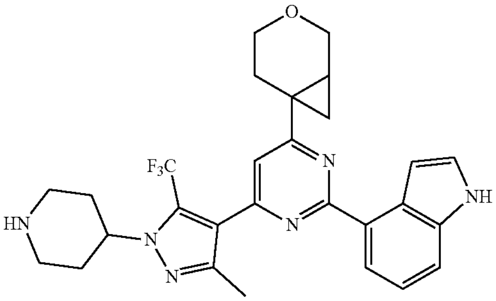
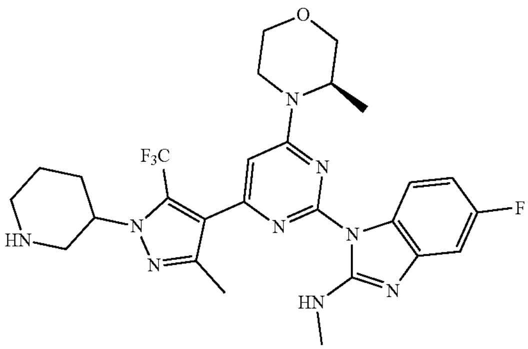

-continued
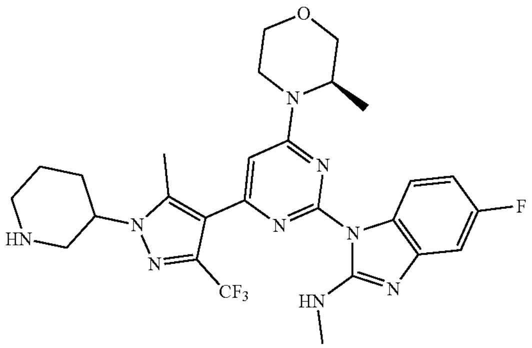
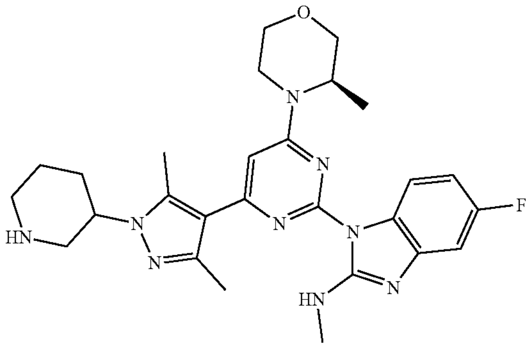
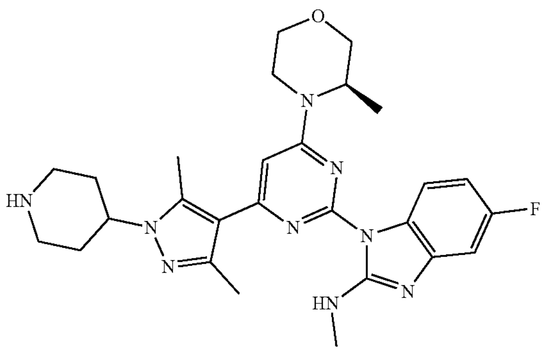
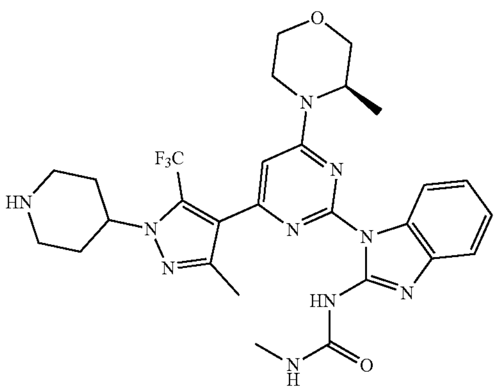
-continued
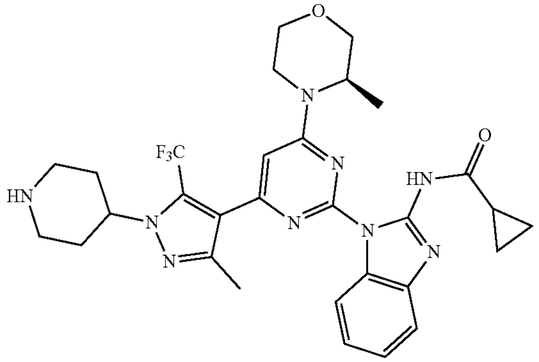
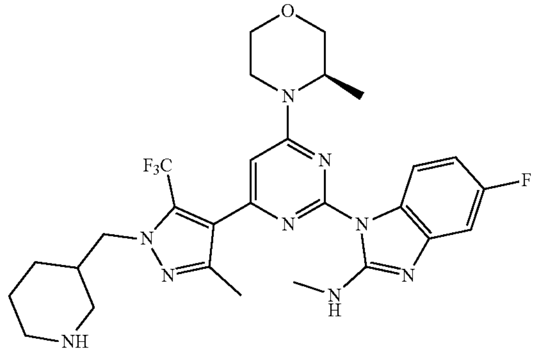
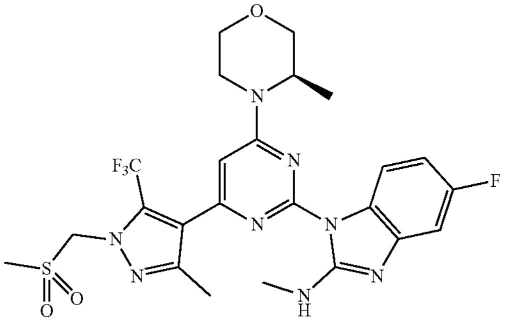
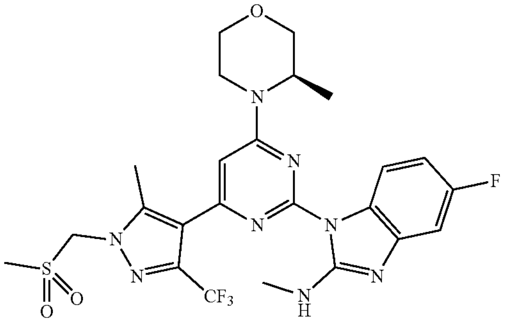
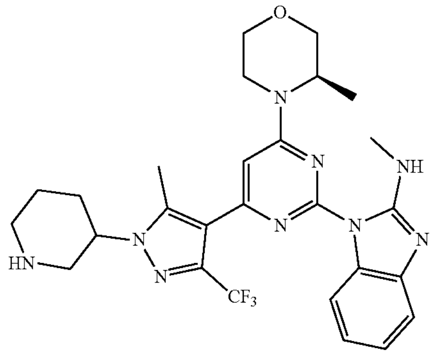

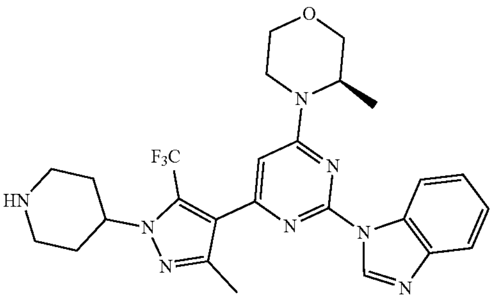
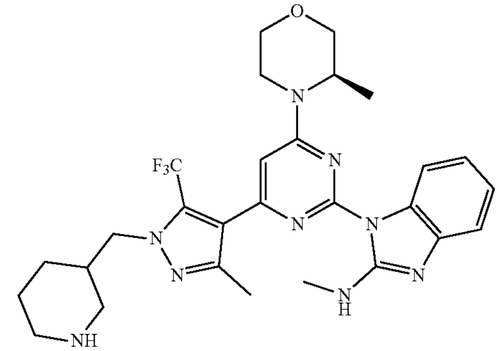
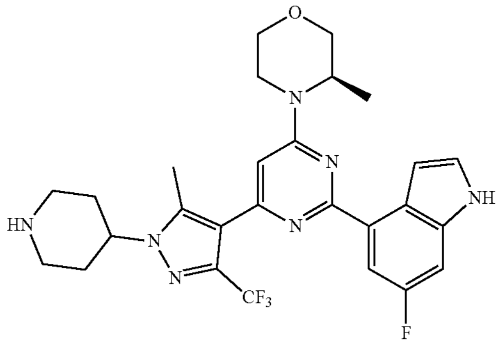
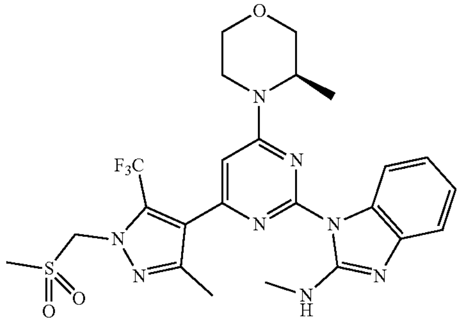
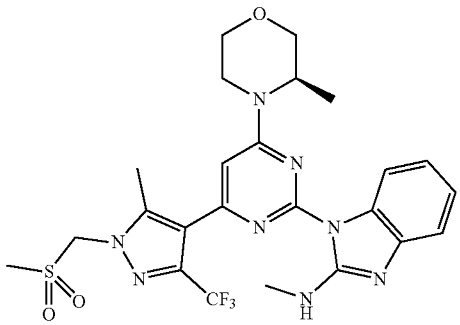
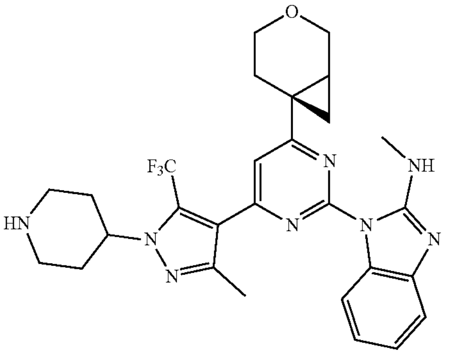
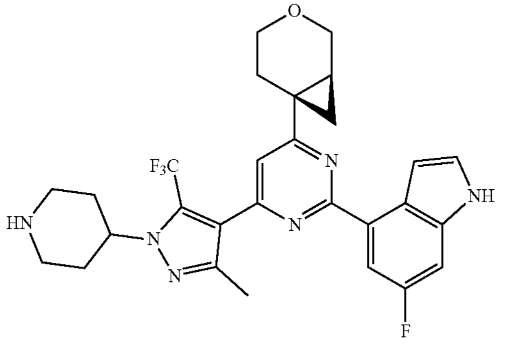
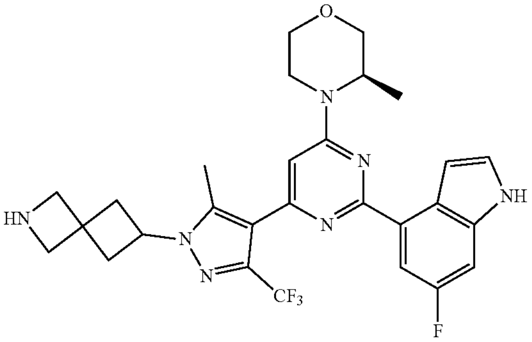
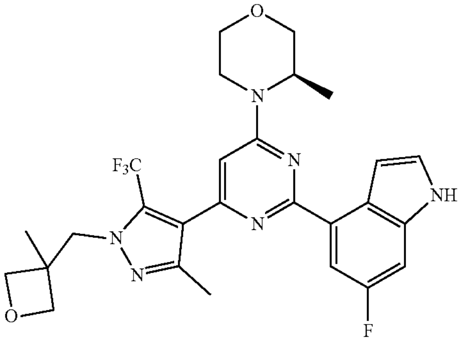
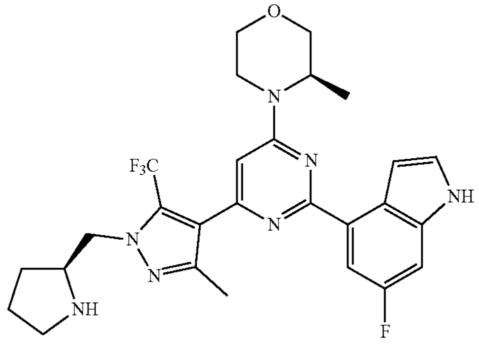

-continued
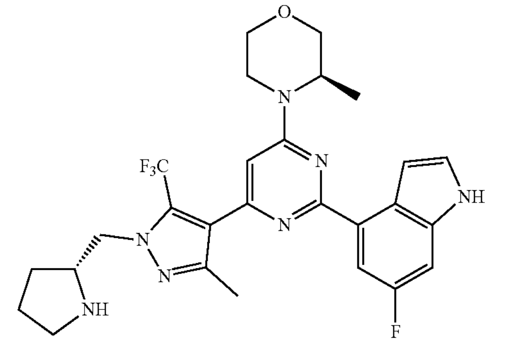
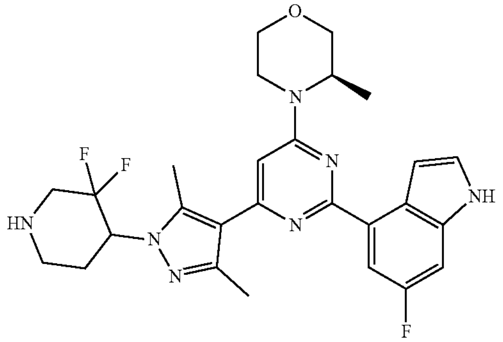
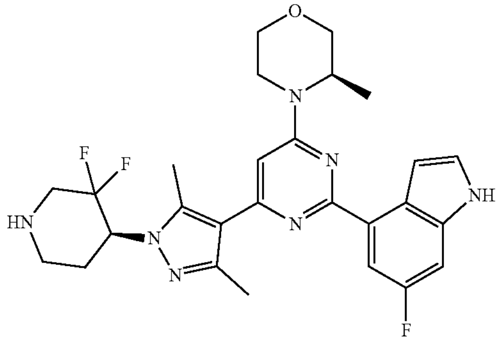
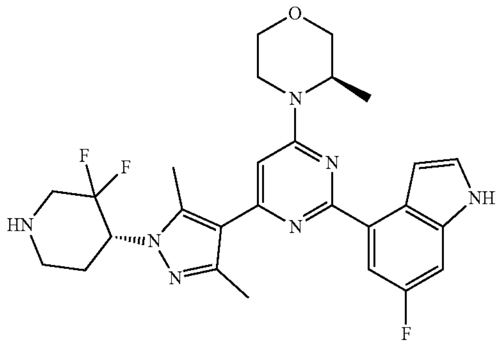
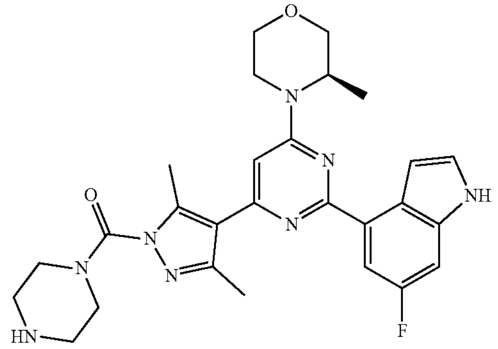
-continued
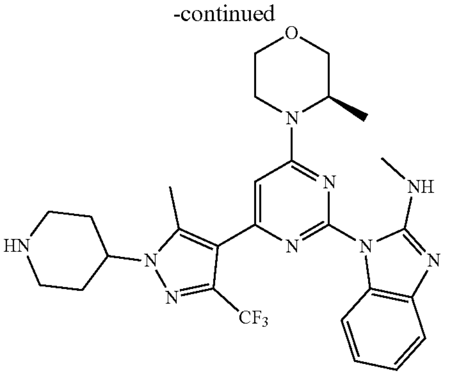
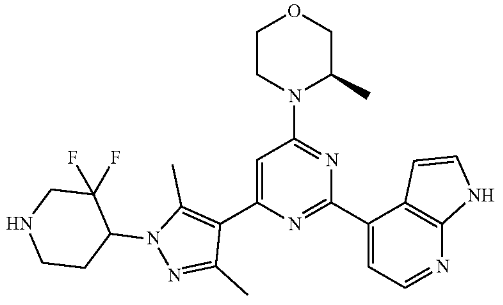
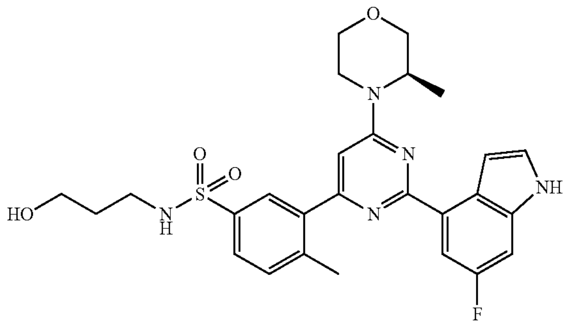
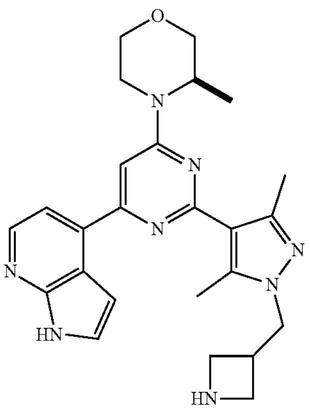

-continued

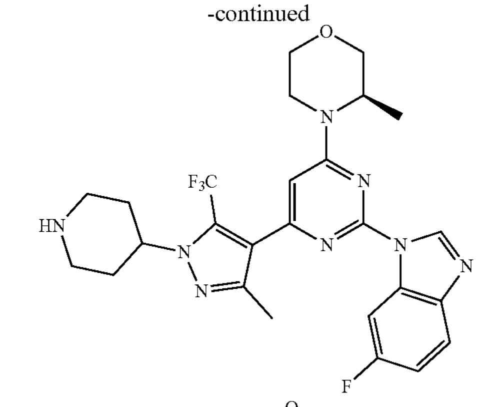

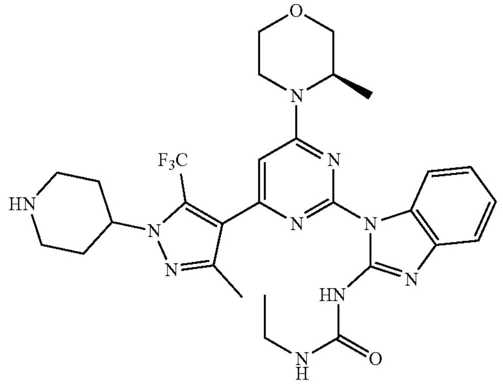

.

15. A pharmaceutical composition, comprising:

the compound, or the pharmaceutically acceptable salt, enantiomer, diastereomer, racemate, solvate, hydrate, polymorph, prodrug or isotopic variant thereof according to claim 1; and a pharmaceutically acceptable excipient;

alternatively, the pharmaceutical composition further comprises one or more other therapeutic agents.

16. A method of treating and/or preventing diseases mediated by ATR kinase in a subject, which comprises administering to the subject the compound, or the pharmaceutically acceptable salt, enantiomer, diastereomer, racemate, solvate, hydrate, polymorph, prodrug or isotopic variant thereof according to claim 1.

17. The method of claim 16, wherein the said diseases mediated by ATR kinase includes: proliferative diseases (such as cancer), especially solid tumors (such as carcinoma and sarcoma), leukemia and lymphoma, especially breast cancer, colorectal cancer, lung cancer (including small cell lung cancer, non-small cell lung cancer and bronchoalveolar cancer), prostate cancer and bile duct cancer, bone cancer, bladder cancer, head and neck cancer, kidney cancer, liver cancer, gastrointestinal cancer, esophageal cancer, ovarian cancer, pancreatic cancer, skin cancer, testicular cancer, thyroid cancer, uterine cancer, cervical cancer and vulvar cancer, and leukemia [including acute lymphoblastic leukemia (ALL) and chronic myeloid leukemia (CML)], multiple myeloma and lymphoma.

* * * * *